US009902739B2

(12) United States Patent
Stewart et al.

(10) Patent No.: US 9,902,739 B2

(45) Date of Patent: Feb. 27, 2018

(54) SMALL MOLECULE INHIBITORS OF G PROTEIN COUPLED RECEPTOR 6 KINASES POLYPEPTIDES

(71) Applicant: Mayo Foundation for Medical Education and Research, Rochester, MN (US)

(72) Inventors: Alexander Keith Stewart, Scottsdale, AZ (US); Brian Rich, San Jose, CA (US); Nikolai Sepetov, Los Gatos, CA (US); Robert Greenhouse, Newark, CA (US); Artem Plekhov, Fremont, CA (US); Wen Yang, San Jose, CA (US); Zhiwei Tong, San Jose, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/305,808

(22) PCT Filed: Apr. 21, 2015

(86) PCT No.: PCT/US2015/026926

§ 371 (c)(1),
(2) Date: Oct. 21, 2016

(87) PCT Pub. No.: WO2015/164411

PCT Pub. Date: Oct. 29, 2015

(65) Prior Publication Data

US 2017/0050979 A1 Feb. 23, 2017

Related U.S. Application Data

(60) Provisional application No. 61/982,184, filed on Apr. 21, 2014, provisional application No. 62/027,651, filed on Jul. 22, 2014.

(51) Int. Cl.

| | |
|---|---|
| ***A61K 31/4196*** | (2006.01) |
| ***A61K 31/4155*** | (2006.01) |
| ***C07D 403/14*** | (2006.01) |
| ***C07D 249/12*** | (2006.01) |
| ***C07D 495/04*** | (2006.01) |
| ***C07D 403/12*** | (2006.01) |
| ***C07D 401/14*** | (2006.01) |
| ***C07D 405/14*** | (2006.01) |
| ***C07D 231/18*** | (2006.01) |
| ***C07D 401/04*** | (2006.01) |
| ***C07D 403/04*** | (2006.01) |
| ***C07D 405/04*** | (2006.01) |
| ***C07D 409/04*** | (2006.01) |
| ***C07D 409/14*** | (2006.01) |
| ***C07D 413/04*** | (2006.01) |
| ***C07D 417/04*** | (2006.01) |
| ***C07D 471/04*** | (2006.01) |
| ***C07D 471/06*** | (2006.01) |

(52) U.S. Cl.

CPC ......... *C07D 495/04* (2013.01); *C07D 231/18* (2013.01); *C07D 401/04* (2013.01); *C07D 401/14* (2013.01); *C07D 403/04* (2013.01); *C07D 403/12* (2013.01); *C07D 405/04* (2013.01); *C07D 405/14* (2013.01); *C07D 409/04* (2013.01); *C07D 409/14* (2013.01); *C07D 413/04* (2013.01); *C07D 417/04* (2013.01); *C07D 471/04* (2013.01); *C07D 471/06* (2013.01)

(58) Field of Classification Search

CPC ................ C07D 403/14; C07D 249/12; A61K 31/4196; A61K 31/4155

See application file for complete search history.

(56) References Cited

U.S. PATENT DOCUMENTS

| | | | |
|---|---|---|---|
| 7,226,941 | B2 | 6/2007 | Park et al. |
| 2002/0034767 | A1 | 3/2002 | Benovic et al. |
| 2005/0288347 | A1 | 12/2005 | Hodge et al. |
| 2006/0029983 | A1 | 2/2006 | Oakley et al. |
| 2006/0100235 | A1 | 5/2006 | Andersen et al. |
| 2006/0173006 | A1 | 8/2006 | Sun et al. |
| 2009/0149389 | A1 | 6/2009 | Panitch et al. |
| 2010/0099683 | A1 | 4/2010 | Tomkinson et al. |
| 2011/0139654 | A1 | 6/2011 | Klein et al. |
| 2011/0257211 | A1 | 10/2011 | Chand et al. |
| 2012/0190708 | A1 | 7/2012 | MacKerell, Jr. et al. |
| 2014/0309185 | A1 | 10/2014 | Stewart |
| 2017/0050939 | A1 | 2/2017 | Stewart et al. |

FOREIGN PATENT DOCUMENTS

| | | |
|---|---|---|
| EP | 0014810 | 9/1980 |
| WO | WO2003032916 | 4/2003 |
| WO | WO2005092873 | 10/2005 |

(Continued)

OTHER PUBLICATIONS

PubChem Compound Summary for CID 43164245, created Jul. 21, 2009.*

Caliper Life Sciences, "Fragment-based screening of enzyme drug targets: Microfluidic mobility shift assay improves confidence in candidate selection." *Caliper Life Sciences White Paper.*, 2010.

CAS RN 77803-55-5, STN Registry Database, entered STN Nov. 16, 1984, Accessed Jun. 23, 2017.

European Communication Pursuant to Article 94(3) EPC in International Application No. 12844282.9, dated Feb. 20, 2017, 9 pages.

European Search Report for International Application No. EP12844282, dated Apr. 14, 2015, 12 pages.

European Search Report for International Application No. EP15782804.7, dated Aug. 21, 2017, 10 pages.

(Continued)

*Primary Examiner* — Rebecca Anderson

*Assistant Examiner* — Karen Cheng

(74) *Attorney, Agent, or Firm* — Fish & Richardson P.C.

(57) ABSTRACT

This document relates to inhibitors of G protein coupled receptor 6 kinase (GRK6) polypeptides as well as methods and materials for using such inhibitors to treat hematological malignancies, inflammation diseases, and autoimmune disorders.

22 Claims, No Drawings

(56) References Cited

FOREIGN PATENT DOCUMENTS

| | | | |
|---|---|---|---|
| WO | WO2005113788 | | 12/2005 |
| WO | WO2009053694 | | 4/2009 |
| WO | WO2010118208 | | 10/2010 |
| WO | WO 2013/063458 | * | 5/2013 |

OTHER PUBLICATIONS

European Search Report for International Application No. EP15783914.3, dated Aug. 24, 2017, 10 pages.
Extended European Search Report for International Application No. EP12844282, dated Jul. 24, 2015, 22 pages.
International Preliminary Report on Patentability for PCT/US2012/062206, dated May 8, 2014, 10 pages.
International Preliminary Report on Patentability in International Application No. PCT/US2015/26926, dated Oct. 25, 2016, 8 pages.
International Search Report and Written Opinion for PCT/US2012/0622006, dated Mar. 28, 2013, 15 pages.
International Search Report and Written Opinion in International Application No. PCT/US2015/26926, dated Oct. 19, 2015, 15 pages.
Invitation to Pay Additional Fees for International Application No. PCT/US2015/26926, dated Aug. 6, 2015, 12 pages.
Karampuri et al., "Structure based molecular design, synthesis and biological evaluation of α-pyrone analogs as anti-HSV agent," *Bioorganic & Medicinal Chemistry Letters*., 22(19):6261-6266, Oct. 2012.
Matysiak, "QSAR of Antiproliferative Activity of N-Substituted 2-Amino-5-(2,4-dihydroxypheny1)-1,3,4-thiadiazoles in Various Human Cancer Cells " *QSAR & Combinatorial Science*, (27)5:607-617, Epub Nov. 13, 2007.
Mazzone et al., "Synthesis and biological evaluation of some 5-aryl-2-amino-1, 3, 4-oxa(thia)diazoles," *Farmaco, Edizione Scientifica*, 37(10):685-700, 1982 (abstract) [online] Retrieved from STN on the Web, Database CA: 98:100754, compound of the formulae I , I I, compounds with RN 35314-01-3, 83796-35-4.
Mazzone et al., "Synthesis of pharmaceutically significant 1-aryl-4H(R)-thiosemicarbazides, the corresponding 5-aryl-4H(R) -1, 2, 4-triazoline-3-thiones and some derivatives," Farmaco, Edizione Scientifica, 36(3):181-196, 1981, (Original in Italian) [English abstract] [on-line] Retrieved from STN on the Web, Database CA: 95:6695, compound of the formula II, compounds with RN 77803-55-5, 77803-57-7.
Pollack et al., "A comparative study of fragment screening methods on the p38α kinase: new methods, new insights," *J Comput Aided Mol Des*., 25(7):677-687, Epub Jul. 6, 2011.
Puglisi et al., "Antiinflammatory and analgesic activities of 3-(carboxymethylthio)-5-aryl-4-methyl-and -4-phenyl-4H-1, 2, 4-triazoles," Farmaco, Edizione Scientifica, 37(9):633-640, 1982, (Original in Italian) [English abstract] [on-line] Retrieved from STN on the Web, Database CA: 97:207757, compound on the formula I, compound with RN 58755-01-4D.
STN search result. See p. 201-203. Wang et al. Study on the nucleophilic substitution of 3-aryl-5-mercapto-1,2,4-tnazoles. Youji Huaxue (1997), 17(6), 535-541. STN search result on Jul. 12, 2015.
Stockman et al., "Identification of allosteric PIF-pocket ligands for PDK1 using NMR-based fragment screening and 1H-15N TROSY experiments," *Chem Biol Drug Des*., 73(2):179-188, Feb. 2009.
Tiedemann et al., "Kinome-wide RNAi studies in human multiple myeloma identify vulnerable kinase targets, including a lymphoid-restricted kinase, GRK6," *Blood*, 115(8):1594-1604, Epub Dec. 7, 2009.
Westwood et al., "Identification of arylamine N-acetyltransferase inhibitors as an approach towards novel anti-tuberculars," *Protein Cell*., 1(1):82-95, Epub Mar. 18, 2010.
Zareef et al., "Synthesis and antimicrobial activity of some derivatives of acylhydrazine including novel benzenidiazasulfonamides," *Eur. J. Med. Chem*., 1:141-152, Jan. 2008.
U.S. Appl. No. 14/354,326, filed Apr. 25, 2014, Stewart et al.
U.S. Appl. No. 15/305,808, filed Oct. 21, 2016, Stewart et al.
U.S. Appl. No. 15/305,809, filed Oct. 21, 2016, Stewart et al.

* cited by examiner

SMALL MOLECULE INHIBITORS OF G PROTEIN COUPLED RECEPTOR 6 KINASES POLYPEPTIDES

CROSS REFERENCE TO RELATED APPLICATIONS

This application is a National Stage application under 35 U.S.C. § 371 of International Application No. PCT/US2015/026926, having an International Filing Date of Apr. 21, 2015, which claims the benefit of U.S. Provisional Application Ser. Nos. 61/982,184, filed Apr. 21, 2014, and 62/027,651, filed Jul. 22, 2014, the disclosures of each of which are incorporated herein by reference in their entirety.

TECHNICAL FIELD

This document relates to inhibitors of G protein coupled receptor 6 kinase (GRK6) polypeptides as well as methods and materials for using such inhibitors to treat hematological malignancies, inflammation diseases, and autoimmune disorders.

BACKGROUND

GRK6 is a member of the enzyme group of kinases. Kinases regulate many different cell proliferation, differentiation, and signaling processes by adding phosphate groups to proteins. The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250-300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI-XI, binds the protein substrate and carries out the transfer of the gamma phosphate from ATP to the hydroxyl group of a serine, threonine, or tyrosine residue. Subdomain V spans the two lobes.

SUMMARY

Provided herein is a compound of Formula I:

Formula I

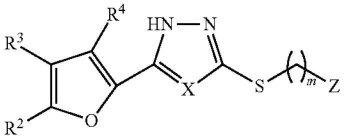

or a pharmaceutically acceptable salt thereof,
wherein:
X is selected from the group consisting of CH and N;

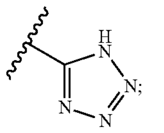 [SMILES: *c1nnn[nH]1]

Z is selected from the group consisting of —C(O)OR$^1$ and
$R^1$ is selected from the group consisting of H and ($C_1$-$C_6$) alkyl;
$R^2$ is selected from the group consisting of: a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, and a substituted or unsubstituted heteroaryl;
$R^3$ and $R^4$ are independently selected from the group consisting of: H, halo, a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, a substituted or unsubstituted heteroaryl, a substituted or unsubstituted aralkyl, and a substituted or unsubstituted heteroaralkyl;
or $R^2$ and $R^3$ or $R^3$ and $R^4$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and
m is an integer from 1 to 2.

In some embodiments, a compound of Formula I can be a compound of Formula IA:

Formula IA

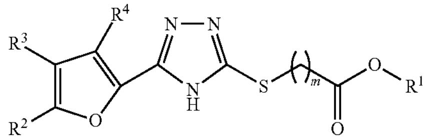

or a pharmaceutically acceptable salt thereof,
wherein:
$R^1$ is selected from the group consisting of H and ($C_1$-$C_6$) alkyl;
$R^2$ is selected from the group consisting of: a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, and a substituted or unsubstituted heteroaryl;
$R^3$ and $R^4$ are independently selected from the group consisting of: H, halo, a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, a substituted or unsubstituted heteroaryl, a substituted or unsubstituted aralkyl, and a substituted or unsubstituted heteroaralkyl;
or $R^2$ and $R^3$ or $R^3$ and $R^4$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and
m is an integer from 1 to 2.

In some embodiments of the compounds of Formula I and/or Formula IA, $R^2$ is a substituted or unsubstituted aryl. In some embodiments, $R^2$ is a substituted or unsubstituted heteroaryl. In some embodiments, $R^2$ is a $(C_1-C_6)$alkyl further substituted by one or more heterocycloalkyls. In some embodiments, $R^2$ is a $(C_1-C_6)$alkyl further substituted by one or more aryl.

In some embodiments of the compounds of Formula I and/or Formula IA, $R^3$ is selected from a group consisting of: a substituted or unsubstituted $(C_1-C_6)$alkynyl, halo, and a substituted or unsubstituted aryl; and $R^4$ is H. In some embodiments, each of $R^1$, $R^3$, and $R^4$ is H; and $R^2$ is a substituted or unsubstituted heteroaryl. For example, $R^2$ can be selected from a group consisting of pyridazinyl, pyridyl, carbazolyl, thiopheneyl, benzothiopheneyl, pyrrolyl, indolyl, quinolinyl, furanyl, and benzofuranyl.

In some embodiments of a compound of Formula IA, each of $R^1$ and $R^4$ is H; $R^2$ is selected from a group consisting of a substituted or unsubstituted aryl and a substituted or unsubstituted heteroaryl; and $R^3$ is selected from a group consisting of halo, a substituted $(C_1-C_6)$alkynyl, and a substituted or unsubstituted aryl.

Non-limiting examples of a compound of Formula I and/or IA include:

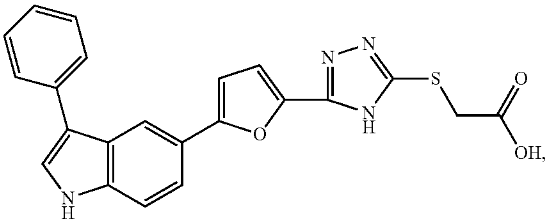
,
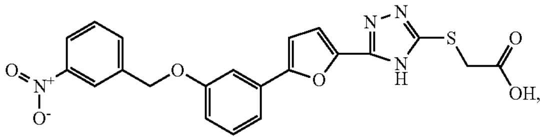
,
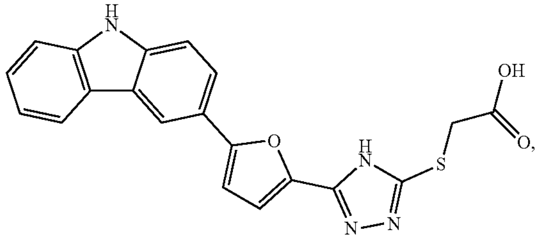
,
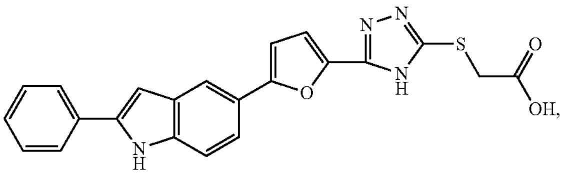
,
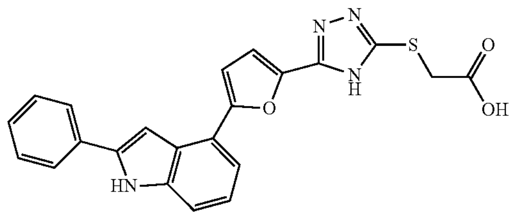

-continued

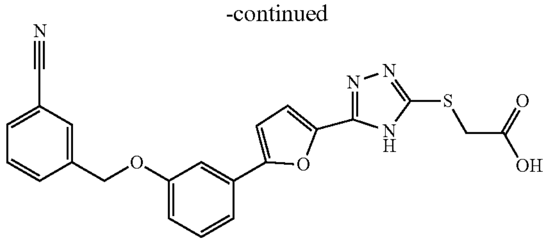

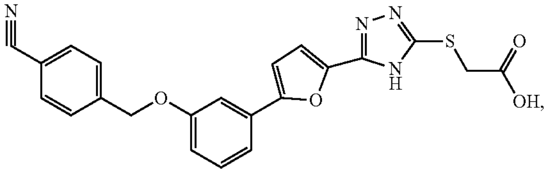
,
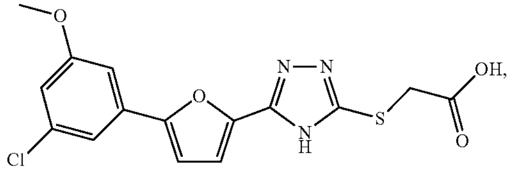
,
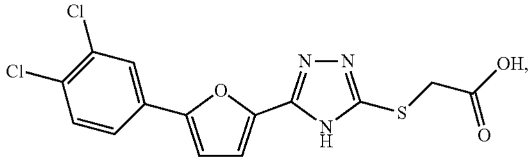
,
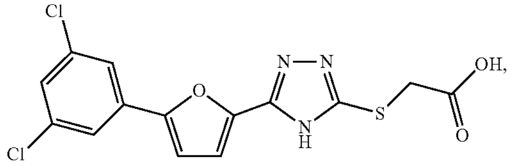
,
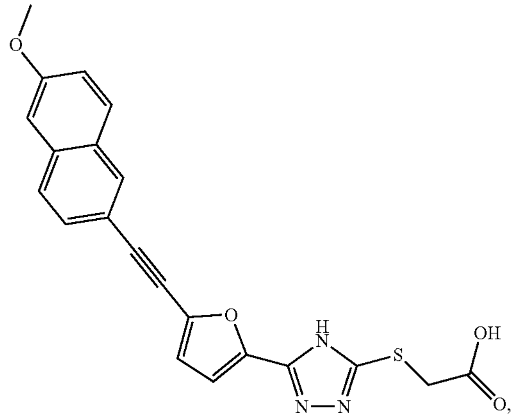
,
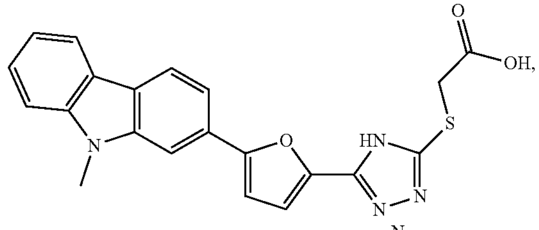
,
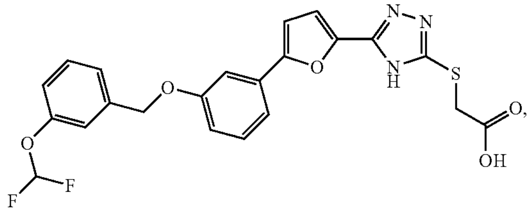
, -continued
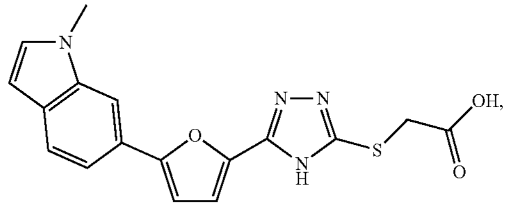
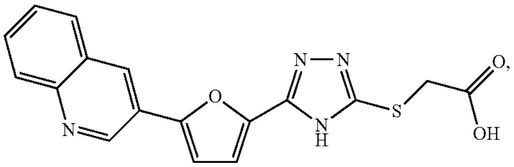
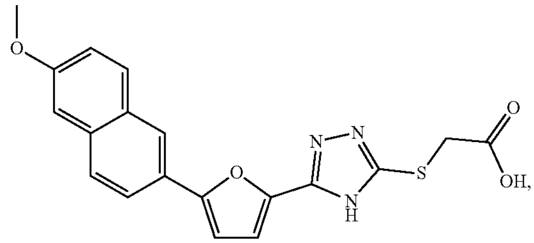
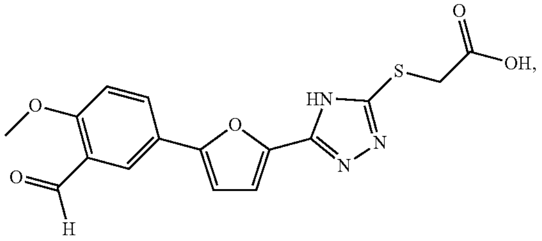
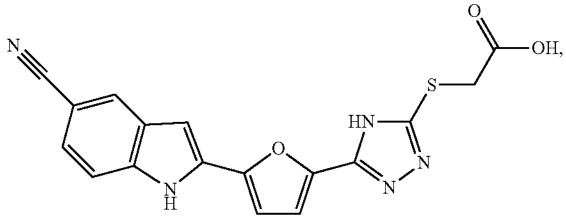
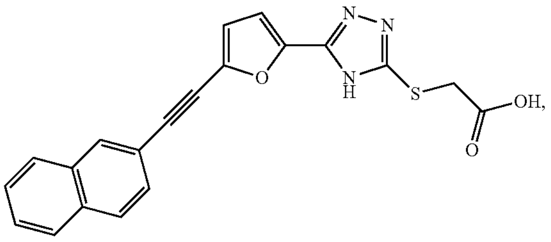
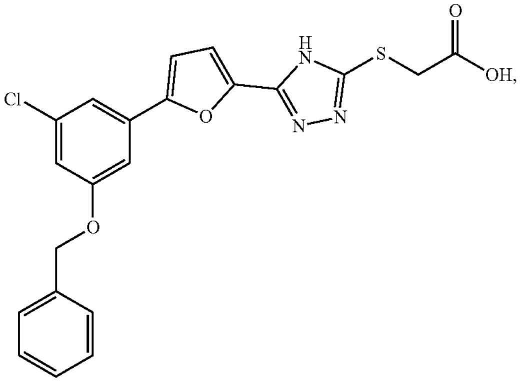
-continued
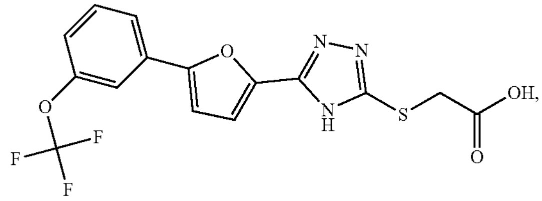
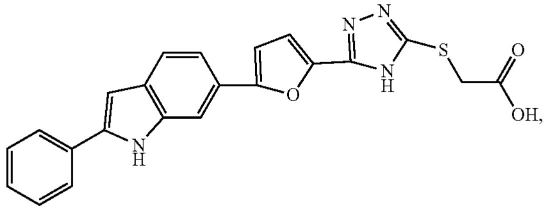
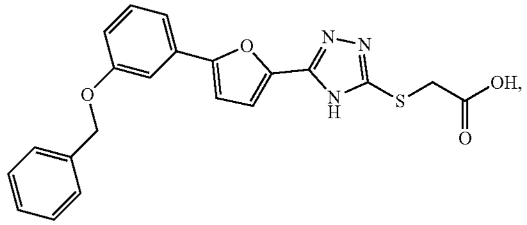
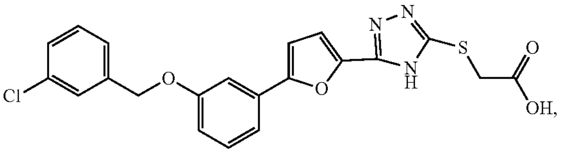
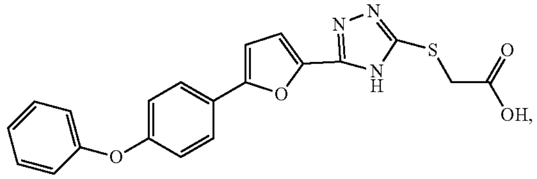
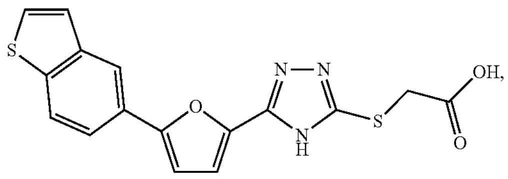
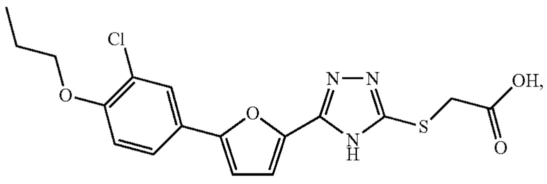
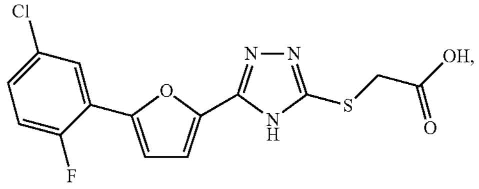
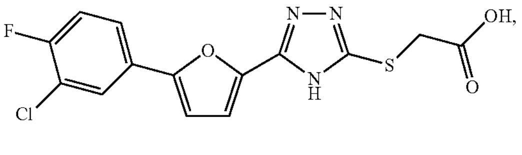

-continued
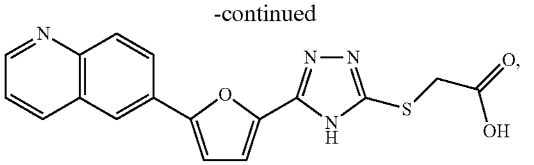
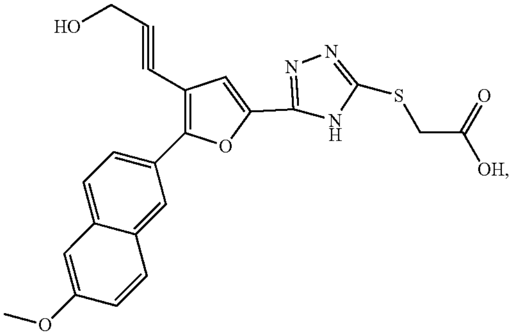
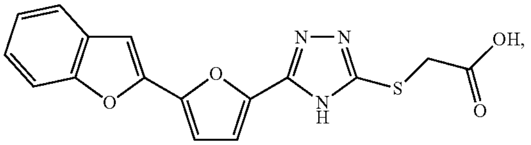
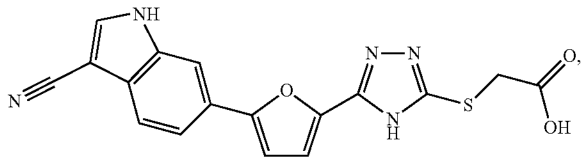
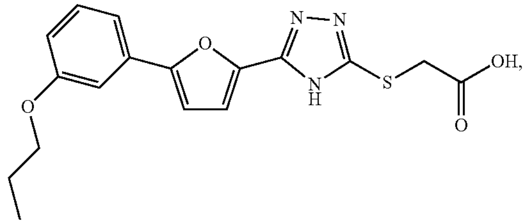
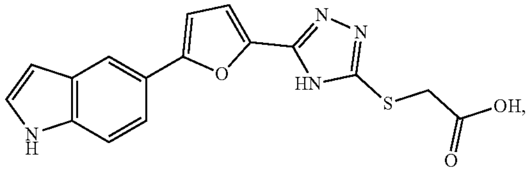
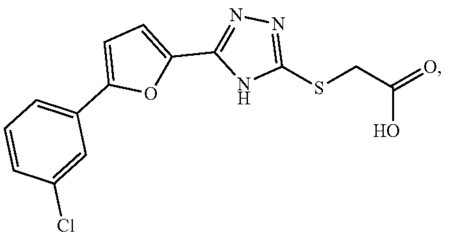
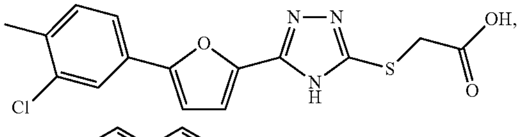
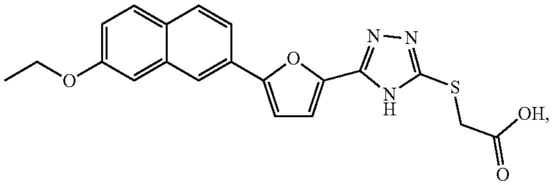
-continued
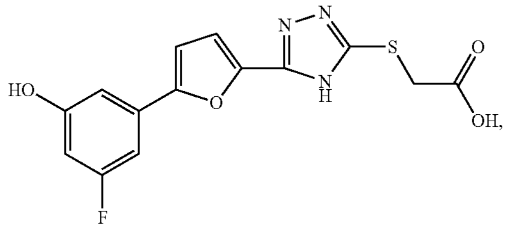
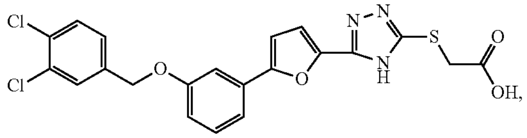
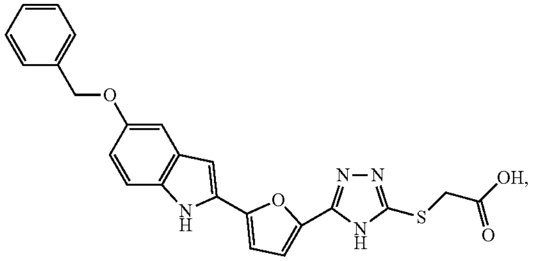
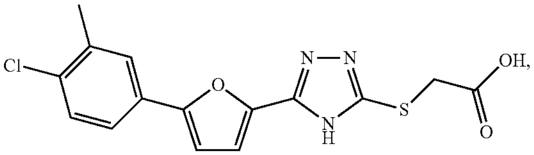
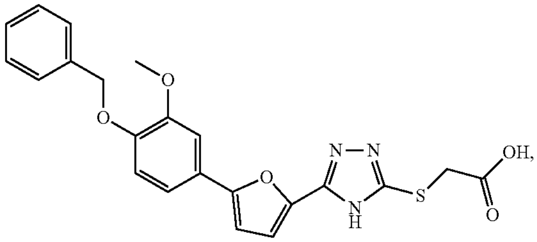
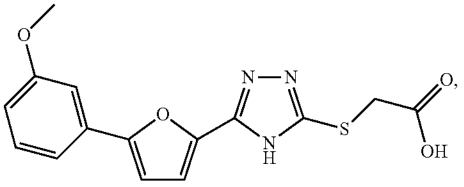
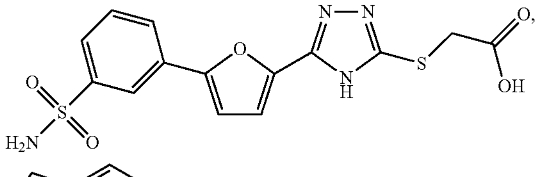
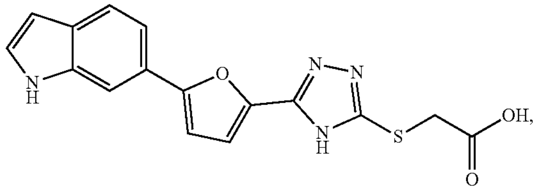
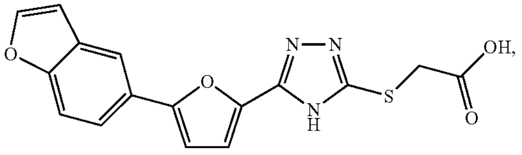

-continued
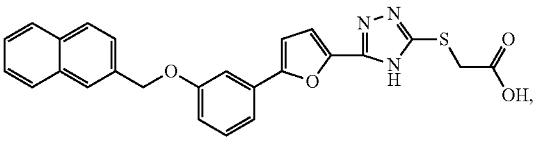
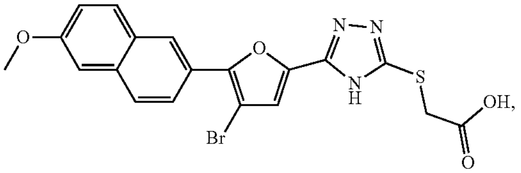
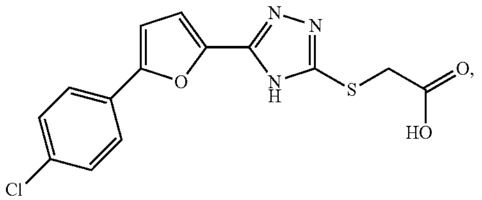
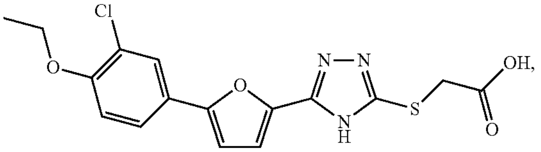
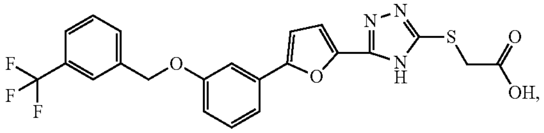
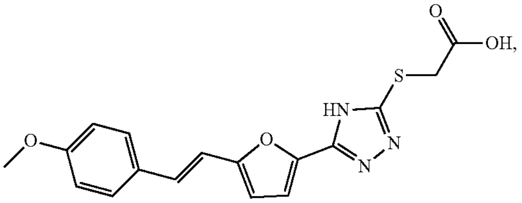
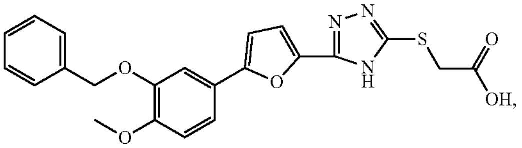
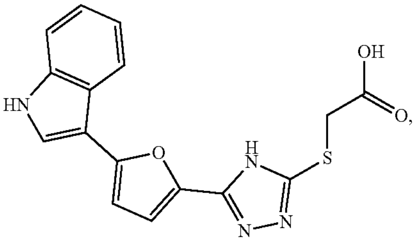
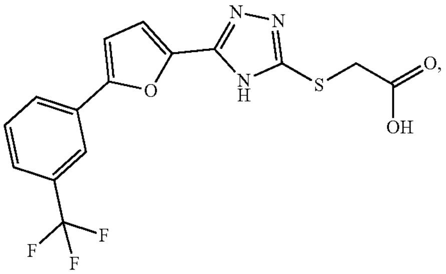
-continued
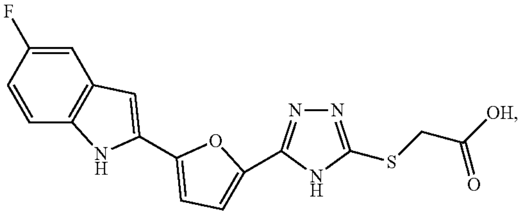
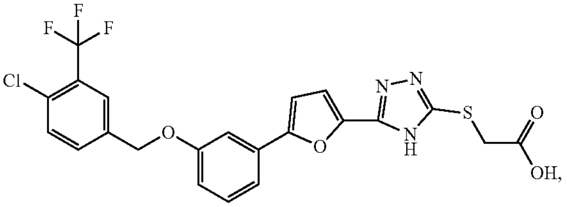
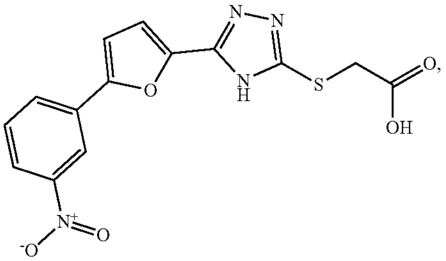
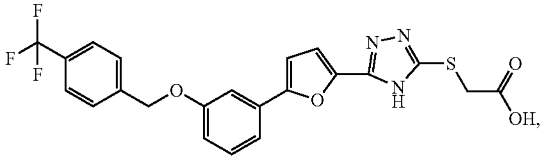
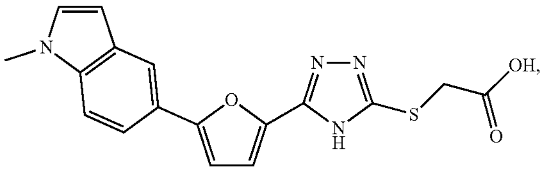
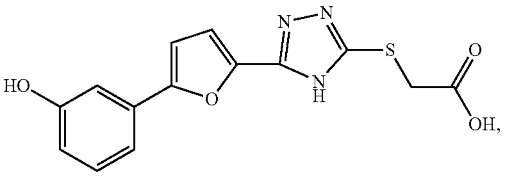
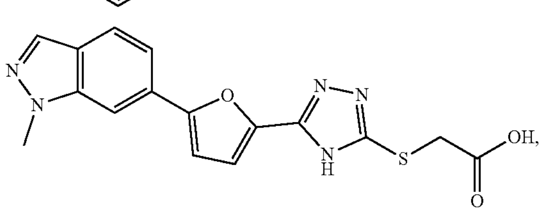
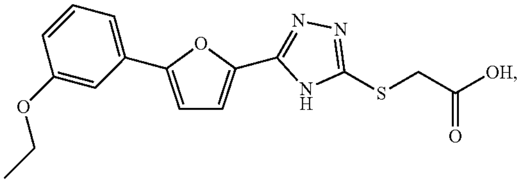

-continued
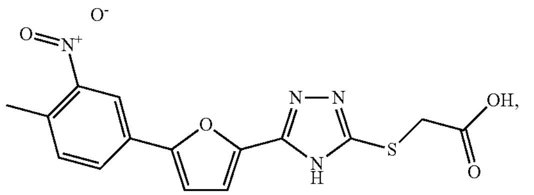
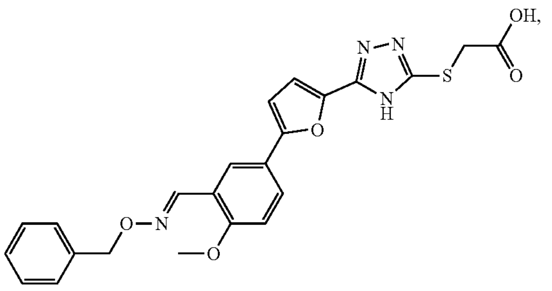
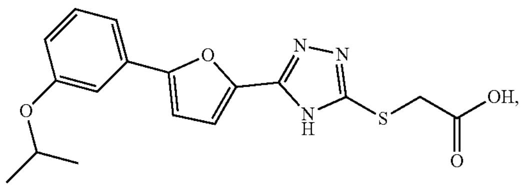
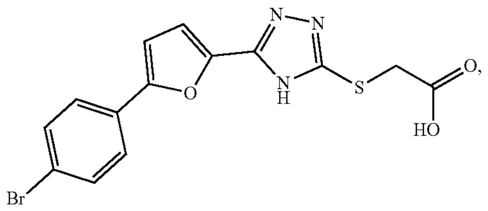
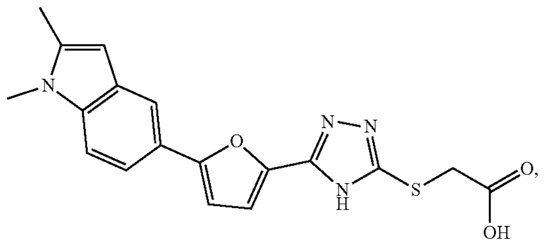
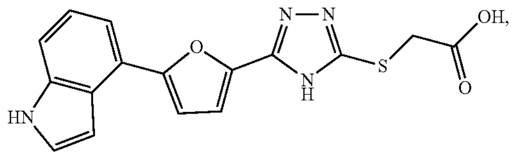
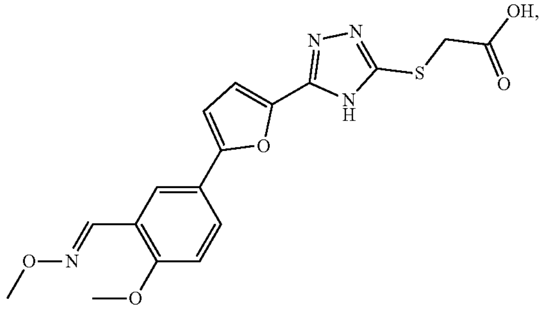
-continued
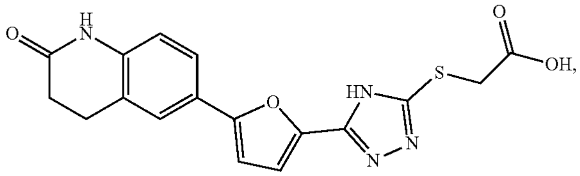
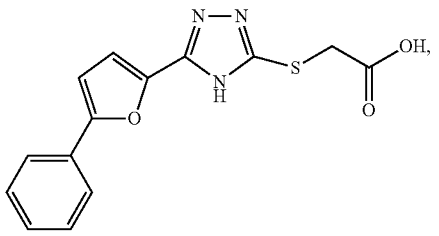
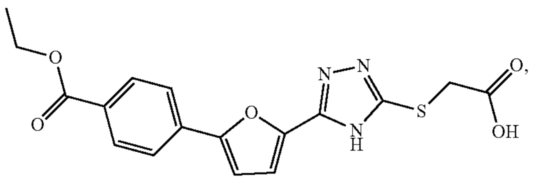
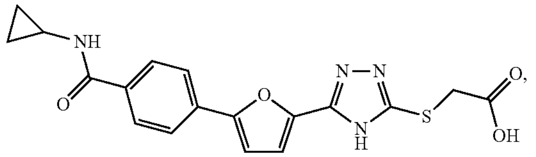
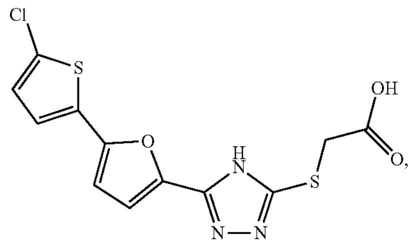
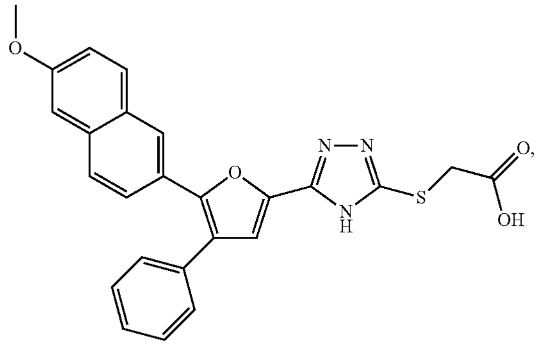
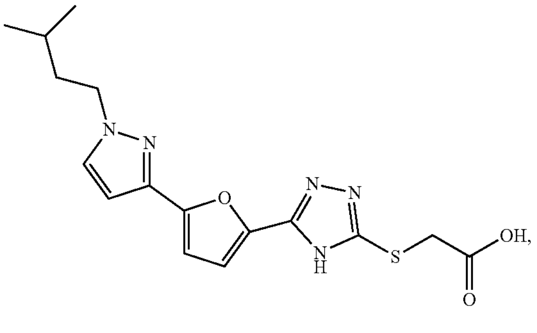

-continued
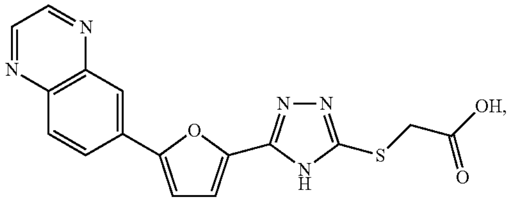
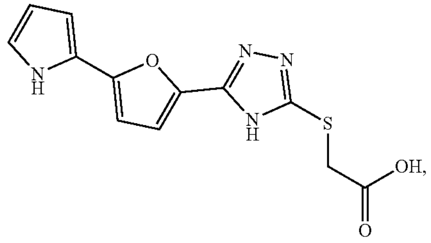
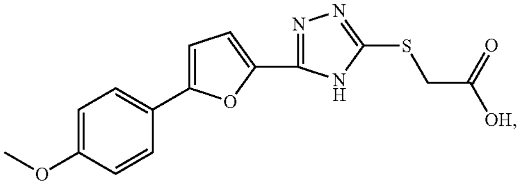
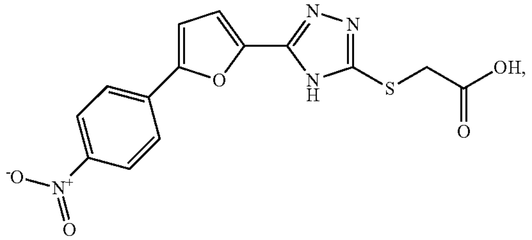
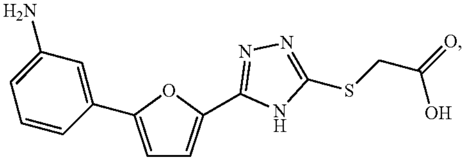
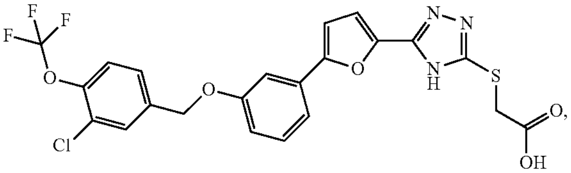
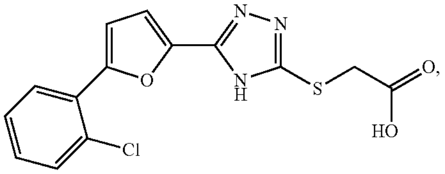
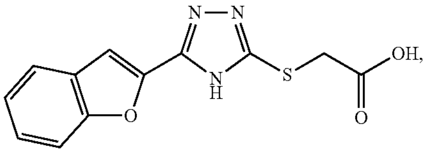
-continued
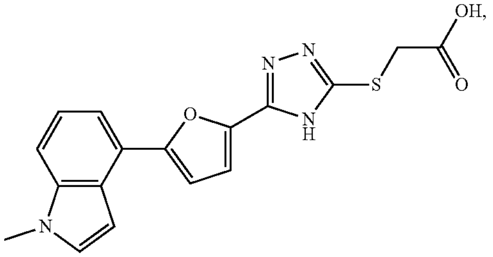
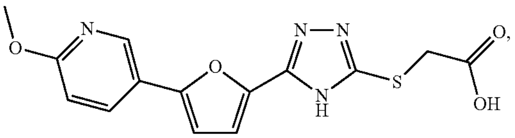
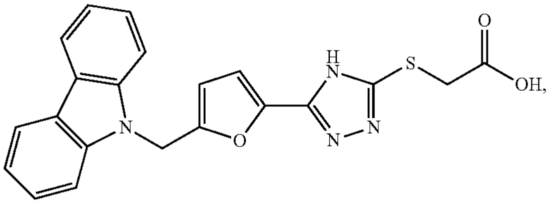
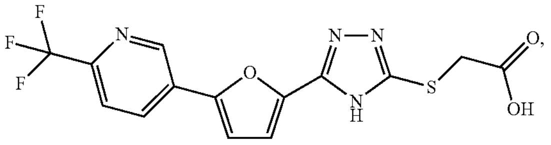
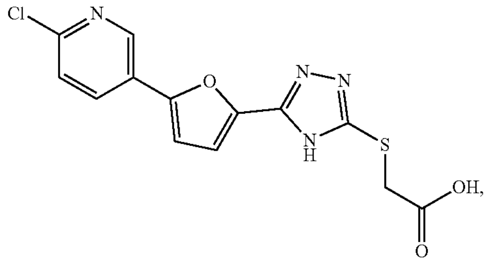
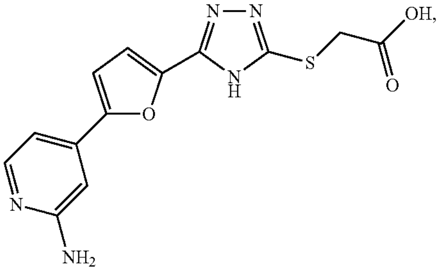
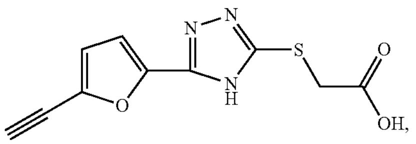
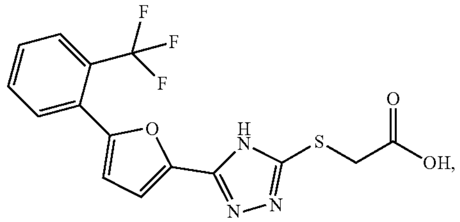

-continued
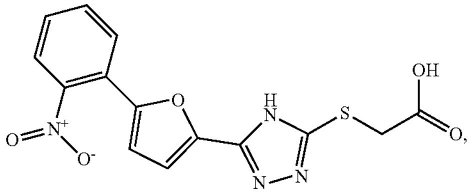
,
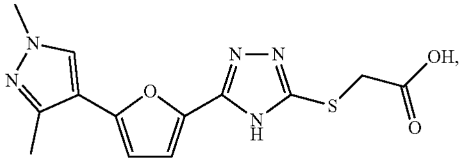
,
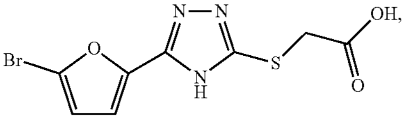
,
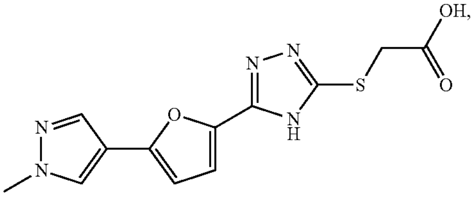
,
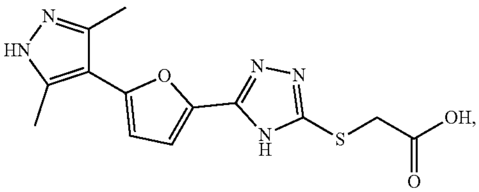
,
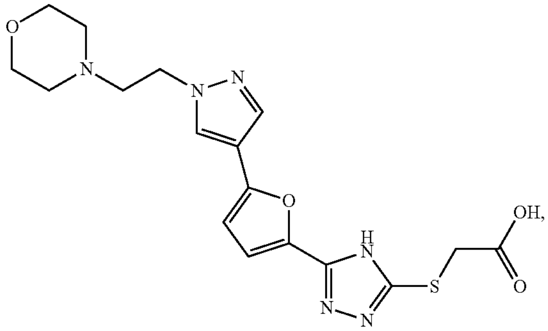
,
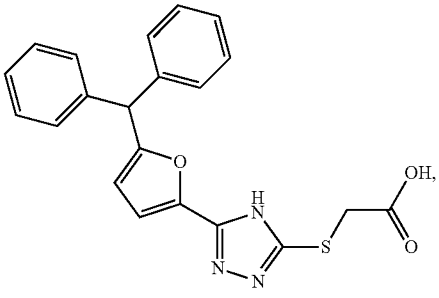
,
-continued
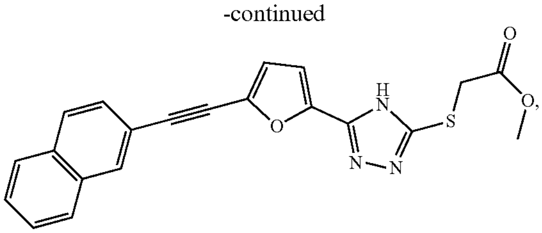
,
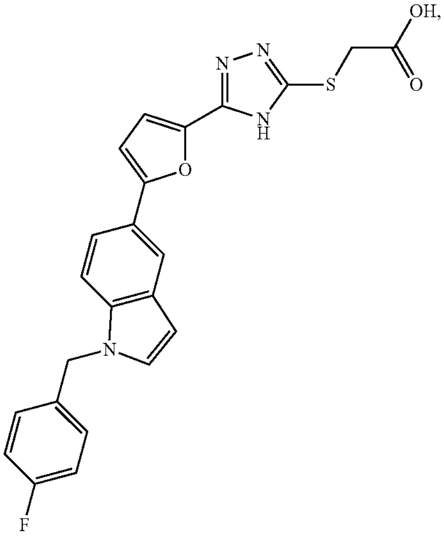
,
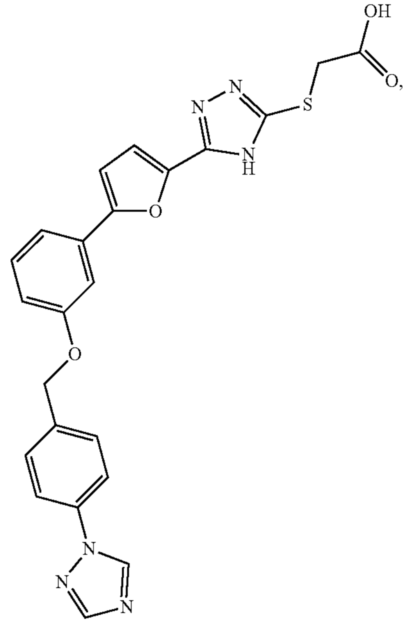
,
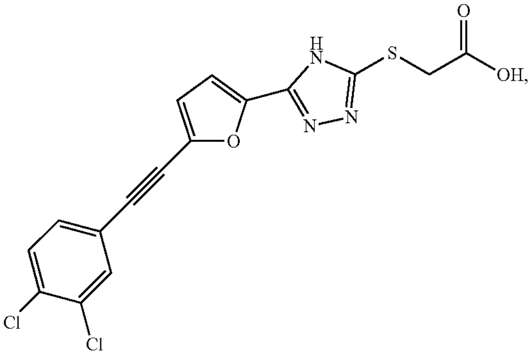
, and -continued

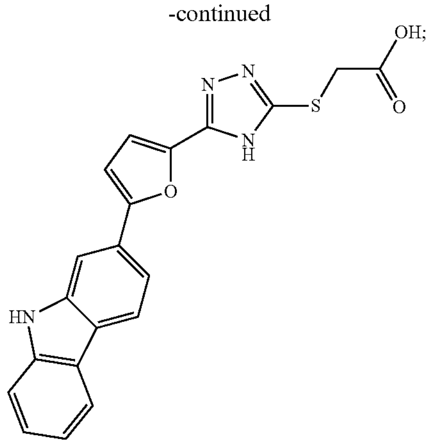

or a pharmaceutically acceptable salt thereof.

In some embodiments, a compound of Formula I can be a compound of Formula IB:

Formula IB

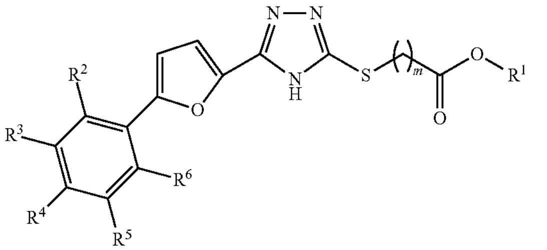

or a pharmaceutically acceptable salt thereof, wherein:

$R^1$ is selected from the group consisting of H and $(C_1-C_6)$alkyl;

each of $R^2$, $R^3$, $R^4$, $R^5$, and $R^6$ are independently selected from the group consisting of: H, halo, $(C_1-C_6)$alkyl, $(C_1-C_6)$haloalkyl, $OR^7$, CN, $NO_2$, $C(O)R^8$, $NR^9R^{10}$, $—S(O)_2NR^9R^{10}$, $—S(O)NR^9R^{10}$, $—C(NR^{11})R^{12}$, $—C(O)NR^{13}R^{14}$, a substituted or unsubstituted aryl, a substituted or unsubstituted heteroaryl, a substituted or unsubstituted cycloalkyl, and a substituted or unsubstituted heterocycloalkyl;

or $R^2$ and $R^3$, $R^3$ and $R^4$, $R^4$ and $R^5$, or $R^5$ and $R^6$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring;

each $R^7$ is independently selected from the group consisting of H, $(C_1-C_6)$alkyl, $(C_1-C_6)$haloalkyl, $(C_1-C_6)$aralkyl, $(C_1-C_6)$heteroaralkyl, a substituted or unsubstituted aryl, and a substituted or unsubstituted heteroaryl;

each $R^8$ is independently selected from a group consisting of H, OH, $(C_1-C_6)$alkyl, $(C_1-C_6)$haloalkyl, $OR^{8a}$, $—NR^{8a}R^{8b}$, wherein $R^{8a}$ and $R^{8b}$ are independently selected from a group consisting of H and $(C_1-C_6)$alkyl;

each of $R^9$, $R^{10}$, $R^{12}$, $R^{13}$, and $R^{14}$ are independently selected from a group consisting of H and $(C_1-C_6)$alkyl;

each $R^{11}$ is independently selected from a group consisting of H, $(C_1-C_6)$alkyl, and $OR^{11a}$ wherein $R^{11a}$ is independently selected from a group consisting of H, $(C_1-C_6)$alkyl, a substituted or unsubstituted aryl, and a substituted or unsubstituted heteroaryl; and m is an integer from 1 to 2.

In some embodiments, at least one of $R^2$ and $R^3$, $R^3$ and $R^4$, $R^4$ and $R^5$, and $R^5$ and $R^6$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring. In some such embodiments, $R^1$ is H. For example, $R^1$ is H; and $R^3$ is $OR^{3a}$; wherein $R^{3a}$ is selected from a group consisting of H, $(C_1-C_6)$alkyl, $(C_1-C_6)$alkyl, $(C_1-C_6)$haloalkyl, $(C_1-C_6)$aralkyl, $(C_1-C_6)$heteroaralkyl, a substituted or unsubstituted aryl, and a substituted or unsubstituted heteroaryl.

Non-limiting examples of a compound of Formula I and/or IB include:

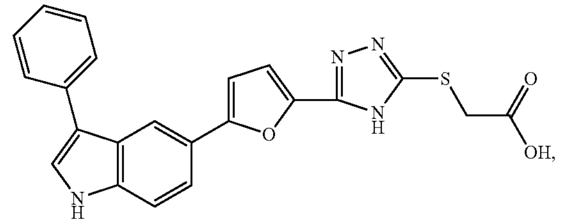

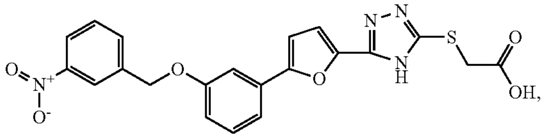

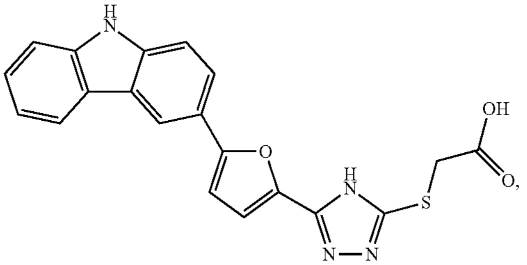

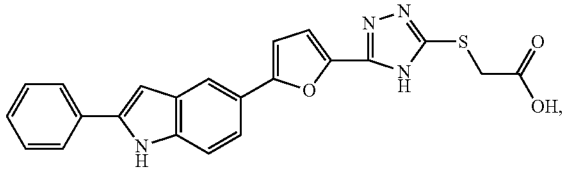

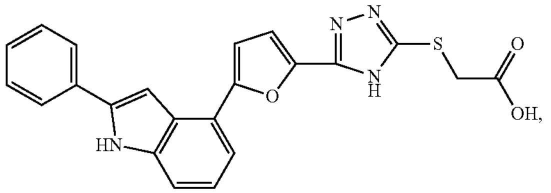

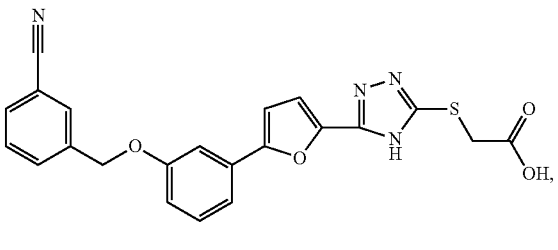

-continued
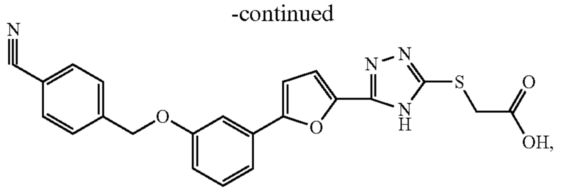
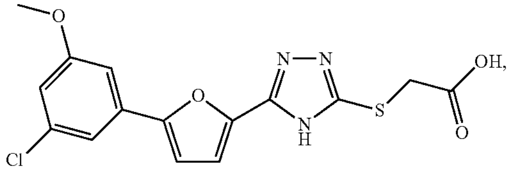
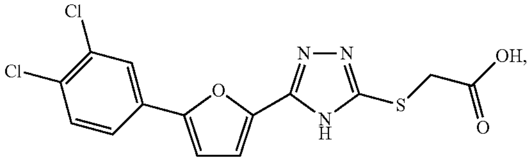
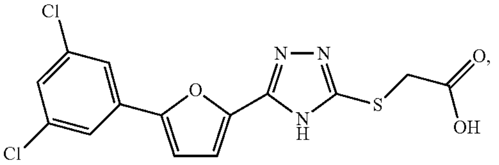
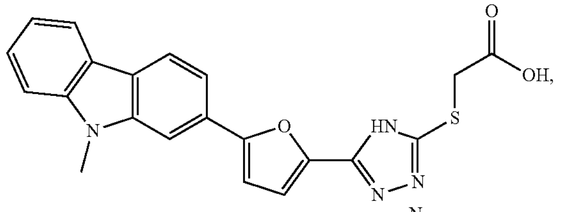
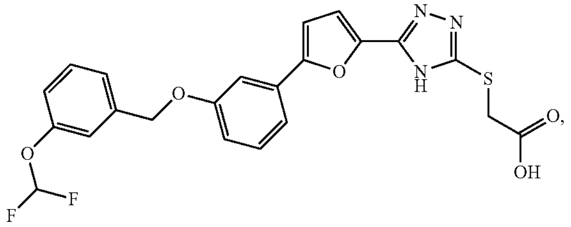
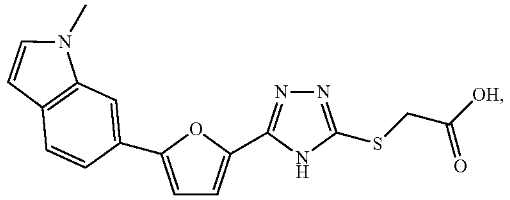
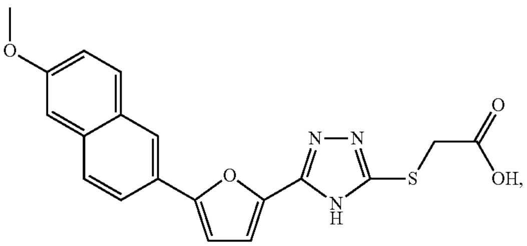
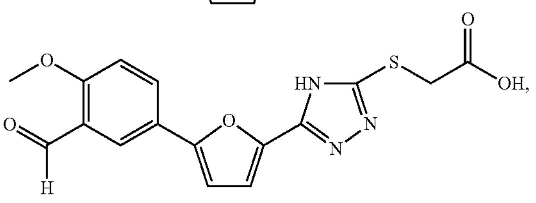
-continued
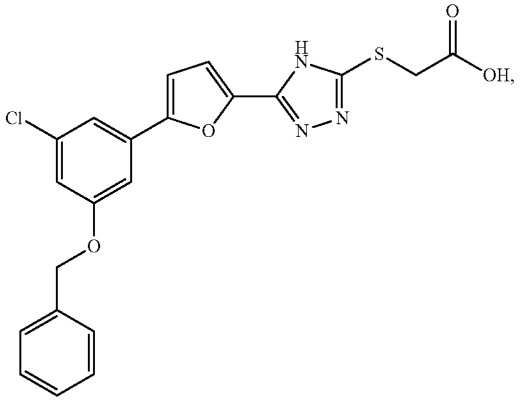
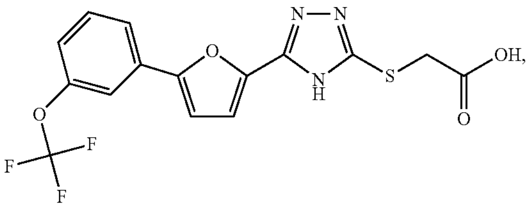
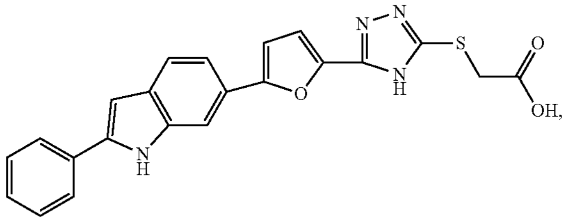
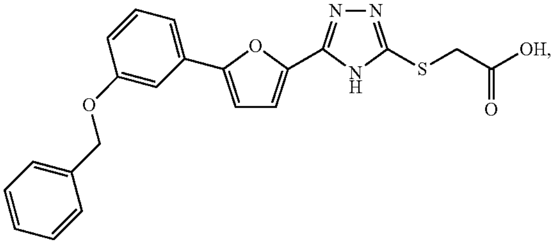
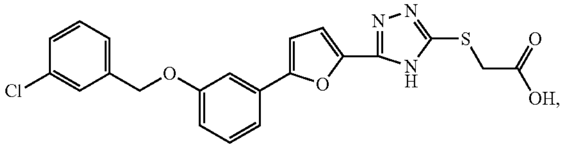
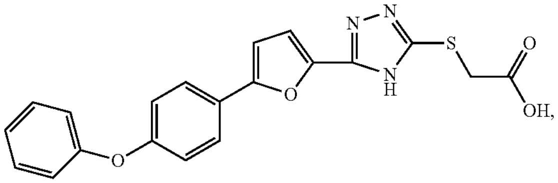
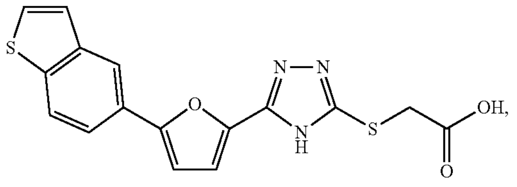

-continued
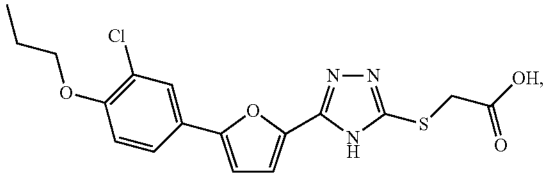
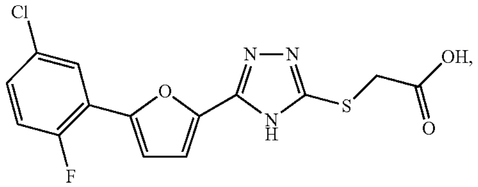
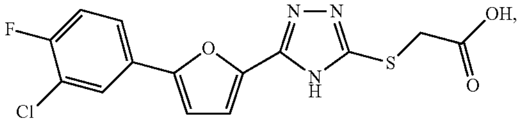
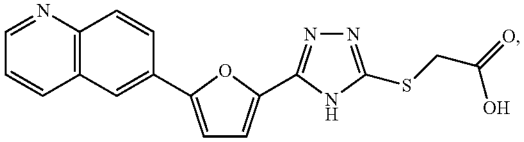
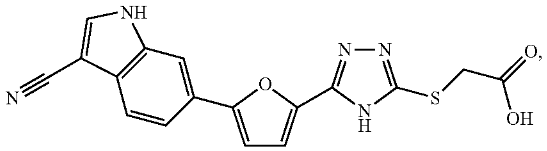
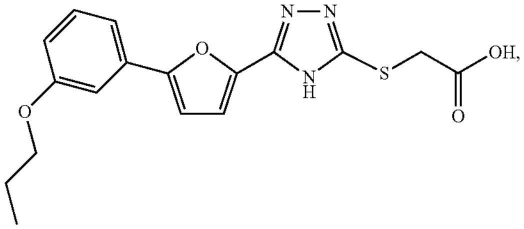
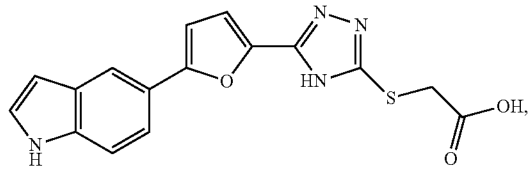
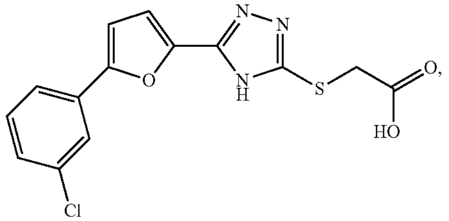
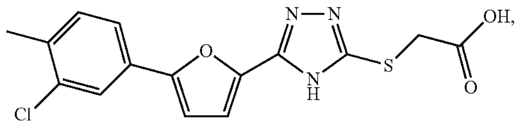
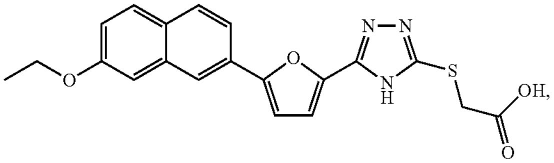
-continued
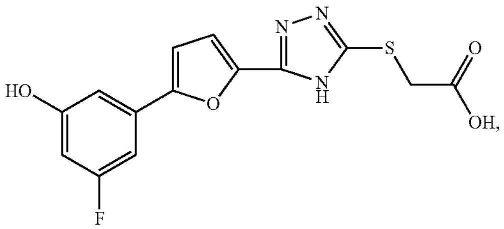
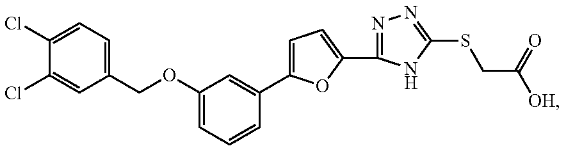
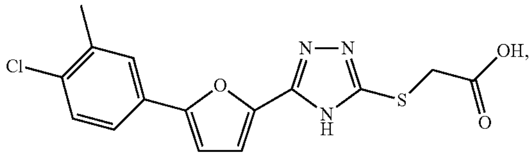
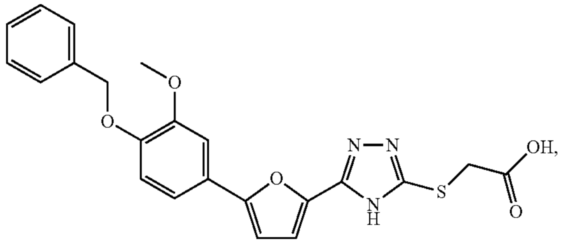
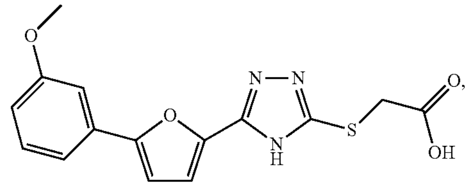
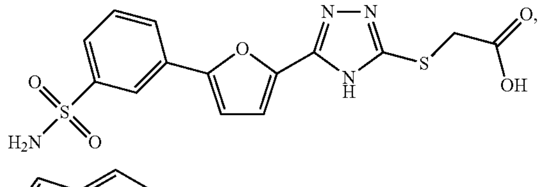
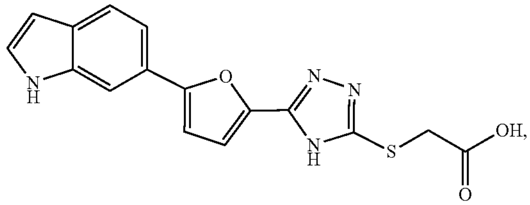
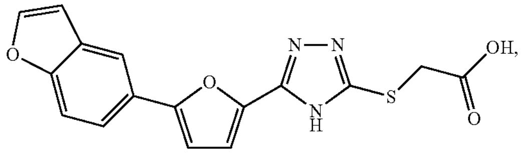
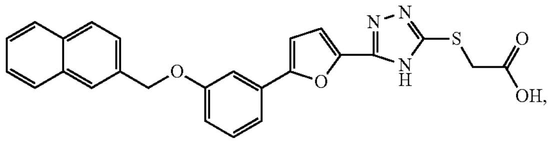

-continued
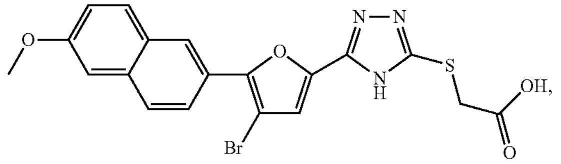
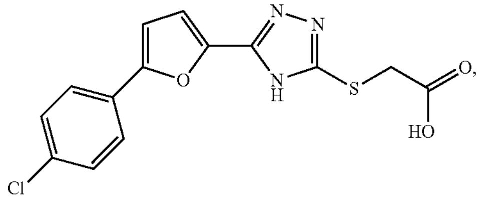
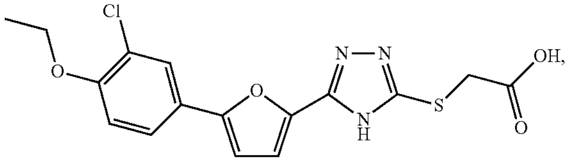
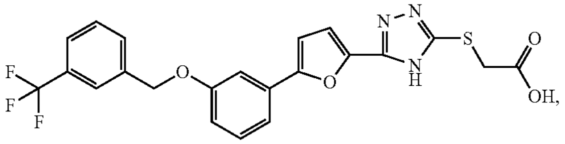
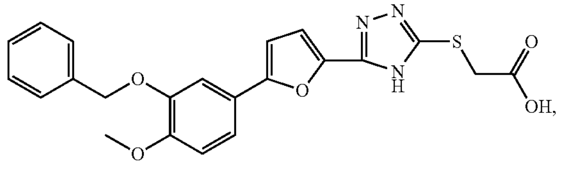
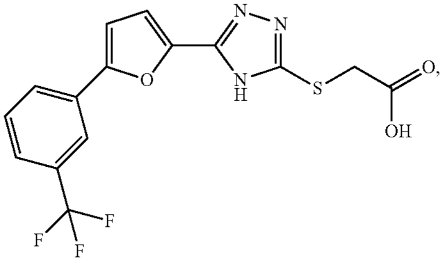
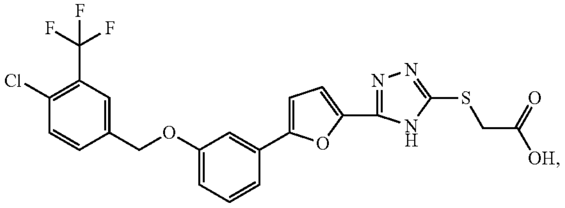
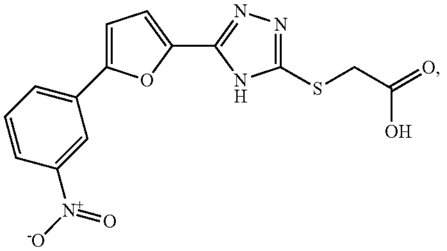
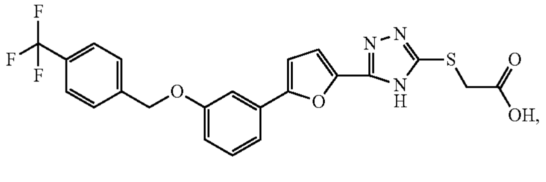
-continued
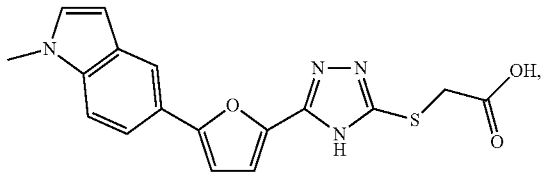
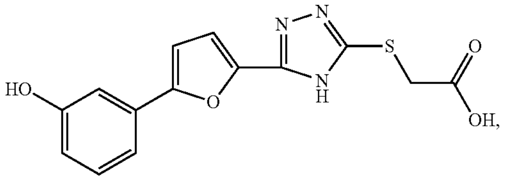
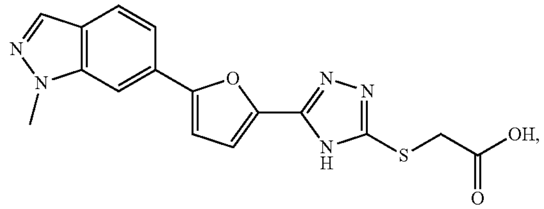
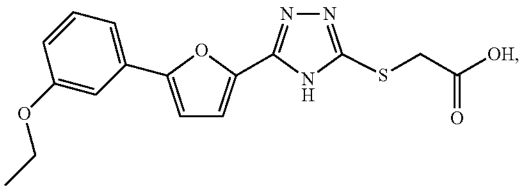
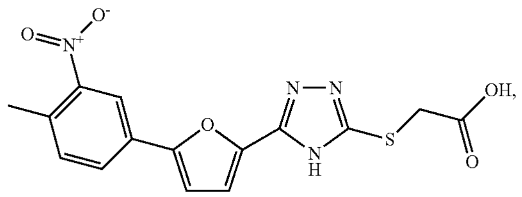
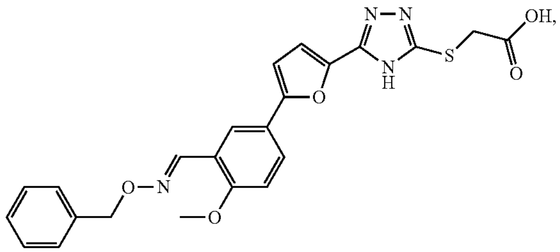
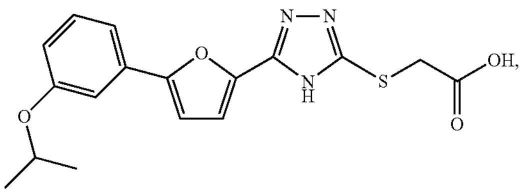
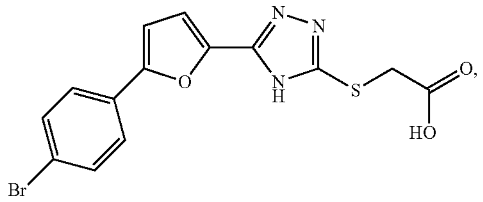

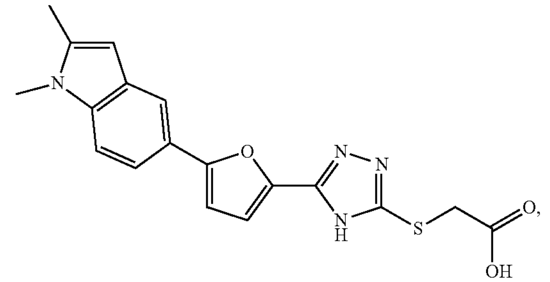
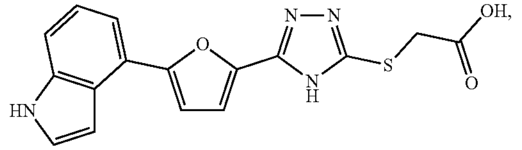
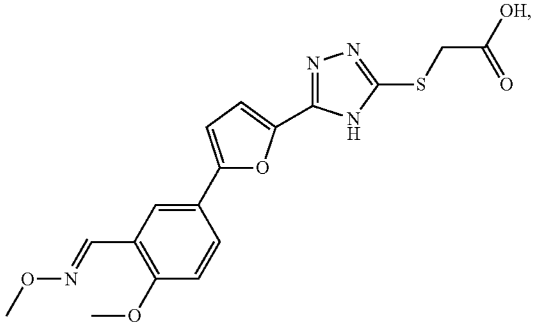
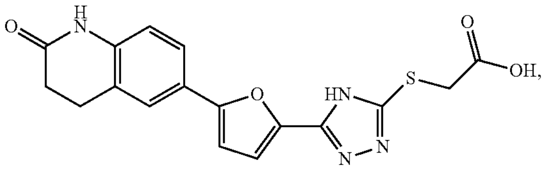
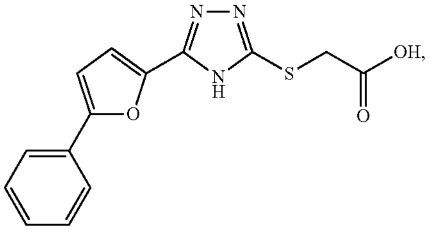
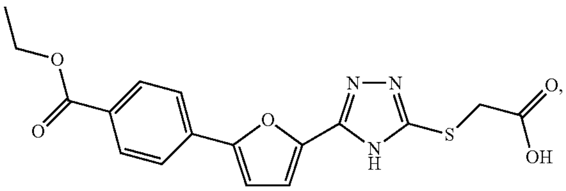
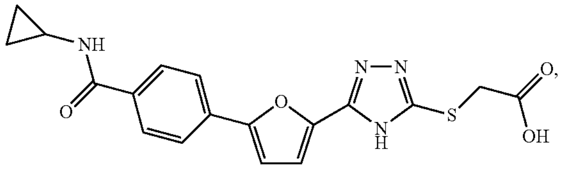
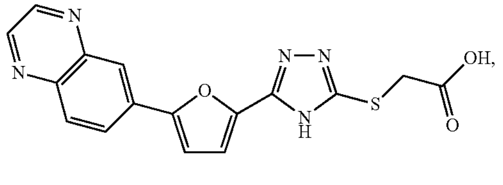
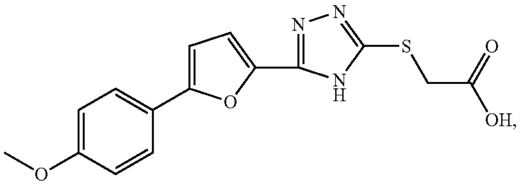
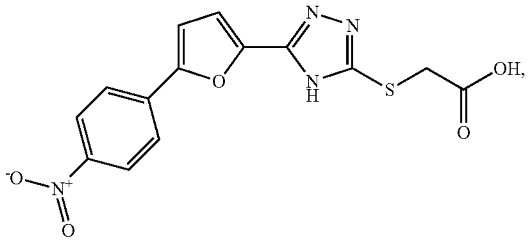
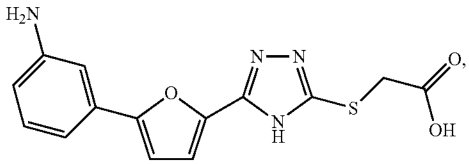
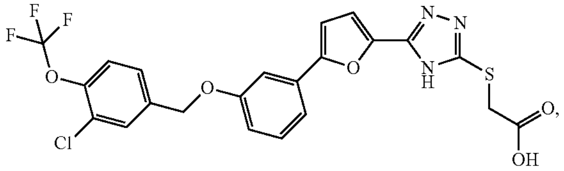
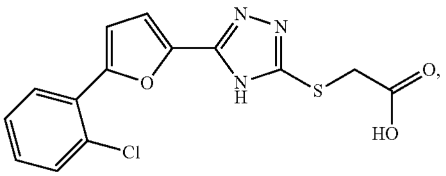
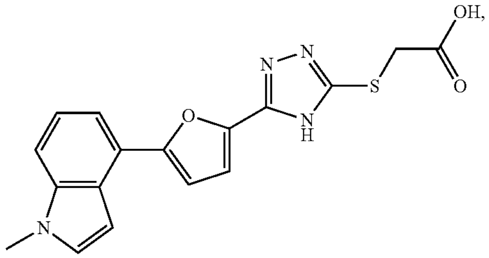
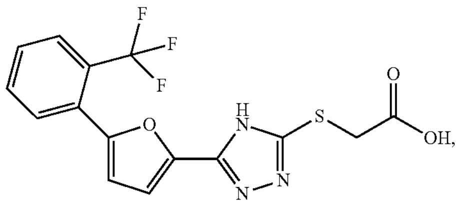
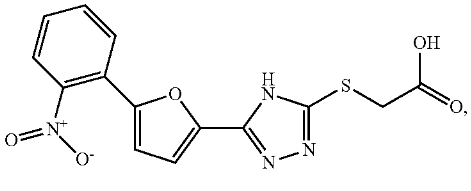

-continued

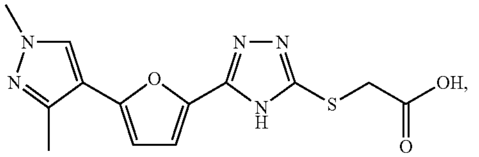

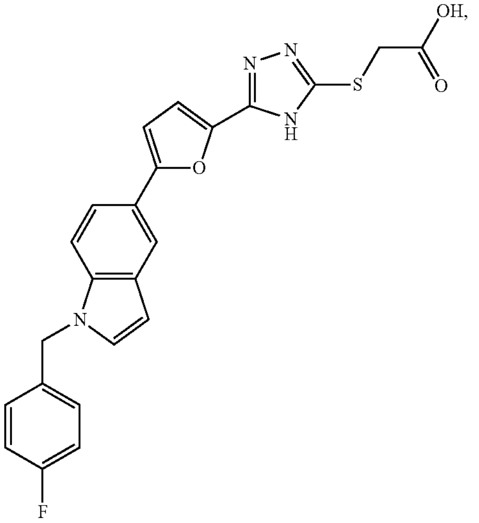

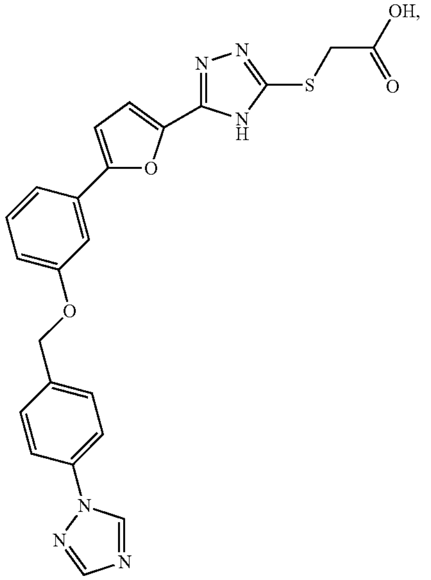

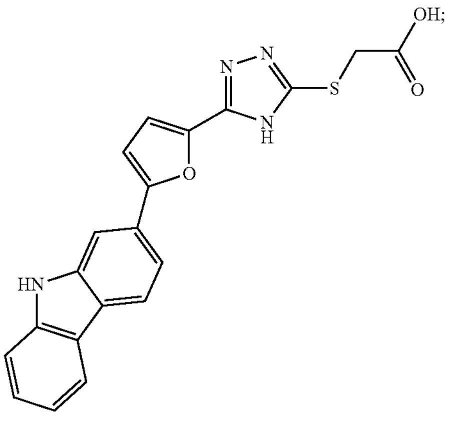

or a pharmaceutically acceptable salt thereof.

Also provided herein is a compound of Formula II:

Formula II

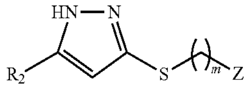

or a pharmaceutically acceptable salt thereof, wherein:

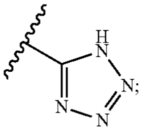 [SMILES: *c1nnn[nH]1]

Z is selected from the group consisting of —C(O)OR$^1$ and

R$^1$ is selected from the group consisting of H and ($C_1$-$C_6$) alkyl;

R$^2$ is a substituted or unsubstituted aryl, a substituted or unsubstituted heteroaryl; and m is an integer from 1 to 2.

In some embodiments, a compound of Formula II can be a compound of Formula IIA:

Formula IIA

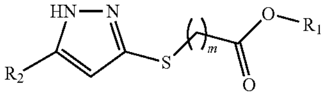

or a pharmaceutically acceptable salt thereof, wherein:

R$^1$ is selected from the group consisting of H and ($C_1$-$C_6$) alkyl;

R$^2$ is a substituted or unsubstituted aryl, a substituted or unsubstituted heteroaryl; and m is an integer from 1 to 2.

In some embodiments of Formula II and/or Formula IIA, R$^1$ is H; and R$^2$ is a substituted or unsubstituted heteroaryl. For example, R$^2$ is a substituted or unsubstituted furanyl, or a substituted or unsubstituted thiopheneyl. In some embodiments, R$^1$ is H; and R$^2$ is a substituted or unsubstituted aryl. For example, R$^2$ is a substituted or unsubstituted phenyl.

Non-limiting examples of a compound of Formula II and/or Formula IIA include:

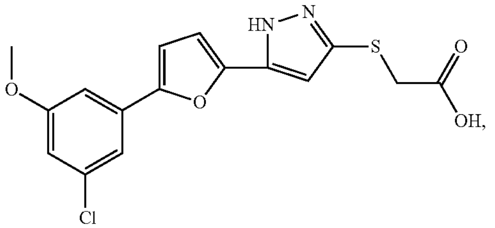

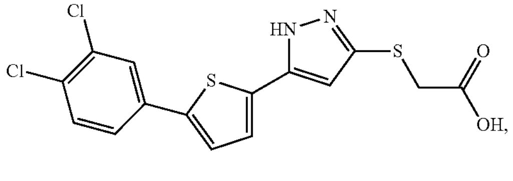

-continued

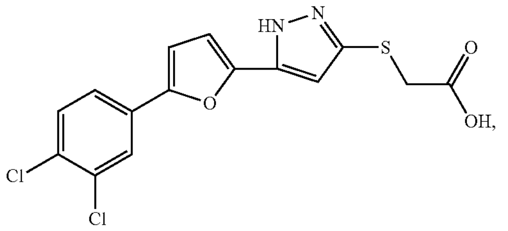

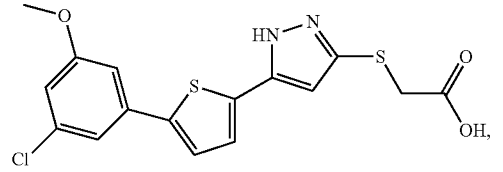

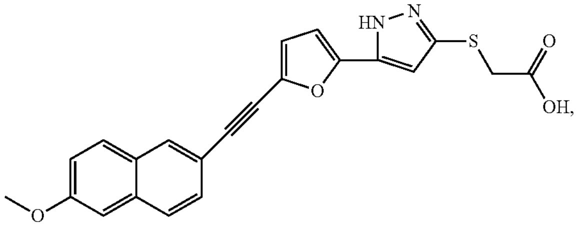

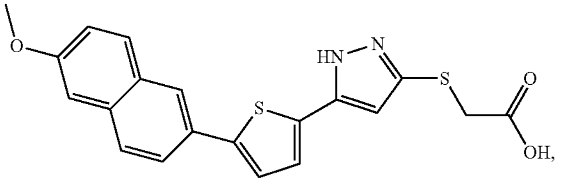

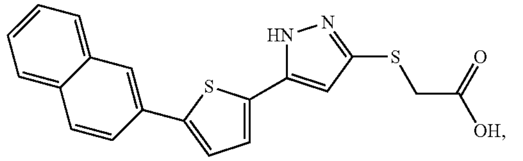

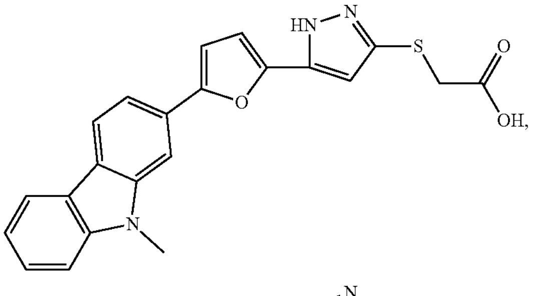

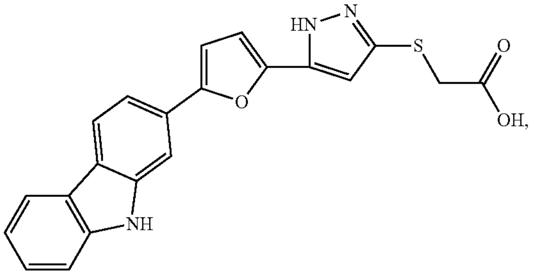

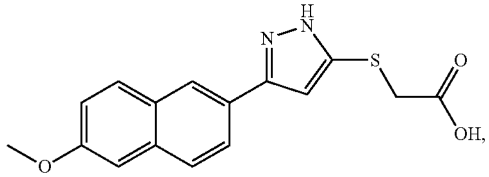

-continued

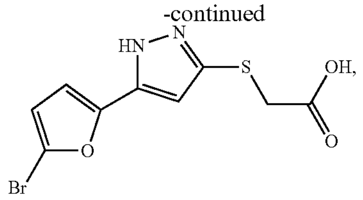

and

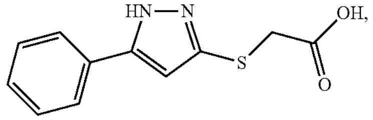

or a pharmaceutically acceptable salt thereof.

Further provided herein is a compound of Formula III:

Formula III

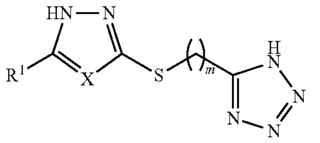

or a pharmaceutically acceptable salt thereof, wherein:

X is selected from the group consisting of CH and N;

$R^1$ is a substituted or unsubstituted aryl or a substituted or unsubstituted heteroaryl; and m is an integer from 1 to 2.

In some embodiments, a compound of Formula III can be a compound of Formula IIIA:

Formula IIIA

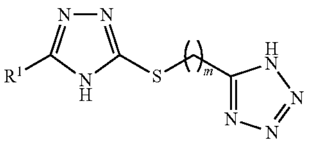

or a pharmaceutically acceptable salt thereof, wherein:

$R^1$ is a substituted or unsubstituted aryl or a substituted or unsubstituted heteroaryl; and m is an integer from 1 to 2.

In some embodiments of Formula III and IIIA, m is 1.

In some embodiments of Formula III and IIIA, $R^1$ can be a substituted or unsubstituted aryl. For example,

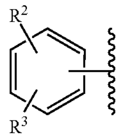

wherein:

each of $R^2$ and $R^3$ are independently selected from the group consisting of: H, halo, $(C_1\text{-}C_6)$alkyl, $(C_1\text{-}C_6)$haloalkyl, $OR^4$, $NO_2$, $NR^4R^5$, CN, a substituted or unsubstituted aryl, and a substituted or unsubstituted heteroaryl; and each of $R^4$ and $R^5$ are independently selected from the group consisting of H, $(C_1\text{-}C_6)$alkyl, and $(C_1\text{-}C_6)$haloalkyl.

In some such embodiments, $R^2$ is H or $NO_2$; and $R^3$ is ($C_1$-$C_6$)alkyl or a substituted or unsubstituted phenyl. In other such embodiments, $R^2$ is H; and $R^3$ is ($C_1$-$C_6$)alkyl. For example, $R^3$ is methyl. In other such embodiments, $R^2$ is $NO_2$; and $R^3$ is a substituted or unsubstituted phenyl.

In some embodiments of Formula III and Formula IIIA, $R^1$ is:

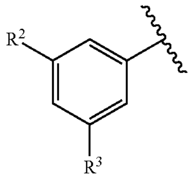

In some such embodiments, $R^2$ is $NO_2$; and $R^3$ is:

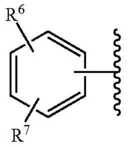

wherein:

each of $R^6$ and $R^7$ are independently selected from a group consisting of: H, halo, ($C_1$-$C_6$)alkyl, ($C_1$-$C_6$)haloalkyl, $OR^{4a}$, $NO_2$, $NR^{4a}R^{5a}$, CN, a substituted or unsubstituted aryl, and a substituted or unsubstituted heteroaryl; and each of $R^{4a}$ and $R^{5a}$ are independently selected from the group consisting of H, ($C_1$-$C_6$)alkyl, and ($C_1$-$C_6$)haloalkyl.

For example, $R^3$ can be:

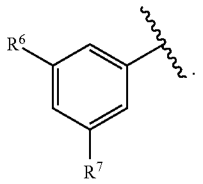

In some such embodiments, $R^6$ is halo; and $R^7$ is $OR^c$; wherein $R^c$ is selected from a group consisting of H, ($C_1$-$C_6$)alkyl, and ($C_1$-$C_6$)haloalkyl.

In some embodiments of Formula III and IIIA, $R^1$ is selected from the group consisting of:

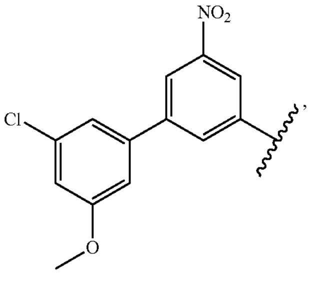,

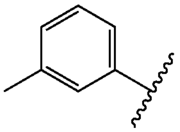

In some embodiments of Formula III and IIIA, $R^1$ is a substituted or unsubstituted heteroaryl. For example, $R^1$ can be:

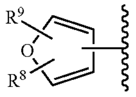

wherein:

each of $R^8$ and $R^9$ are independently selected from a group consisting of: H, halo, ($C_1$-$C_6$)alkyl, ($C_1$-$C_6$)haloalkyl, $OR^{4b}$, $NO_2$, $NR^{4b}R^{5b}$, CN, a substituted or unsubstituted aryl, and a substituted or unsubstituted heteroaryl; and each of $R^{4b}$ and $R^{5b}$ are independently selected from the group consisting of H, ($C_1$-$C_6$)alkyl, and ($C_1$-$C_6$)haloalkyl.

For example, $R^1$ can be:

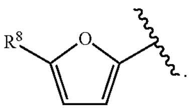

In some such embodiments, $R^8$ is a substituted or unsubstituted aryl. For example, $R^8$ can be:

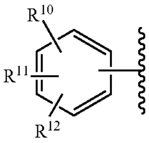

wherein:

each of $R^{10}$, $R^{11}$, and $R^{12}$ are independently selected from a group consisting of: H, halo, ($C_1$-$C_6$)haloalkyl, CN, $NO_2$, $OR^{13}$, $NR^{14}R^{15}$, $C(O)R^{16}$, $C(O)OR^{16}$, $—NR^{17}S(O)_2R^{18}$, $—S(O)_2NR^{19}R^{20}$, $—NR^{17}S(O)R^{18}$, $—S(O)_2NR^{19}R^{20}$, $—S(O)NR^{19}R^{20}$, $—NR^{21}C(O)R^{22}$, a substituted or unsubstituted aryl, a substituted or unsubstituted heteroaryl, and a substituted or unsubstituted heterocycloalkyl; or two of the groups $R^{10}$, $R^{11}$, and $R^{12}$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and each of $R^{13}$, $R^{14}$, $R^{15}$, $R^{16}$, $R^{17}$, $R^{18}$, $R^{19}$, $R^{20}$, $R^{21}$, and $R^{22}$ are independently selected from a group consisting of H, ($C_1$-$C_6$)alkyl, and ($C_1$-$C_6$)haloalkyl.

In some embodiments, $R^8$ is a substituted or unsubstituted heteroaryl. For example, $R^8$ can be selected from a group consisting of a substituted or unsubstituted quinolinyl, a substituted or unsubstituted indolyl, and a substituted or unsubstituted pyridyl.

$R^1$ can be selected from:

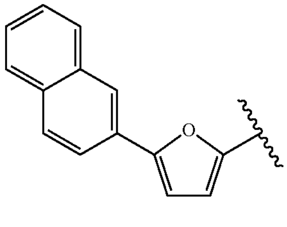,

-continued
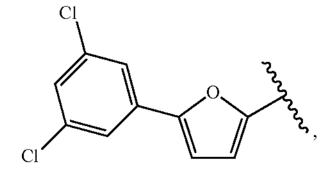,
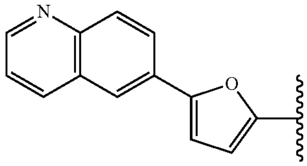,
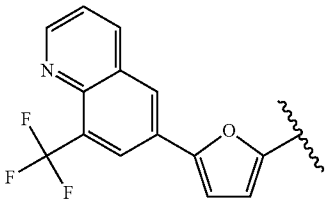,
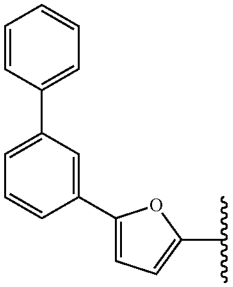,
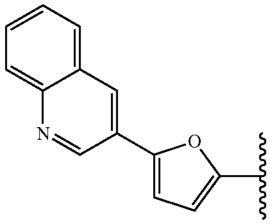,
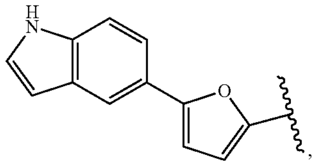,
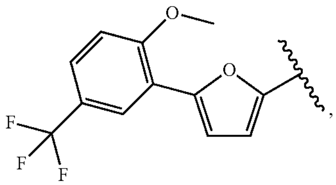,
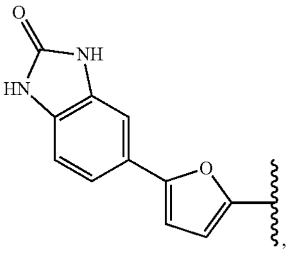,
-continued
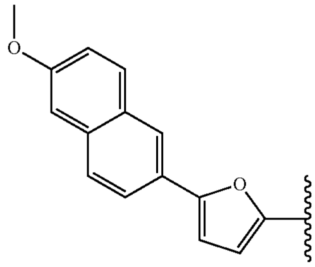,
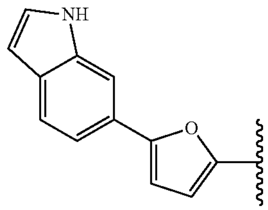,
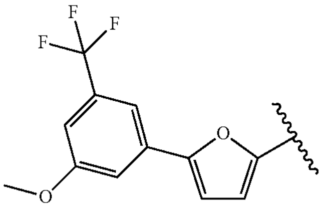,
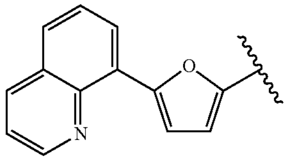,
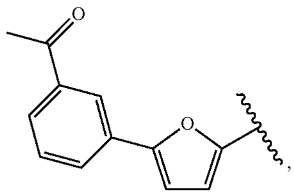,
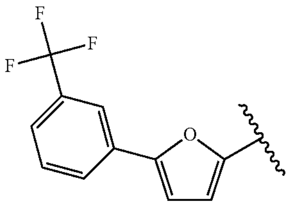,
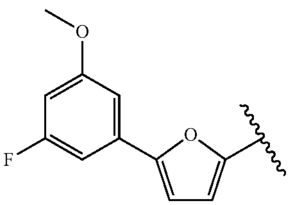,
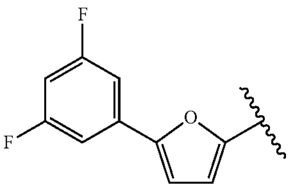, -continued
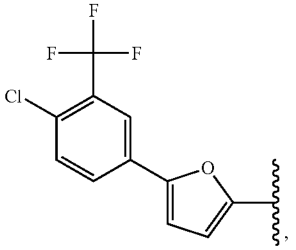
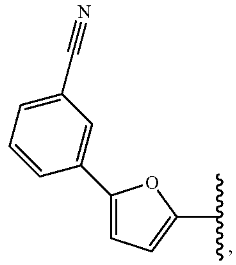
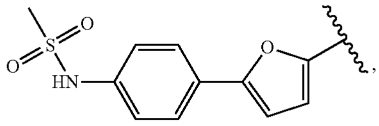
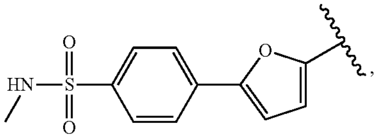
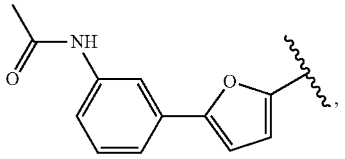
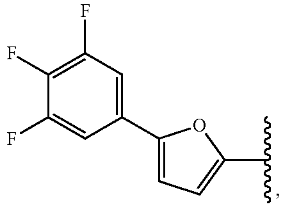
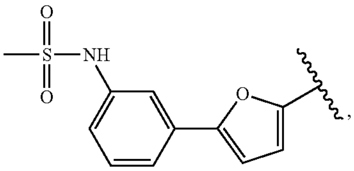
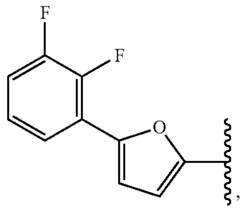
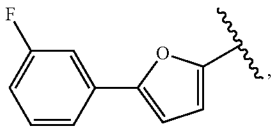
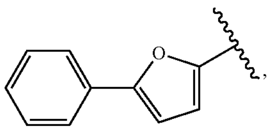
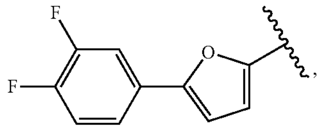
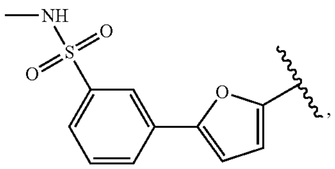
-continued
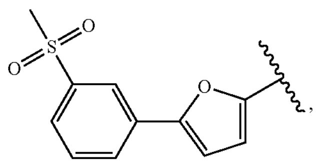
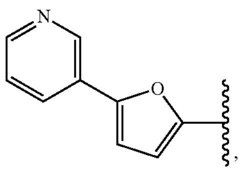
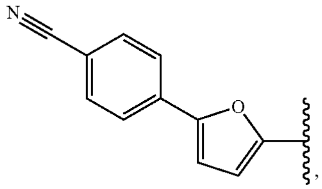
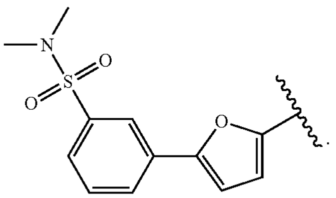 [SMILES: *c1ccc(-c2cccc(S(=O)(=O)N(C)C)c2)o1]
Non-limiting examples of a compound of Formula III and/or IIIA include:
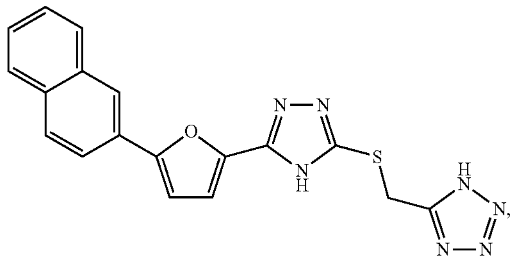
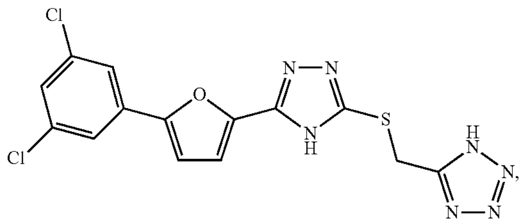
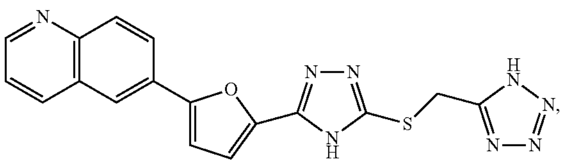

-continued
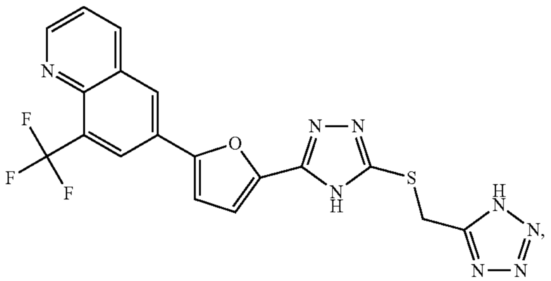
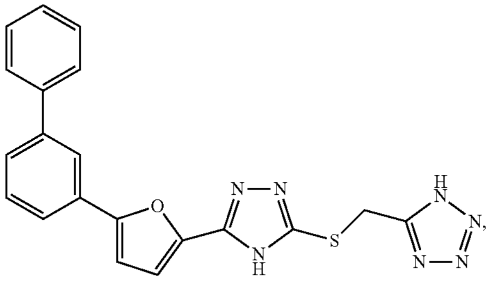
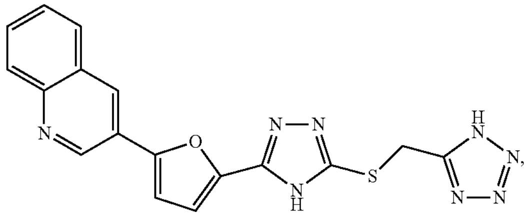
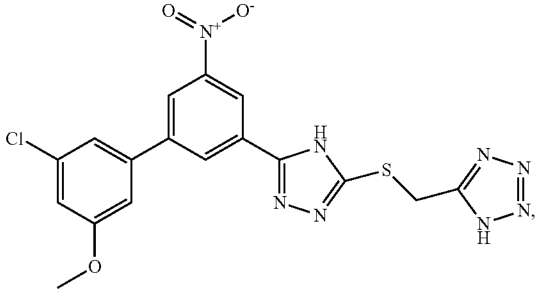
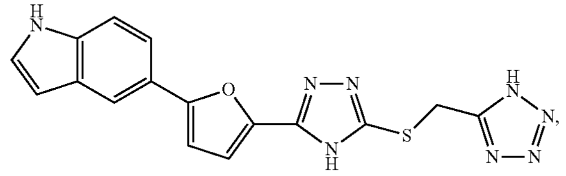
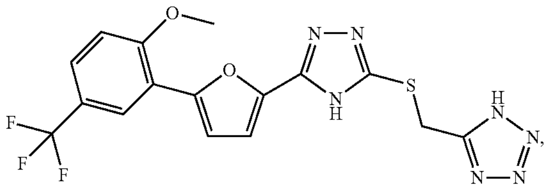
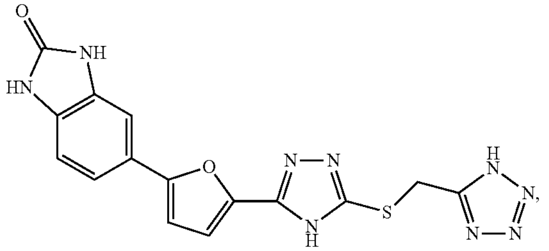
-continued
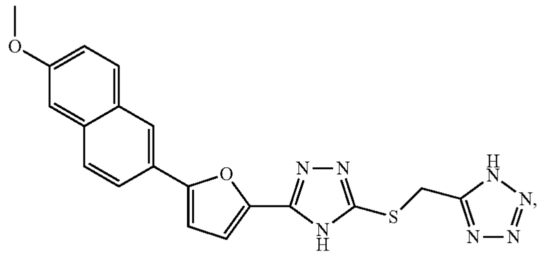
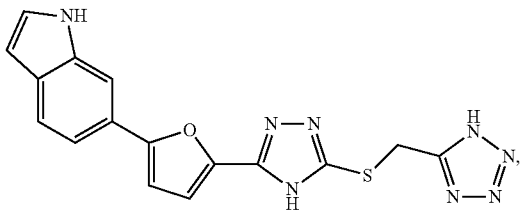
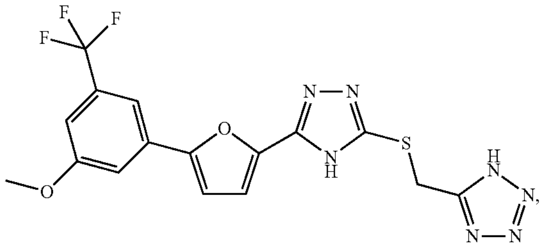
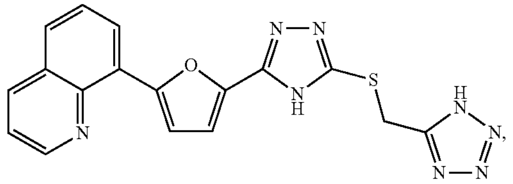
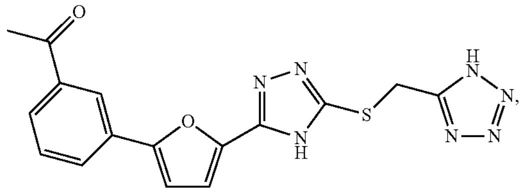
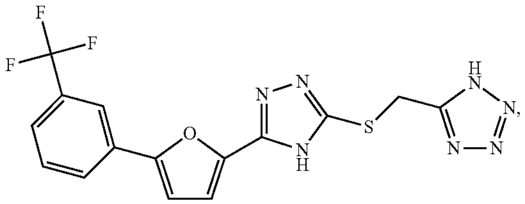
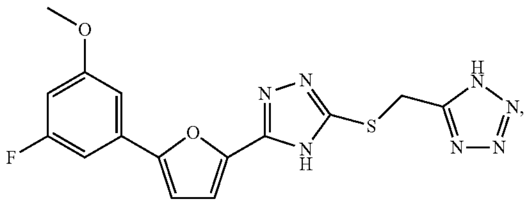
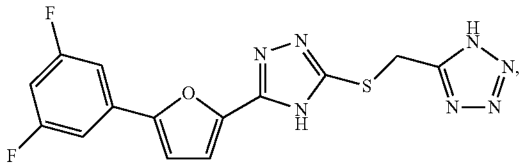

-continued
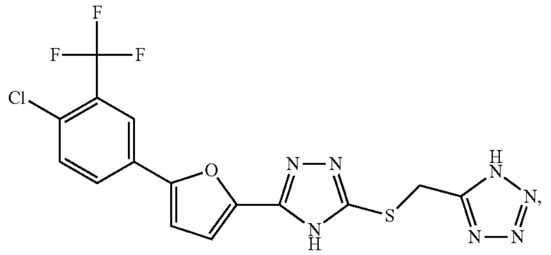
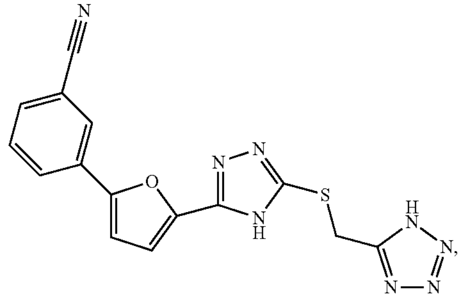
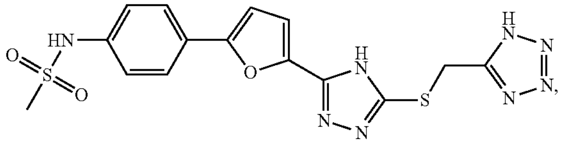
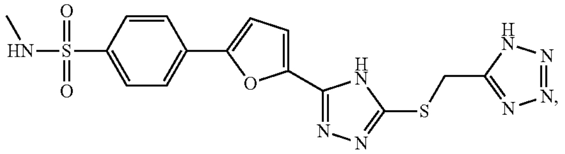
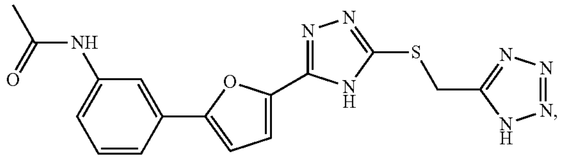
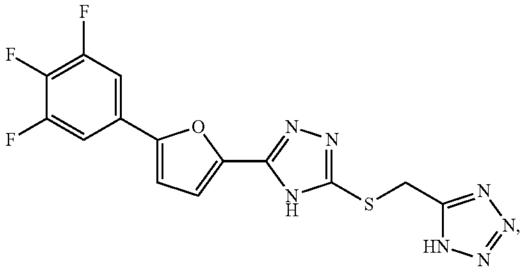
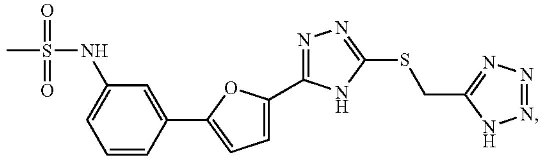
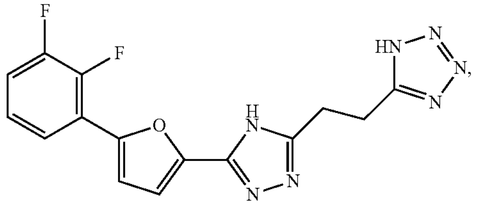
-continued
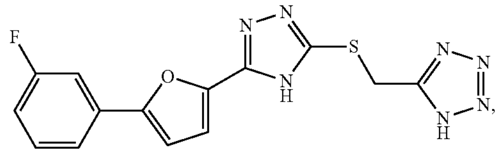
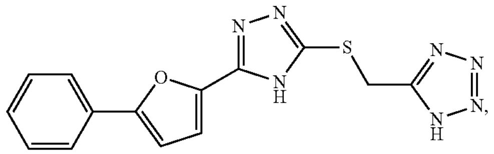
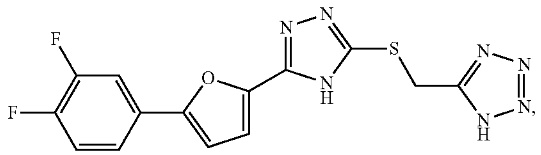
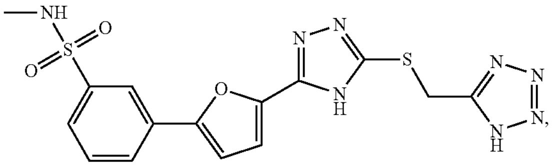
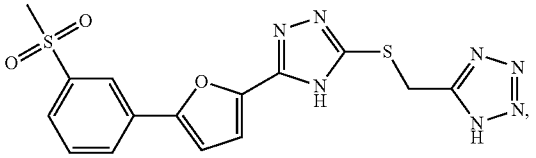
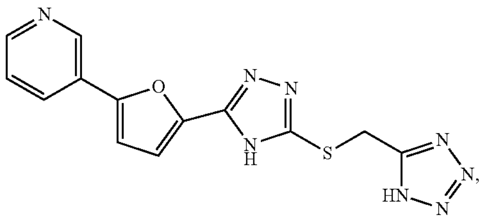
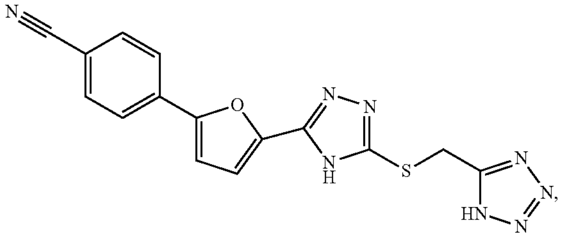
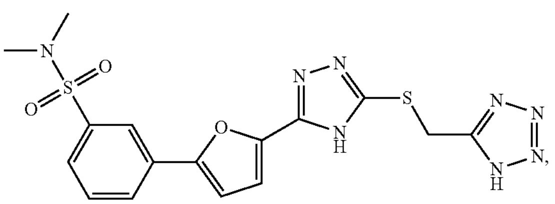
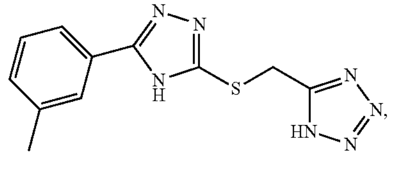
and -continued
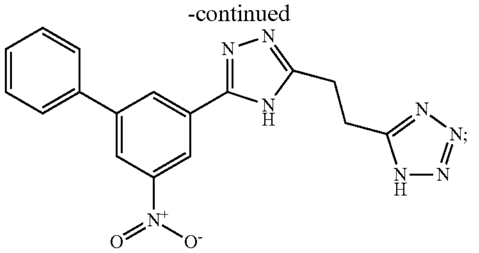
or a pharmaceutically acceptable salt thereof.
Also provided herein are compounds selected from the group consisting of:
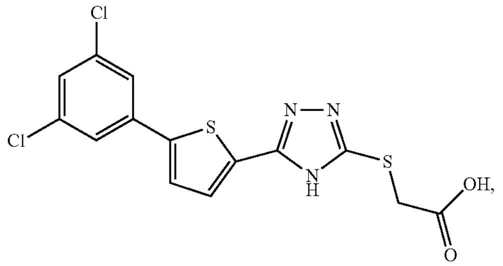
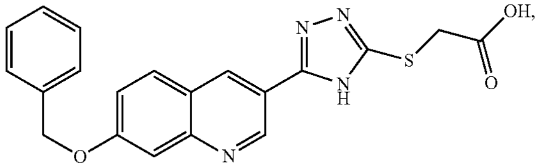
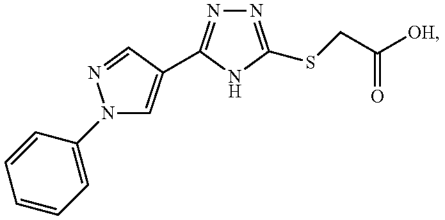
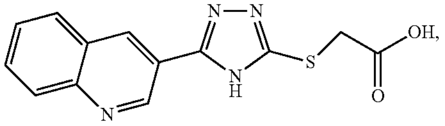
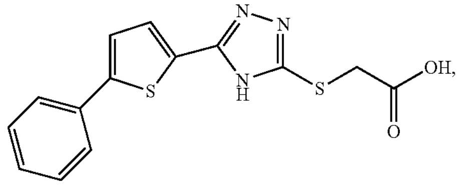
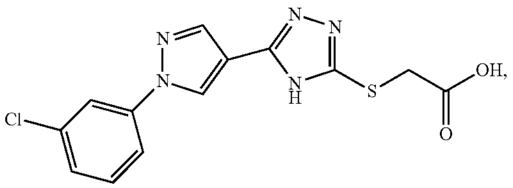
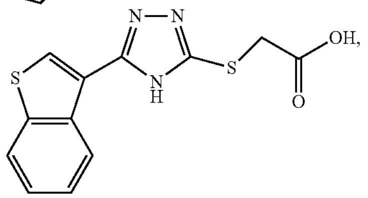
-continued
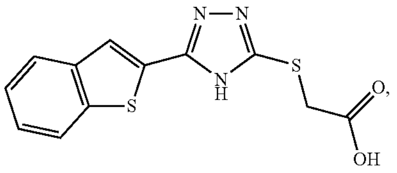
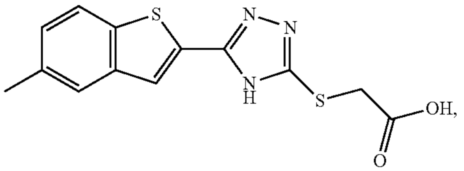
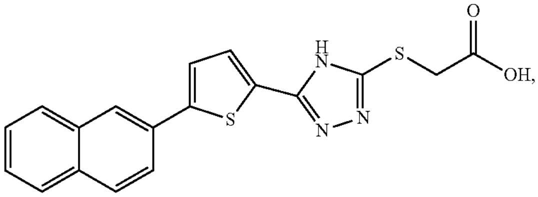
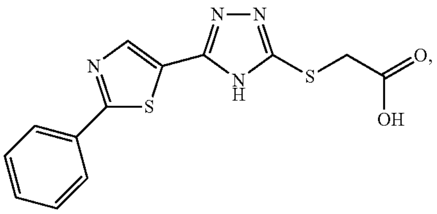
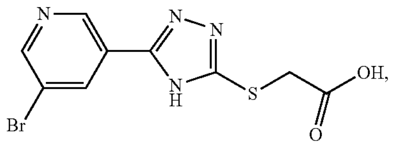
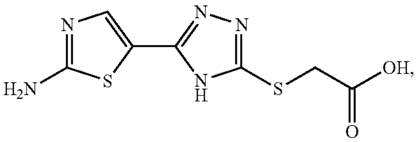
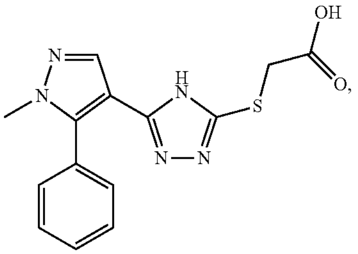
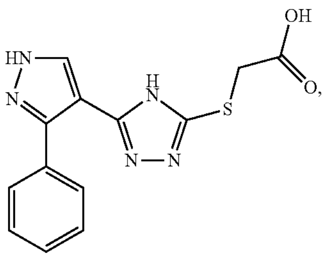
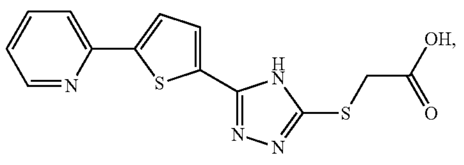

-continued
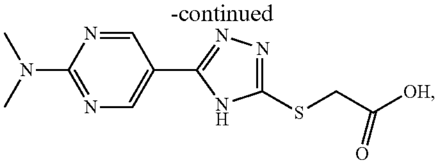
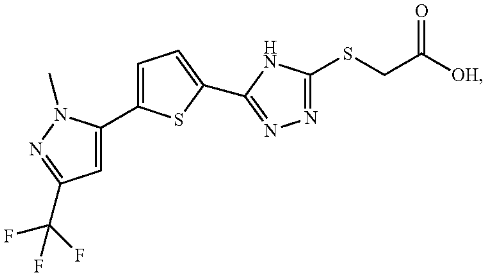
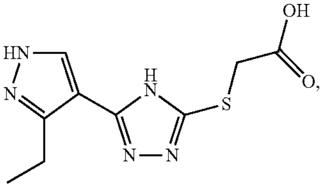
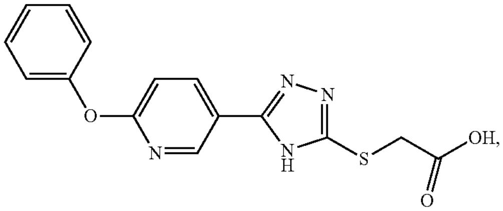
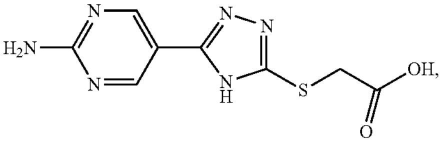
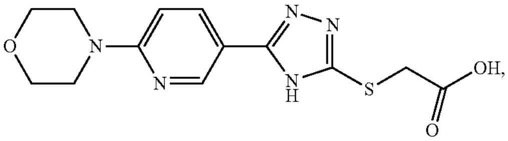
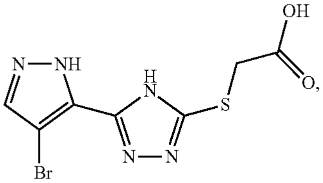
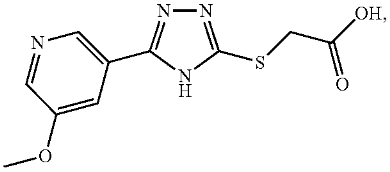
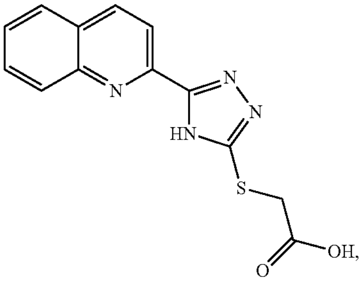
-continued
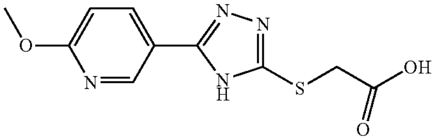
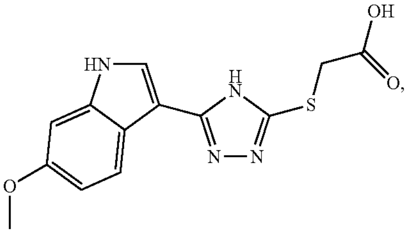
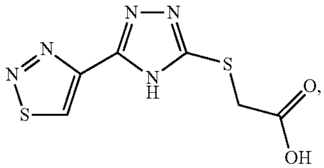
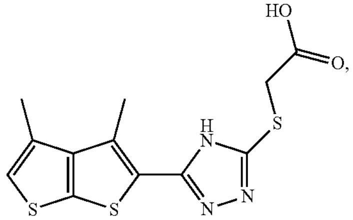
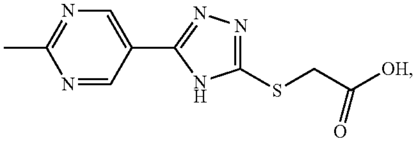
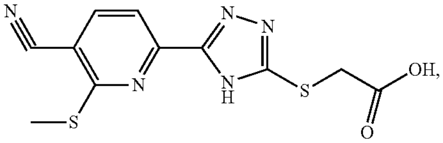
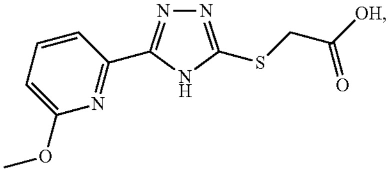
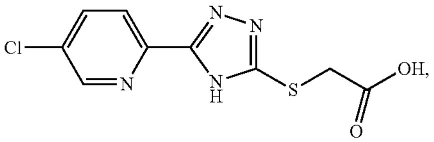
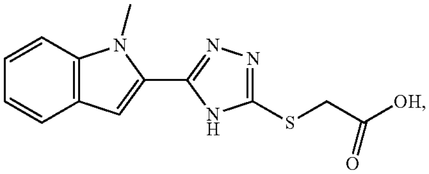
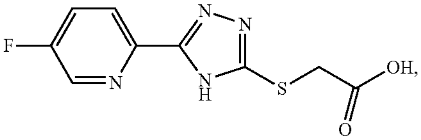

-continued
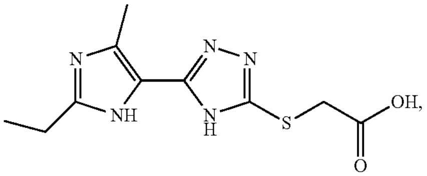
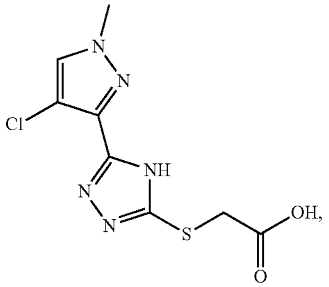
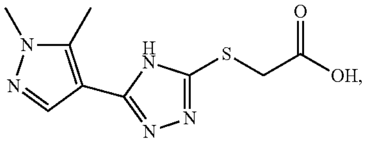
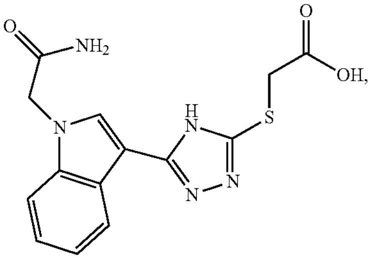
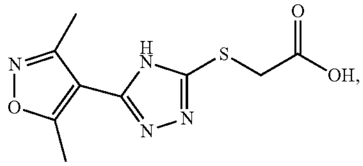
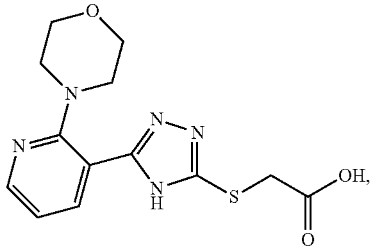
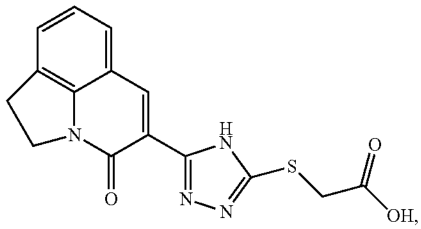
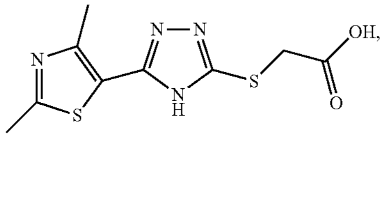
-continued
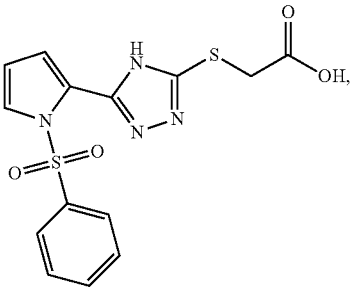
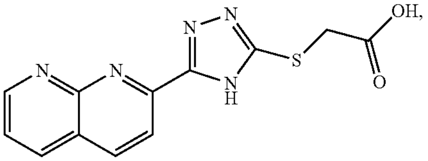
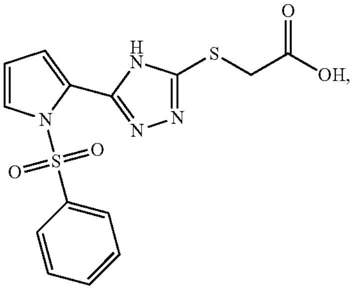
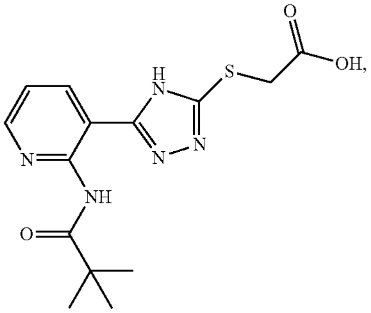
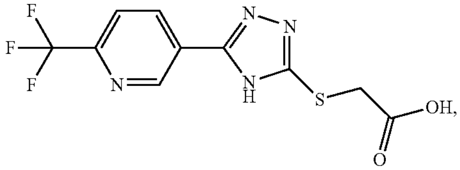
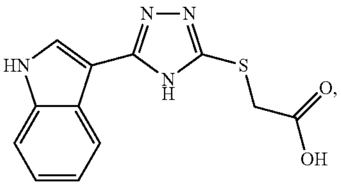
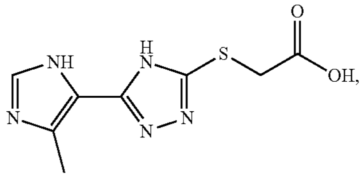

-continued

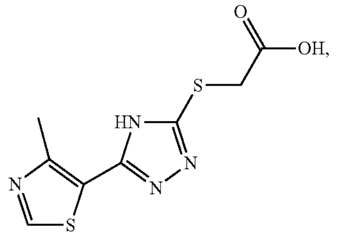

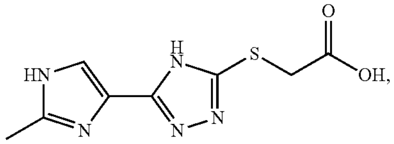

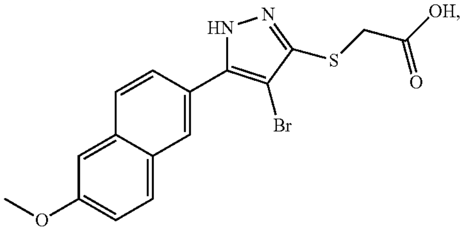

and

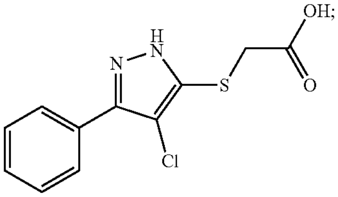

or a pharmaceutically acceptable salt thereof.

The compounds provided herein can also be present in a pharmaceutical composition comprising a compound provided herein, or a pharmaceutically acceptable salt thereof, and a pharmaceutically acceptable carrier.

The compounds provided herein are also useful in methods for inhibiting a G protein coupled receptor 6 kinase polypeptide in a patient. In some embodiments, the method can include administering to the patient a therapeutically effective amount of a compound provided herein, or a pharmaceutically acceptable salt thereof. The compounds provided herein are also useful for inhibiting a G protein coupled receptor 6 kinase polypeptide in a cell. In some embodiments, such methods include contacting the cell with an effective amount of a compound provided herein, or a pharmaceutically acceptable salt thereof. In some such embodiments, the cell is a cancerous cell. For example, a B cell cancerous cell.

Also provided herein are methods for treating a hematological malignancy in a patient, the method comprising administering to the patient a therapeutically effective amount of a compound provided herein, or a pharmaceutically acceptable salt thereof. In some embodiments, the hematological malignancy is a B cell cancer. For example, the B cell cancer can be selected from the group consisting of: a small lymphocytic lymphoma (SLL), a mantle cell lymphoma, a Burkitt's lymphoma, a follicle centre cell lymphoma, a follicular lymphoma, a Burkitt-like lymphoma, a marginal zone B-cell lymphoma (MZBCL), a nodal marginal zone B cell lymphoma, an extra-nodal marginal zone B cell lymphoma, a splenic marginal zone B cell lymphoma, a lymphoplasmacytic lymphoma, and a diffuse large B cell lymphoma. In some embodiments, the B cell cancer is selected from the group consisting of: a B cell acute lymphocytic leukemia (B-ALL), a precursor B cell acute lymphocytic leukemia (B-ALL), a B cell chronic lymphocytic leukemia (B-CLL), a precursor B-lymphoblastic leukaemia, a precursor B-lymphoblastic lymphoma, a small lymphocytic lymphoma, a B cell prolymphocytic leukemia, an undifferentiated B cell lymphoma, a hairy cell leukemia, a mediastinal large B-cell lymphoma, a plasma cell myeloma, a plasmacytoma, a primary effusive lymphoma, a Burkitt's cell leukemia, and a B cell diffuse mixed lymphoma.

Further provided herein are methods for treating an inflammation disease in a patient, the method comprising administering to the patient a therapeutically effective amount of a compound provided herein, or a pharmaceutically acceptable salt thereof. In some embodiments, the inflammatory disease can be selected from the group consisting of: encephalitis, inflammatory eye disease, otitis, pharyngitis, pneumonia, gastritis, enteritis, hepatitis, pancreatitis, nephritis, cystitis, urethritis, endometritis, vaginitis, arthritis, peripheral neuritis, malignant tumor, infectious diseases, autoimmune diseases, ischemic diseases, metabolic diseases, injury, scald, chemical corrosion, and neurodegenerative diseases.

In some embodiments, an autoimmune disease can be selected from the group consisting of: rheumatism, systemic lupus erythematosus, and sarcoidosis.

In some embodiments, an ischemic disease can be selected from the group consisting of: myocardial infarction and cerebral infarction.

In some embodiments, a metabolic disease can be selected from the group consisting of: diabetes and gout.

In some embodiments, a neurodegenerative can be Alzheimer's disease.

The compounds provided herein are also useful for suppressing an immune response in a patient, the method comprising administering to the patient a therapeutically effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Definitions

For the terms "for example" and "such as," and grammatical equivalences thereof, the phrase "and without limitation" is understood to follow unless explicitly stated otherwise. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "patient," as used herein, includes both humans and other animals, particularly mammals. Thus, the methods are applicable to both human therapy and veterinary applications. In some embodiments, the patient is a mammal, for example, a primate. In some embodiments, the patient is a human.

The terms "treating" and "treatment" mean causing a therapeutically beneficial effect, such as ameliorating one or more existing symptoms and/or reducing the severity of symptoms that will or are expected to develop.

A "therapeutically effective" amount of the inhibitors described herein is typically one which is sufficient to achieve the desired effect and may vary according to the nature and severity of the disease condition, and the potency of the inhibitor. It will be appreciated that different concentrations may be employed for prophylaxis than for treatment of an active disease.

The term "contacting" means bringing at least two moieties together, whether in an in vitro system or an in vivo system.

The term "inhibition" with respect to a GRK6 polypeptide refers to inhibition of a GRK6 polypeptide and its biological activities associated with a GRK6 polypeptide pathway. Inhibition of GRK6 polypeptide can include antagonizing or inactivation. The mode of action of a GRK6 polypeptide inhibitor can be direct, e.g., through binding to a GRK6 polypeptide as a ligand. The mode of action of an inhibitor can be indirect, e.g., through binding to and/or modifying another molecule that otherwise binds to and activates a GRK6 polypeptide.

As used herein, "administration" refers to delivery of an inhibitor or composition comprising an inhibitor provided herein by any external route, including, without limitation, IV, intramuscular, SC, intranasal, inhalation, transdermal, oral, buccal, rectal, sublingual, and parenteral administration.

The term "cancerous B cell" is used herein to refer to a B cell that is cancerous. By "cancerous cell" or "cancer cell" is meant a cell that shows aberrant cell growth, such as increased cell growth. A cancerous cell may be a hyperplastic cell, a cell that shows a lack of contact inhibition of growth in vitro, a tumor cell that is incapable of metastasis in vivo, or a metastatic cell that is capable of metastasis in vivo.

An inhibitor provided herein can also incorporate one or more isotopes of the atoms occurring in the inhibitor. Isotopes include, for example, those atoms having the same atomic number but different mass numbers. For example, carbon atoms can include carbon-12, carbon-13, and/or carbon-14 and hydrogen atoms can include hydrogen, deuterium, and/or tritium.

The term, "inhibitor," as used herein is meant to include all stereoisomers, geometric isomers, and tautomers of the structures depicted. Inhibitors herein identified by name or structure as one particular tautomeric form are intended to include other tautomeric forms unless otherwise specified. For example, triazole and pyrazole inhibitors provided herein are intended to include the appropriate equivalent tautomeric forms shown below.

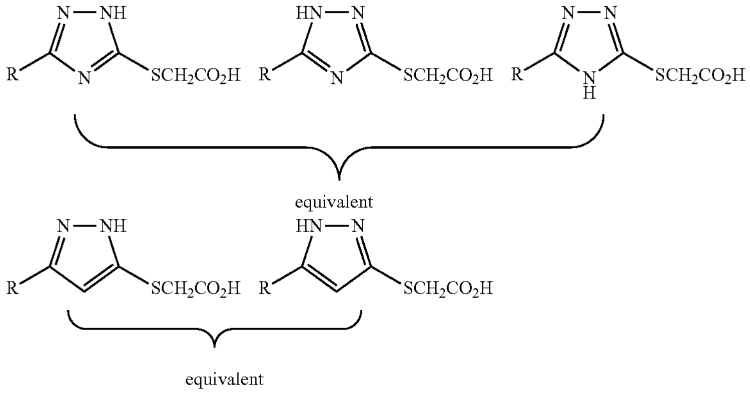

One of ordinary skill will also realize that the pyrazole inhibitors provided are not intended to include the structure shown below, which is not an appropriate tautomeric form of a pyrazole ring.

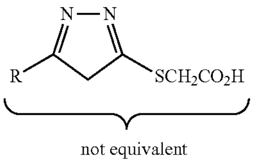

In some embodiments, an inhibitor provided herein, or salt thereof, is substantially isolated. By "substantially isolated" is meant that the inhibitor is at least partially or substantially separated from the environment in which it was formed or detected. Partial separation can include, for example, a composition enriched in the inhibitor provided herein. Substantial separation can include compositions containing at least about 50%, at least about 60%, at least about 70%, at least about 80%, at least about 90%, at least about 95%, at least about 97%, or at least about 99% by weight of the inhibitors provided herein, or salt thereof. Methods for isolating inhibitors and their salts are routine in the art.

The phrase "pharmaceutically acceptable" is used herein to refer to those inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "alkyl" includes a substituted or unsubstituted straight-chain alkyl groups (e.g., methyl, ethyl, propyl, butyl, pentyl, hexyl, heptyl, octyl, nonyl, decyl, etc.) and branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_{1-6}$ for straight chain; $C_{3-6}$ for branched chain). The term $C_{1-6}$ includes alkyl groups containing 1 to 6 carbon atoms.

The term "alkenyl" includes a substituted or unsubstituted aliphatic groups that may or may not be substituted, as described above for alkyls, containing at least one double bond and at least two carbon atoms. For example, the term "alkenyl" includes straight-chain alkenyl groups (e.g., ethylenyl, propenyl, butenyl, pentenyl, hexenyl, heptenyl, octenyl, nonenyl, and decenyl) and branched-chain alkenyl groups. In certain embodiments, a straight chain or branched chain alkenyl group has six or fewer carbon atoms in its backbone (e.g., $C_{2-6}$ for straight chain; $C_{3-6}$ for branched chain). The term $C_{2-6}$ includes alkenyl groups containing 2 to 6 carbon atoms.

The term "alkynyl" includes a substituted or unsubstituted unsaturated aliphatic group analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has six or fewer carbon atoms in its backbone (e.g., $C_{2-6}$ for straight chain; $C_{3-6}$ for branched chain). The term $C_{2-6}$ includes alkynyl groups containing 2 to 6 carbon atoms.

As used herein, "haloalkyl" means a hydrocarbon substituent, which is a linear or branched or cyclic alkyl, alkenyl or alkynyl substituted with one or more chloro, bromo, fluoro, or iodo atom(s). In some embodiments, a haloalkyl is a fluoroalkyl, wherein one or more of the hydrogen atoms have been substituted by fluoro. In some embodiments, haloalkyls are of 1 to about 3 carbons in length (e.g., 1 to about 2 carbons in length or 1 carbon in length).

The term "cycloalkyl" includes a substituted or unsubstituted cyclic aliphatic group which may be saturated or unsaturated. For example, cycloalkyl groups include cyclopropyl, cyclopentyl, cyclohexyl, cycloheptyl, and cyclooctyl. In some embodiments, cycloalkyls can have from 3-8 carbon atoms in their ring structure, for example, they can have 3, 4, 5, or 6 carbons in the ring structure.

In general, the term "aryl" includes substituted or unsubstituted aromatic rings, including 5- and 6-membered single-ring aromatic groups, such as benzene and phenyl. Furthermore, the term "aryl" includes multicyclic aryl groups, e.g., tricyclic, bicyclic, such as naphthalene and anthracene. In some embodiments, the aryl is a $C_6$-$C_{14}$ aryl group. In some embodiments, the aryl is a $C_6$-$C_{10}$ aryl group. In some embodiments, the aryl is a $C_5$-$C_6$ aryl group. In some embodiments, the aryl is a substituted or unsubstituted phenyl. In some embodiments, the aryl is substituted phenyl. In some embodiments, the aryl is unsubstituted phenyl.

As used herein, "arylalkyl" means an aryl-alkyl-group in which the aryl and alkyl moieties are as previously described. Preferred arylalkyl groups contain a $C_{1-4}$alkyl moiety. Exemplary arylalkyl groups include benzyl and 2-phenethyl.

The term "heteroaryl" means a substituted or unsubstituted mono-, bi-, tri- or polycyclic group having 5 to 14 ring atoms, alternatively 5, 6, 9, or 10 ring atoms; having 6, 10, or 14 pi electrons shared in a cyclic array; wherein at least one ring in the system is aromatic, and at least one ring in the system contains one or more heteroatoms independently selected from the group consisting of N, O, and S. Exemplary heteroaryl groups include, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine In some embodiments, the heteroaryl group is unsubstituted. In some embodiments, the heteroaryl group is substituted. In some embodiments, the heteroaryl group is a 5-14 membered heteroaryl group. In some embodiments, the heteroaryl group is a 5-10 membered heteroaryl group. In some embodiments, the heteroaryl is a 5-6 membered heteroaryl group.

As used herein, "heteroarylalkyl" means a heteroaryl-alkyl-group in which the heteroaryl and alkyl moieties are as previously described. Preferred heteroarylalkyl groups contain a $C_{1-4}$ alkyl moiety. Exemplary heteroarylalkyl groups include pyridylmethyl.

The term "heterocycloalkyl" includes substituted or unsubstituted groups, including but not limited to, 3- to 10-membered single or multiple rings having one to five heteroatoms, for example, piperazine, pyrrolidine, piperidine, or homopiperazine. In some embodiments, the heterocycloalkyl is a 3-10 membered heterocycloalkyl group. In some embodiments, the heterocycloalkyl is a 5-10 membered heterocycloalkyl group. In some embodiments, the heterocycloalkyl is a 5-7 membered heterocycloalkyl group. In some embodiments, the heterocycloalkyl is a 5-6 membered heterocycloalkyl group.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered cycloalkyl or heterocycloalkyl ring. In some embodiments, two sites of substitution may come together to form a 3-10 membered cycloalkyl group, a 5-14 membered aryl group, a 5-14 membered heteroaryl group, or a 3-10 membered heterocycloalkyl group. Non-limiting examples of substituents include: ($C_1$-$C_6$)alkyl, halo, ($C_1$-$C_6$)haloalkyl, —CN, —$NR^8R^9$, —$NO_2$, —O($C_1$-$C_6$)haloalkyl, —$OR^8$, —OC(O)$R^8$, —C(O)$R^8$, —C(O)O$R^8$, —C(O)N$R^8R^9$, —S$R^8$, —S(O)$R^8$, —$SO_2R^8$, —$SO_2NR^8R^9$, ($C_3$-$C_7$) cycloalkyl, ($C_3$-$C_7$) heterocycloalkyl, ($C_5$-$C_{14}$)aryl, and ($C_5$-$C_{14}$)heteroaryl, wherein $R^8$ and $R^9$ are independently selected from H and ($C_1$-$C_6$)alkyl.

Inhibitors

This, document provides inhibitors of GRK6 polypeptides as well as methods and materials for using such inhibitors to treat hematological malignancies, inflammation diseases, and autoimmune disorders.

Provided herein is a compound of Formula I:

Formula I

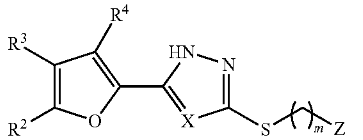

or a pharmaceutically acceptable salt thereof, wherein:

X is selected from the group consisting of CH and N;

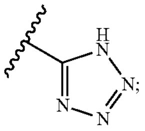 [SMILES: *c1nnn[nH]1]

Z is selected from the group consisting of —C(O)O$R^1$ and $R^1$ is selected from the group consisting of H and ($C_1$-$C_6$) alkyl;

$R^2$ is selected from the group consisting of: a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, and a substituted or unsubstituted heteroaryl;

$R^3$ and $R^4$ are independently selected from the group consisting of: H, halo, a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, a substituted or unsubstituted heteroaryl, a substituted or unsubstituted aralkyl, and a substituted or unsubstituted heteroaralkyl;

or $R^2$ and $R^3$ or $R^3$ and $R^4$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and m is an integer from 1 to 2.

In some embodiments, $R^2$ is a substituted or unsubstituted aryl. In some embodiments, $R^2$ is a substituted or unsubstituted heteroaryl. In some embodiments, $R^2$ is a ($C_1$-$C_6$)alkyl further substituted by one or more heterocycloalkyls. In some embodiments, $R^2$ is a ($C_1$-$C_6$)alkyl further substituted by one or more aryl. In some embodiments, $R^2$ is a substituted or unsubstituted phenyl. In some embodiments, $R^2$ is a substituted ($C_2$-$C_6$)alkynyl. In some embodiments, $R^2$ is a ($C_2$-$C_6$)alkynyl further substituted by a substituted aryl group. In some embodiments, $R^2$ is a ($C_2$-$C_6$)alkynyl further substituted by a dichlorophenyl group. In some embodiments, $R^2$ is a heteroaryl selected from a group consisting of pyridazinyl, pyridyl, carbazolyl, thiopheneyl, benzothiopheneyl, pyrrolyl, indolyl, quinolinyl, furanyl, benzofuranyl, and carbazole, each of which may be optionally substituted.

In some embodiments, $R^3$ is selected from a group consisting of: a substituted or unsubstituted ($C_1$-$C_6$)alkynyl, halo, and a substituted or unsubstituted aryl; and $R^4$ is H. In some embodiments, each of $R^1$, $R^3$, and $R^4$ is H; and $R^2$ is a substituted or unsubstituted heteroaryl. For example, $R^2$ can be a heteroaryl selected from a group consisting of pyridazinyl, pyridyl, carbazolyl, thiopheneyl, benzothiopheneyl, pyrrolyl, indolyl, quinolinyl, furanyl, and benzofuranyl. In some embodiments, $R^2$ is a carbazole.

In some embodiments, a compound of Formula I is a compound of Formula IA:

Formula IA

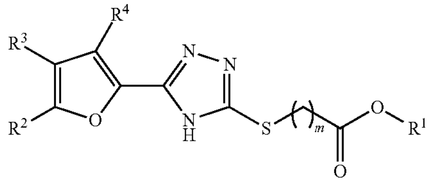

or a pharmaceutically acceptable salt thereof, wherein:

$R^1$ is selected from the group consisting of H and ($C_1$-$C_6$) alkyl;

$R^2$ is selected from the group consisting of: a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, and a substituted or unsubstituted heteroaryl;

$R^3$ and $R^4$ are independently selected from the group consisting of: H, halo, a substituted ($C_1$-$C_6$)alkyl, a substituted or unsubstituted ($C_2$-$C_6$)alkenyl, a substituted or unsubstituted ($C_2$-$C_6$)alkynyl, ($C_1$-$C_6$)haloalkyl, a substituted or unsubstituted cycloalkyl, a substituted or unsubstituted heterocycloalkyl, a substituted or unsubstituted aryl, a substituted or unsubstituted heteroaryl, a substituted or unsubstituted aralkyl, and a substituted or unsubstituted heteroaralkyl;

or $R^2$ and $R^3$ or $R^3$ and $R^4$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and m is an integer from 1 to 2.

In some embodiments, $R^2$ is a substituted or unsubstituted aryl. In some embodiments, $R^2$ is a substituted or unsubstituted heteroaryl. In some embodiments, $R^2$ is a ($C_1$-$C_6$)alkyl further substituted by one or more heterocycloalkyls. In some embodiments, $R^2$ is a ($C_1$-$C_6$)alkyl further substituted by one or more aryl. In some embodiments, $R^2$ is a substituted or unsubstituted phenyl. In some embodiments, $R^2$ is a substituted ($C_1$-$C_6$)alkynyl. In some embodiments, $R^2$ is a ($C_2$-$C_6$)alkynyl further substituted by a substituted aryl group. In some embodiments, $R^2$ is a ($C_2$-$C_6$)alkynyl further substituted by a dichlorophenyl group. In some embodiments, $R^2$ is a heteroaryl selected from a group consisting of pyridazinyl, pyridyl, carbazolyl, thiopheneyl, benzothiopheneyl, pyrrolyl, indolyl, quinolinyl, furanyl, benzofuranyl, and carbazole, each of which may be optionally substituted.

In some embodiments, $R^3$ is selected from a group consisting of: a substituted or unsubstituted $(C_1\text{-}C_6)$alkynyl, halo, and a substituted or unsubstituted aryl; and $R^4$ is H. In some embodiments, each of $R^1$, $R^3$, and $R^4$ is H; and $R^2$ is a substituted or unsubstituted heteroaryl. For example, $R^2$ can be a heteroaryl selected from a group consisting of pyridazinyl, pyridyl, carbazolyl, thiopheneyl, benzothiopheneyl, pyrrolyl, indolyl, quinolinyl, furanyl, and benzofuranyl. In some embodiments, $R^2$ is a carbazole.

In some embodiments, each of $R^1$ and $R^4$ is H; $R^2$ is selected from a group consisting of a substituted or unsubstituted aryl and a substituted or unsubstituted heteroaryl; and $R^3$ is selected from a group consisting of halo, a substituted $(C_1\text{-}C_6)$alkynyl, and a substituted or unsubstituted aryl.

In some embodiments, a compound of Formula I includes a compound of Formula IB:

Formula IB

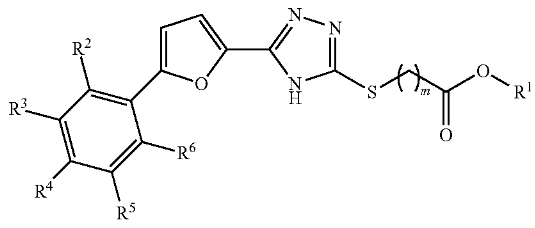

or a pharmaceutically acceptable salt thereof, wherein:

$R^1$ is selected from the group consisting of H and $(C_1\text{-}C_6)$ alkyl;

each of $R^2$, $R^3$, $R^4$, $R^5$, and $R^6$ are independently selected from the group consisting of: H, halo, $(C_1\text{-}C_6)$alkyl, $(C_1\text{-}C_6)$haloalkyl, $OR^7$, CN, $NO_2$, $C(O)R^8$, $NR^9R^{10}$, $—S(O)_2NR^9R^{10}$, $—S(O)NR^9R^{10}$, $—C(NR^{11})R^{12}$, $—C(O)NR^{13}R^{14}$, a substituted or unsubstituted aryl, a substituted or unsubstituted heteroaryl, a substituted or unsubstituted cycloalkyl, and a substituted or unsubstituted heterocycloalkyl;

or $R^2$ and $R^3$, $R^3$ and $R^4$, $R^4$ and $R^5$, or $R^5$ and $R^6$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring;

each $R^7$ is independently selected from the group consisting of H, $(C_1\text{-}C_6)$alkyl, $(C_1\text{-}C_6)$haloalkyl, $(C_1\text{-}C_6)$aralkyl, $(C_1\text{-}C_6)$heteroaralkyl, a substituted or unsubstituted aryl, and a substituted or unsubstituted heteroaryl;

each $R^8$ is independently selected from a group consisting of H, OH, $(C_1\text{-}C_6)$alkyl, $(C_1\text{-}C_6)$haloalkyl, $OR^{8a}$, $—NR^{8a}R^{8b}$, wherein $R^{8a}$ and $R^{8b}$ are independently selected from a group consisting of H and $(C_1\text{-}C_6)$alkyl;

each of $R^9$, $R^{10}$, $R^{12}$, $R^{13}$, and $R^{14}$ are independently selected from a group consisting of H and $(C_1\text{-}C_6)$alkyl;

each $R^{11}$ is independently selected from a group consisting of H, $(C_1\text{-}C_6)$alkyl, and $OR^{11a}$ wherein $R^{11a}$ is independently selected from a group consisting of H, $(C_1\text{-}C_6)$ alkyl, a substituted or unsubstituted aryl, and a substituted or unsubstituted heteroaryl; and m is an integer from 1 to 2.

In some embodiments, at least one of $R^2$ and $R^3$, $R^3$ and $R^4$, $R^4$ and $R^5$, and $R^5$ and $R^6$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring.

In some embodiments, $R^1$ is H. In some such embodiments, $R^1$ is H; and $R^3$ is $OR^{3a}$; wherein $R^{3a}$ is selected from a group consisting of H, $(C_1\text{-}C_6)$alkyl, $(C_1\text{-}C_6)$alkyl, $(C_1\text{-}C_6)$haloalkyl, $(C_1\text{-}C_6)$aralkyl, $(C_1\text{-}C_6)$heteroaralkyl, a substituted or unsubstituted aryl, and a substituted or unsubstituted heteroaryl.

Non-limiting examples of a compound of Formula I, IA, and/or IB include the compounds in Table 1, or a pharmaceutically acceptable salt thereof.

TABLE 1

| # | Compound Structure |
|---|---|
| 1-1 | 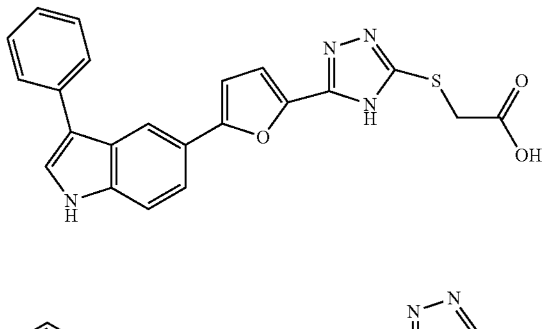 |
| 1-2 | 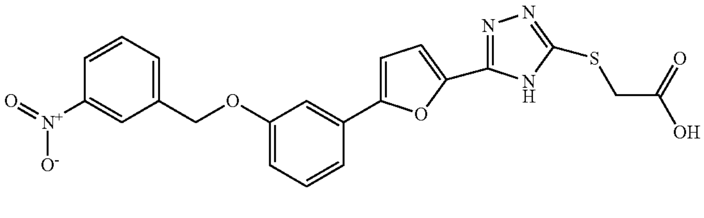 [SMILES: O=C(O)CSc1nnc(-c2ccc(-c3cccc(OCc4cccc([N+](=O)[O-])c4)c3)o2)[nH]1] |

TABLE 1-continued
| # | Compound Structure |
|---|---|
| 1-3 | 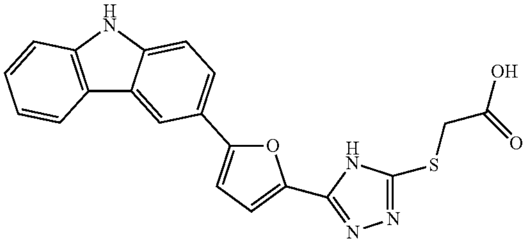 [SMILES: O=C(O)CSc1nnc(-c2ccc(-c3ccc4[nH]c5ccccc5c4c3)o2)[nH]1] |
| 1-4 | 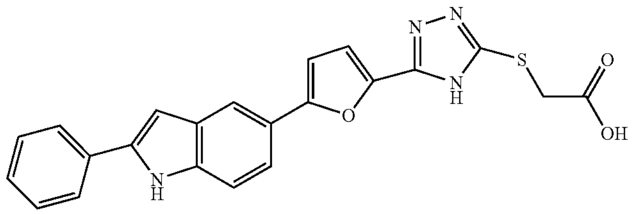 [SMILES: O=C(O)CSc1nnc(-c2ccc(-c3ccc4[nH]c(-c5ccccc5)cc4c3)o2)[nH]1] |
| 1-5 | 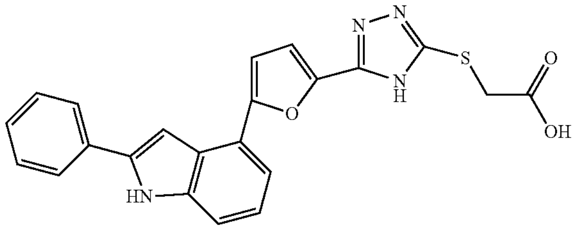 [SMILES: O=C(O)CSc1nnc(-c2ccc(-c3cccc4[nH]c(-c5ccccc5)cc34)o2)[nH]1] |
| 1-6 | 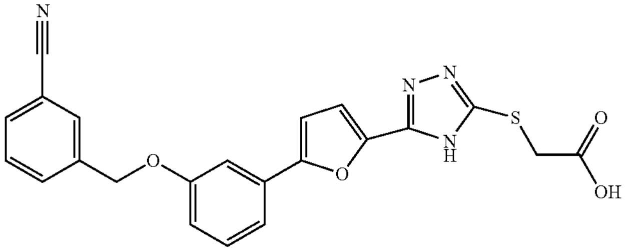 [SMILES: N#Cc1cccc(COc2cccc(-c3ccc(-c4nnc(SCC(=O)O)[nH]4)o3)c2)c1] |
| 1-7 | 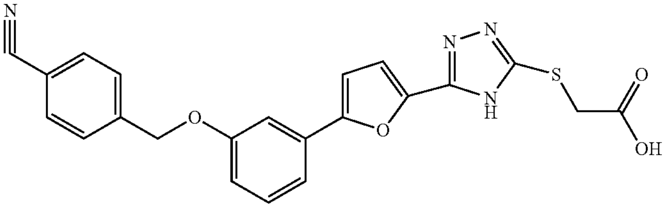 [SMILES: N#Cc1ccc(COc2cccc(-c3ccc(-c4nnc(SCC(=O)O)[nH]4)o3)c2)cc1] |
| 1-8 | 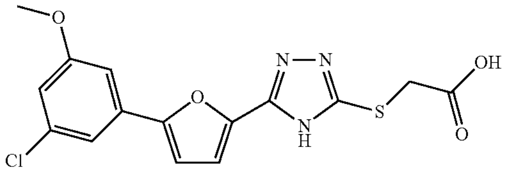 [SMILES: COc1cc(Cl)cc(-c2ccc(-c3nnc(SCC(=O)O)[nH]3)o2)c1] |
| 1-9 | 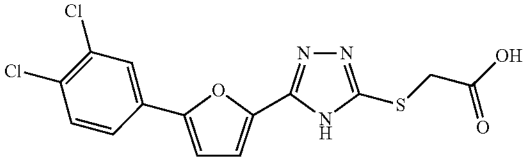 [SMILES: O=C(O)CSc1nnc(-c2ccc(-c3ccc(Cl)c(Cl)c3)o2)[nH]1] |

TABLE 1-continued
| # | Compound Structure |
|---|---|
| 1-10 | 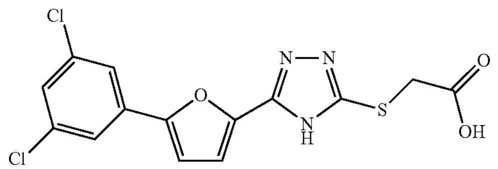 [SMILES: O=C(O)CSc1nnc(-c2ccc(-c3cc(Cl)cc(Cl)c3)o2)[nH]1] |
| 1-11 | 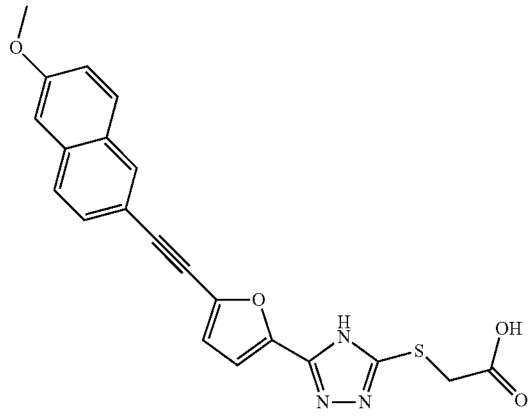 [SMILES: COc1ccc2cc(C#Cc3ccc(-c4nnc(SCC(=O)O)[nH]4)o3)ccc2c1] |
| 1-12 | 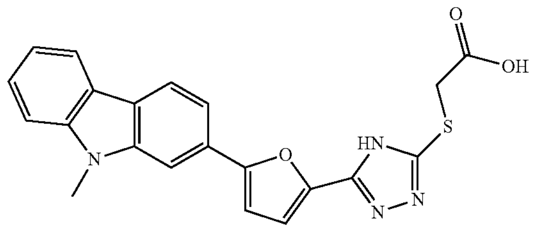 [SMILES: Cn1c2ccccc2c2ccc(-c3ccc(-c4nnc(SCC(=O)O)[nH]4)o3)cc21] |
| 1-13 | 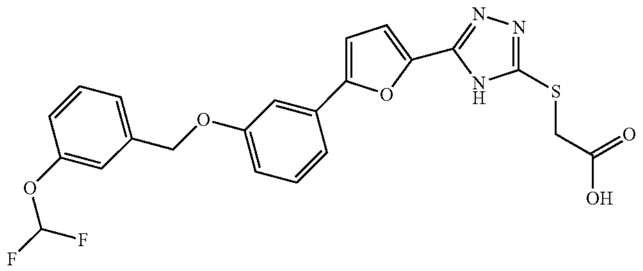 [SMILES: O=C(O)CSc1nnc(-c2ccc(-c3cccc(OCc4cccc(OC(F)F)c4)c3)o2)[nH]1] |
| 1-14 | 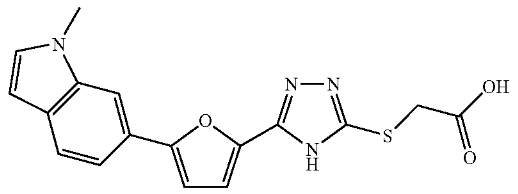 [SMILES: Cn1ccc2ccc(-c3ccc(-c4nnc(SCC(=O)O)[nH]4)o3)cc21] |
| 1-15 | 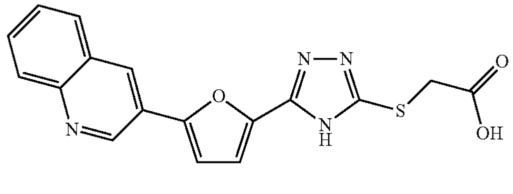 [SMILES: O=C(O)CSc1nnc(-c2ccc(-c3cnc4ccccc4c3)o2)[nH]1] |

TABLE 1-continued
| # | Compound Structure |
|---|---|
| 1-16 | 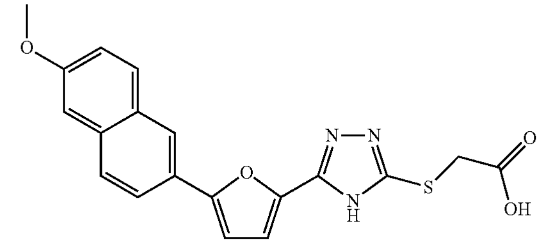 [SMILES: COc1ccc2cc(-c3ccc(-c4nnc(SCC(=O)O)[nH]4)o3)ccc2c1] |
| 1-17 | 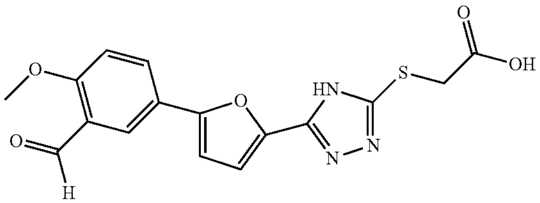 [SMILES: COc1ccc(-c2ccc(-c3nnc(SCC(=O)O)[nH]3)o2)cc1C=O] |
| 1-18 | 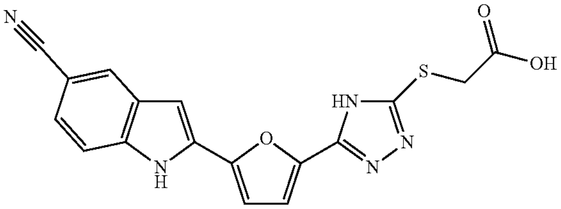 [SMILES: N#Cc1ccc2[nH]c(-c3ccc(-c4nnc(SCC(=O)O)[nH]4)o3)cc2c1] |
| 1-19 | 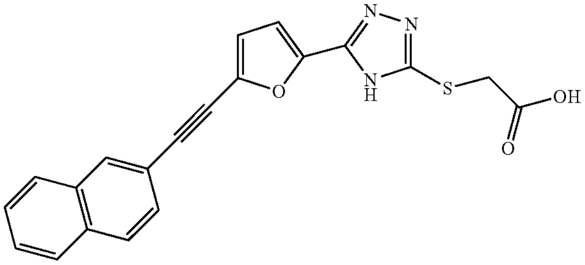 [SMILES: O=C(O)CSc1nnc(-c2ccc(C#Cc3ccc4ccccc4c3)o2)[nH]1] |
| 1-20 | 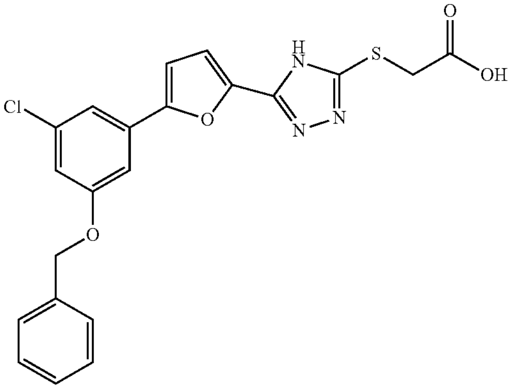 [SMILES: O=C(O)CSc1nnc(-c2ccc(-c3cc(Cl)cc(OCc4ccccc4)c3)o2)[nH]1] |
| 1-21 | 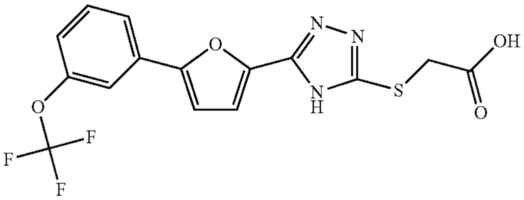 [SMILES: O=C(O)CSc1nnc(-c2ccc(-c3cccc(OC(F)(F)F)c3)o2)[nH]1] |

TABLE 1-continued
| # | Compound Structure |
|---|---|
| 1-22 | 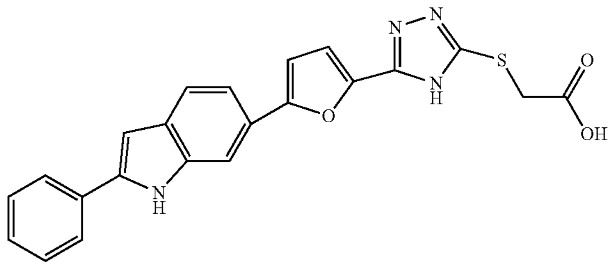 [SMILES: O=C(O)CSc1nnc(-c2ccc(-c3ccc4cc(-c5ccccc5)[nH]c4c3)o2)[nH]1] |
| 1-23 | 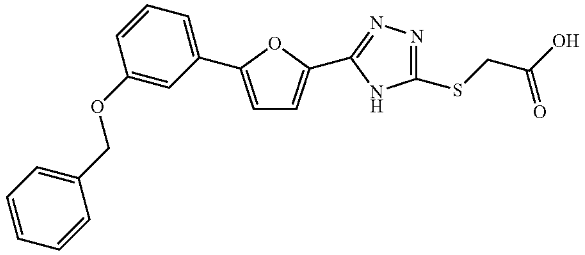 [SMILES: O=C(O)CSc1nnc(-c2ccc(-c3cccc(OCc4ccccc4)c3)o2)[nH]1] |
| 1-24 | 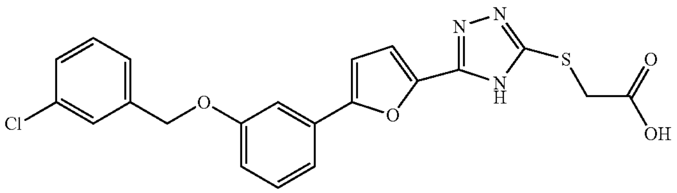 [SMILES: O=C(O)CSc1nnc(-c2ccc(-c3cccc(OCc4cccc(Cl)c4)c3)o2)[nH]1] |
| 1-25 | 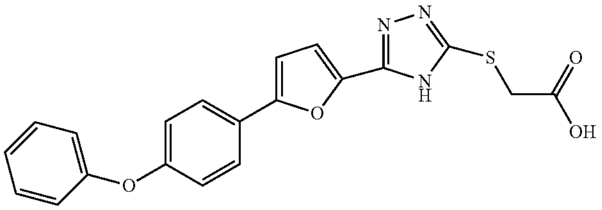 [SMILES: O=C(O)CSc1nnc(-c2ccc(-c3ccc(Oc4ccccc4)cc3)o2)[nH]1] |
| 1-26 | 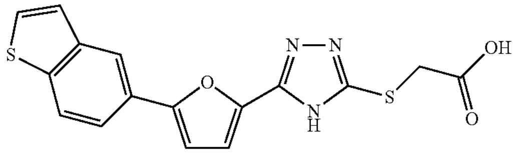 [SMILES: O=C(O)CSc1nnc(-c2ccc(-c3ccc4sccc4c3)o2)[nH]1] |
| 1-27 | 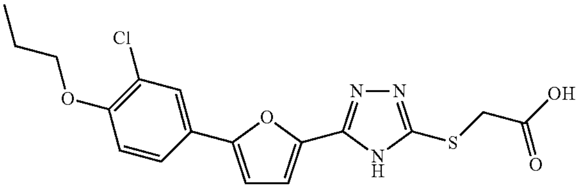 [SMILES: CCCOc1ccc(-c2ccc(-c3nnc(SCC(=O)O)[nH]3)o2)cc1Cl] |
| 1-28 | 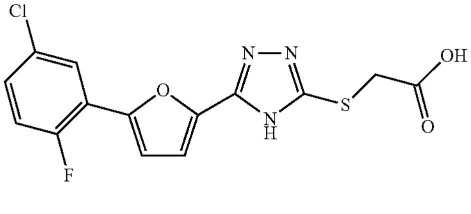 [SMILES: O=C(O)CSc1nnc(-c2ccc(-c3cc(Cl)ccc3F)o2)[nH]1] |

TABLE 1-continued
| # | Compound Structure |
| --- | --- |
| 1-29 | 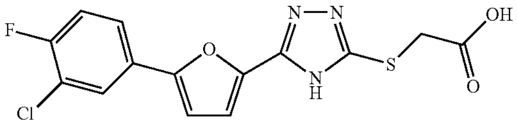 [SMILES: O=C(O)CSc1nnc(-c2ccc(-c3ccc(F)c(Cl)c3)o2)[nH]1] |
| 1-30 | 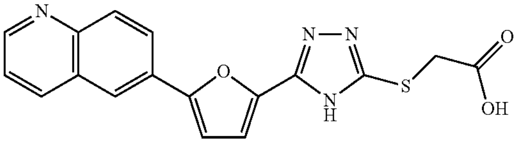 [SMILES: O=C(O)CSc1nnc(-c2ccc(-c3ccc4ncccc4c3)o2)[nH]1] |
| 1-31 | 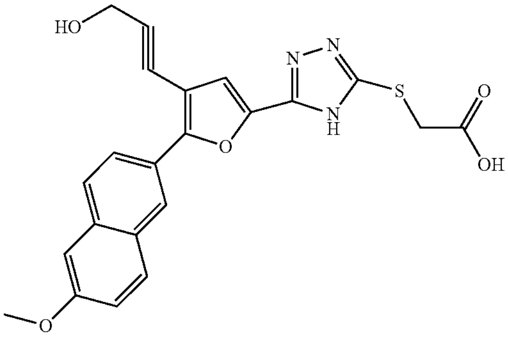 [SMILES: COc1ccc2cc(-c3oc(-c4nnc(SCC(=O)O)[nH]4)cc3C#CCO)ccc2c1] |
| 1-32 | 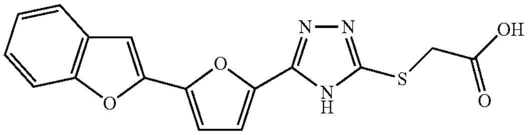 [SMILES: O=C(O)CSc1nnc(-c2ccc(-c3cc4ccccc4o3)o2)[nH]1] |
| 1-33 | 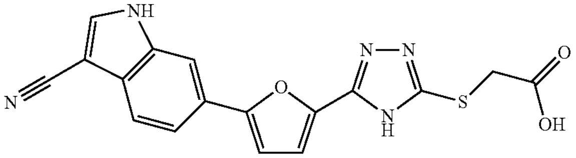 [SMILES: N#Cc1c[nH]c2cc(-c3ccc(-c4nnc(SCC(=O)O)[nH]4)o3)ccc12] |
| 1-34 | 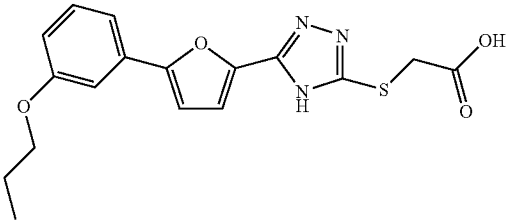 [SMILES: CCCOc1cccc(-c2ccc(-c3nnc(SCC(=O)O)[nH]3)o2)c1] |
| 1-35 | 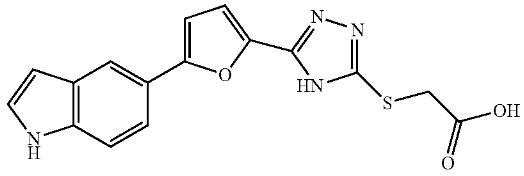 [SMILES: O=C(O)CSc1nnc(-c2ccc(-c3ccc4[nH]ccc4c3)o2)[nH]1] |
| 1-36 | 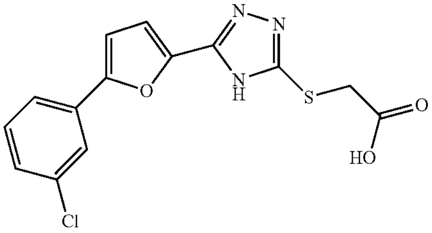 [SMILES: O=C(O)CSc1nnc(-c2ccc(-c3cccc(Cl)c3)o2)[nH]1] |

TABLE 1-continued
| # | Compound Structure |
| --- | --- |
| 1-37 | 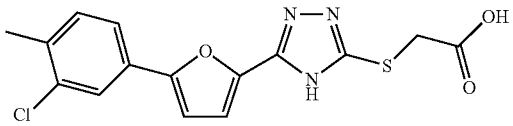 [SMILES: Cc1ccc(-c2ccc(-c3nnc(SCC(=O)O)[nH]3)o2)cc1Cl] |
| 1-38 | 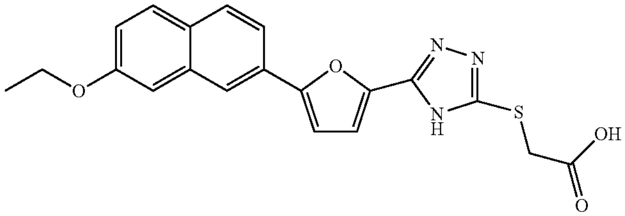 [SMILES: CCOc1ccc2ccc(-c3ccc(-c4nnc(SCC(=O)O)[nH]4)o3)cc2c1] |
| 1-39 | 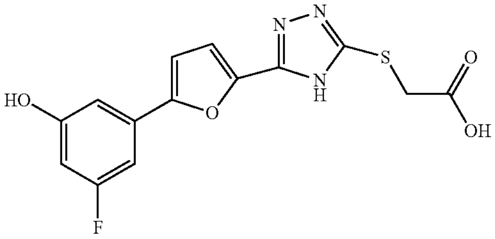 [SMILES: O=C(O)CSc1nnc(-c2ccc(-c3cc(O)cc(F)c3)o2)[nH]1] |
| 1-40 | 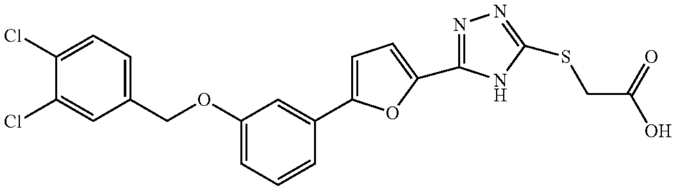 [SMILES: O=C(O)CSc1nnc(-c2ccc(-c3cccc(OCc4ccc(Cl)c(Cl)c4)c3)o2)[nH]1] |
| 1-41 | 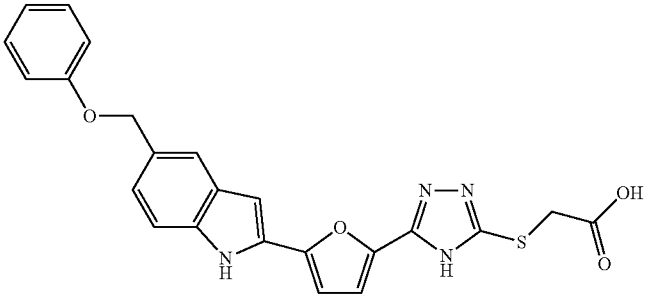 [SMILES: O=C(O)CSc1nnc(-c2ccc(-c3cc4cc(COc5ccccc5)ccc4[nH]3)o2)[nH]1] |
| 1-42 | 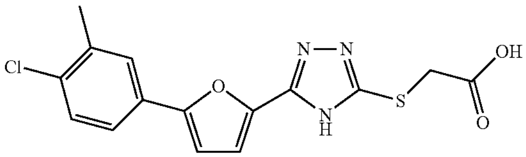 [SMILES: Cc1cc(-c2ccc(-c3nnc(SCC(=O)O)[nH]3)o2)ccc1Cl] |
| 1-43 | 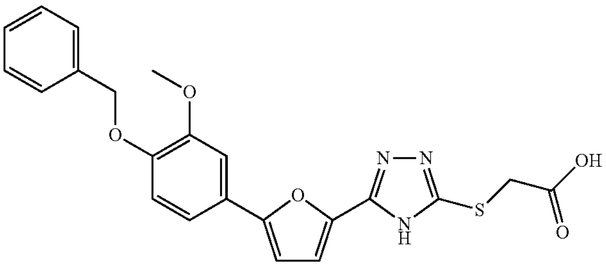 [SMILES: COc1cc(-c2ccc(-c3nnc(SCC(=O)O)[nH]3)o2)ccc1OCc1ccccc1] |

TABLE 1-continued
| # | Compound Structure |
|---|---|
| 1-44 | 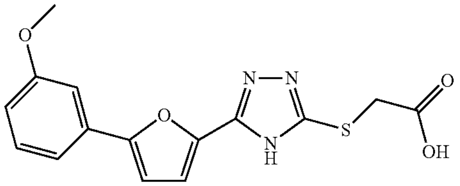 [SMILES: COc1cccc(-c2ccc(-c3nnc(SCC(=O)O)[nH]3)o2)c1] |
| 1-45 | 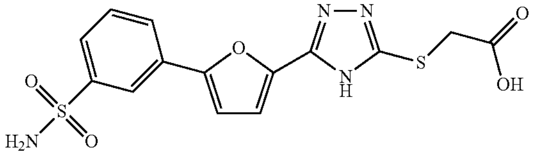 [SMILES: NS(=O)(=O)c1cccc(-c2ccc(-c3nnc(SCC(=O)O)[nH]3)o2)c1] |
| 1-46 | 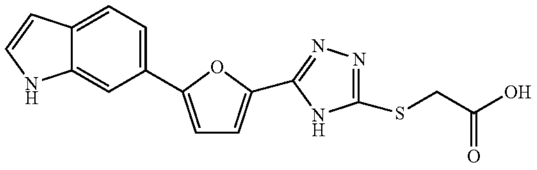 [SMILES: O=C(O)CSc1nnc(-c2ccc(-c3ccc4cc[nH]c4c3)o2)[nH]1] |
| 1-47 | 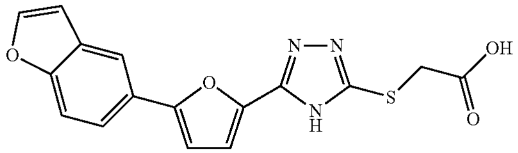 [SMILES: O=C(O)CSc1nnc(-c2ccc(-c3ccc4occc4c3)o2)[nH]1] |
| 1-48 | 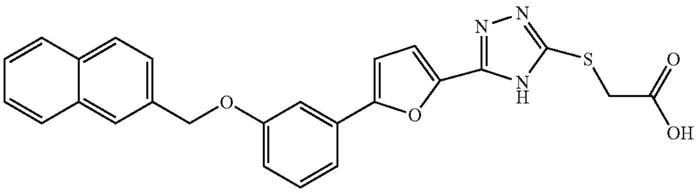 [SMILES: O=C(O)CSc1nnc(-c2ccc(-c3cccc(OCc4ccc5ccccc5c4)c3)o2)[nH]1] |
| 1-49 | 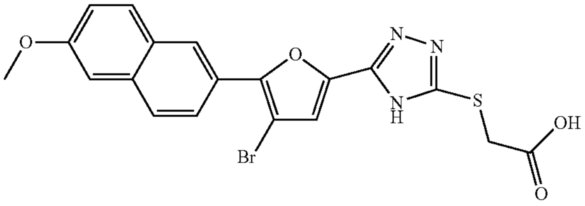 [SMILES: COc1ccc2cc(-c3oc(-c4nnc(SCC(=O)O)[nH]4)cc3Br)ccc2c1] |
| 1-50 | 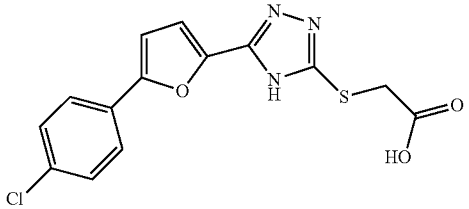 [SMILES: O=C(O)CSc1nnc(-c2ccc(-c3ccc(Cl)cc3)o2)[nH]1] |
| 1-51 | 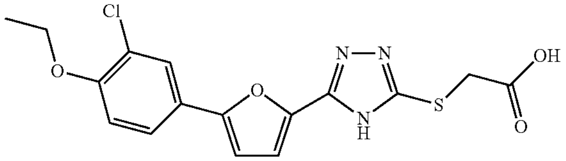 [SMILES: CCOc1ccc(-c2ccc(-c3nnc(SCC(=O)O)[nH]3)o2)cc1Cl] |

TABLE 1-continued
| # | Compound Structure |
|---|---|
| 1-52 | 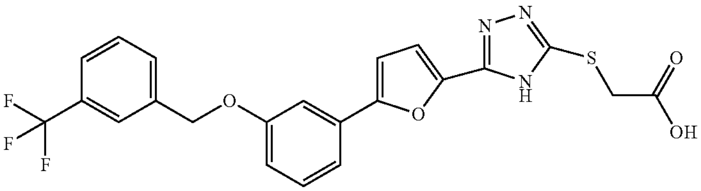 [SMILES: O=C(O)CSc1nnc(-c2ccc(-c3cccc(OCc4cccc(C(F)(F)F)c4)c3)o2)[nH]1] |
| 1-53 | 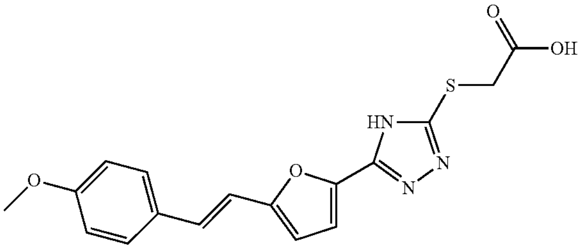 [SMILES: COc1ccc(/C=C/c2ccc(-c3nnc(SCC(=O)O)[nH]3)o2)cc1] |
| 1-54 | 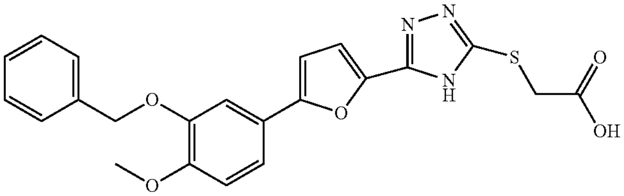 [SMILES: COc1ccc(-c2ccc(-c3nnc(SCC(=O)O)[nH]3)o2)cc1OCc1ccccc1] |
| 1-55 | 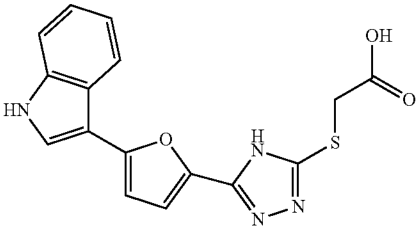 [SMILES: O=C(O)CSc1nnc(-c2ccc(-c3c[nH]c4ccccc34)o2)[nH]1] |
| 1-56 | 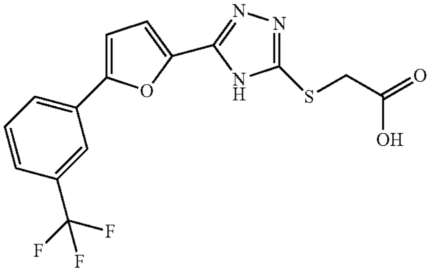 [SMILES: O=C(O)CSc1nnc(-c2ccc(-c3cccc(C(F)(F)F)c3)o2)[nH]1] |
| 1-57 | 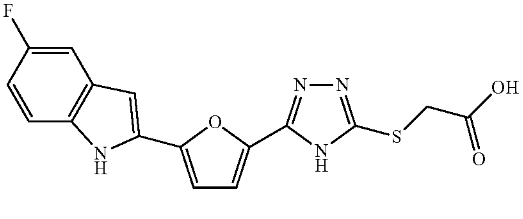 [SMILES: O=C(O)CSc1nnc(-c2ccc(-c3cc4cc(F)ccc4[nH]3)o2)[nH]1] |

TABLE 1-continued
| # | Compound Structure |
|---|---|
| 1-58 | 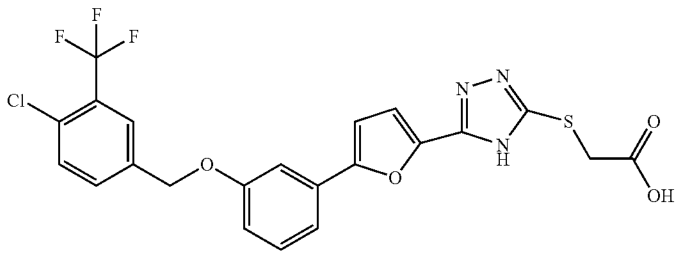 [SMILES: O=C(O)CSc1nnc(-c2ccc(-c3cccc(OCc4ccc(Cl)c(C(F)(F)F)c4)c3)o2)[nH]1] |
| 1-59 | 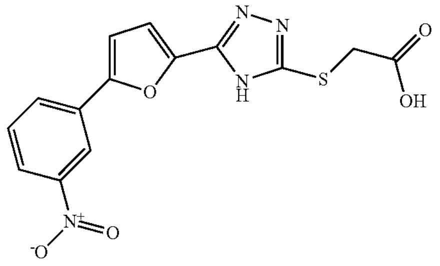 |
| 1-60 | 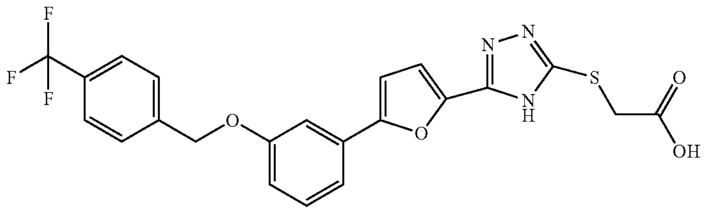 [SMILES: O=C(O)CSc1nnc(-c2ccc(-c3cccc(OCc4ccc(C(F)(F)F)cc4)c3)o2)[nH]1] |
| 1-61 | 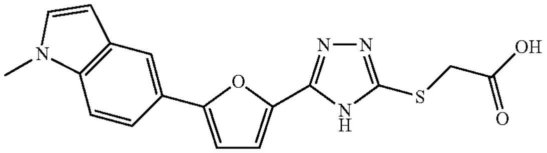 [SMILES: Cn1ccc2cc(-c3ccc(-c4nnc(SCC(=O)O)[nH]4)o3)ccc21] |
| 1-62 | 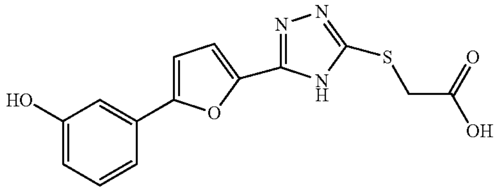 [SMILES: O=C(O)CSc1nnc(-c2ccc(-c3cccc(O)c3)o2)[nH]1] |
| 1-63 | 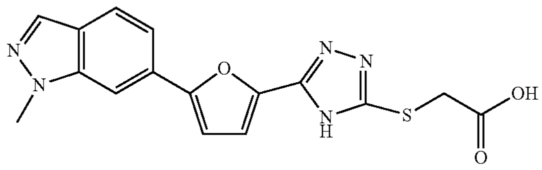 [SMILES: Cn1ncc2ccc(-c3ccc(-c4nnc(SCC(=O)O)[nH]4)o3)cc21] |
| 1-64 | 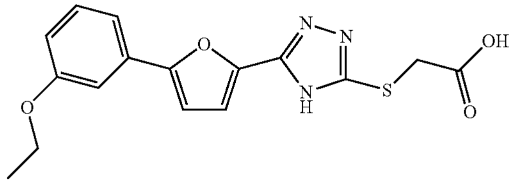 [SMILES: CCOc1cccc(-c2ccc(-c3nnc(SCC(=O)O)[nH]3)o2)c1] |

TABLE 1-continued
| # | Compound Structure |
|---|---|
| 1-65 | 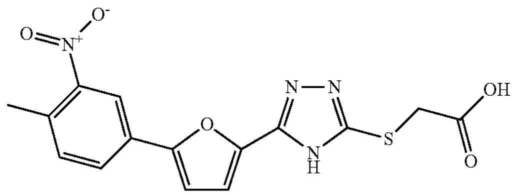 [SMILES: Cc1ccc(-c2ccc(-c3nnc(SCC(=O)O)[nH]3)o2)cc1[N+](=O)[O-]] |
| 1-66 | 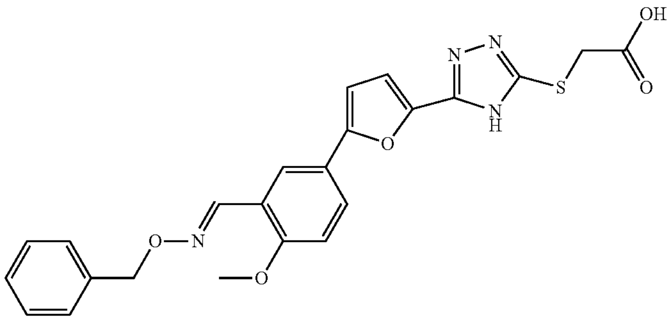 [SMILES: COc1ccc(-c2ccc(-c3nnc(SCC(=O)O)[nH]3)o2)cc1/C=N/OCc1ccccc1] |
| 1-67 | 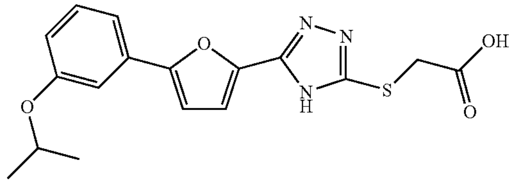 [SMILES: CC(C)Oc1cccc(-c2ccc(-c3nnc(SCC(=O)O)[nH]3)o2)c1] |
| 1-68 | 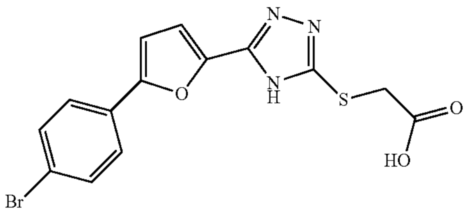 |
| 1-69 | 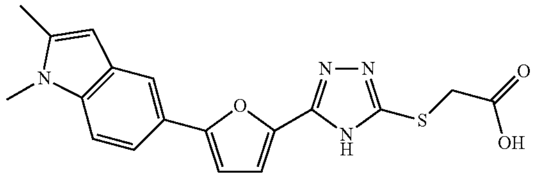 [SMILES: Cc1cc2cc(-c3ccc(-c4nnc(SCC(=O)O)[nH]4)o3)ccc2n1C] |
| 1-70 | 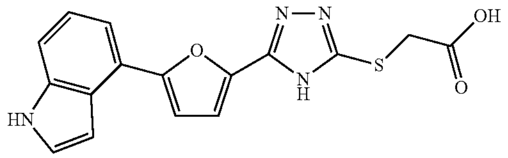 [SMILES: O=C(O)CSc1nnc(-c2ccc(-c3cccc4[nH]ccc34)o2)[nH]1] |
| 1-71 | 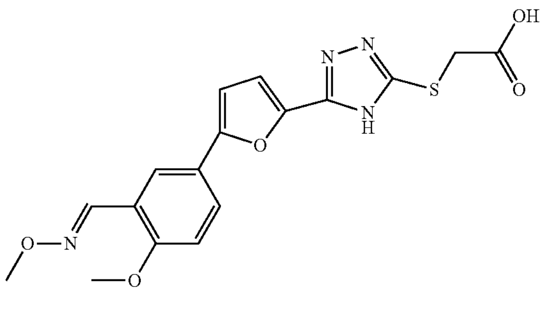 [SMILES: CO/N=C/c1cc(-c2ccc(-c3nnc(SCC(=O)O)[nH]3)o2)ccc1OC] |

TABLE 1-continued
| # | Compound Structure |
|---|---|
| 1-72 | 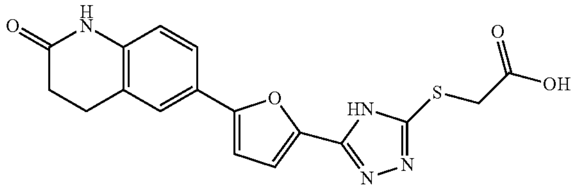 [SMILES: O=C(O)CSc1nnc(-c2ccc(-c3ccc4c(c3)CCC(=O)N4)o2)[nH]1] |
| 1-73 | 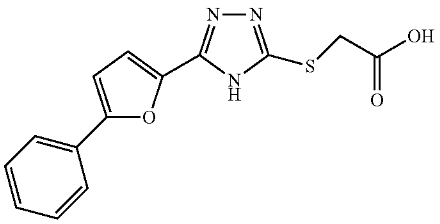 [SMILES: O=C(O)CSc1nnc(-c2ccc(-c3ccccc3)o2)[nH]1] |
| 1-74 | 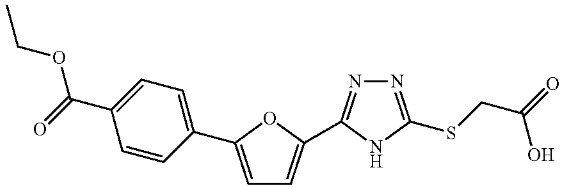 [SMILES: CCOC(=O)c1ccc(-c2ccc(-c3nnc(SCC(=O)O)[nH]3)o2)cc1] |
| 1-75 | 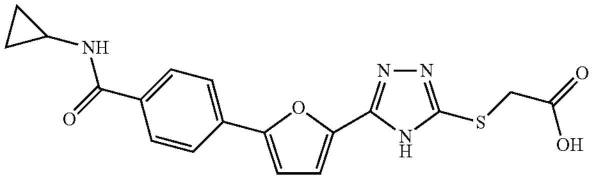 [SMILES: O=C(O)CSc1nnc(-c2ccc(-c3ccc(C(=O)NC4CC4)cc3)o2)[nH]1] |
| 1-76 | 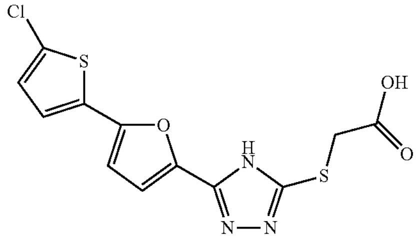 [SMILES: O=C(O)CSc1nnc(-c2ccc(-c3ccc(Cl)s3)o2)[nH]1] |
| 1-77 | 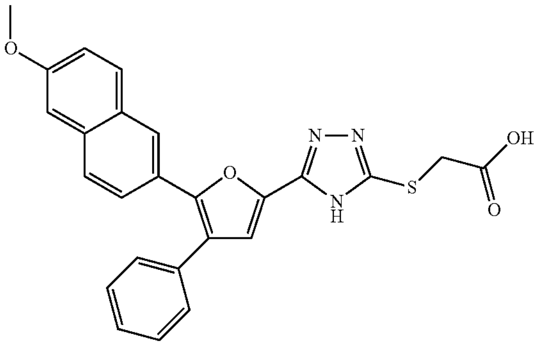 [SMILES: COc1ccc2cc(-c3oc(-c4nnc(SCC(=O)O)[nH]4)cc3-c3ccccc3)ccc2c1] |

TABLE 1-continued
| # | Compound Structure |
|---|---|
| 1-78 | 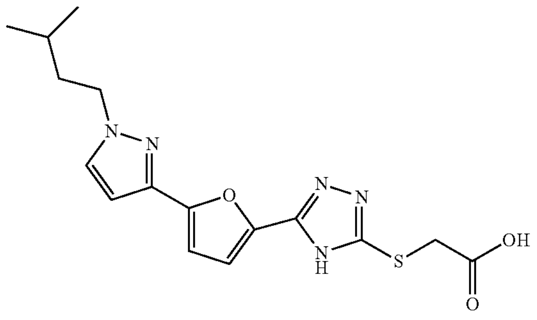 |
| 1-79 | 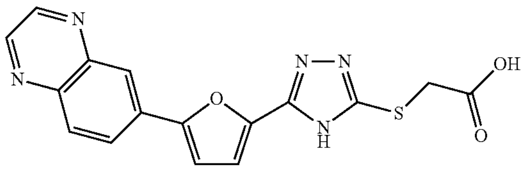 [SMILES: O=C(O)CSc1nnc(-c2ccc(-c3ccc4nccnc4c3)o2)[nH]1] |
| 1-80 | 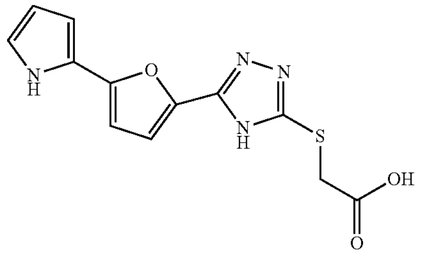 [SMILES: O=C(O)CSc1nnc(-c2ccc(-c3ccc[nH]3)o2)[nH]1] |
| 1-81 | 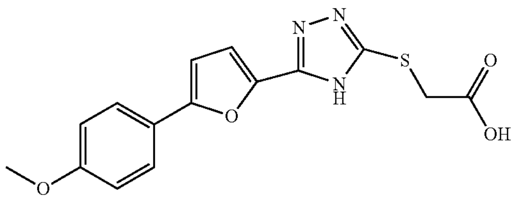 [SMILES: COc1ccc(-c2ccc(-c3nnc(SCC(=O)O)[nH]3)o2)cc1] |
| 1-82 | 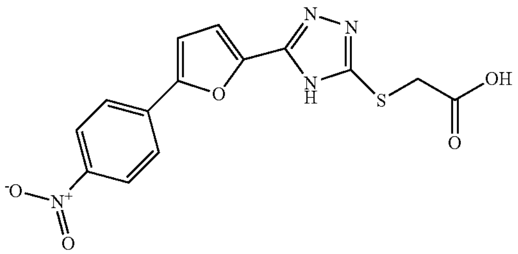 |
| 1-83 | 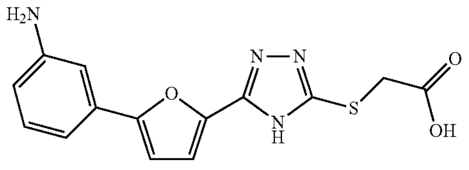 [SMILES: Nc1cccc(-c2ccc(-c3nnc(SCC(=O)O)[nH]3)o2)c1]

TABLE 1-continued
| # | Compound Structure |
|---|---|
| 1-84 | 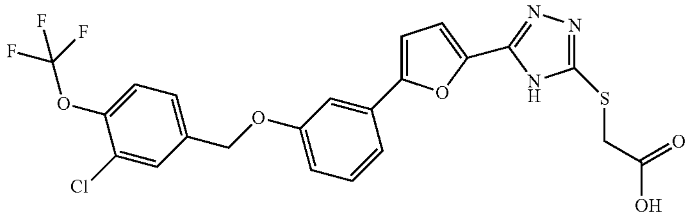 [SMILES: O=C(O)CSc1nnc(-c2ccc(-c3cccc(OCc4ccc(OC(F)(F)F)c(Cl)c4)c3)o2)[nH]1] |
| 1-85 | 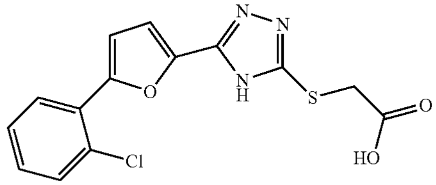 [SMILES: O=C(O)CSc1nnc(-c2ccc(-c3ccccc3Cl)o2)[nH]1] |
| 1-86 | 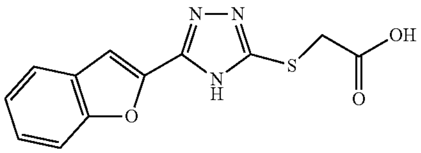 [SMILES: O=C(O)CSc1nnc(-c2cc3ccccc3o2)[nH]1] |
| 1-87 | 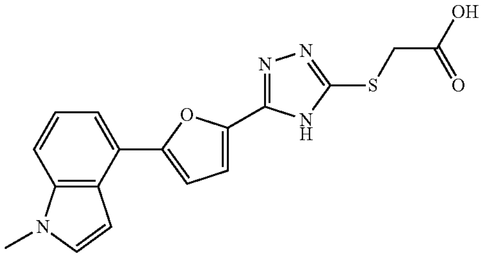 [SMILES: Cn1ccc2c(-c3ccc(-c4nnc(SCC(=O)O)[nH]4)o3)cccc21] |
| 1-88 | 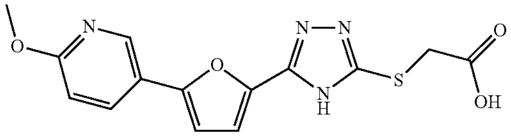 [SMILES: COc1ccc(-c2ccc(-c3nnc(SCC(=O)O)[nH]3)o2)cn1] |
| 1-89 | 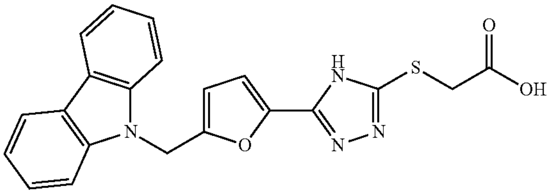 [SMILES: O=C(O)CSc1nnc(-c2ccc(Cn3c4ccccc4c4ccccc43)o2)[nH]1] |
| 1-90 | 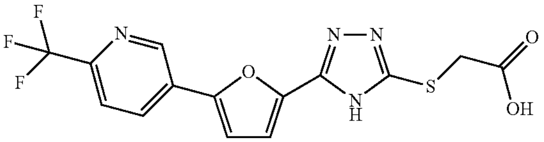 [SMILES: O=C(O)CSc1nnc(-c2ccc(-c3ccc(C(F)(F)F)nc3)o2)[nH]1] |

TABLE 1-continued
| # | Compound Structure |
| --- | --- |
| 1-91 | 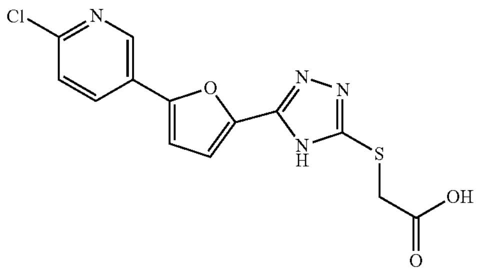 [SMILES: O=C(O)CSc1nnc(-c2ccc(-c3ccc(Cl)nc3)o2)[nH]1] |
| 1-92 | 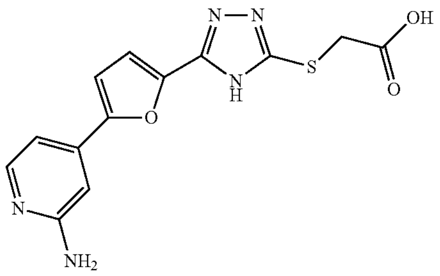 [SMILES: Nc1cc(-c2ccc(-c3nnc(SCC(=O)O)[nH]3)o2)ccn1] |
| 1-93 | 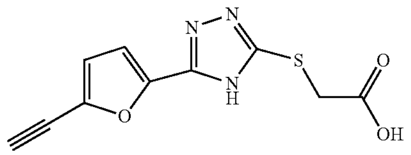 [SMILES: C#Cc1ccc(-c2nnc(SCC(=O)O)[nH]2)o1] |
| 1-94 | 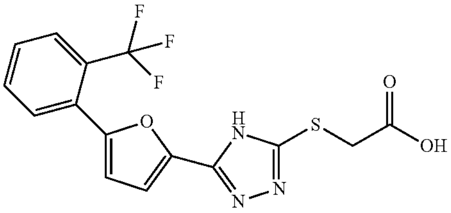 [SMILES: O=C(O)CSc1nnc(-c2ccc(-c3ccccc3C(F)(F)F)o2)[nH]1] |
| 1-95 | 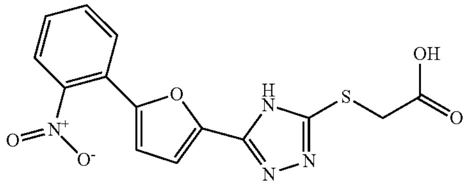 [SMILES: O=C(O)CSc1nnc(-c2ccc(-c3ccccc3[N+](=O)[O-])o2)[nH]1] |
| 1-96 | 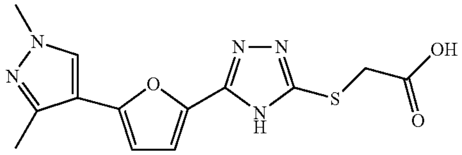 [SMILES: Cc1nn(C)cc1-c1ccc(-c2nnc(SCC(=O)O)[nH]2)o1] |
| 1-97 | 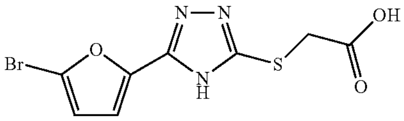 [SMILES: O=C(O)CSc1nnc(-c2ccc(Br)o2)[nH]1] |

TABLE 1-continued
| # | Compound Structure |
|---|---|
| 1-98 | 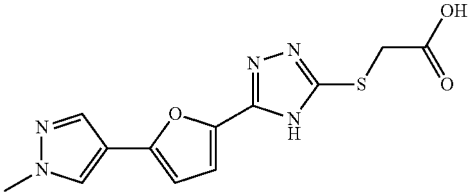 [SMILES: Cn1cc(-c2ccc(-c3nnc(SCC(=O)O)[nH]3)o2)cn1] |
| 1-99 | 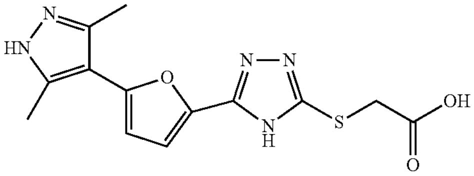 [SMILES: Cc1n[nH]c(C)c1-c1ccc(-c2nnc(SCC(=O)O)[nH]2)o1] |
| 1-100 | 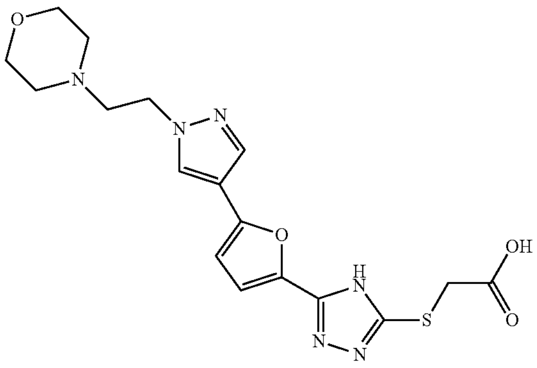 [SMILES: O=C(O)CSc1nnc(-c2ccc(-c3cnn(CCN4CCOCC4)c3)o2)[nH]1] |
| 1-101 | 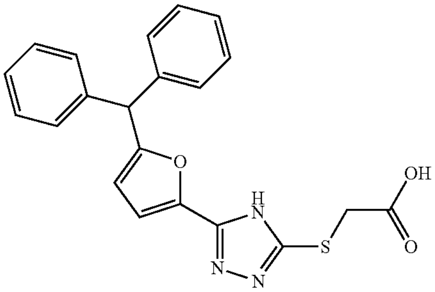 [SMILES: O=C(O)CSc1nnc(-c2ccc(C(c3ccccc3)c3ccccc3)o2)[nH]1] |
| 1-102 | 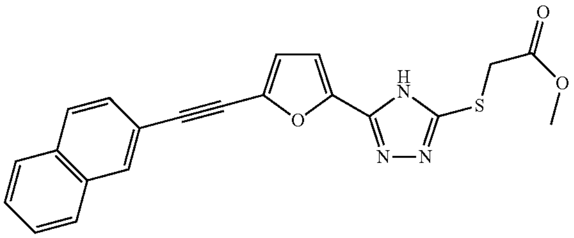 [SMILES: COC(=O)CSc1nnc(-c2ccc(C#Cc3ccc4ccccc4c3)o2)[nH]1] |

TABLE 1-continued
| # | Compound Structure |
| --- | --- |
| 1-103 | 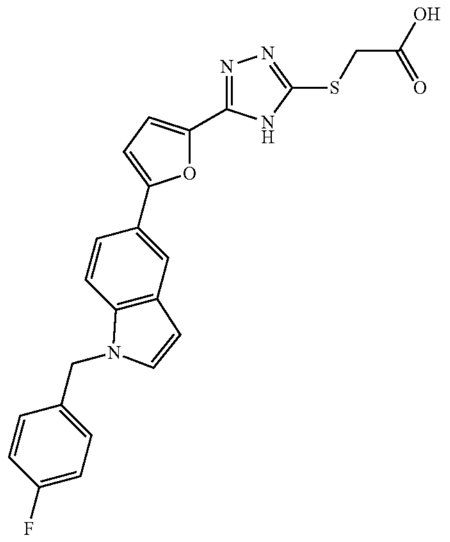 [SMILES: O=C(O)CSc1nnc(-c2ccc(-c3ccc4c(ccn4Cc4ccc(F)cc4)c3)o2)[nH]1] |
| 1-104 | 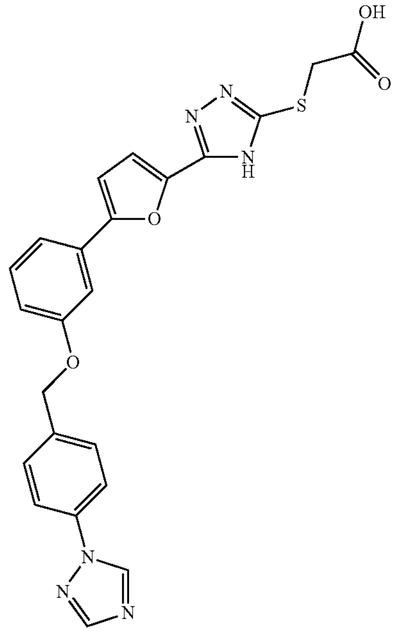 [SMILES: O=C(O)CSc1nnc(-c2ccc(-c3cccc(OCc4ccc(-n5cncn5)cc4)c3)o2)[nH]1] |
| 1-105 | 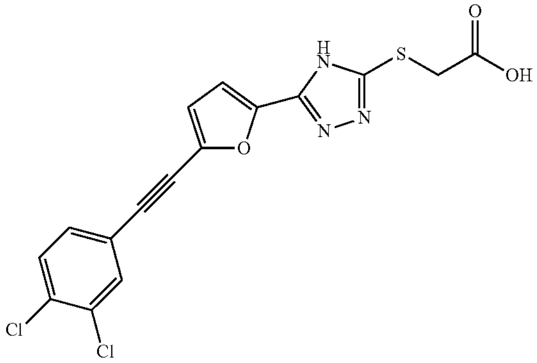 [SMILES: O=C(O)CSc1nnc(-c2ccc(C#Cc3ccc(Cl)c(Cl)c3)o2)[nH]1] |

TABLE 1-continued

| # | Compound Structure |
| --- | --- |
| 1-106 | 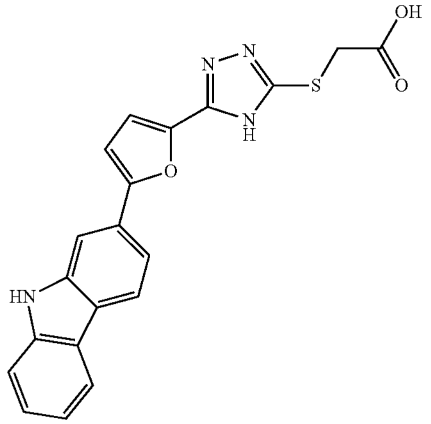 [SMILES: O=C(O)CSc1nnc(-c2ccc(-c3ccc4c(c3)[nH]c3ccccc34)o2)[nH]1] |

Also provided herein are compounds of Formula II:

Formula II

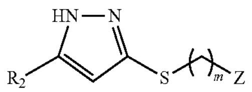

or a pharmaceutically acceptable salt thereof,
wherein:

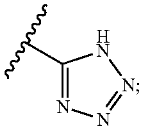 [SMILES: *c1nnn[nH]1]

Z is selected from the group consisting of —C(O)OR$^1$ and

R$^1$ is selected from the group consisting of H and ($C_1$-$C_6$) alkyl;

R$^2$ is a substituted or unsubstituted aryl, a substituted or unsubstituted heteroaryl; and m is an integer from 1 to 2.

In some embodiments, R$^2$ is a substituted or unsubstituted furanyl, or a substituted or unsubstituted thiopheneyl.

In some embodiments, a compound of Formula II includes a compound of Formula IIA:

Formula IIA

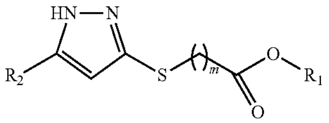

or a pharmaceutically acceptable salt thereof,
wherein:

R$^1$ is selected from the group consisting of H and ($C_1$-$C_6$) alkyl;

R$^2$ is a substituted or unsubstituted aryl, a substituted or unsubstituted heteroaryl; and m is an integer from 1 to 2.

In some embodiments, R$^1$ is H; and R$^2$ is a substituted or unsubstituted heteroaryl. In some embodiments, R$^2$ is a substituted or unsubstituted furanyl, or a substituted or unsubstituted thiopheneyl. In some embodiments, R$^1$ is H; and R$^2$ is a substituted or unsubstituted aryl. For example, R$^2$ can be a substituted or unsubstituted phenyl.

Non-limiting examples of a compound of Formula II or IIA include the compounds in Table 2, or a pharmaceutically acceptable salt thereof.

TABLE 2

| # | Compound Structure |
| --- | --- |
| 2-1 | 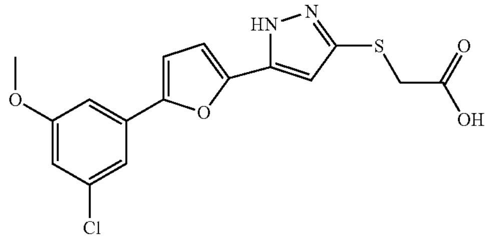 [SMILES: COc1cc(Cl)cc(-c2ccc(-c3cc(SCC(=O)O)n[nH]3)o2)c1] |
| 2-2 | 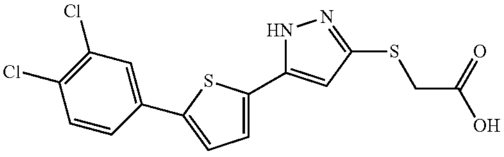 [SMILES: O=C(O)CSc1cc(-c2ccc(-c3ccc(Cl)c(Cl)c3)s2)[nH]n1] |

TABLE 2-continued
| # | Compound Structure |
|---|---|
| 2-3 | 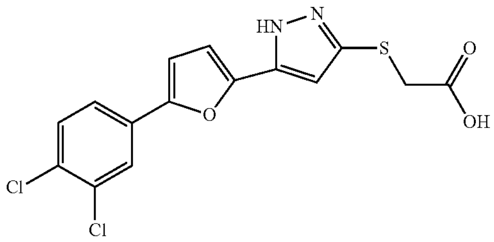 [SMILES: O=C(O)CSc1cc(-c2ccc(-c3ccc(Cl)c(Cl)c3)o2)[nH]n1] |
| 2-4 | 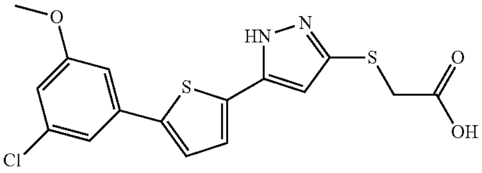 [SMILES: COc1cc(Cl)cc(-c2ccc(-c3cc(SCC(=O)O)n[nH]3)s2)c1] |
| 2-5 | 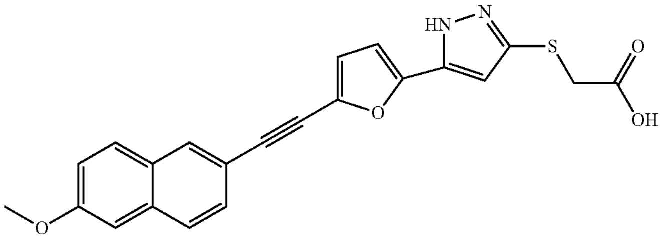 [SMILES: COc1ccc2cc(C#Cc3ccc(-c4cc(SCC(=O)O)n[nH]4)o3)ccc2c1] |
| 2-6 | 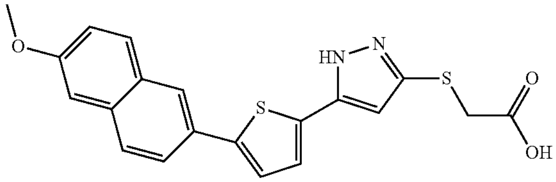 [SMILES: COc1ccc2cc(-c3ccc(-c4cc(SCC(=O)O)n[nH]4)s3)ccc2c1] |
| 2-7 | 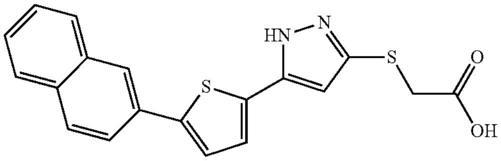 [SMILES: O=C(O)CSc1cc(-c2ccc(-c3ccc4ccccc4c3)s2)[nH]n1] |
| 2-8 | 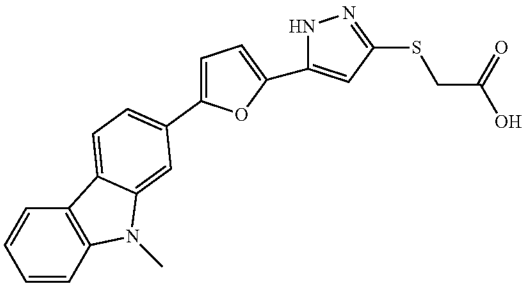 [SMILES: Cn1c2ccccc2c2ccc(-c3ccc(-c4cc(SCC(=O)O)n[nH]4)o3)cc21] |

TABLE 2-continued

| # | Compound Structure |
|---|---|
| 2-9 | 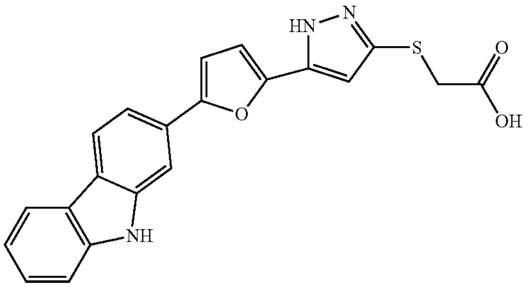 [SMILES: O=C(O)CSc1cc(-c2ccc(-c3ccc4c(c3)[nH]c3ccccc34)o2)[nH]n1] |
| 2-10 | 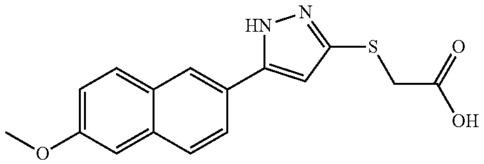 [SMILES: COc1ccc2cc(-c3cc(SCC(=O)O)n[nH]3)ccc2c1] |
| 2-11 | 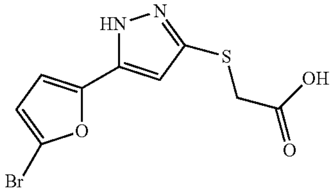 [SMILES: O=C(O)CSc1cc(-c2ccc(Br)o2)[nH]n1] |
| 2-12 | 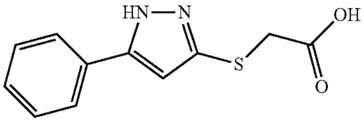 [SMILES: O=C(O)CSc1cc(-c2ccccc2)[nH]n1] |

This disclosure also provides a compound of Formula III:

Formula III

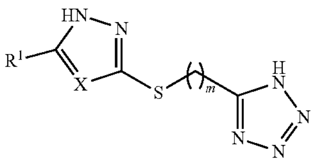

or a pharmaceutically acceptable salt thereof, wherein:

X is selected from the group consisting of CH and N;

$R^1$ is a substituted or unsubstituted aryl or a substituted or unsubstituted heteroaryl; and m is an integer from 1 to 2.

In some embodiments, m is 1.

In some embodiments, $R^1$ is a substituted or unsubstituted aryl. For example, $R^1$ can be:

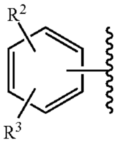

wherein:

each of $R^2$ and $R^3$ are independently selected from the group consisting of: H, halo, $(C_1-C_6)$alkyl, $(C_1-C_6)$haloalkyl, $OR^4$, $NO_2$, $NR^4R^5$, CN, a substituted or unsubstituted aryl, and a substituted or unsubstituted heteroaryl; and each of $R^4$ and $R^5$ are independently selected from the group consisting of H, $(C_1-C_6)$alkyl, and $(C_1-C_6)$haloalkyl.

In some such embodiments, $R^2$ is H or $NO_2$; and $R^3$ is $(C_1-C_6)$alkyl or a substituted or unsubstituted phenyl. For example, $R^2$ can be H; and $R^3$ can be $(C_1-C_6)$alkyl. In some embodiments, $R^3$ is methyl. In other such embodiments, $R^2$ is $NO_2$; and $R^3$ is a substituted or unsubstituted phenyl. For example, $R^1$ can be:

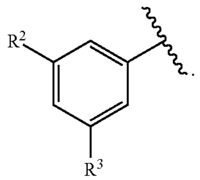

In some such embodiments, $R^2$ is $NO_2$; and $R^3$ is:

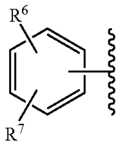

wherein:

each of $R^6$ and $R^7$ are independently selected from a group consisting of: H, halo, $(C_1\text{-}C_6)$alkyl, $(C_1\text{-}C_6)$haloalkyl, $OR^{4a}$, $NO_2$, $NR^{4a}R^{5a}$, CN, a substituted or unsubstituted aryl, and a substituted or unsubstituted heteroaryl; and each of $R^{4a}$ and $R^{5a}$ are independently selected from the group consisting of H, $(C_1\text{-}C_6)$alkyl, and $(C_1\text{-}C_6)$haloalkyl.

For example, $R^3$ can be:

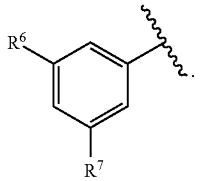

In some embodiments, $R^6$ is halo; and $R^7$ is $OR^c$; wherein $R^c$ is selected from a group consisting of H, $(C_1\text{-}C_6)$alkyl, and $(C_1\text{-}C_6)$haloalkyl.

In some embodiments, $R^1$ is selected from the group consisting of:

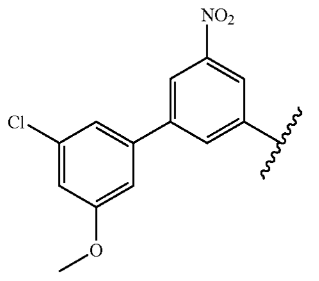

and

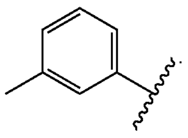

In some embodiments, $R^1$ is a substituted or unsubstituted heteroaryl. For example, $R^1$ can be:

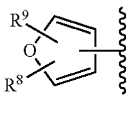

wherein:

each of $R^8$ and $R^9$ are independently selected from a group consisting of: H, halo, $(C_1\text{-}C_6)$alkyl, $(C_1\text{-}C_6)$haloalkyl, $OR^{4b}$, $NO_2$, $NR^{4b}R^{5b}$, CN, a substituted or unsubstituted aryl, and a substituted or unsubstituted heteroaryl; and each of $R^{4b}$ and $R^{5b}$ are independently selected from the group consisting of H, $(C_1\text{-}C_6)$alkyl, and $(C_1\text{-}C_6)$haloalkyl.

In some such embodiments, $R^1$ is:

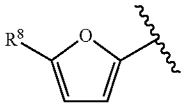

For example, $R^8$ can be a substituted or unsubstituted aryl. In some embodiments, $R^8$ is:

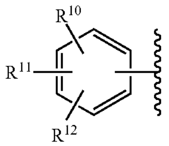

wherein:

each of $R^{10}$, $R^{11}$, and $R^{12}$ are independently selected from a group consisting of: H, halo, $(C_1\text{-}C_6)$alkyl, $(C_1\text{-}C_6)$haloalkyl, CN, $NO_2$, $OR^{13}$, $NR^{14}R^{15}$, $C(O)R^{16}$, $C(O)OR^{16}$, $—NR^{17}S(O)_2R^{18}$, $—S(O)_2NR^{19}R^{20}$, $—NR^{17}S(O)R^{18}$, $—S(O)_2NR^{19}R^{20}$, $—S(O)NR^{19}R^{20}$, $—NR^{21}C(O)R^{22}$, a substituted or unsubstituted aryl, a substituted or unsubstituted heteroaryl, and a substituted or unsubstituted heterocycloalkyl; or two of the groups $R^{10}$, $R^{11}$, and $R^{12}$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and each of $R^{13}$, $R^{14}$, $R^{15}$, $R^{16}$, $R^{17}$, $R^{18}$, $R^{19}$, $R^{20}$, $R^{21}$, and $R^{22}$ are independently selected from a group consisting of H, $(C_1\text{-}C_6)$alkyl, and $(C_1\text{-}C_6)$haloalkyl.

In some embodiments, $R^8$ is a substituted or unsubstituted heteroaryl. For example, $R^8$ can be selected from a group consisting of a substituted or unsubstituted quinolinyl, a substituted or unsubstituted indolyl, and a substituted or unsubstituted pyridyl. In some embodiments, $R^8$ is a substituted or unsubstituted quinolinyl. In some embodiments, $R^8$ is a substituted or unsubstituted indolyl. In some embodiments, $R^8$ is a substituted or unsubstituted pyridyl.

In some embodiments, $R^1$ is selected from the group consisting of:

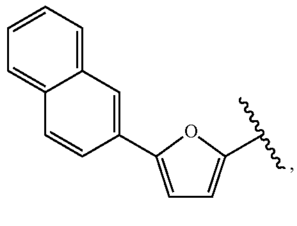

,

-continued
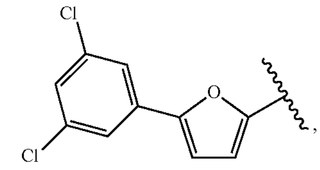
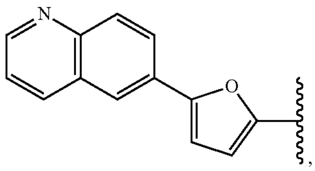
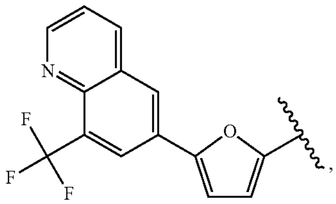
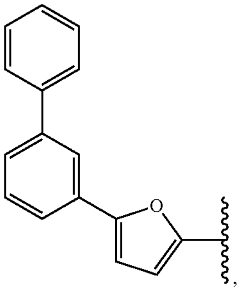
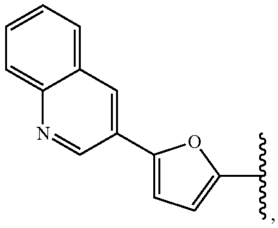
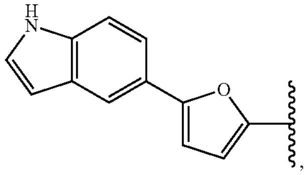
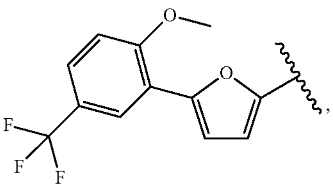
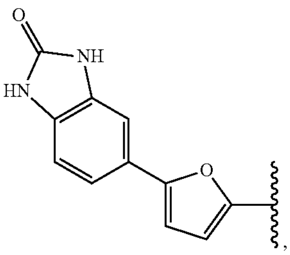
-continued
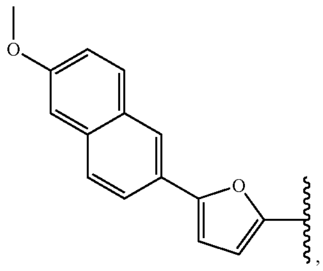
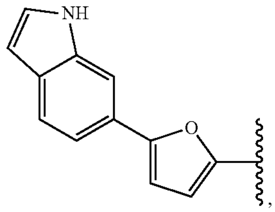
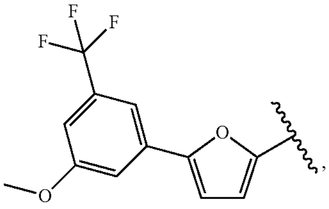
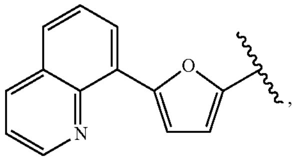
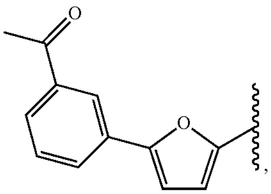
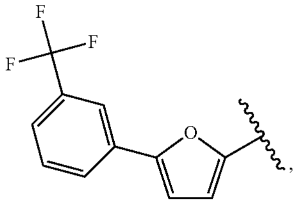
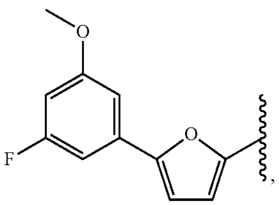
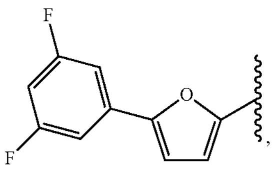

-continued

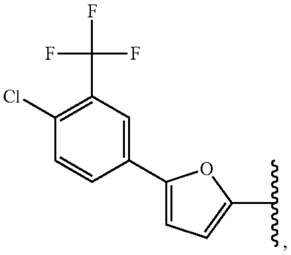

,

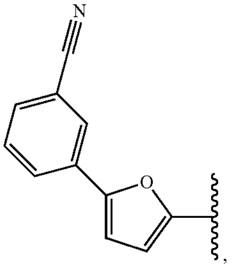

,

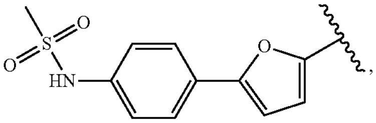

,

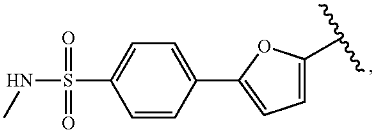

,

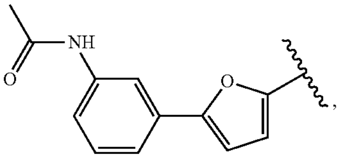

,

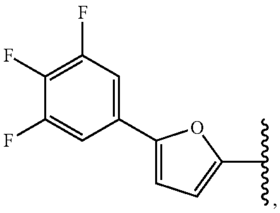

,

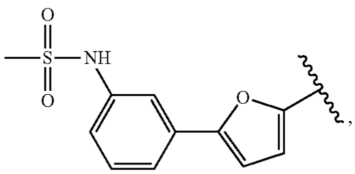

,

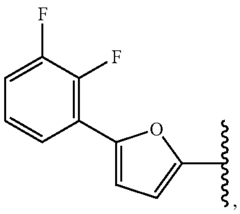

,

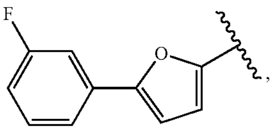

,

-continued

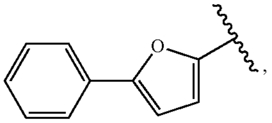

,

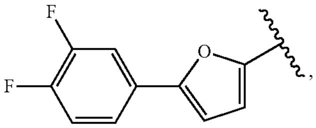

,

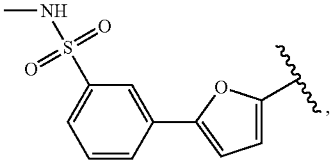

,

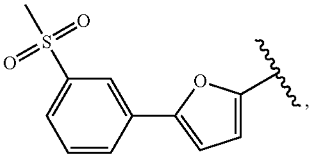

,

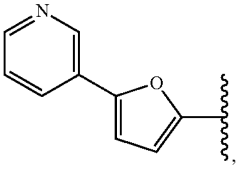

,

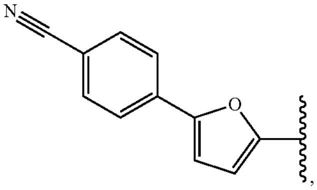

,

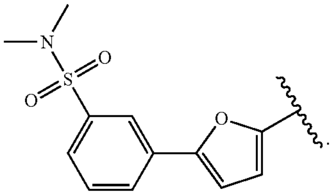

.

In some embodiments, a compound of Formula III is a compound of Formula IIIA:

Formula IIIA

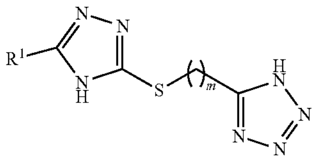

or a pharmaceutically acceptable salt thereof, wherein:

$R^1$ is a substituted or unsubstituted aryl or a substituted or unsubstituted heteroaryl; and m is an integer from 1 to 2.

In some embodiments, m is 1.

In some embodiments, $R^1$ is a substituted or unsubstituted aryl. For example, $R^1$ can be:

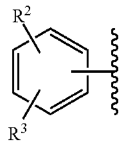

wherein:

each of $R^2$ and $R^3$ are independently selected from the group consisting of: H, halo, $(C_1\text{-}C_6)$alkyl, $(C_1\text{-}C_6)$haloalkyl, $OR^4$, $NO_2$, $NR^4R^5$, CN, a substituted or unsubstituted aryl, and a substituted or unsubstituted heteroaryl; and each of $R^4$ and $R^5$ are independently selected from the group consisting of H, $(C_1\text{-}C_6)$alkyl, and $(C_1\text{-}C_6)$haloalkyl.

In some such embodiments, $R^2$ is H or $NO_2$; and $R^3$ is $(C_1\text{-}C_6)$alkyl or a substituted or unsubstituted phenyl. For example, $R^2$ can be H; and $R^3$ can be $(C_1\text{-}C_6)$alkyl. In some embodiments, $R^3$ is methyl. In other such embodiments, $R^2$ is $NO_2$; and $R^3$ is a substituted or unsubstituted phenyl. For example, $R^1$ can be:

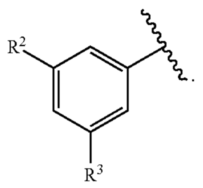

In some such embodiments, $R^2$ is $NO_2$; and $R^3$ is:

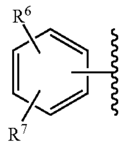

wherein:

each of $R^6$ and $R^7$ are independently selected from a group consisting of: H, halo, $(C_1\text{-}C_6)$alkyl, $(C_1\text{-}C_6)$haloalkyl, $OR^{4a}$, $NO_2$, $NR^{4a}R^{5a}$, CN, a substituted or unsubstituted aryl, and a substituted or unsubstituted heteroaryl; and each of $R^{4a}$ and $R^{5a}$ are independently selected from the group consisting of H, $(C_1\text{-}C_6)$alkyl, and $(C_1\text{-}C_6)$haloalkyl.

For example, $R^3$ can be:

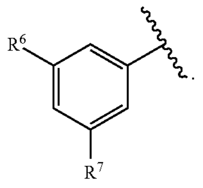

In some embodiments, $R^6$ is halo; and $R^7$ is $OR^c$; wherein $R^c$ is selected from a group consisting of H, $(C_1\text{-}C_6)$alkyl, and $(C_1\text{-}C_6)$haloalkyl.

In some embodiments, $R^1$ is selected from the group consisting of:

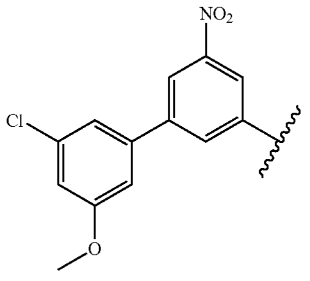

and

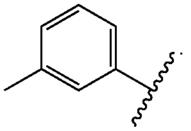

In some embodiments, $R^1$ is a substituted or unsubstituted heteroaryl. For example, $R^1$ can be:

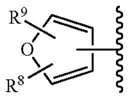

wherein:

each of $R^8$ and $R^9$ are independently selected from a group consisting of: H, halo, $(C_1\text{-}C_6)$alkyl, $(C_1\text{-}C_6)$haloalkyl, $OR^{4b}$, $NO_2$, $NR^{4b}R^{5b}$, CN, a substituted or unsubstituted aryl, and a substituted or unsubstituted heteroaryl; and each of $R^{4b}$ and $R^{5b}$ are independently selected from the group consisting of H, $(C_1\text{-}C_6)$alkyl, and $(C_1\text{-}C_6)$haloalkyl.

In some such embodiments, $R^1$ is:

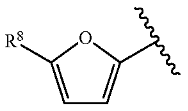

For example, $R^8$ can be a substituted or unsubstituted aryl. In some embodiments, $R^8$ is:

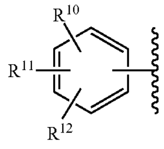

wherein:

each of $R^{10}$, $R^{11}$, and $R^{12}$ are independently selected from a group consisting of: H, halo, $(C_1\text{-}C_6)$alkyl, $(C_1\text{-}C_6)$haloalkyl, CN, $NO_2$, $OR^{13}$, $NR^{14}R^{15}$, $C(O)R^{16}$, $C(O)OR^{16}$, $—NR^{17}S(O)_2R^{18}$, $—S(O)_2NR^{19}R^{20}$, $—NR^{17}S(O)R^{18}$, $—S(O)_2NR^{19}R^{20}$, $—S(O)NR^{19}R^{20}$, $—NR^{21}C(O)R^{22}$, a substituted or unsubstituted aryl, a substituted or unsubstituted heteroaryl, and a substituted or unsubstituted heterocycloalkyl; or two of the groups $R^{10}$, $R^{11}$, and $R^{12}$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and each of $R^{13}$, $R^{14}$, $R^{15}$, $R^{16}$, $R^{17}$, $R^{18}$, $R^{19}$, $R^{20}$, $R^{21}$, and $R^{22}$ are independently selected from a group consisting of H, $(C_1\text{-}C_6)$alkyl, and $(C_1\text{-}C_6)$haloalkyl.

In some embodiments, $R^8$ is a substituted or unsubstituted heteroaryl. For example, $R^8$ can be selected from a group consisting of a substituted or unsubstituted quinolinyl, a substituted or unsubstituted indolyl, and a substituted or unsubstituted pyridyl. In some embodiments, $R^8$ is a substituted or unsubstituted quinolinyl. In some embodiments, $R^8$ is a substituted or unsubstituted indolyl. In some embodiments, $R^8$ is a substituted or unsubstituted pyridyl.

In some embodiments, $R^1$ is selected from the group consisting of:

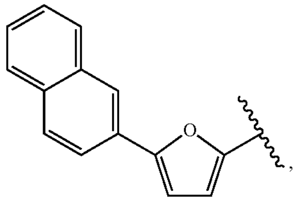,

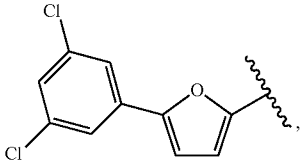,

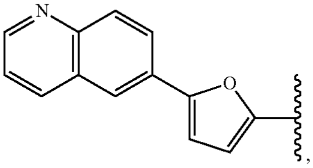,

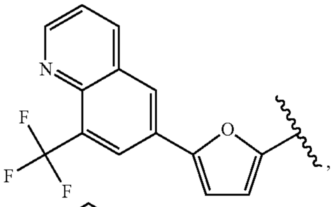,

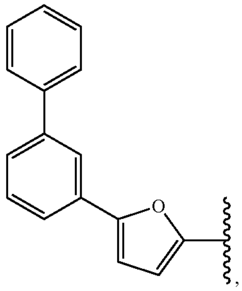,

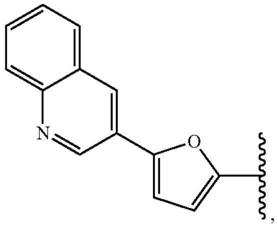,

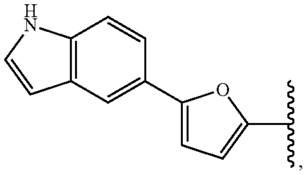,

-continued

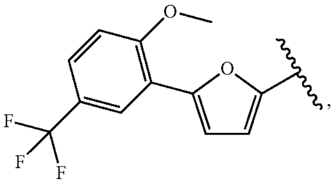,

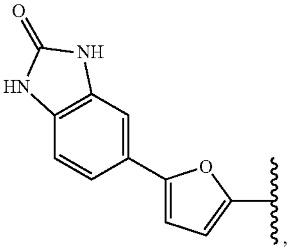,

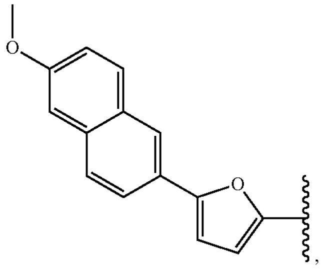,

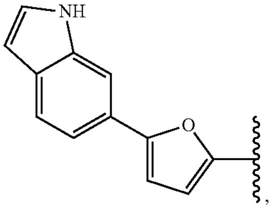,

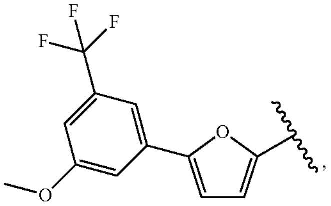,

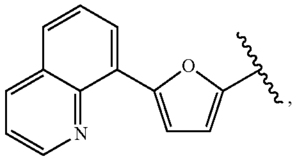,

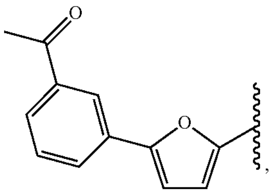,

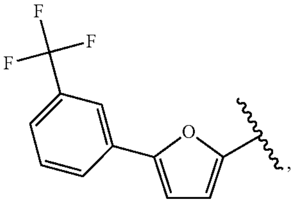,

-continued
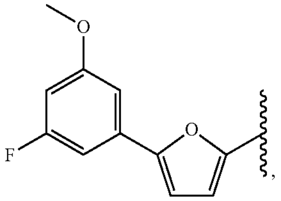,
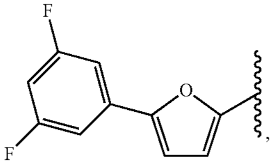,
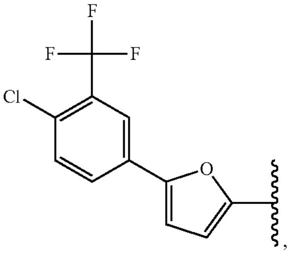,
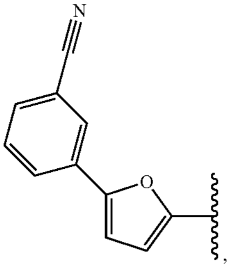,
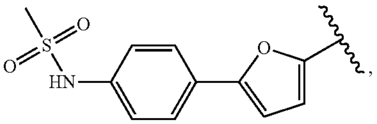,
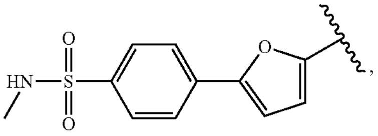,
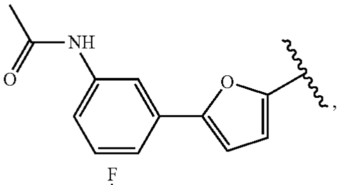,
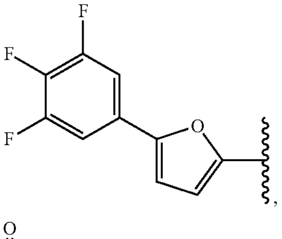,
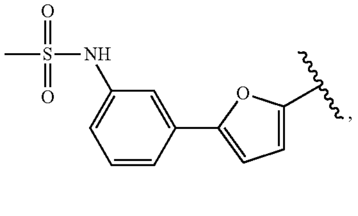,
-continued
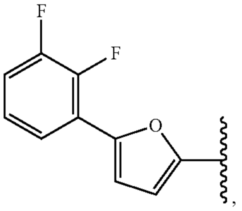,
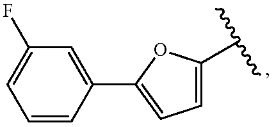,
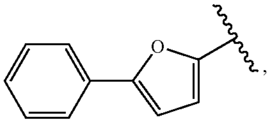,
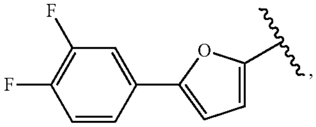,
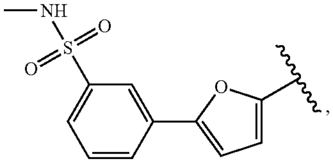,
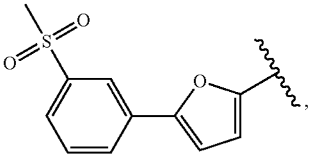,
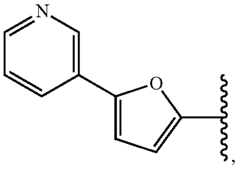,
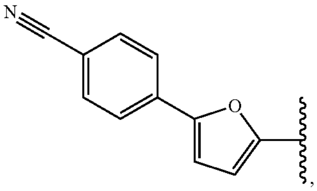,
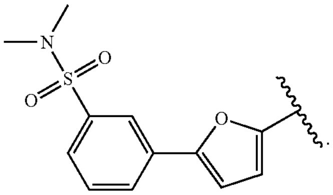.
Non-limiting examples of a compound of Formula III and/or IIIA include the compounds in Table 3, or a pharmaceutically acceptable salt thereof.

TABLE 3
| # | Compound Structure |
|---|---|
| 3-1 | 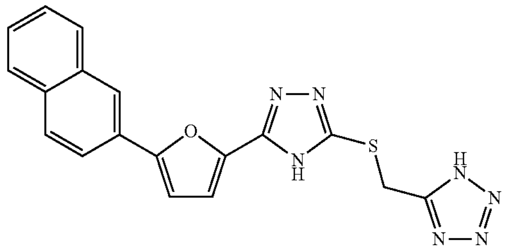 [SMILES: c1ccc2cc(-c3ccc(-c4nnc(SCc5nnn[nH]5)[nH]4)o3)ccc2c1] |
| 3-2 | 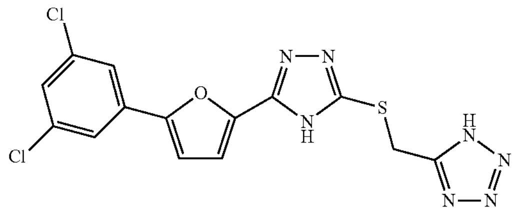 [SMILES: Clc1cc(Cl)cc(-c2ccc(-c3nnc(SCc4nnn[nH]4)[nH]3)o2)c1] |
| 3-3 | 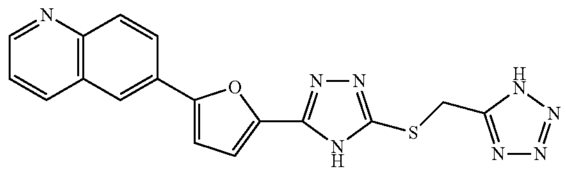 [SMILES: c1cnc2ccc(-c3ccc(-c4nnc(SCc5nnn[nH]5)[nH]4)o3)cc2c1] |
| 3-4 | 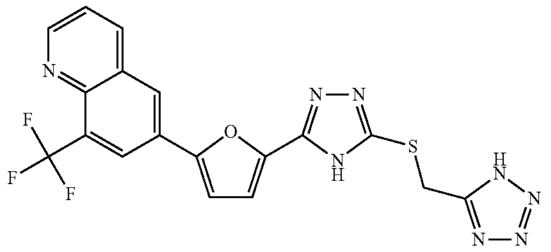 [SMILES: FC(F)(F)c1cc(-c2ccc(-c3nnc(SCc4nnn[nH]4)[nH]3)o2)cc2cccnc12] |
| 3-5 | 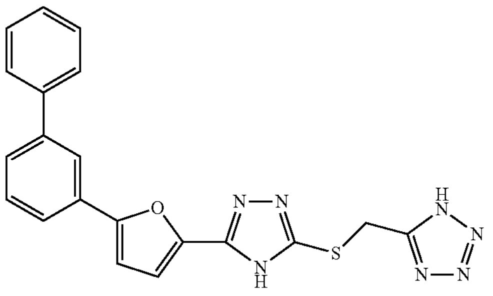 [SMILES: c1ccc(-c2cccc(-c3ccc(-c4nnc(SCc5nnn[nH]5)[nH]4)o3)c2)cc1] |
| 3-6 | 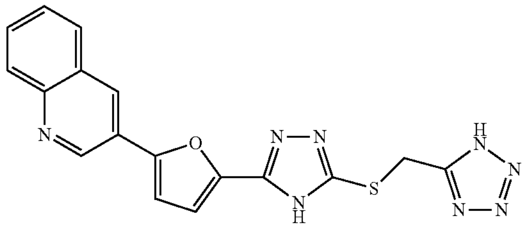 [SMILES: c1ccc2ncc(-c3ccc(-c4nnc(SCc5nnn[nH]5)[nH]4)o3)cc2c1] |

TABLE 3-continued
| # | Compound Structure |
|---|---|
| 3-7 | 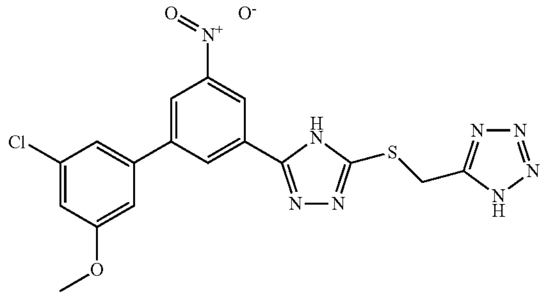 |
| 3-8 | 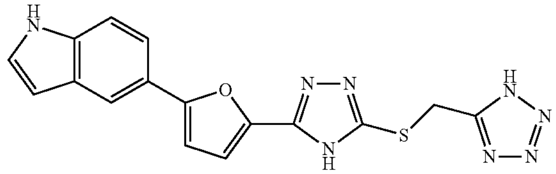 [SMILES: c1cc2cc(-c3ccc(-c4nnc(SCc5nnn[nH]5)[nH]4)o3)ccc2[nH]1] |
| 3-9 | 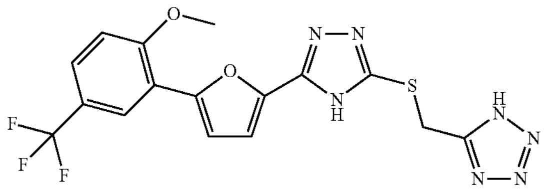 [SMILES: COc1ccc(C(F)(F)F)cc1-c1ccc(-c2nnc(SCc3nnn[nH]3)[nH]2)o1] |
| 3-10 | 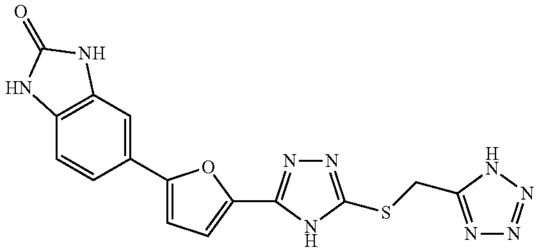 [SMILES: O=c1[nH]c2ccc(-c3ccc(-c4nnc(SCc5nnn[nH]5)[nH]4)o3)cc2[nH]1] |
| 3-11 | 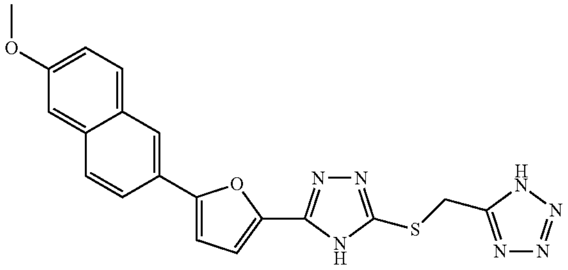 [SMILES: COc1ccc2cc(-c3ccc(-c4nnc(SCc5nnn[nH]5)[nH]4)o3)ccc2c1] |
| 3-12 | 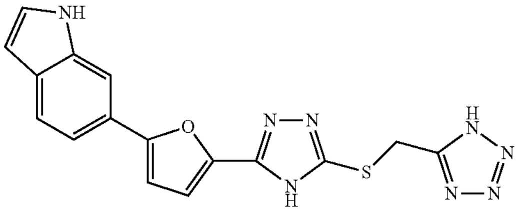 [SMILES: c1cc2ccc(-c3ccc(-c4nnc(SCc5nnn[nH]5)[nH]4)o3)cc2[nH]1] |

TABLE 3-continued
| # | Compound Structure |
| --- | --- |
| 3-13 | 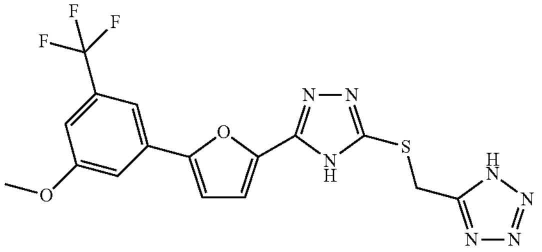 [SMILES: COc1cc(-c2ccc(-c3nnc(SCc4nnn[nH]4)[nH]3)o2)cc(C(F)(F)F)c1] |
| 3-14 | 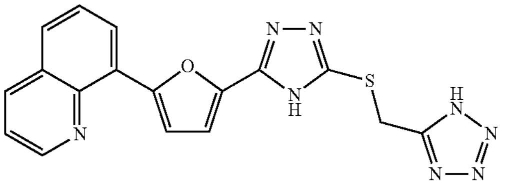 [SMILES: c1cnc2c(-c3ccc(-c4nnc(SCc5nnn[nH]5)[nH]4)o3)cccc2c1] |
| 3-15 | 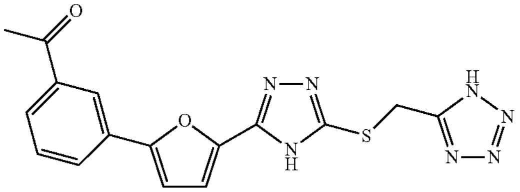 [SMILES: CC(=O)c1cccc(-c2ccc(-c3nnc(SCc4nnn[nH]4)[nH]3)o2)c1] |
| 3-16 | 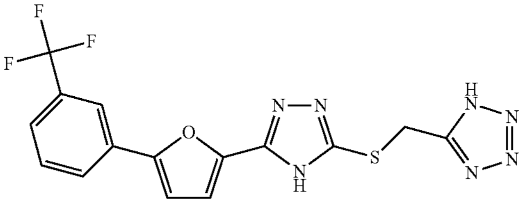 [SMILES: FC(F)(F)c1cccc(-c2ccc(-c3nnc(SCc4nnn[nH]4)[nH]3)o2)c1] |
| 3-17 | 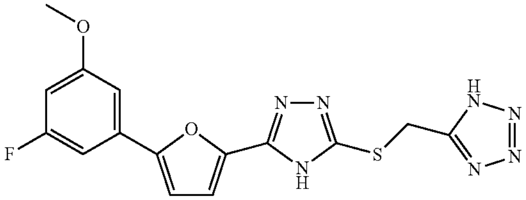 [SMILES: COc1cc(F)cc(-c2ccc(-c3nnc(SCc4nnn[nH]4)[nH]3)o2)c1] |
| 3-18 | 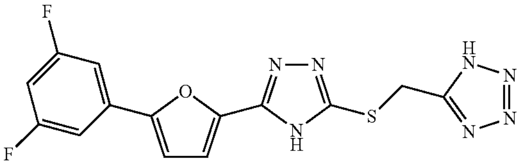 [SMILES: Fc1cc(F)cc(-c2ccc(-c3nnc(SCc4nnn[nH]4)[nH]3)o2)c1] |
| 3-19 | 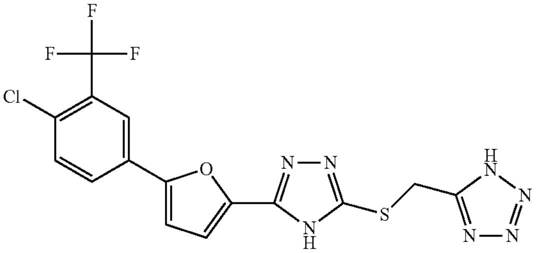 [SMILES: FC(F)(F)c1cc(-c2ccc(-c3nnc(SCc4nnn[nH]4)[nH]3)o2)ccc1Cl] |

TABLE 3-continued
| # | Compound Structure |
|---|---|
| 3-20 | 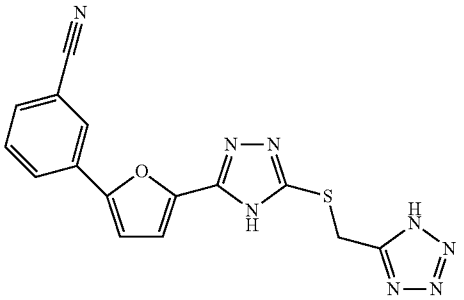 [SMILES: N#Cc1cccc(-c2ccc(-c3nnc(SCc4nnn[nH]4)[nH]3)o2)c1] |
| 3-21 | 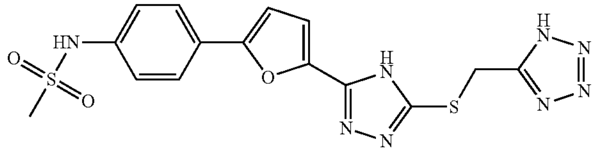 [SMILES: CS(=O)(=O)Nc1ccc(-c2ccc(-c3nnc(SCc4nnn[nH]4)[nH]3)o2)cc1] |
| 3-22 | 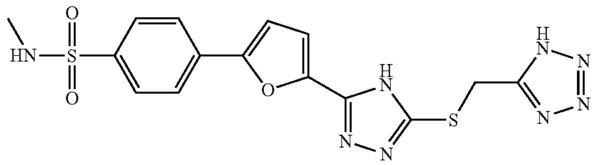 [SMILES: CNS(=O)(=O)c1ccc(-c2ccc(-c3nnc(SCc4nnn[nH]4)[nH]3)o2)cc1] |
| 3-23 | 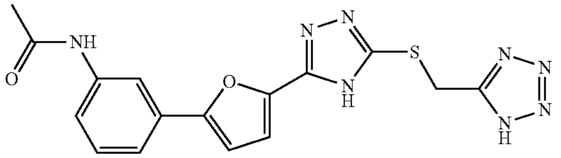 [SMILES: CC(=O)Nc1cccc(-c2ccc(-c3nnc(SCc4nnn[nH]4)[nH]3)o2)c1] |
| 3-24 | 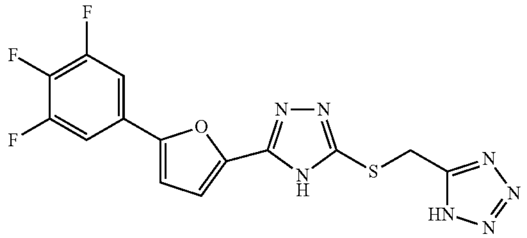 [SMILES: Fc1cc(-c2ccc(-c3nnc(SCc4nnn[nH]4)[nH]3)o2)cc(F)c1F] |
| 3-25 | 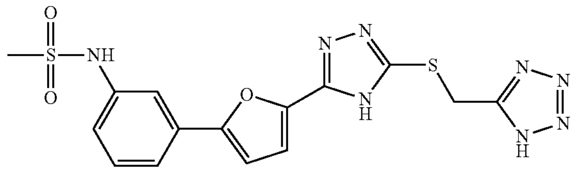 [SMILES: CS(=O)(=O)Nc1cccc(-c2ccc(-c3nnc(SCc4nnn[nH]4)[nH]3)o2)c1] |
| 3-26 | 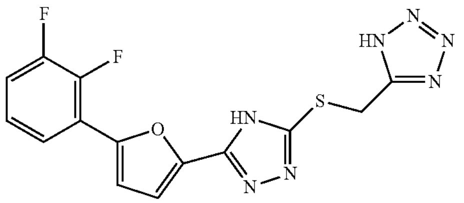 [SMILES: Fc1cccc(-c2ccc(-c3nnc(SCc4nnn[nH]4)[nH]3)o2)c1F] |
| 3-27 | 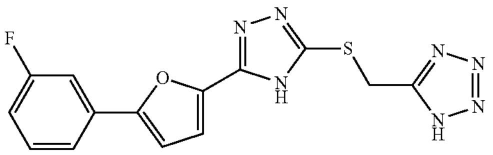 [SMILES: Fc1cccc(-c2ccc(-c3nnc(SCc4nnn[nH]4)[nH]3)o2)c1] |

TABLE 3-continued
| # | Compound Structure |
|---|---|
| 3-28 | 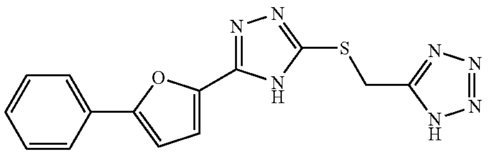 [SMILES: c1ccc(-c2ccc(-c3nnc(SCc4nnn[nH]4)[nH]3)o2)cc1] |
| 3-29 | 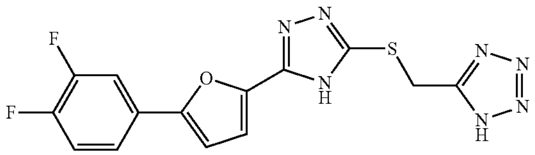 [SMILES: Fc1ccc(-c2ccc(-c3nnc(SCc4nnn[nH]4)[nH]3)o2)cc1F] |
| 3-30 | 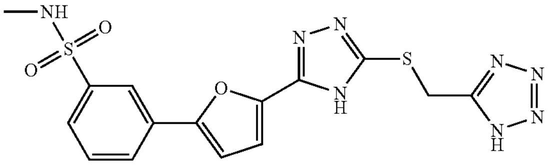 [SMILES: CNS(=O)(=O)c1cccc(-c2ccc(-c3nnc(SCc4nnn[nH]4)[nH]3)o2)c1] |
| 3-31 | 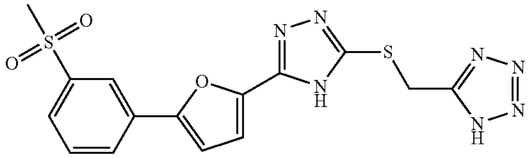 [SMILES: CS(=O)(=O)c1cccc(-c2ccc(-c3nnc(SCc4nnn[nH]4)[nH]3)o2)c1] |
| 3-32 | 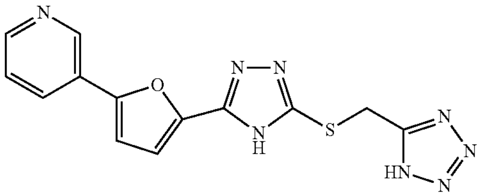 [SMILES: c1cncc(-c2ccc(-c3nnc(SCc4nnn[nH]4)[nH]3)o2)c1] |
| 3-33 | 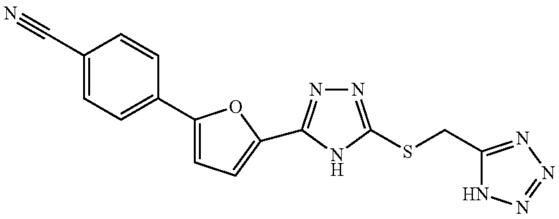 [SMILES: N#Cc1ccc(-c2ccc(-c3nnc(SCc4nnn[nH]4)[nH]3)o2)cc1] |
| 3-34 | 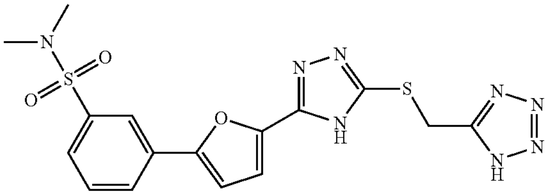 [SMILES: CN(C)S(=O)(=O)c1cccc(-c2ccc(-c3nnc(SCc4nnn[nH]4)[nH]3)o2)c1] |
| 3-35 | 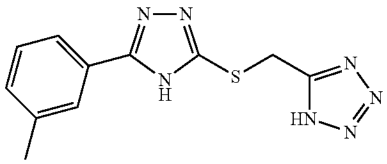 [SMILES: Cc1cccc(-c2nnc(SCc3nnn[nH]3)[nH]2)c1] |

TABLE 3-continued

| # | Compound Structure |
|---|---|
| 3-36 | 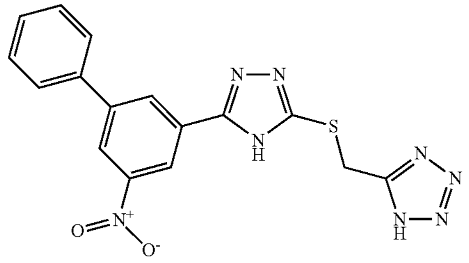 [SMILES: O=[N+]([O-])c1cc(-c2ccccc2)cc(-c2nnc(SCc3nnn[nH]3)[nH]2)c1] |

Also provided herein is a compound of Formula IV:

Formula IV

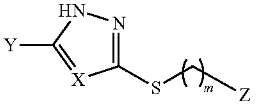

or a pharmaceutically acceptable salt thereof, wherein:

X is selected from the group consisting of CH and N;

Y is a substituted or unsubstituted heteroaryl;

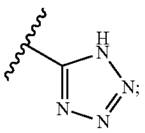 [SMILES: *c1nnn[nH]1]

Z is selected from the group consisting of —C(O)$OR^1$ and $R^1$ is selected from the group consisting of H and ($C_1$-$C_6$) alkyl; and m is an integer from 1 to 2.

In some embodiments, m is 1.

In some embodiments, a compound of Formula IV is a compound of Formula IVA:

Formula IVA

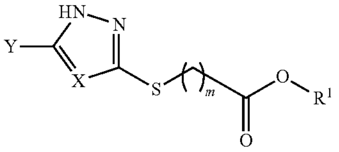

or a pharmaceutically acceptable salt thereof, wherein:

X is selected from the group consisting of CH and N;

Y is a substituted or unsubstituted heteroaryl;

$R^1$ is selected from the group consisting of H and ($C_1$-$C_6$) alkyl; and m is an integer from 1 to 2.

Non-limiting examples of a compound of Formula IV and/or IVA include the compounds in Table 4, or a pharmaceutically acceptable salt thereof.

TABLE 4

| # | Compound Structure |
|---|---|
| 4-1 | 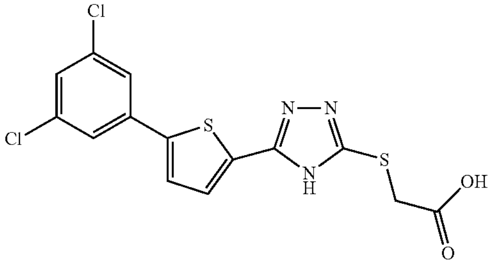 [SMILES: O=C(O)CSc1nnc(-c2ccc(-c3cc(Cl)cc(Cl)c3)s2)[nH]1] |
| 4-2 | 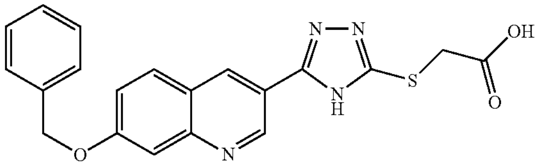 [SMILES: O=C(O)CSc1nnc(-c2cnc3cc(OCc4ccccc4)ccc3c2)[nH]1] |
| 4-3 | 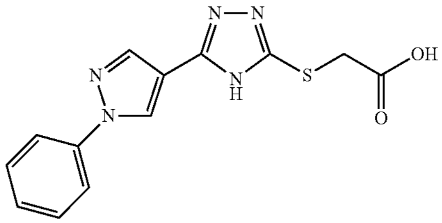 [SMILES: O=C(O)CSc1nnc(-c2cnn(-c3ccccc3)c2)[nH]1] |
| 4-4 | 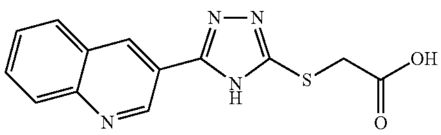 [SMILES: O=C(O)CSc1nnc(-c2cnc3ccccc3c2)[nH]1] |
| 4-5 | 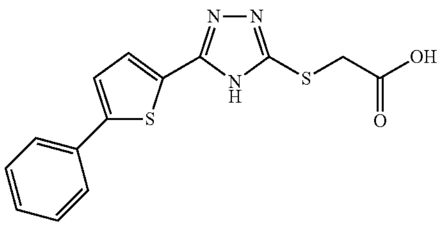 [SMILES: O=C(O)CSc1nnc(-c2ccc(-c3ccccc3)s2)[nH]1] |

TABLE 4-continued
| # | Compound Structure |
|---|---|
| 4-6 | 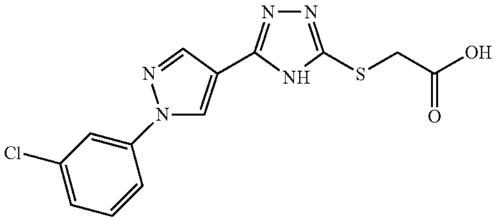 [SMILES: O=C(O)CSc1nnc(-c2cnn(-c3cccc(Cl)c3)c2)[nH]1] |
| 4-7 | 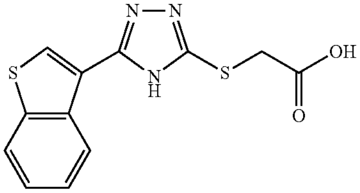 [SMILES: O=C(O)CSc1nnc(-c2csc3ccccc23)[nH]1] |
| 4-8 | 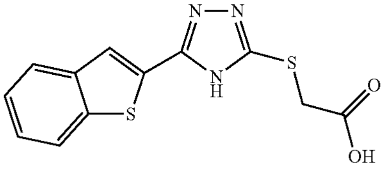 [SMILES: O=C(O)CSc1nnc(-c2cc3ccccc3s2)[nH]1] |
| 4-9 | 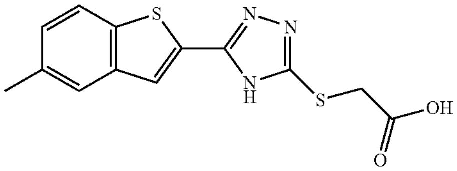 [SMILES: Cc1ccc2sc(-c3nnc(SCC(=O)O)[nH]3)cc2c1] |
| 4-10 | 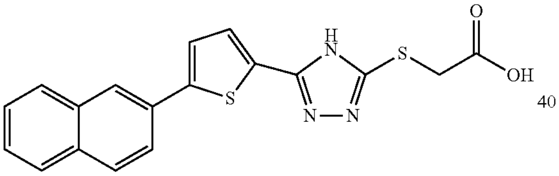 |
| 4-11 | 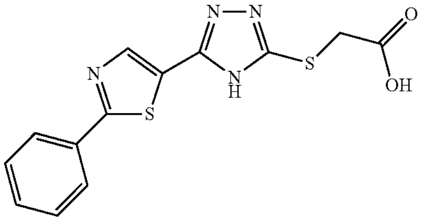 [SMILES: O=C(O)CSc1nnc(-c2cnc(-c3ccccc3)s2)[nH]1] |
| 4-12 | 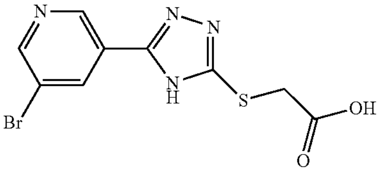 [SMILES: O=C(O)CSc1nnc(-c2cncc(Br)c2)[nH]1] |
| 4-13 | 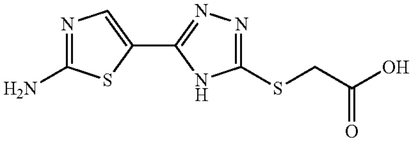 [SMILES: Nc1ncc(-c2nnc(SCC(=O)O)[nH]2)s1] |
| 4-14 | 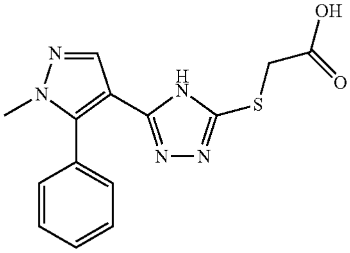 [SMILES: Cn1ncc(-c2nnc(SCC(=O)O)[nH]2)c1-c1ccccc1] |
| 4-15 | 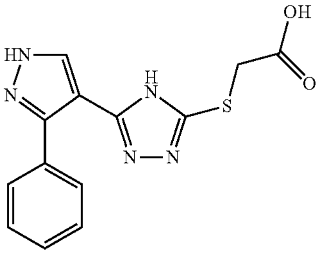 [SMILES: O=C(O)CSc1nnc(-c2c[nH]nc2-c2ccccc2)[nH]1] |
| 4-16 | 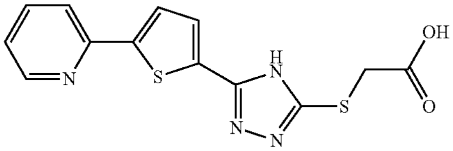 [SMILES: O=C(O)CSc1nnc(-c2ccc(-c3ccccn3)s2)[nH]1] |
| 4-17 | 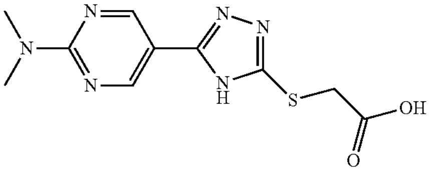 [SMILES: CN(C)c1ncc(-c2nnc(SCC(=O)O)[nH]2)cn1] |
| 4-18 | 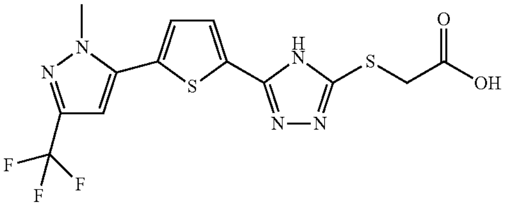 [SMILES: Cn1nc(C(F)(F)F)cc1-c1ccc(-c2nnc(SCC(=O)O)[nH]2)s1] |
| 4-19 | 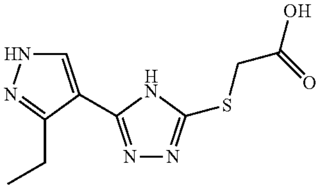 [SMILES: CCc1n[nH]cc1-c1nnc(SCC(=O)O)[nH]1] |
| 4-20 | 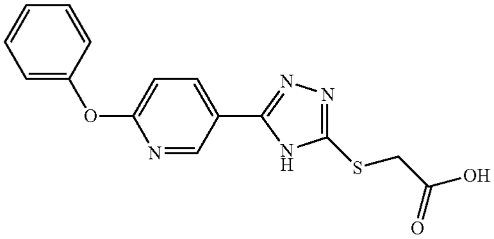 [SMILES: O=C(O)CSc1nnc(-c2ccc(Oc3ccccc3)nc2)[nH]1] |

TABLE 4-continued
| # | Compound Structure |
| --- | --- |
| 4-21 | 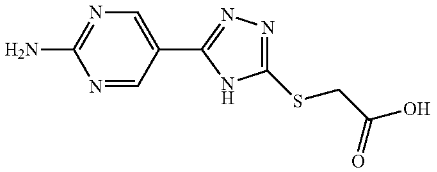 [SMILES: Nc1ncc(-c2nnc(SCC(=O)O)[nH]2)cn1] |
| 4-22 | 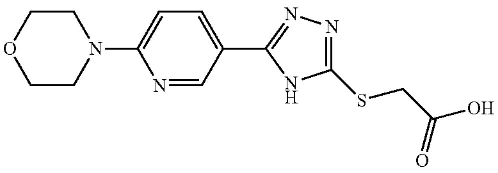 [SMILES: O=C(O)CSc1nnc(-c2ccc(N3CCOCC3)nc2)[nH]1] |
| 4-23 | 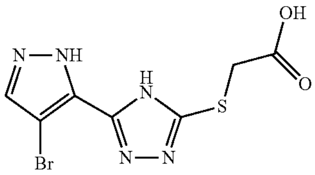 [SMILES: O=C(O)CSc1nnc(-c2[nH]ncc2Br)[nH]1] |
| 4-24 | 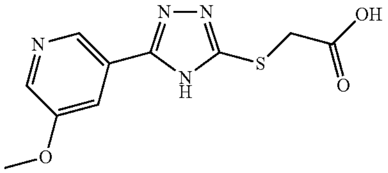 [SMILES: COc1cncc(-c2nnc(SCC(=O)O)[nH]2)c1] |
| 4-25 | 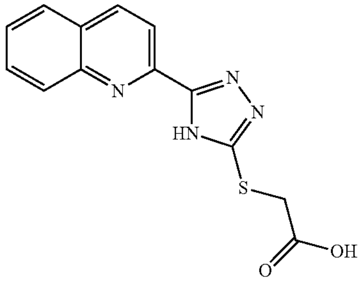 [SMILES: O=C(O)CSc1nnc(-c2ccc3ccccc3n2)[nH]1] |
| 4-26 | 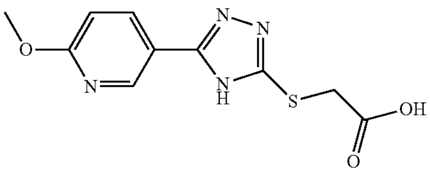 [SMILES: COc1ccc(-c2nnc(SCC(=O)O)[nH]2)cn1] |
| 4-27 | 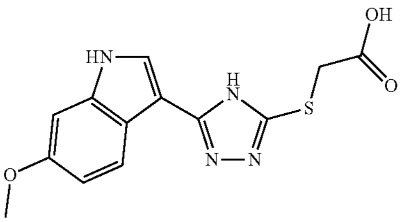 [SMILES: COc1ccc2c(-c3nnc(SCC(=O)O)[nH]3)c[nH]c2c1] |
| 4-28 | 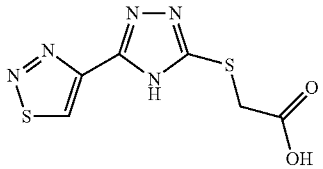 [SMILES: O=C(O)CSc1nnc(-c2csnn2)[nH]1] |
| 4-29 | 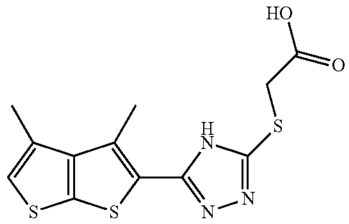 [SMILES: Cc1csc2sc(-c3nnc(SCC(=O)O)[nH]3)c(C)c12] |
| 4-30 | 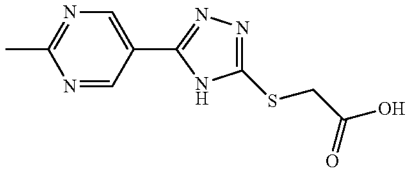 [SMILES: Cc1ncc(-c2nnc(SCC(=O)O)[nH]2)cn1] |
| 4-31 | 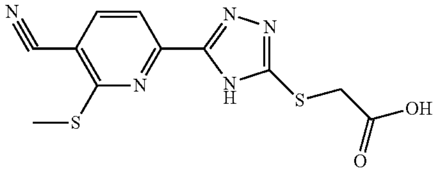 [SMILES: CSc1nc(-c2nnc(SCC(=O)O)[nH]2)ccc1C#N] |
| 4-32 | 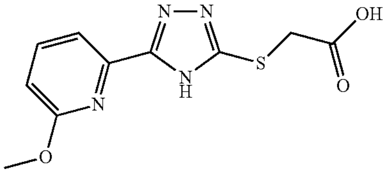 [SMILES: COc1cccc(-c2nnc(SCC(=O)O)[nH]2)n1] |
| 4-33 | 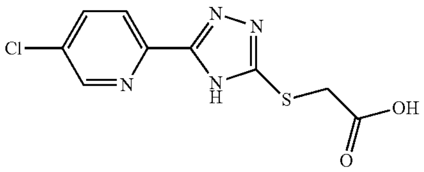 [SMILES: O=C(O)CSc1nnc(-c2ccc(Cl)cn2)[nH]1] |
| 4-34 | 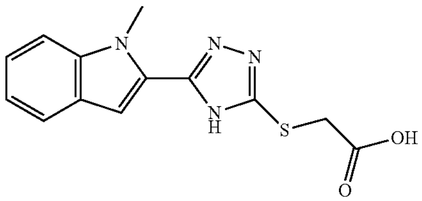 [SMILES: Cn1c(-c2nnc(SCC(=O)O)[nH]2)cc2ccccc21] |
| 4-35 | 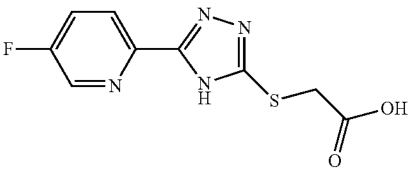 [SMILES: O=C(O)CSc1nnc(-c2ccc(F)cn2)[nH]1] |
| 4-36 | 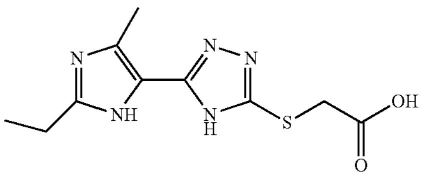 [SMILES: CCc1nc(C)c(-c2nnc(SCC(=O)O)[nH]2)[nH]1] |

TABLE 4-continued
| # | Compound Structure |
| --- | --- |
| 4-37 | 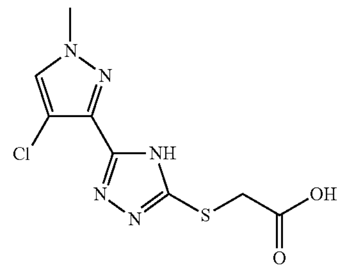 [SMILES: Cn1cc(Cl)c(-c2nnc(SCC(=O)O)[nH]2)n1] |
| 4-38 | 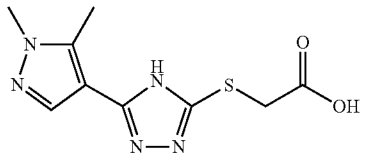 [SMILES: Cc1c(-c2nnc(SCC(=O)O)[nH]2)cnn1C] |
| 4-39 | 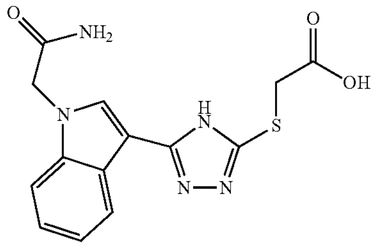 [SMILES: NC(=O)Cn1cc(-c2nnc(SCC(=O)O)[nH]2)c2ccccc21] |
| 4-40 | 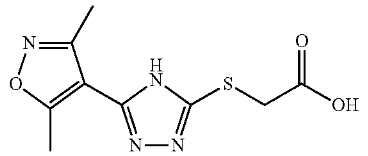 [SMILES: Cc1noc(C)c1-c1nnc(SCC(=O)O)[nH]1] |
| 4-41 | 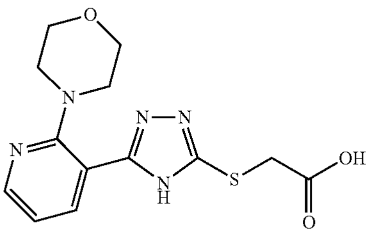 [SMILES: O=C(O)CSc1nnc(-c2cccnc2N2CCOCC2)[nH]1] |
| 4-42 | 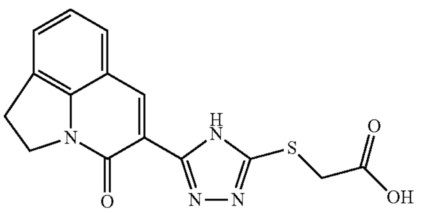 [SMILES: O=C(O)CSc1nnc(-c2cc3cccc4c3n(c2=O)CC4)[nH]1] |
| 4-43 | 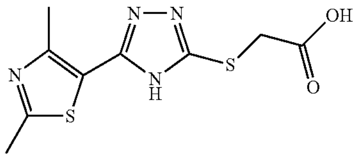 [SMILES: Cc1nc(C)c(-c2nnc(SCC(=O)O)[nH]2)s1] |
TABLE 4-continued
| # | Compound Structure |
| --- | --- |
| 4-44 | 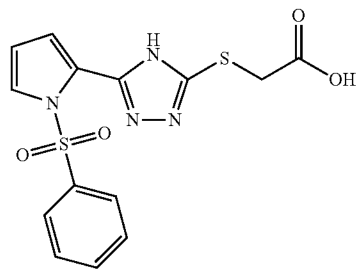 [SMILES: O=C(O)CSc1nnc(-c2cccn2S(=O)(=O)c2ccccc2)[nH]1] |
| 4-45 | 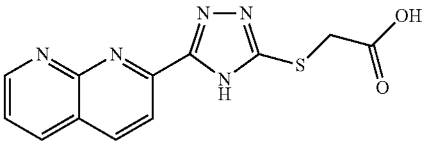 [SMILES: O=C(O)CSc1nnc(-c2ccc3cccnc3n2)[nH]1] |
| 4-46 | 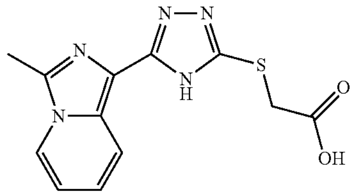 [SMILES: Cc1nc(-c2nnc(SCC(=O)O)[nH]2)c2ccccn12] |
| 4-47 | 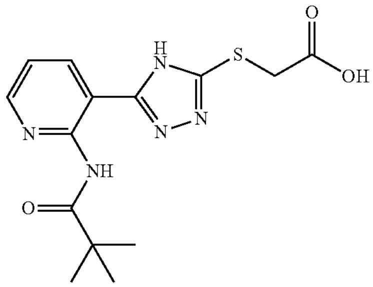 [SMILES: CC(C)(C)C(=O)Nc1ncccc1-c1nnc(SCC(=O)O)[nH]1] |
| 4-48 | 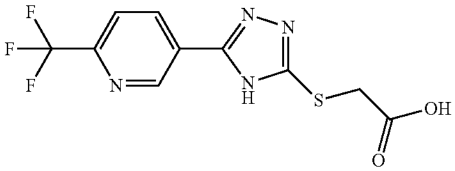 [SMILES: O=C(O)CSc1nnc(-c2ccc(C(F)(F)F)nc2)[nH]1] |
| 4-49 | 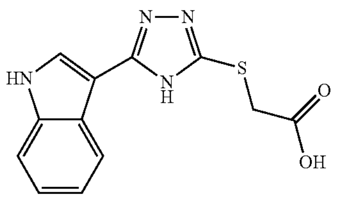 [SMILES: O=C(O)CSc1nnc(-c2c[nH]c3ccccc23)[nH]1] |
| 4-50 | 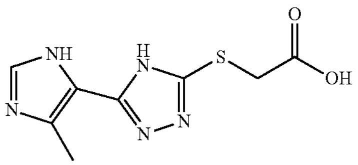 [SMILES: Cc1nc[nH]c1-c1nnc(SCC(=O)O)[nH]1] |

TABLE 4-continued

| # | Compound Structure |
|---|---|
| 4-51 | 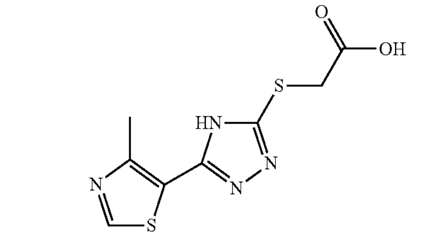 [SMILES: Cc1ncsc1-c1nnc(SCC(=O)O)[nH]1] |
| 4-52 | 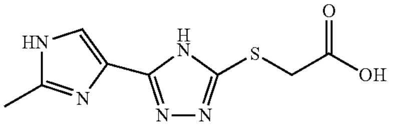 [SMILES: Cc1nc(-c2nnc(SCC(=O)O)[nH]2)c[nH]1] |
| 4-53 | 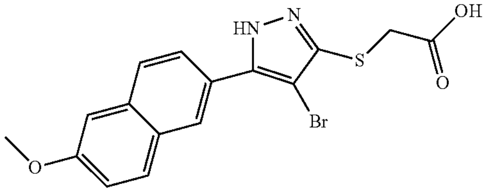 [SMILES: COc1ccc2cc(-c3[nH]nc(SCC(=O)O)c3Br)ccc2c1] |
| 4-54 | 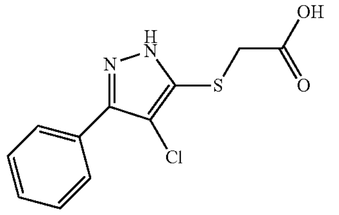 [SMILES: O=C(O)CSc1[nH]nc(-c2ccccc2)c1Cl] |

An inhibitor provided herein, including a pharmaceutically acceptable salt thereof, can be purchased commercially or prepared using known organic synthesis techniques. See, for example, Examples 1-17.

A reaction for preparing an inhibitor provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of an inhibitor can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1st Ed., Oxford University Press, 2000; and *March's Advanced Organic chemistry: Reactions, Mechanisms, and Structure*, 5th Ed., Wiley-Interscience Publication, 2001 (each of which is incorporated herein by reference in their entirety).

Pharmaceutically Acceptable Salts and Compositions

This document also provides pharmaceutically acceptable salts of the inhibitors provided herein. Examples of pharmaceutically acceptable salts of the inhibitors provided herein include acid addition salts and base salts of the inhibitors.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate, and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, and zinc salts.

Hemisalts of acids and bases may also be formed, for example, hemisulphate and hemicalcium salts.

An inhibitor provided herein intended for pharmaceutical use may be administered as a crystalline or amorphous product. In some cases, such a product may be obtained, for example, as a solid plug, powder, or film by methods such as precipitation, crystallization, freeze drying, spray drying, or evaporative drying. Microwave or radio frequency drying may be used for this purpose.

An inhibitor may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated is the installation of an inhibitor in the body of the patient in a controlled formulation, with systemic or local release of an inhibitor to occur at a later time. For example, an inhibitor can be localized in a depot for controlled release to the circulation, or for release to a local site. Advantageously, an inhibitor can be administered in the form of a pharmaceutical composition.

An inhibitor may be administered alone or in combination with one or more other inhibitors provided herein or in combination with one or more other drugs (or as any combination thereof). Generally, an inhibitor will be administered as a formulation in association with one or more pharmaceutically acceptable excipients. The term "excipient" is used herein to describe any ingredient other than an inhibitor(s) provided herein. The choice of excipient will to a large extent depend on factors such as the particular mode of administration, the effect of the excipient on solubility and stability, and the nature of the dosage form.

Non-limiting examples of pharmaceutical excipients suitable for administration of the inhibitors provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of an inhibitor provided herein. In some embodiments, the excipient is a physiologically acceptable saline solution.

A pharmaceutical composition can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal ointments, creams, gels, and patch preparations and dry powder inhalers (see, e.g., *Ansel Introduction to Pharmaceutical Dosage Forms, Fourth Edition* 1985, 126).

The concentration of an inhibitor in a pharmaceutical composition will depend on absorption, inactivation, and excretion rates of the inhibitor, the physicochemical characteristics of the inhibitor, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the inhibitors. The pharmaceutically therapeutically active inhibitors are, in one embodiment, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active inhibitor sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an inhibitor as provided herein and optional pharmaceutical adjuvants in a carrier, such as, for example, water, saline, aqueous dextrose, glycerol, glycols, ethanol, and the like, to thereby form a solution or suspension. If desired, a pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing an inhibitor provided herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of inhibitor provided herein and methods for their preparation will be readily apparent to those skilled in the art. Such compositions and methods for their preparation may be found, for example, in *Remington's Pharmaceutical Sciences,* 19th Edition (Mack Publishing Company, 1995).

Methods of Use

This document also provides methods and materials for using inhibitors of G protein couple receptor 6 kinase (GRK6) polypeptides. In some cases, an inhibitor provided herein may be used to treat any disease or disorder which involves the inhibition of a GRK6 polypeptide or a GRK6 polypeptide pathway. For example, a GRK6 polypeptide can be inhibited in a patient by administering a therapeutically effective amount of an inhibitor provided herein. In addition, a GRK6 polypeptide can be inhibited in a cell by contacting the cell with an effective amount of an inhibitor provided herein.

An inhibitor provided herein can have an $IC_{50}$ value in a GRK6 polypeptide inhibition assay ranging from about 0.1 μM to greater than about 20 μM. For example, see Examples 18-21.

Diseases and disorders which involve overexpression or over-activation of a GRK6 polypeptide can include, for example, hematological malignancies, inflammation diseases, and autoimmune disorders.

Hematological malignancies that may be treated by the inhibitors, compositions and methods described herein include, but are not limited to, cancers of the bone marrow, blood, and lymph nodes. For example, hematological malignancies can include, for example, malignant lymphoma (reticulum cell sarcoma), multiple myeloma, acute myeloid leukemia, chronic myeloid leukemia, acute lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), harry cell leukemia, and Waldenström's macroglobulinemia.

Hematological malignancies may be solid tumors that may or may not be metastatic. Cancers may also occur, as in leukemia, as a diffuse tissue. Thus, the term "tumor cell", as provided herein, includes a cell afflicted by any one of the above identified disorders.

In some embodiments, the hematological malignancy is a B cell cancer. For example, the B cell cancer is a B cell Non-Hodgkin Lymphoma. B cell Non-Hodgkin's Lymphomas can include mediastinal large B-cell lymphoma, lymphoblastic B cell lymphoma, Waldenstrom's macroglobulinaemia, and follicular lymphoma. Thus, in some embodiments, the B cell Non-Hodgkin's Lymphoma is small lymphocytic lymphoma (SLL), a mantle cell lymphoma, a Burkitt's lymphoma, a follicle centre cell lymphoma, a follicular lymphoma, a Burkitt-like lymphoma, a marginal zone B-cell lymphoma (MZBCL), a nodal marginal zone B cell lymphoma, an extra-nodal marginal zone B cell lymphoma, a splenic marginal zone B cell lymphoma, a lymphoplasmacytic lymphoma, or a diffuse large B cell lymphoma. In some embodiments, the B cell cancer is myeloma.

In some embodiments, the B cell cancer is a B cell acute lymphocytic leukemia (B-ALL), a precursor B cell acute lymphocytic leukemia (B-ALL), a B cell chronic lymphocytic leukemia (B-CLL), a precursor B-lymphoblastic leukaemia, a precursor B-lymphoblastic lymphoma, a small lymphocytic lymphoma, a B cell prolymphocytic leukemia, an undifferentiated B cell lymphoma, a hairy cell leukemia, a mediastinal large B-cell lymphoma, a plasma cell myeloma, a plasmacytoma, a primary effusive lymphoma, a Burkitt's cell leukemia, or a B cell diffuse mixed lymphoma.

An inhibitor provided herein can also be administered in combination with existing methods of treating hematological malignancies, for example by chemotherapy, irradiation, or surgery. Thus, there is further provided a method of treating hematological malignancies comprising administering an effective amount of an inhibitor described herein, or a pharmaceutically acceptable salt form thereof, to a patient, wherein a therapeutically effective amount of one or more additional cancer chemotherapeutic agents are administered to the patient.

The inhibitors provided herein are also useful in treating an inflammatory disease in a patient. Examples of inflammatory diseases treated by an inhibitor provided herein include, but are not limited to, general inflammatory diseases such as encephalitis, inflammatory eye disease, otitis, pharyngitis, pneumonia, gastritis, enteritis, hepatitis, pancreatitis, nephritis, cystitis, urethritis, endometritis, vaginitis, arthritis, and peripheral neuritis, and further include inflammatory diseases that secondarily cause inflammation, such as malignant tumor, infectious diseases, allergic diseases, autoimmune diseases (such as rheumatism, systemic lupus erythematosus, and sarcoidosis), ischemic diseases (such as myocardial infarction and cerebral infarction), metabolic diseases (such as diabetes and gout), injury, scald, chemical corrosion, and neurodegenerative diseases (such as Alzheimer's disease).

For example, an inhibitor provided herein can be used to treat an autoimmune disease or disorder. The term "autoimmune" refers to the process by which immune system components such as antibodies or lymphocytes attack or harm molecules, cells, or tissues of the organism producing them. The term "autoimmune disorders" refers to diseases where damage, such as tissue damage, or pathogenesis is, at least partially, a result of an autoimmune process.

In some embodiments, suppression of the immune response is useful in the treatment of patients suffering from autoimmune diseases as well as adverse immune reactions associated with organ transplantations.

Autoimmune diseases include allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, psoriasis, rheumatoid arthritis, sarcoidosis, scleroderma, and systemic lupus erythematosus.

Inhibitors provided herein are effective to inhibit a GRK6 polypeptide in a cell, for example, in a cancer cell (e.g., in a cell from a hematological malignancy). Therefore there is also provided a method of inhibiting a GRK6 polypeptide in a cell comprising contacting the cell with an effective amount of an inhibitor provided herein, or a pharmaceutically acceptable salt form thereof. The method may be performed by contacting the cell with an inhibitor as described herein, or a pharmaceutically acceptable salt form thereof, in vitro, thereby inhibiting a GRK6 polypeptide in vitro. Uses of such an in vitro method of inhibiting a GRK6 polypeptide include, but are not limited to use in a screening assay (for example, wherein an inhibitor described herein is used as a positive control or standard compared to compounds of unknown activity or potency in inhibiting a GRK6polypeptide).

EXAMPLES

Example 1

Preparation of 2-((5-(5-bromofuran-2-yl)-1H-1,2,4-triazol-3-yl)thio)acetic acid t-butyl ester (a3)

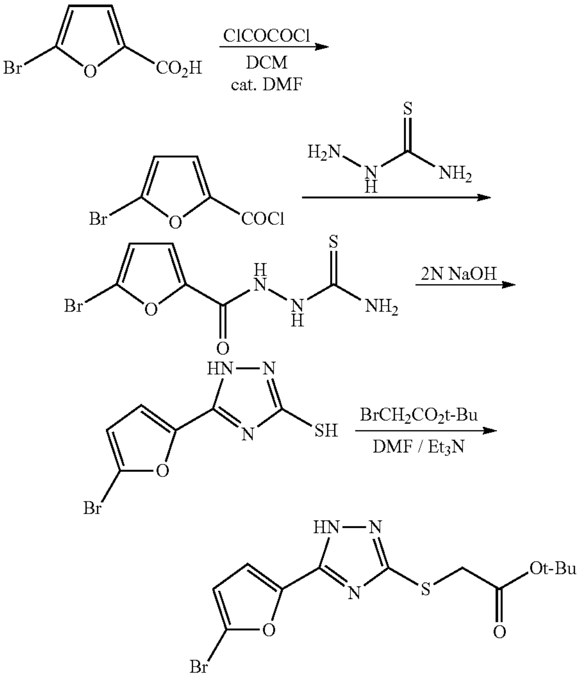

Step 1: To a stirred suspension of 5-bromo-2-furoic acid (12.0 g) in dry dichloromethane (100 mL), oxalyl chloride (11.0 mL) was added in portions over 10 min at 0° C. Upon completion, DMF (20 μL) was added and the ice bath was removed. When the solution became homogeneous and bubbling ceased, stirring was stopped and the solvent and excess reagent was removed under reduced pressure. The crude acid chloride was used without purification in the next reaction.

Step 2: Thiosemicarbazide (7.4 g) was suspended in dry pyridine (60 mL). The reaction mixture was cooled in ice and the crude acid chloride (Step 1) in THF/pyridine was slowly added and the reaction was set to stir overnight. The solvent was then removed and the crude residue washed with water and dried.

Step 3: The crude aroylthiosemicarbazide (Step 2) was treated with 2 M sodium hydroxide at 85° C. overnight. After cooling, the solution was acidified with hydrochloric acid and the precipitate was filtered, washed with water, and dried.

Step 4: The crude product of Step 3 was dissolved in dry DMF (100 mL) and treated with triethylamine (2 eq.) and t-butyl bromoacetate (1 eq.). The mixture was stirred at room temperature for 4 h and then briefly heated to 50° C. The reaction mixture was poured over ice and extracted with ethyl acetate. The organic layer was subsequently washed with water and evaporated to dryness to give the title compound.

Example 2

Preparation of Additional Compounds

The following examples (Table 5) can be prepared as described above for 2-((5-(5-bromofuran-2-yl)-1H-1,2,4-triazol-3-yl)thio)acetic acid t-butyl ester (Example 1) by substituting ethylbromoacetate (a1), 5-(chloromethyl)-1H-tetrazole (a2), or bromoacetic acid (1-97), for t-butylbromoacetate (a3).

TABLE 5

| # | Compound Structure | MW |
|---|---|---|
| a1 | 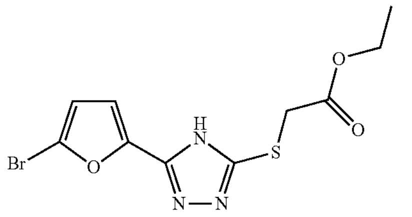 [SMILES: CCOC(=O)CSc1nnc(-c2ccc(Br)o2)[nH]1] | 332.18 |
| a2 | 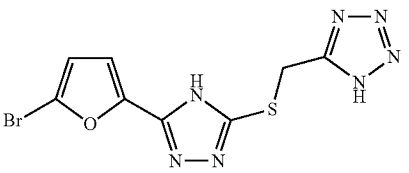 [SMILES: Brc1ccc(-c2nnc(SCc3nnn[nH]3)[nH]2)o1] | 328.15 |
| a3 | 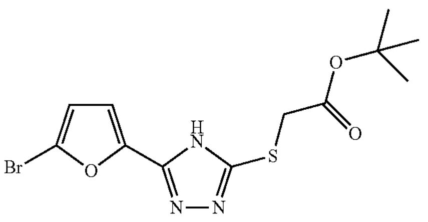 [SMILES: CC(C)(C)OC(=O)CSc1nnc(-c2ccc(Br)o2)[nH]1] | 360.23 |
| 1-97 | 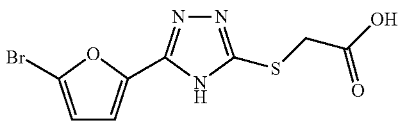 [SMILES: O=C(O)CSc1nnc(-c2ccc(Br)o2)[nH]1] | 304.12 |

Example 3

Preparation of 2-((3-(5-(quinolin-6-yl)furan-2-yl)-1H-1,2,4-triazol-5-yl)thio)acetic acid (1-30)

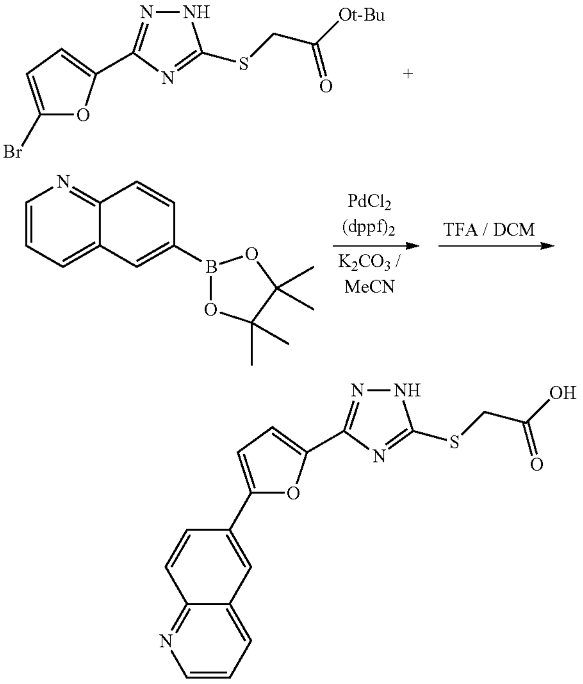

Tert-butyl 2-((3-(5-bromofuran-2-yl)-1H-1,2,4-triazol-5-yl)thio)acetate (58 mg), 6-(4,4,5,5-tetra-methyl-1,3,2-dioxaborolan-2-yl)quinolone (45.2 mg), and 1,1'-bis(diphenylphosphino)ferrocene palladium dichloride (11.8 mg) were added to a mixture of acetonitrile (1.6 mL) and potassium carbonate (1.6 mL, 2 M aqueous). The reaction mixture was heated at 120° C. in a microwave reactor for 30 minutes. Reaction mixture was poured into ethyl acetate and washed with water. The organic phase was then collected and evaporated to dryness. The resulting residue was purified by HPLC to afford a yellow solid. The solid was treated with a 1:1 mixture of dichloromethane and trifluoroacetic acid to give the title compound.

Example 4

Preparation of 2-((5-(5-(1-methyl-1H-indazol-6-yl)furan-2-yl)-4H-1,2,4-triazol-3-yl)thio)acetic acid (1-63)

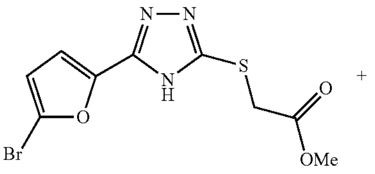

-continued

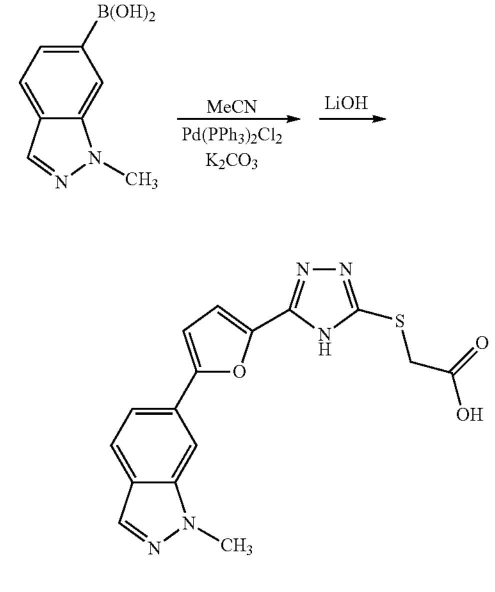

[5-(5-Bromo-furan-2-yl)-4H-[1,2,4]triazol-3-ylsulfanyl] acetic acid methyl ester (37 mg, 0.116 mmol) was dissolved in $CH_3CN$ (1 mL) in a microwave vessel, followed by addition of (dppf)$PdCl_2$ (5 mg,), $K_2CO_3$ (0.5 mL, 1 N aq. 0.5 mmol) and (1-methyl-1H-indazol-6-yl)boronic acid (30 mg, 0.12 mmol). The mixture was heated under microwave irradiation at 130° C. for 30 min. The mixture was subsequently concentrated and the residue was treated with aqueous LiOH in THF for 2 h. The mixture was then concentrated and the residue was purified by prep HPLC to give the title compound (0.9 mg). MS: (m/z) calcd. 355.1, observed ($M+H^+$) 356.3.

Example 5

Preparation of 2-((5-(5-(2-aminopyridin-4-yl)furan-2-yl)-4H-1,2,4-triazol-3-yl)thio)acetic acid (1-92)

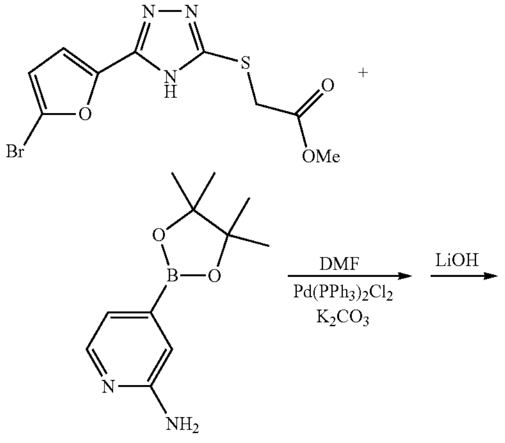

-continued

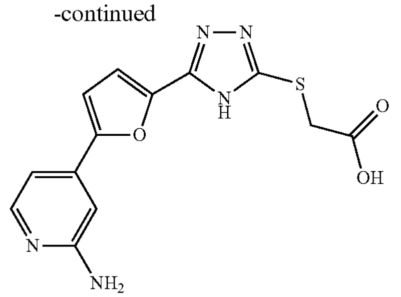

[5-(5-Bromo-furan-2-yl)-4H-[1,2,4]triazol-3-ylsulfanyl] acetic acid methyl ester (155 mg, 0.145 mmol) was dissolved in DMF (1 mL) in a microwave vessel, followed by addition of (dppf)$PdCl_2$ (20 mg), $K_2CO_3$ (2.5 mL, 1 N aq 2.5 mmol), and 2-aminopyridine-4-boronic acid pinacol ester (108 mg, 0.22 mmol). The mixture was heated under microwave irradiation at 130° C. for 30 min. The mixture was subsequently concentrated and the residue was treated with aqueous LiOH in THF for 2 h. The mixture was then concentrated and the residue was purified by prep HPLC to give the title compound (0.9 mg). MS: (m/z) calcd. 317.0, observed ($M+H^+$) 318.1.

Example 6

Preparation of 2-((5-(5-(5-chlorothiophen-2-yl)furan-2-yl)-4H-1,2,4-triazol-3-yl)thio)acetic acid (1-76)

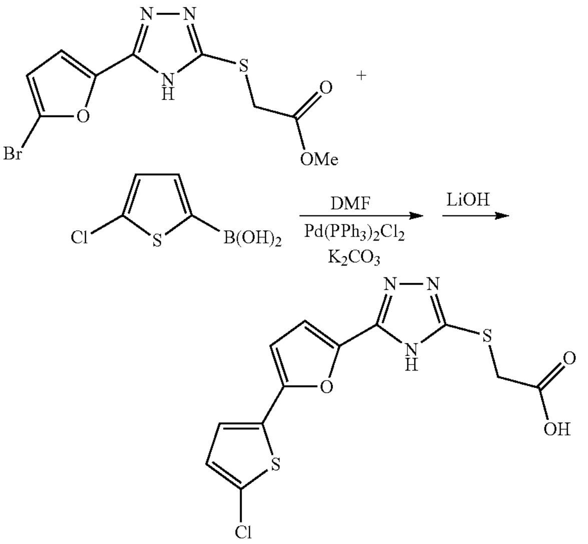

[5-(5-Bromo-furan-2-yl)-4H-[1,2,4]triazol-3-ylsulfanyl] acetic acid methyl ester (46 mg, 0.145 mmol) was dissolved in DMF (1 mL) in a microwave vessel followed by addition of $Pd(PPh_3)_4$ (12 mg, 0.01 mmol), $K_2CO_3$ (30 mg, 0.22 mmol), and 5-chlorothiophene-2-boronic acid (36 mg, 0.22 mmol). The mixture was heated under microwave irradiation at 130° C. for 30 min. The mixture was subsequently concentrated and the residue was treated with aqueous LiOH in THF for 2 h. The mixture was then concentrated and the residue was purified by prep HPLC to give the title compound (0.9 mg). MS: (m/z) calcd. 340.9, observed ($M+H^+$) 342.2.

Example 7

Preparation of 2-((5-(5-(naphthalen-2-ylethynyl)furan-2-yl)-4H-1,2,4-triazol-3-yl)thio)acetic acid (1-19)

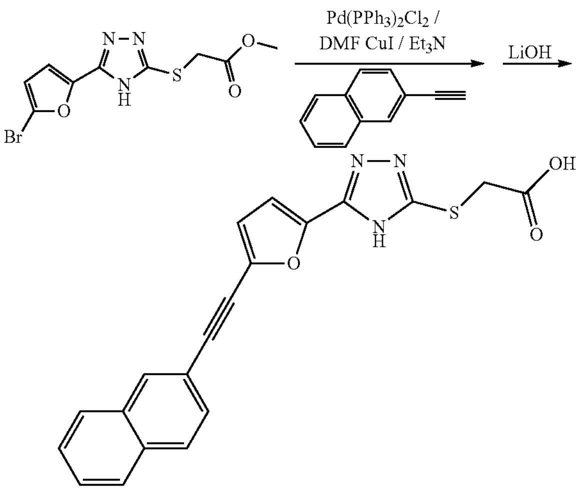

[5-(5-Bromo-furan-2-yl)-4H-[1,2,4]triazol-3-ylsulfanyl]acetic acid methyl ester (50 mg, 0.157 mmol) was dissolved in DMF (1 mL) at RT followed by addition of 2-ethynyl-naphthalene (28 mg, 0.189 mmol), $Pd(PPh_3)_2Cl_2$ (2.2 mg), CuI (1.2 mg) and $NEt_3$ (0.2 mL). The mixture was stirred at 80° C. for 2 h. The reaction mixture was then concentrated and treated with aqueous LiOH and THF. After removal of all volatiles, the residue was purified by prep HPLC to give the title compound (0.3 mg). MS: (m/z) calcd. 375.0, observed ($M+H^+$) 376.1.

Example 8

Preparation of Additional Ethynyl Furanyl Derivatives

The following examples (Table 6) can be prepared as described above for the preparation of 2-((5-(5-(naphthalen-2-ylethynyl)furan-2-yl)-4H-1,2,4-triazol-3-yl)thio)acetic acid (Example 7) by substituting the appropriate starting materials.

TABLE 6

| # | Compound Structure | MW |
|---|---|---|
| 1-11 | 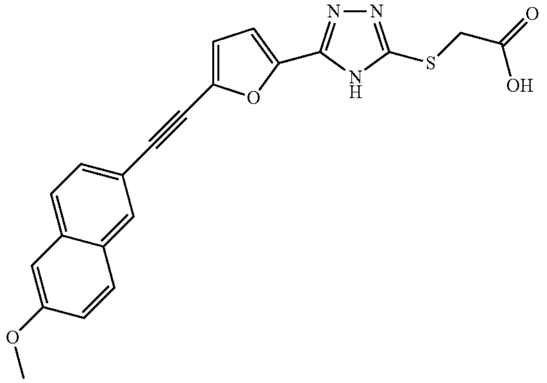 [SMILES: COc1ccc2cc(C#Cc3ccc(-c4nnc(SCC(=O)O)[nH]4)o3)ccc2c1] | 405.43 |
| 1-19 | 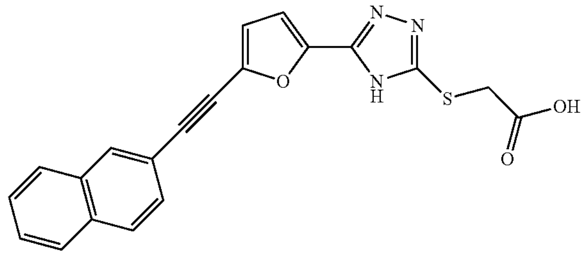 [SMILES: O=C(O)CSc1nnc(-c2ccc(C#Cc3ccc4ccccc4c3)o2)[nH]1] | 375.40 |
| 1-93 | 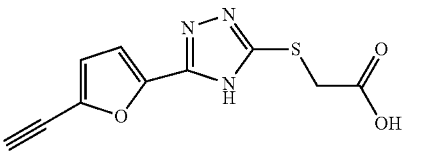 [SMILES: C#Cc1ccc(-c2nnc(SCC(=O)O)[nH]2)o1] | 249.25 |

TABLE 6-continued

| # | Compound Structure | MW |
|---|---|---|
| 1-102 | 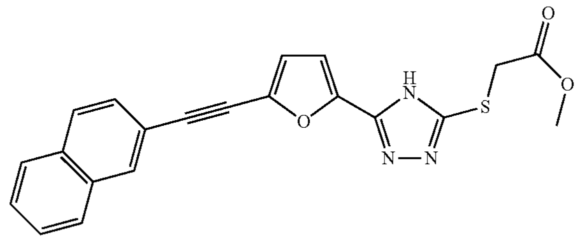 [SMILES: COC(=O)CSc1nnc(-c2ccc(C#Cc3ccc4ccccc4c3)o2)[nH]1] | 389.43 |

Example 9

General Synthetic Scheme for the Preparation of 5-heterocyclic- and hetero-biaryl Substituted 2-(1H-1,2,4-triazol-3-yl)thio)acetic acid Derivatives

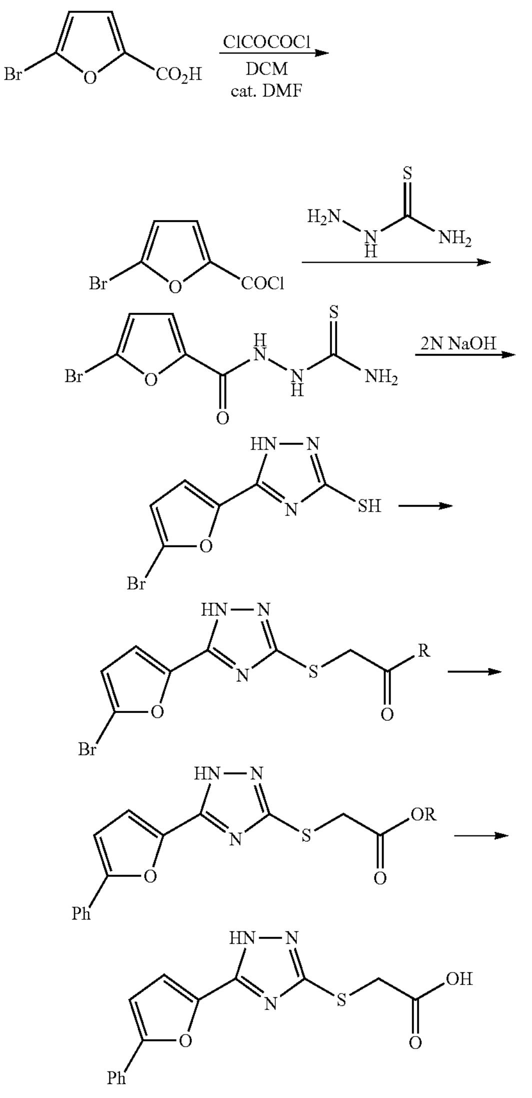

R = t-Bu, Et, etc.

Example 10

Alternative General Scheme for the Preparation of 5-heterocyclic- and hetero-biaryl Substituted 2-(1H-1,2,4-triazol-3-yl)thio)acetic acid Derivatives

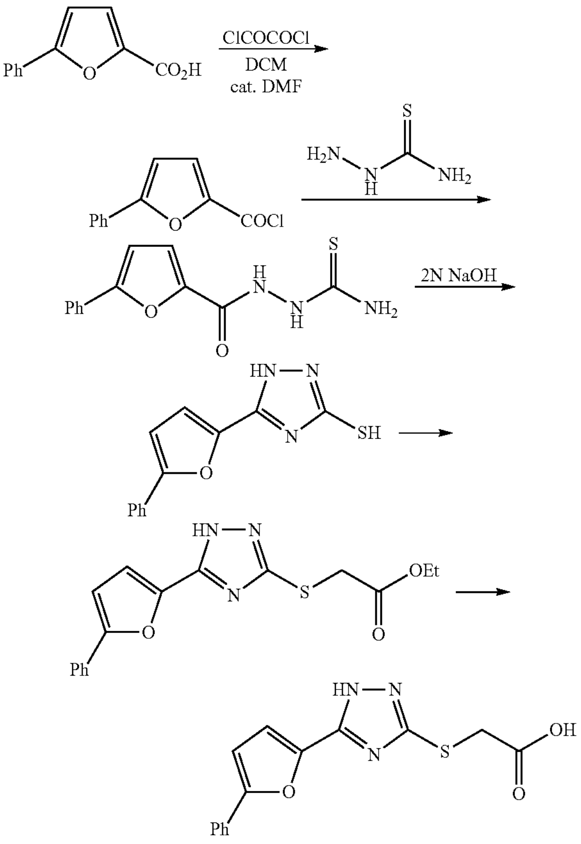

Example 11

Preparation of Additional Furanyl Derivatives

The following examples (Table 7) can be prepared as shown above using the general synthetic scheme for the preparation of 5-heterocyclic- and hetero-biaryl substituted 2-(1H-1,2,4-triazol-3-yl)thio)acetic acid derivatives (Example 9) or the alternative general scheme for the preparation of 5-heterocyclic- and hetero-biaryl substituted 2-(1H-1,2,4-triazol-3-yl)thio)acetic acid derivatives (Example 10).

TABLE 7
| # | Compound Structure | MW |
|---|---|---|
| 1-1 | 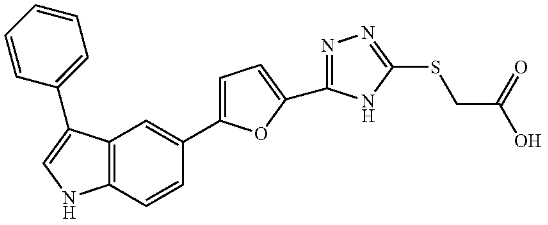 [SMILES: O=C(O)CSc1nnc(-c2ccc(-c3ccc4[nH]cc(-c5ccccc5)c4c3)o2)[nH]1] | 416.45 |
| 1-2 | 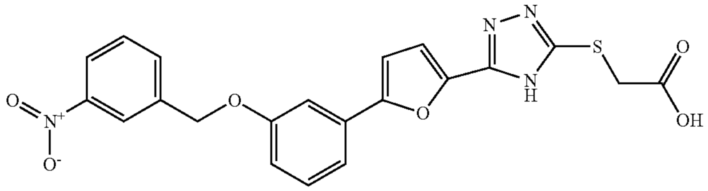 [SMILES: O=C(O)CSc1nnc(-c2ccc(-c3cccc(OCc4cccc([N+](=O)[O-])c4)c3)o2)[nH]1] | 452.44 |
| 1-3 | 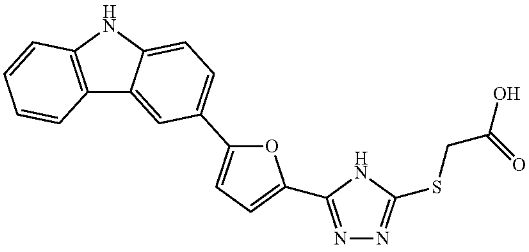 [SMILES: O=C(O)CSc1nnc(-c2ccc(-c3ccc4[nH]c5ccccc5c4c3)o2)[nH]1] | 390.42 |
| 1-4 | 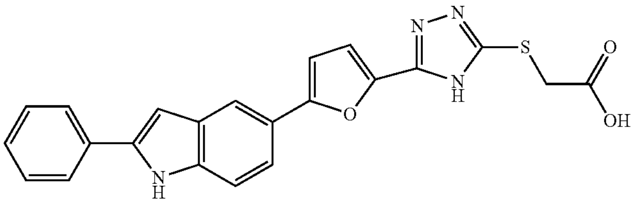 [SMILES: O=C(O)CSc1nnc(-c2ccc(-c3ccc4[nH]c(-c5ccccc5)cc4c3)o2)[nH]1] | 416.45 |
| 1-5 | 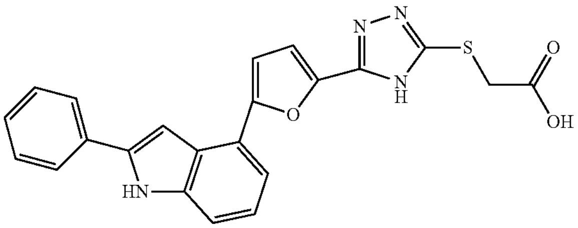 [SMILES: O=C(O)CSc1nnc(-c2ccc(-c3cccc4[nH]c(-c5ccccc5)cc34)o2)[nH]1] | 416.45 |
| 1-6 | 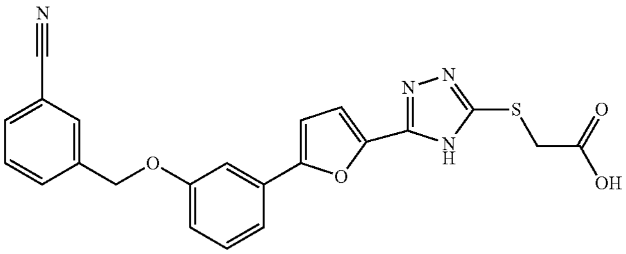 [SMILES: N#Cc1cccc(COc2cccc(-c3ccc(-c4nnc(SCC(=O)O)[nH]4)o3)c2)c1] | 432.45 |

TABLE 7-continued
| # | Compound Structure | MW |
| --- | --- | --- |
| 1-7 | 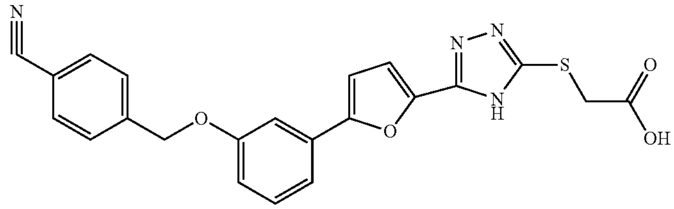 [SMILES: N#Cc1ccc(COc2cccc(-c3ccc(-c4nnc(SCC(=O)O)[nH]4)o3)c2)cc1] | 432.45 |
| 1-8 | 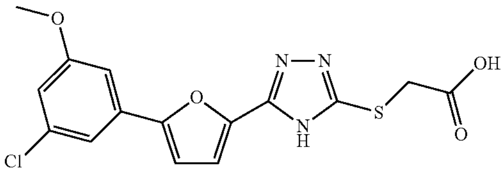 [SMILES: COc1cc(Cl)cc(-c2ccc(-c3nnc(SCC(=O)O)[nH]3)o2)c1] | 365.80 |
| 1-9 | 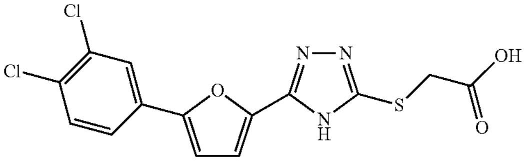 [SMILES: O=C(O)CSc1nnc(-c2ccc(-c3ccc(Cl)c(Cl)c3)o2)[nH]1] | 370.23 |
| 1-10 | 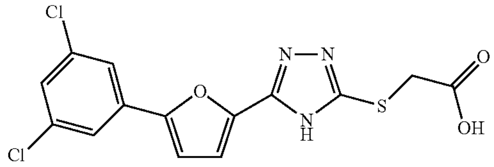 [SMILES: O=C(O)CSc1nnc(-c2ccc(-c3cc(Cl)cc(Cl)c3)o2)[nH]1] | 370.23 |
| 1-12 | 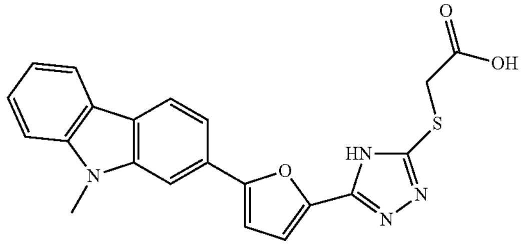 [SMILES: Cn1c2ccccc2c2ccc(-c3ccc(-c4nnc(SCC(=O)O)[nH]4)o3)cc21] | 404.44 |
| 1-13 | 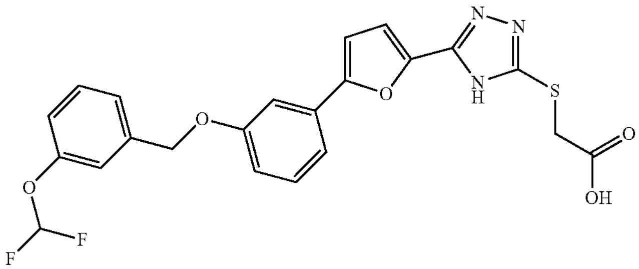 [SMILES: O=C(O)CSc1nnc(-c2ccc(-c3cccc(OCc4cccc(OC(F)F)c4)c3)o2)[nH]1] | 473.45 |
| 1-14 | 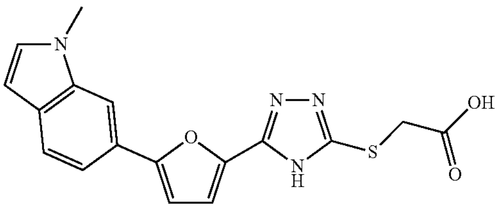 [SMILES: Cn1ccc2ccc(-c3ccc(-c4nnc(SCC(=O)O)[nH]4)o3)cc21] | 354.39 |

TABLE 7-continued
| # | Compound Structure | MW |
|---|---|---|
| 1-15 | 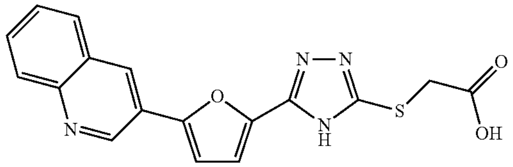 [SMILES: O=C(O)CSc1nnc(-c2ccc(-c3cnc4ccccc4c3)o2)[nH]1] | 352.37 |
| 1-16 | 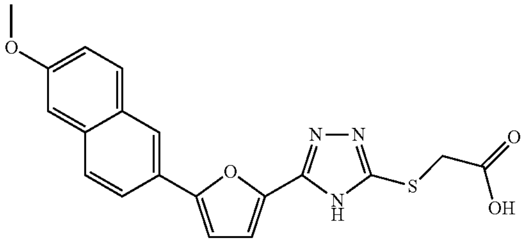 [SMILES: COc1ccc2cc(-c3ccc(-c4nnc(SCC(=O)O)[nH]4)o3)ccc2c1] | 381.41 |
| 1-17 | 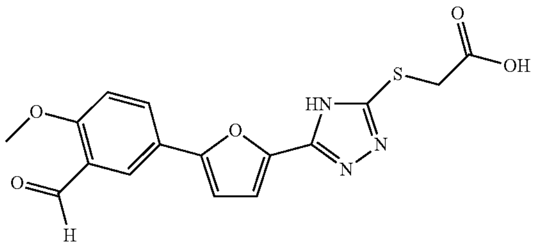 [SMILES: COc1ccc(-c2ccc(-c3nnc(SCC(=O)O)[nH]3)o2)cc1C=O] | 359.36 |
| 1-18 | 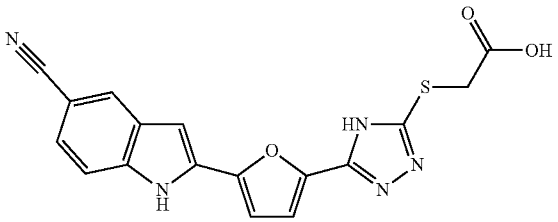 [SMILES: N#Cc1ccc2[nH]c(-c3ccc(-c4nnc(SCC(=O)O)[nH]4)o3)cc2c1] | 365.37 |
| 1-20 | 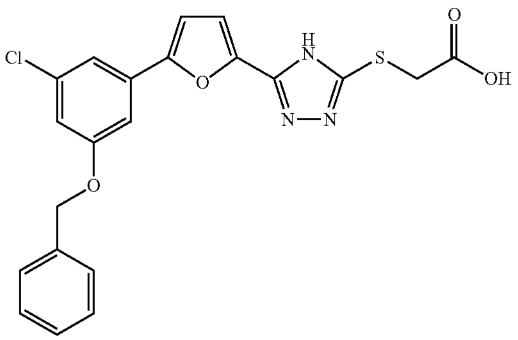 [SMILES: O=C(O)CSc1nnc(-c2ccc(-c3cc(Cl)cc(OCc4ccccc4)c3)o2)[nH]1] | 441.90 |
| 1-21 | 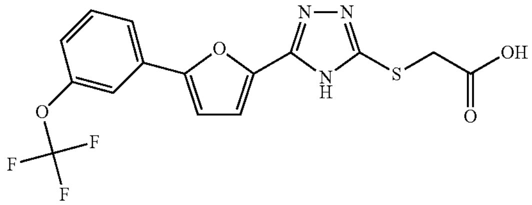 [SMILES: O=C(O)CSc1nnc(-c2ccc(-c3cccc(OC(F)(F)F)c3)o2)[nH]1] | 385.32 |

TABLE 7-continued
| # | Compound Structure | MW |
|---|---|---|
| 1-22 | 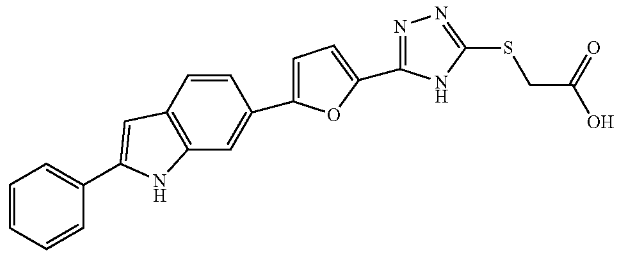 [SMILES: O=C(O)CSc1nnc(-c2ccc(-c3ccc4cc(-c5ccccc5)[nH]c4c3)o2)[nH]1] | 416.45 |
| 1-23 | 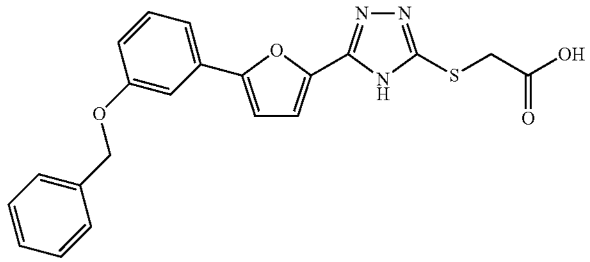 [SMILES: O=C(O)CSc1nnc(-c2ccc(-c3cccc(OCc4ccccc4)c3)o2)[nH]1] | 407.44 |
| 1-24 | 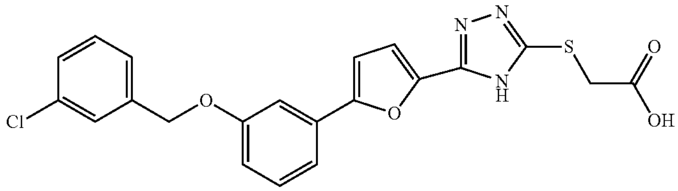 [SMILES: O=C(O)CSc1nnc(-c2ccc(-c3cccc(OCc4cccc(Cl)c4)c3)o2)[nH]1] | 441.90 |
| 1-25 | 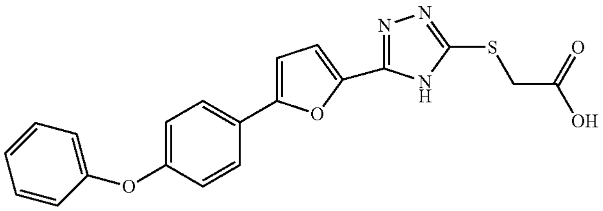 [SMILES: O=C(O)CSc1nnc(-c2ccc(-c3ccc(Oc4ccccc4)cc3)o2)[nH]1] | 393.42 |
| 1-26 | 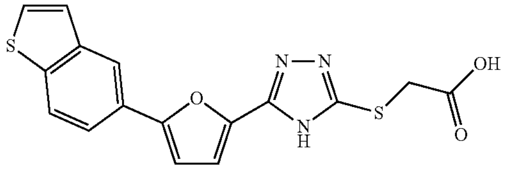 [SMILES: O=C(O)CSc1nnc(-c2ccc(-c3ccc4sccc4c3)o2)[nH]1] | 357.41 |
| 1-27 | 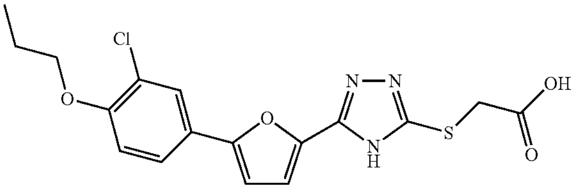 [SMILES: CCCOc1ccc(-c2ccc(-c3nnc(SCC(=O)O)[nH]3)o2)cc1Cl] | 393.86 |
| 1-28 | 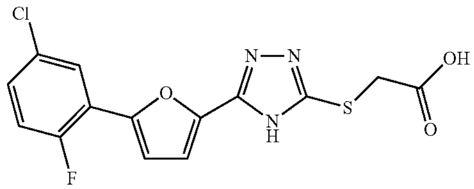 [SMILES: O=C(O)CSc1nnc(-c2ccc(-c3cc(Cl)ccc3F)o2)[nH]1] | 353.77 |

TABLE 7-continued
| # | Compound Structure | MW |
|---|---|---|
| 1-29 | 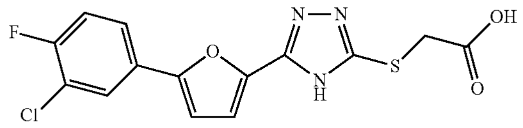 [SMILES: O=C(O)CSc1nnc(-c2ccc(-c3ccc(F)c(Cl)c3)o2)[nH]1] | 353.77 |
| 1-30 | 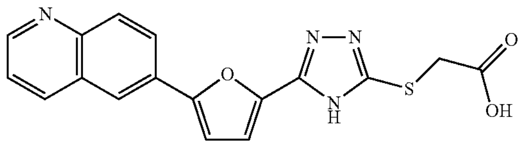 [SMILES: O=C(O)CSc1nnc(-c2ccc(-c3ccc4ncccc4c3)o2)[nH]1] | 352.37 |
| 1-31 | 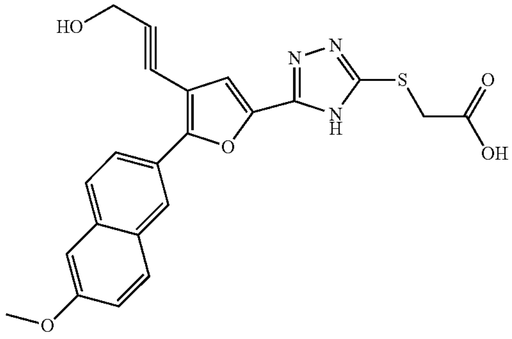 [SMILES: COc1ccc2cc(-c3oc(-c4nnc(SCC(=O)O)[nH]4)cc3C#CCO)ccc2c1] | 435.45 |
| 1-32 | 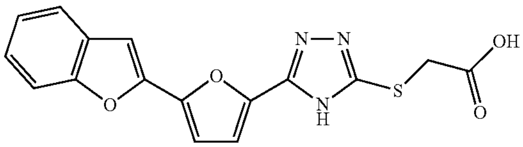 [SMILES: O=C(O)CSc1nnc(-c2ccc(-c3cc4ccccc4o3)o2)[nH]1] | 341.34 |
| 1-33 | 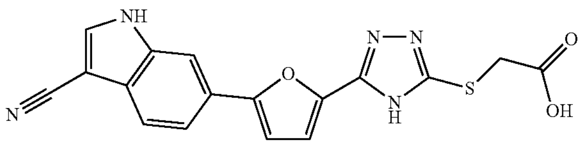 [SMILES: N#Cc1c[nH]c2cc(-c3ccc(-c4nnc(SCC(=O)O)[nH]4)o3)ccc12] | 365.37 |
| 1-34 | 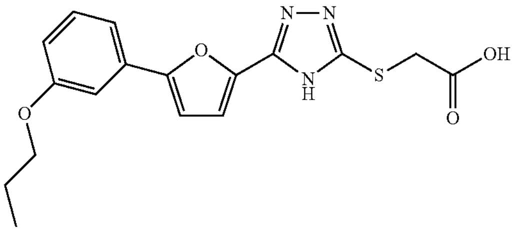 [SMILES: CCCOc1cccc(-c2ccc(-c3nnc(SCC(=O)O)[nH]3)o2)c1] | 359.40 |
| 1-35 | 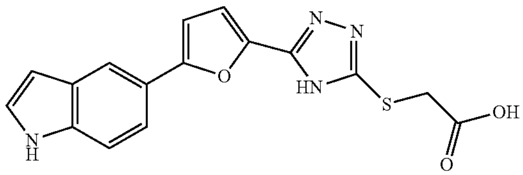 [SMILES: O=C(O)CSc1nnc(-c2ccc(-c3ccc4[nH]ccc4c3)o2)[nH]1] | 340.36 |
| 1-36 | 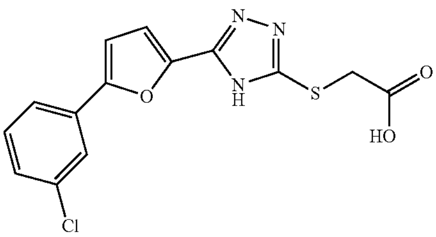 [SMILES: O=C(O)CSc1nnc(-c2ccc(-c3cccc(Cl)c3)o2)[nH]1] | 335.78 |

TABLE 7-continued
| # | Compound Structure | MW |
|---|---|---|
| 1-37 | 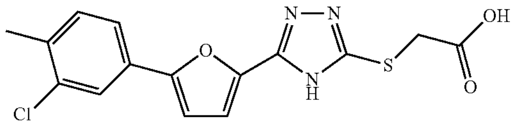 [SMILES: Cc1ccc(-c2ccc(-c3nnc(SCC(=O)O)[nH]3)o2)cc1Cl] | 349.80 |
| 1-38 | 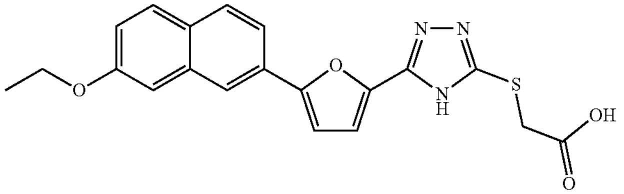 [SMILES: CCOc1ccc2ccc(-c3ccc(-c4nnc(SCC(=O)O)[nH]4)o3)cc2c1] | 395.43 |
| 1-39 | 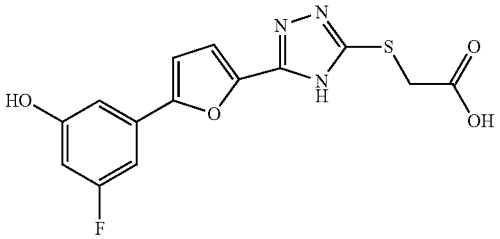 [SMILES: O=C(O)CSc1nnc(-c2ccc(-c3cc(O)cc(F)c3)o2)[nH]1] | 335.31 |
| 1-40 | 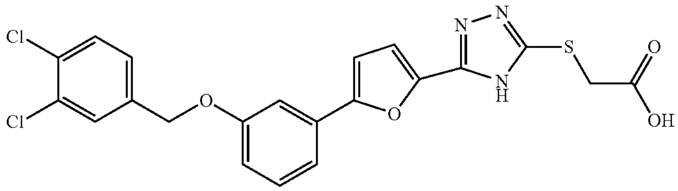 [SMILES: O=C(O)CSc1nnc(-c2ccc(-c3cccc(OCc4ccc(Cl)c(Cl)c4)c3)o2)[nH]1] | 476.35 |
| 1-41 | 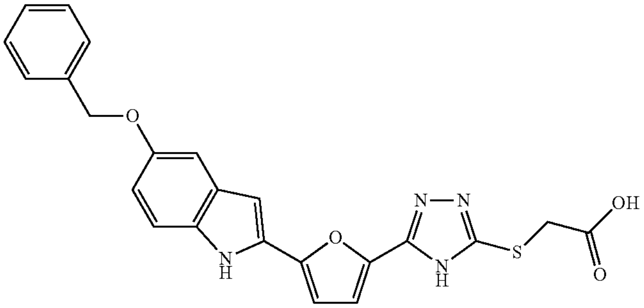 [SMILES: O=C(O)CSc1nnc(-c2ccc(-c3cc4cc(OCc5ccccc5)ccc4[nH]3)o2)[nH]1] | 446.48 |
| 1-42 | 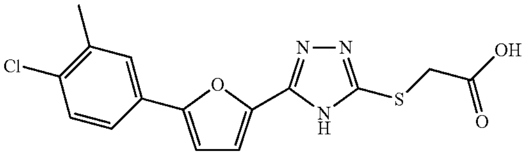 [SMILES: Cc1cc(-c2ccc(-c3nnc(SCC(=O)O)[nH]3)o2)ccc1Cl] | 349.80 |
| 1-43 | 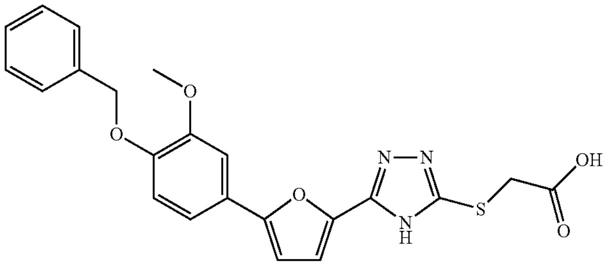 [SMILES: COc1cc(-c2ccc(-c3nnc(SCC(=O)O)[nH]3)o2)ccc1OCc1ccccc1] | 437.47 |

TABLE 7-continued
| # | Compound Structure | MW |
|---|---|---|
| 1-44 | 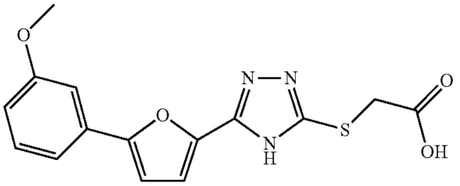 [SMILES: COc1cccc(-c2ccc(-c3nnc(SCC(=O)O)[nH]3)o2)c1] | 331.35 |
| 1-45 | 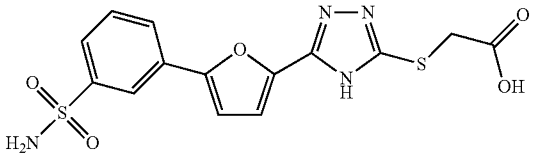 [SMILES: NS(=O)(=O)c1cccc(-c2ccc(-c3nnc(SCC(=O)O)[nH]3)o2)c1] | 380.40 |
| 1-46 | 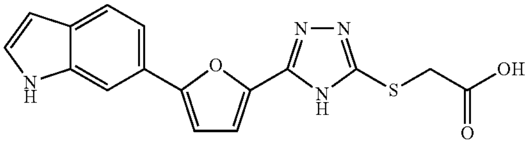 [SMILES: O=C(O)CSc1nnc(-c2ccc(-c3ccc4cc[nH]c4c3)o2)[nH]1] | 340.36 |
| 1-47 | 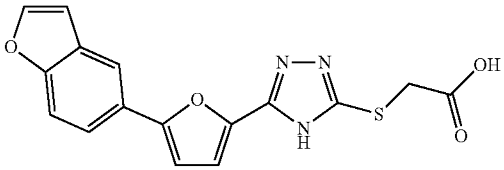 [SMILES: O=C(O)CSc1nnc(-c2ccc(-c3ccc4occc4c3)o2)[nH]1] | 341.34 |
| 1-48 | 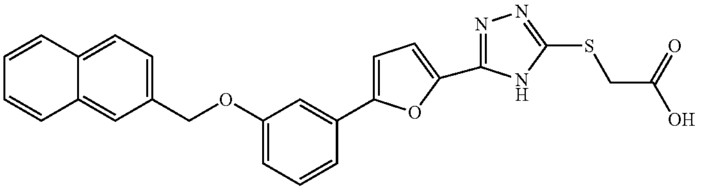 [SMILES: O=C(O)CSc1nnc(-c2ccc(-c3cccc(OCc4ccc5ccccc5c4)c3)o2)[nH]1] | 457.50 |
| 1-49 | 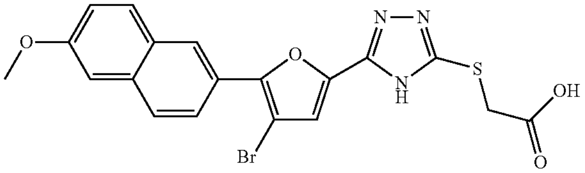 [SMILES: COc1ccc2cc(-c3oc(-c4nnc(SCC(=O)O)[nH]4)cc3Br)ccc2c1] | 460.30 |
| 1-50 | 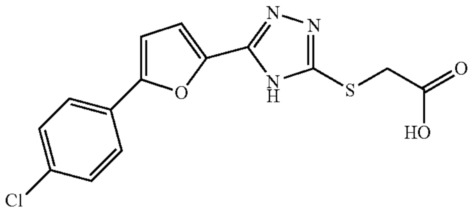 [SMILES: O=C(O)CSc1nnc(-c2ccc(-c3ccc(Cl)cc3)o2)[nH]1] | 335.78 |
| 1-51 | 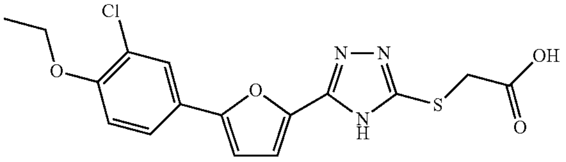 [SMILES: CCOc1ccc(-c2ccc(-c3nnc(SCC(=O)O)[nH]3)o2)cc1Cl] | 379.83 |

TABLE 7-continued
| # | Compound Structure | MW |
|---|---|---|
| 1-52 | 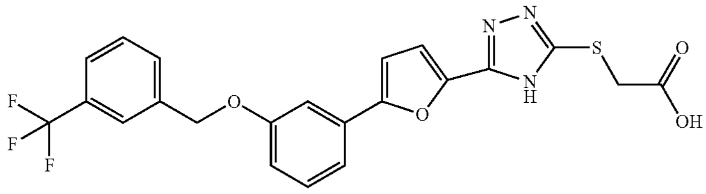 [SMILES: O=C(O)CSc1nnc(-c2ccc(-c3cccc(OCc4cccc(C(F)(F)F)c4)c3)o2)[nH]1] | 475.44 |
| 1-53 | 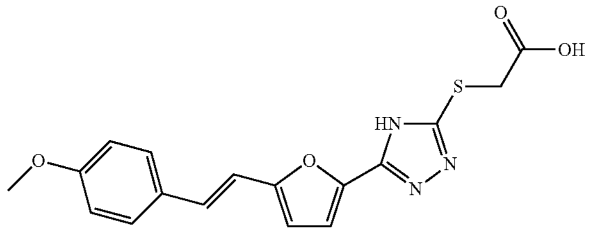 [SMILES: COc1ccc(/C=C/c2ccc(-c3nnc(SCC(=O)O)[nH]3)o2)cc1] | 357.39 |
| 1-54 | 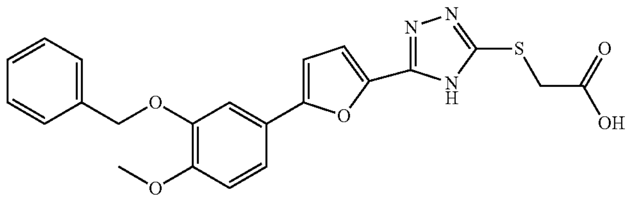 [SMILES: COc1ccc(-c2ccc(-c3nnc(SCC(=O)O)[nH]3)o2)cc1OCc1ccccc1] | 437.47 |
| 1-55 | 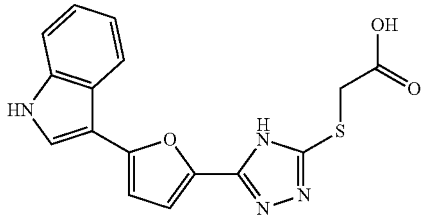 [SMILES: O=C(O)CSc1nnc(-c2ccc(-c3c[nH]c4ccccc34)o2)[nH]1] | 340.36 |
| 1-56 | 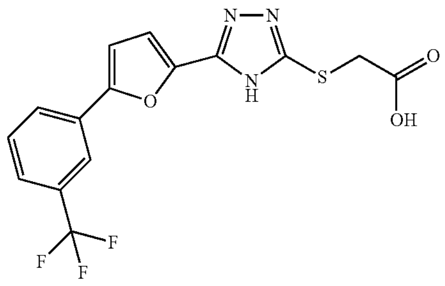 [SMILES: O=C(O)CSc1nnc(-c2ccc(-c3cccc(C(F)(F)F)c3)o2)[nH]1] | 369.32 |
| 1-57 | 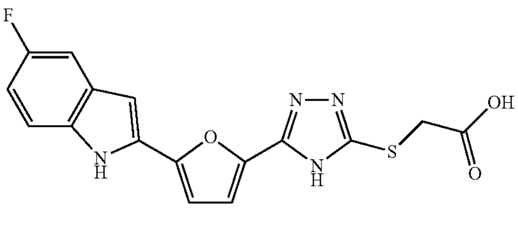 [SMILES: O=C(O)CSc1nnc(-c2ccc(-c3cc4cc(F)ccc4[nH]3)o2)[nH]1] | 358.35 |

TABLE 7-continued
| # | Compound Structure | MW |
| --- | --- | --- |
| 1-58 | 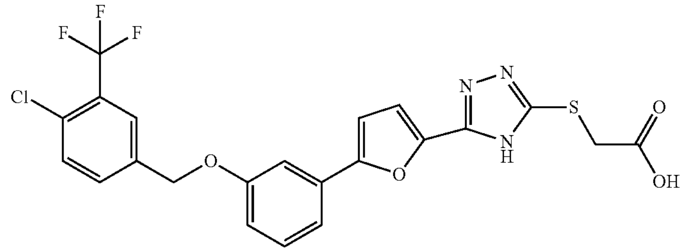 [SMILES: O=C(O)CSc1nnc(-c2ccc(-c3cccc(OCc4ccc(Cl)c(C(F)(F)F)c4)c3)o2)[nH]1] | 509.90 |
| 1-59 | 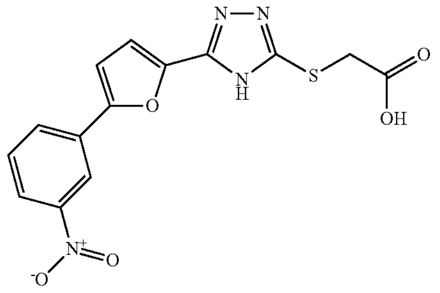 | 346.32 |
| 1-60 | 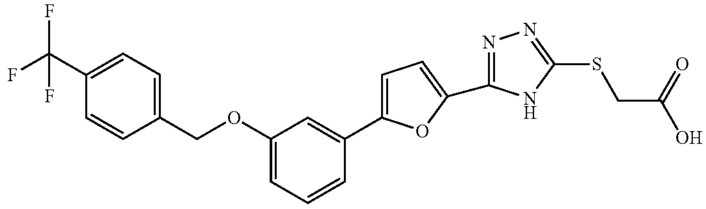 [SMILES: O=C(O)CSc1nnc(-c2ccc(-c3cccc(OCc4ccc(C(F)(F)F)cc4)c3)o2)[nH]1] | 475.44 |
| 1-61 | 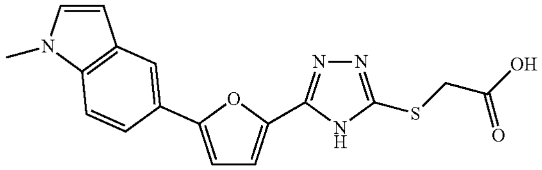 [SMILES: Cn1ccc2cc(-c3ccc(-c4nnc(SCC(=O)O)[nH]4)o3)ccc21] | 354.39 |
| 1-62 | 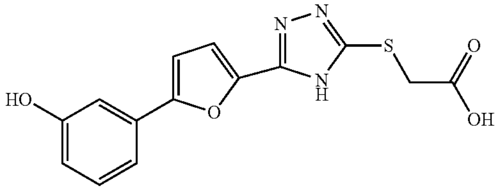 [SMILES: O=C(O)CSc1nnc(-c2ccc(-c3cccc(O)c3)o2)[nH]1] | 317.32 |
| 1-63 | 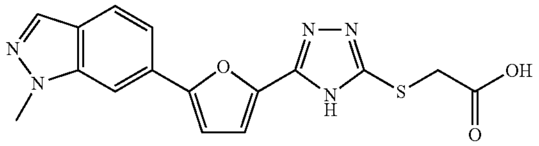 [SMILES: Cn1ncc2ccc(-c3ccc(-c4nnc(SCC(=O)O)[nH]4)o3)cc21] | 355.37 |
| 1-64 | 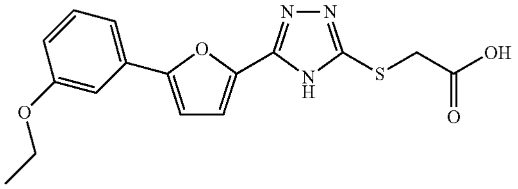 [SMILES: CCOc1cccc(-c2ccc(-c3nnc(SCC(=O)O)[nH]3)o2)c1] | 345.38 |

TABLE 7-continued
| # | Compound Structure | MW |
|---|---|---|
| 1-65 | 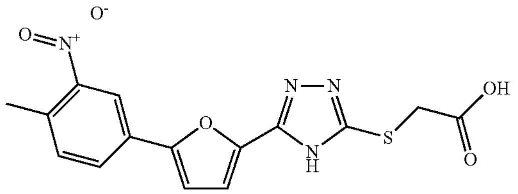 | 360.35 |
| 1-66 | 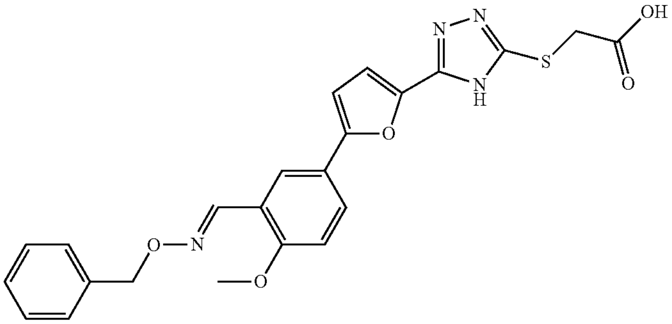 [SMILES: COc1ccc(-c2ccc(-c3nnc(SCC(=O)O)[nH]3)o2)cc1/C=N/OCc1ccccc1] | 464.50 |
| 1-67 | 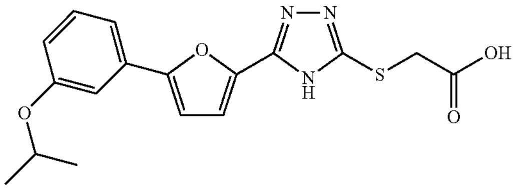 [SMILES: CC(C)Oc1cccc(-c2ccc(-c3nnc(SCC(=O)O)[nH]3)o2)c1] | 359.40 |
| 1-68 | 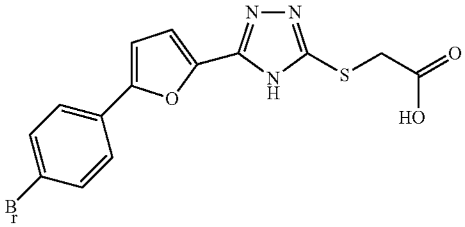 [SMILES: O=C(O)CSc1nnc(-c2ccc(-c3ccc(Br)cc3)o2)[nH]1] | 380.22 |
| 1-69 | 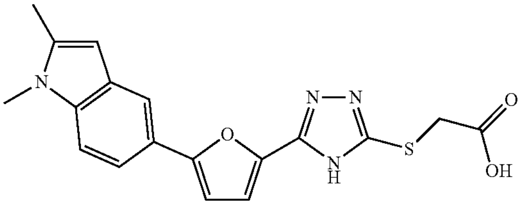 [SMILES: Cc1cc2cc(-c3ccc(-c4nnc(SCC(=O)O)[nH]4)o3)ccc2n1C] | 368.41 |
| 1-70 | 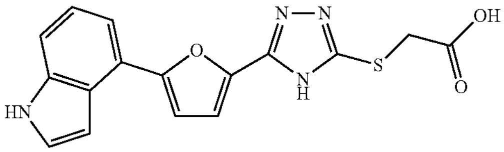 [SMILES: O=C(O)CSc1nnc(-c2ccc(-c3cccc4[nH]ccc34)o2)[nH]1] | 340.36 |

TABLE 7-continued
| # | Compound Structure | MW |
| --- | --- | --- |
| 1-71 | 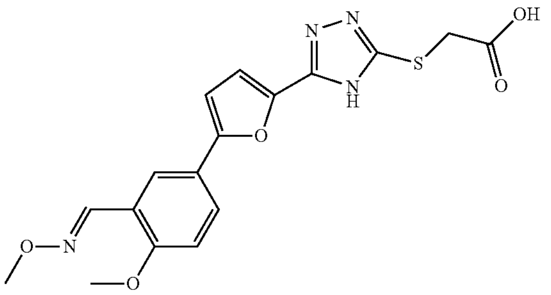 [SMILES: CO/N=C/c1cc(-c2ccc(-c3nnc(SCC(=O)O)[nH]3)o2)ccc1OC] | 388.40 |
| 1-72 | 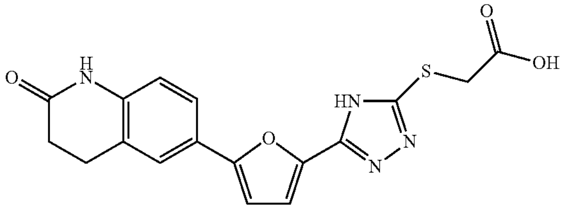 [SMILES: O=C(O)CSc1nnc(-c2ccc(-c3ccc4c(c3)CCC(=O)N4)o2)[nH]1] | 370.38 |
| 1-73 | 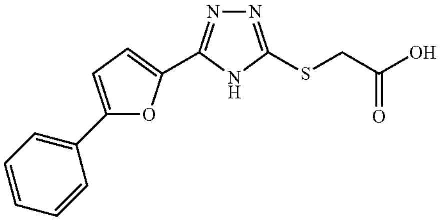 | 301.32 |
| 1-74 | 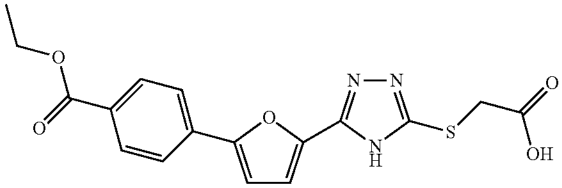 [SMILES: CCOC(=O)c1ccc(-c2ccc(-c3nnc(SCC(=O)O)[nH]3)o2)cc1] | 373.39 |
| 1-75 | 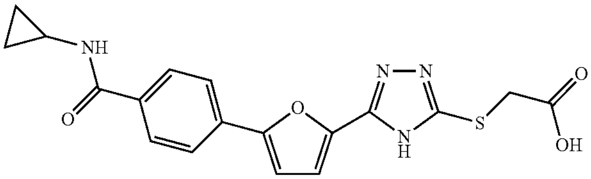 [SMILES: O=C(O)CSc1nnc(-c2ccc(-c3ccc(C(=O)NC4CC4)cc3)o2)[nH]1] | 384.41 |
| 1-76 | 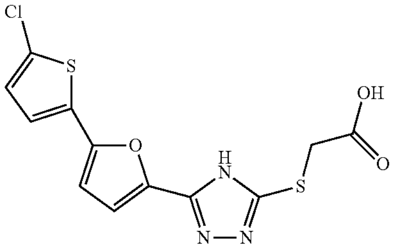 [SMILES: O=C(O)CSc1nnc(-c2ccc(-c3ccc(Cl)s3)o2)[nH]1] | 341.81 |

TABLE 7-continued
| # | Compound Structure | MW |
| --- | --- | --- |
| 1-77 | 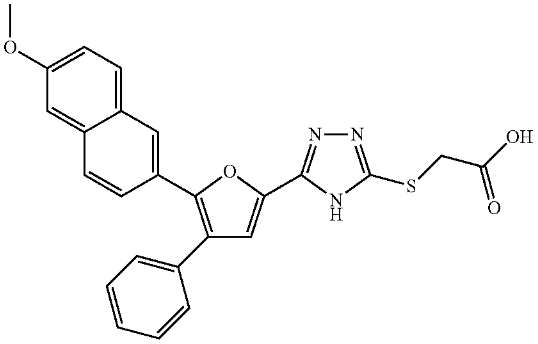 [SMILES: COc1ccc2cc(-c3oc(-c4nnc(SCC(=O)O)[nH]4)cc3-c3ccccc3)ccc2c1] | 457.50 |
| 1-78 | 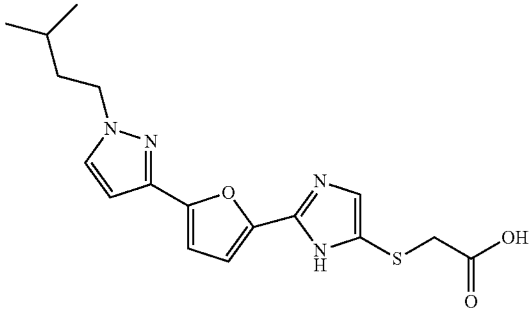 [SMILES: CC(C)CCn1ccc(-c2ccc(-c3ncc(SCC(=O)O)[nH]3)o2)n1] | 361.42 |
| 1-79 | 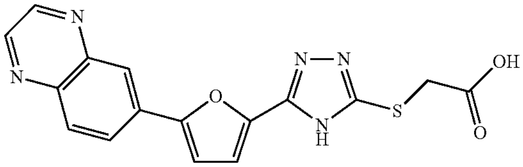 [SMILES: O=C(O)CSc1nnc(-c2ccc(-c3ccc4nccnc4c3)o2)[nH]1] | 353.36 |
| 1-80 | 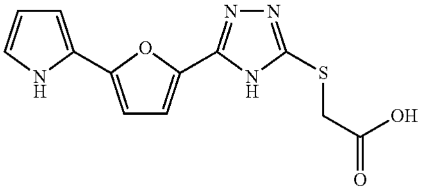 [SMILES: O=C(O)CSc1nnc(-c2ccc(-c3ccc[nH]3)o2)[nH]1] | 290.30 |
| 1-81 | 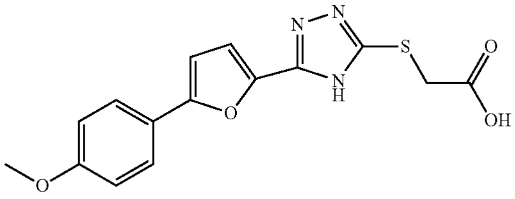 [SMILES: COc1ccc(-c2ccc(-c3nnc(SCC(=O)O)[nH]3)o2)cc1] | 331.35 |
| 1-82 | 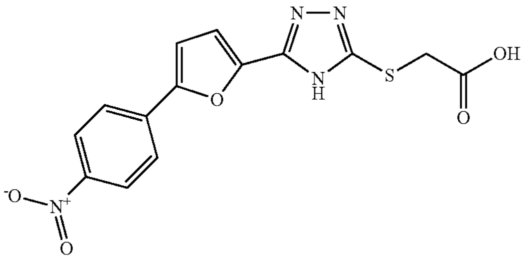 | 346.32 |

TABLE 7-continued
| # | Compound Structure | MW |
|---|---|---|
| 1-83 | 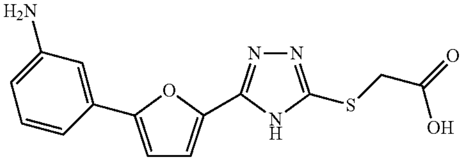 [SMILES: Nc1cccc(-c2ccc(-c3nnc(SCC(=O)O)[nH]3)o2)c1] | 316.34 |
| 1-84 | 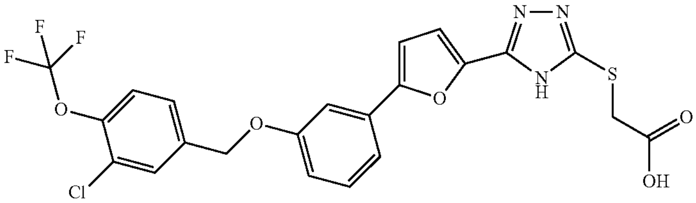 [SMILES: O=C(O)CSc1nnc(-c2ccc(-c3cccc(OCc4ccc(OC(F)(F)F)c(Cl)c4)c3)o2)[nH]1] | 525.90 |
| 1-85 | 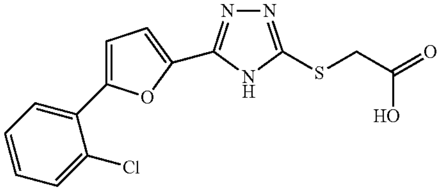 [SMILES: O=C(O)CSc1nnc(-c2ccc(-c3ccccc3Cl)o2)[nH]1] | 335.78 |
| 1-86 | 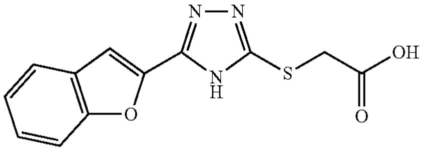 [SMILES: O=C(O)CSc1nnc(-c2cc3ccccc3o2)[nH]1] | 275.28 |
| 1-87 | 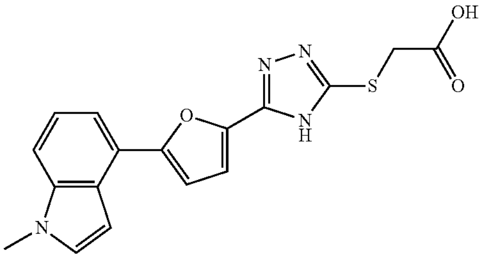 [SMILES: Cn1ccc2c(-c3ccc(-c4nnc(SCC(=O)O)[nH]4)o3)cccc21] | 354.39 |
| 1-88 | 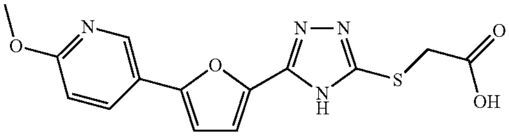 [SMILES: COc1ccc(-c2ccc(-c3nnc(SCC(=O)O)[nH]3)o2)cn1] | 332.34 |
| 1-89 | 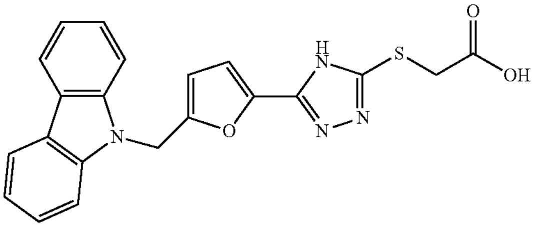 [SMILES: O=C(O)CSc1nnc(-c2ccc(Cn3c4ccccc4c4ccccc43)o2)[nH]1] | 404.44 |
| 1-90 | 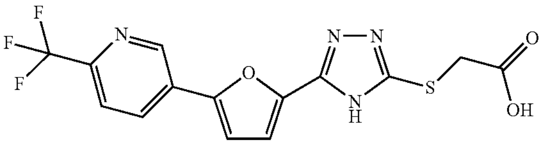 [SMILES: O=C(O)CSc1nnc(-c2ccc(-c3ccc(C(F)(F)F)nc3)o2)[nH]1] | 370.31 |

TABLE 7-continued
| # | Compound Structure | MW |
| --- | --- | --- |
| 1-91 | 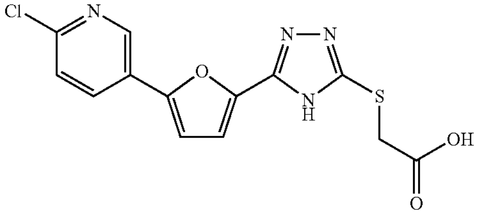 [SMILES: O=C(O)CSc1nnc(-c2ccc(-c3ccc(Cl)nc3)o2)[nH]1] | 336.76 |
| 1-92 | 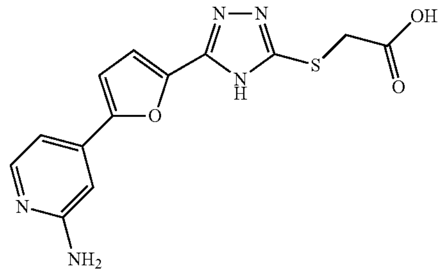 [SMILES: Nc1cc(-c2ccc(-c3nnc(SCC(=O)O)[nH]3)o2)ccn1] | 317.32 |
| 1-94 | 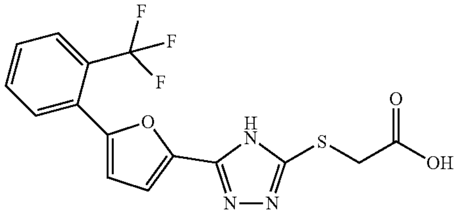 [SMILES: O=C(O)CSc1nnc(-c2ccc(-c3ccccc3C(F)(F)F)o2)[nH]1] | 369.32 |
| 1-95 | 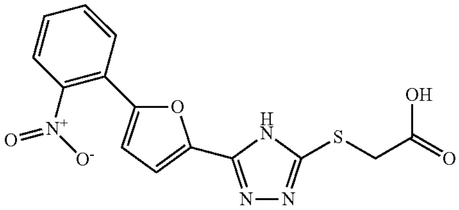 [SMILES: O=C(O)CSc1nnc(-c2ccc(-c3ccccc3[N+](=O)[O-])o2)[nH]1] | 346.32 |
| 1-96 | 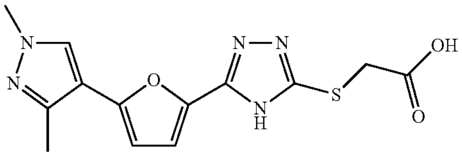 [SMILES: Cc1nn(C)cc1-c1ccc(-c2nnc(SCC(=O)O)[nH]2)o1] | 319.34 |
| 1-98 | 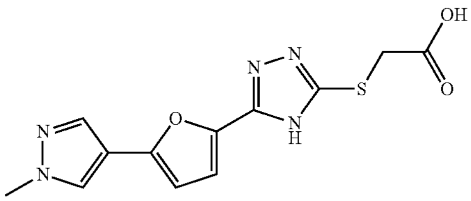 [SMILES: Cn1cc(-c2ccc(-c3nnc(SCC(=O)O)[nH]3)o2)cn1] | 305.31 |

TABLE 7-continued

| # | Compound Structure | MW |
|---|---|---|
| 1-99 | 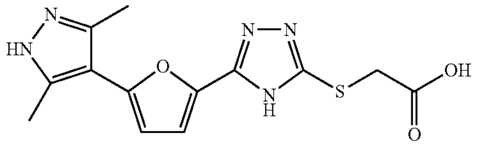 [SMILES: Cc1n[nH]c(C)c1-c1ccc(-c2nnc(SCC(=O)O)[nH]2)o1] | 319.34 |
| 2-100 | 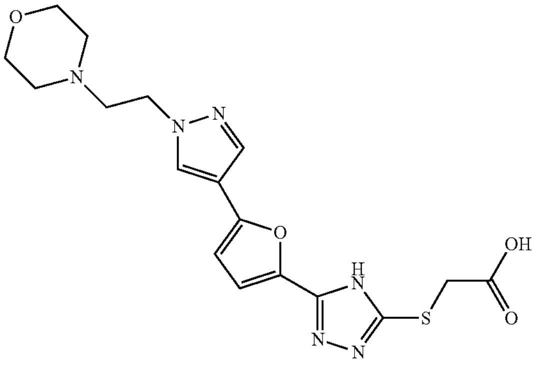 [SMILES: O=C(O)CSc1nnc(-c2ccc(-c3cnn(CCN4CCOCC4)c3)o2)[nH]1] | 404.45 |
| 2-101 | 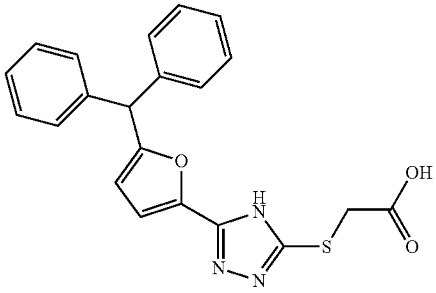 [SMILES: O=C(O)CSc1nnc(-c2ccc(C(c3ccccc3)c3ccccc3)o2)[nH]1] | 391.45 |

Example 12

Preparation of 2-[(5-phenyl-1H-pyrazol-3-yl)sulfanyl]acetic acid (2-12)

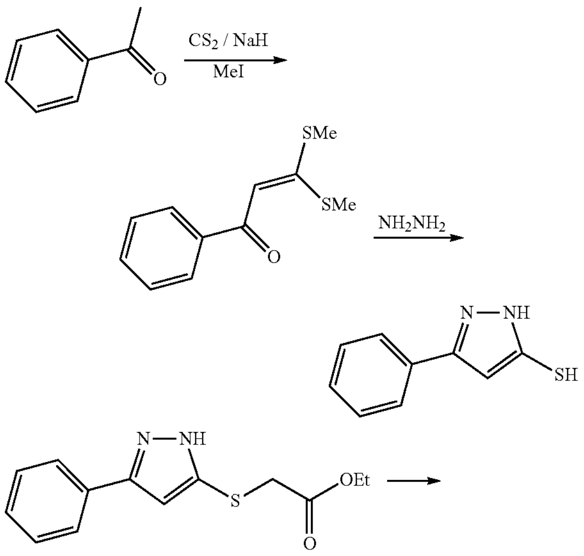

-continued

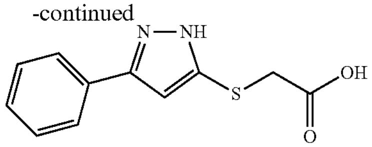

The title compound was prepared using procedures previously reported in Bioorganic & Medicinal Chemistry Letters, volume 22, issue 19, pages 6261-6266, and EP 14810 A2, Example 19, which are incorporated by reference in their entirety herein.

Example 13

Preparation of Additional Pyrazole Derivatives

The following examples (Table 8) can be prepared as described above for the preparation of 2-[(5-phenyl-1H-pyrazol-3-yl)sulfanyl]acetic acid (Example 12) using procedures previously reported in Bioorganic & Medicinal Chemistry Letters, volume 22, issue 19, pages 6261-6266, and EP 14810 A2, Example 19, which are incorporated by reference in their entirety herein.

TABLE 8
| # | Compound Structure | MW |
|---|---|---|
| 2-1 | 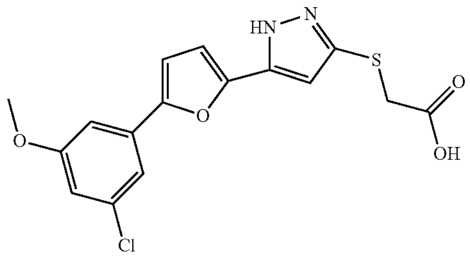 [SMILES: COc1cc(Cl)cc(-c2ccc(-c3cc(SCC(=O)O)n[nH]3)o2)c1] | 364.81 |
| 2-2 | 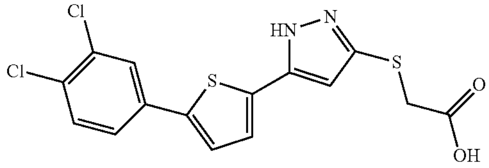 [SMILES: O=C(O)CSc1cc(-c2ccc(-c3ccc(Cl)c(Cl)c3)s2)[nH]n1] | 385.31 |
| 2-3 | 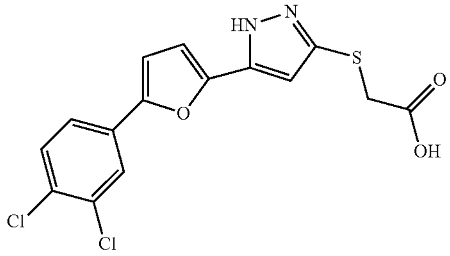 [SMILES: O=C(O)CSc1cc(-c2ccc(-c3ccc(Cl)c(Cl)c3)o2)[nH]n1] | 369.24 |
| 2-4 | 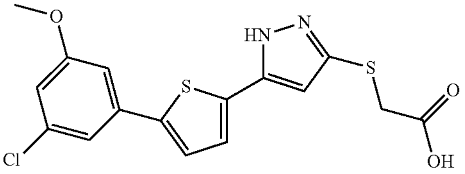 [SMILES: COc1cc(Cl)cc(-c2ccc(-c3cc(SCC(=O)O)n[nH]3)s2)c1] | 380.88 |
| 2-5 | 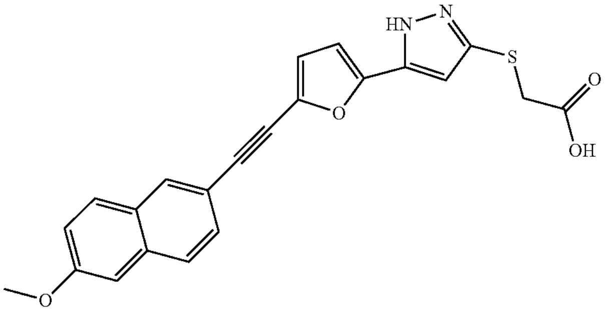 [SMILES: COc1ccc2cc(C#Cc3ccc(-c4cc(SCC(=O)O)n[nH]4)o3)ccc2c1] | 404.44 |
| 2-6 | 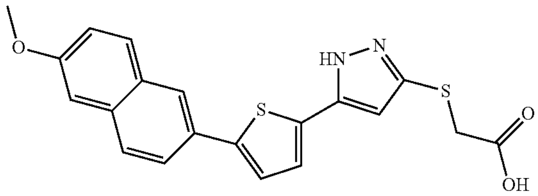 [SMILES: COc1ccc2cc(-c3ccc(-c4cc(SCC(=O)O)n[nH]4)s3)ccc2c1] | 396.49 |
| 2-7 | 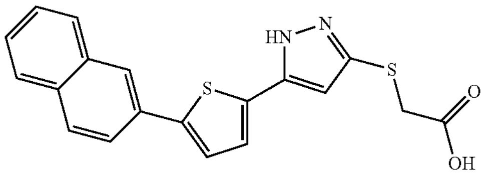 [SMILES: O=C(O)CSc1cc(-c2ccc(-c3ccc4ccccc4c3)s2)[nH]n1] | 366.46 |

TABLE 8-continued
| # | Compound Structure | MW |
| --- | --- | --- |
| 2-8 | 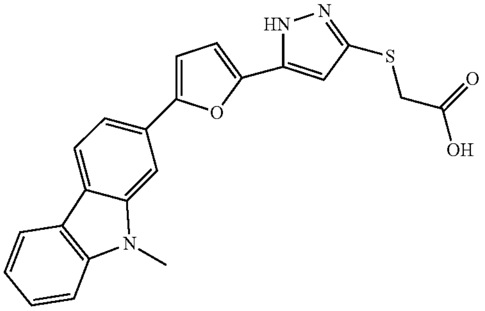 [SMILES: Cn1c2ccccc2c2ccc(-c3ccc(-c4cc(SCC(=O)O)n[nH]4)o3)cc21] | 403.46 |
| 2-9 | 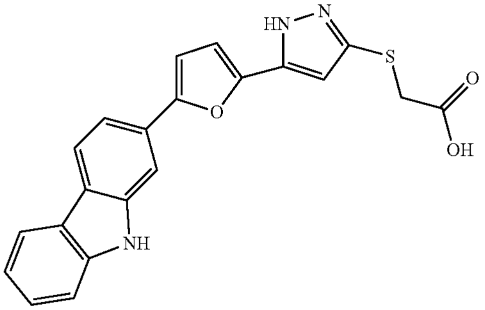 [SMILES: O=C(O)CSc1cc(-c2ccc(-c3ccc4c(c3)[nH]c3ccccc34)o2)[nH]n1] | 389.43 |
| 2-10 | 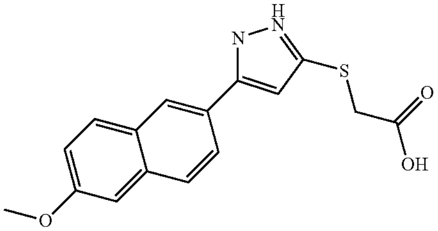 | 314.36 |
| 2-11 | 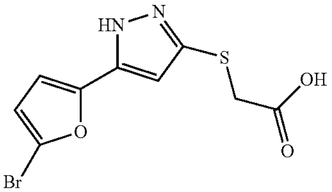 [SMILES: O=C(O)CSc1cc(-c2ccc(Br)o2)[nH]n1] | 303.13 |
| 2-12 | 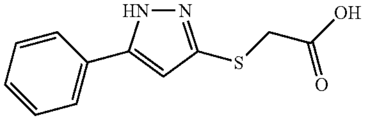 [SMILES: O=C(O)CSc1cc(-c2ccccc2)[nH]n1] | 234.28 |
Example 14
Preparation of 5-(((5-(m-tolyl)-1H-1,2,4-triazol-3-yl)thio)methyl)-1H-tetrazole (3-35)
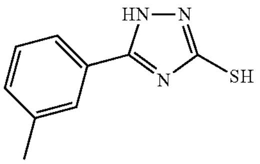
+
-continued
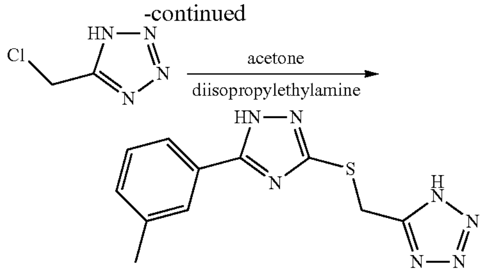
5-(m-tolyl)-1H-1,2,4-triazole-3-thiol (95 mg) and 5-(chloromethyl)-1H-tetrazole (60 mg) were mixed in acetone (1 mL), followed by addition of diisopropylethylamine (130 μL). The mixture was warmed to 50° C. for 1 h and quenched by pouring into water/ethyl acetate. The residue, upon removal of the organic solvent, was purified by HPLC to afford the title compound.

Example 15

Preparation of Additional Tetrazole Derivatives

The following examples (Table 9) can be prepared as described above for the preparation of 2-((5-(5-(5-chlorothiophen-2-yl)furan-2-yl)-4H-1,2,4-triazol-3-yl)thio)acetic acid (Example 6) by substituting 5-(((5-(5-bromofuran-2-yl)-1H-1,2,4-triazol-3-yl)thio)methyl)-1H-tetrazole and the appropriate starting materials, or as described above for the preparation of 5-(((5-(m-tolyl)-1H-1,2,4-triazol-3-yl)thio)methyl)-1H-tetrazole (Example 14) by substituting 5-(3-nitrophenyl)-1H-1,2,4-triazole-3-thiol and the appropriate starting materials.

TABLE 9

| # | Compound Structure | MW |
|---|---|---|
| 3-1 | 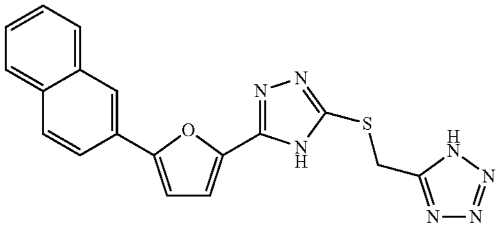 [SMILES: c1ccc2cc(-c3ccc(-c4nnc(SCc5nnn[nH]5)[nH]4)o3)ccc2c1] | 375.41 |
| 3-2 | 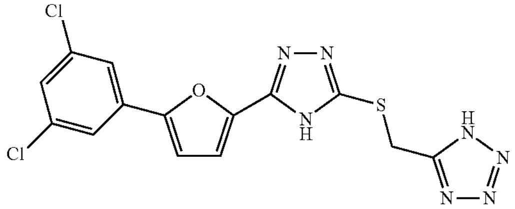 [SMILES: Clc1cc(Cl)cc(-c2ccc(-c3nnc(SCc4nnn[nH]4)[nH]3)o2)c1] | 394.26 |
| 3-3 | 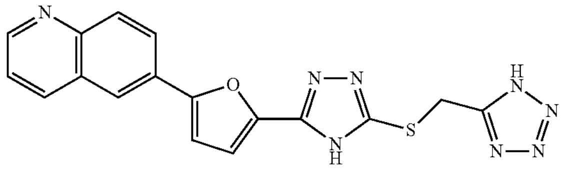 [SMILES: c1cnc2ccc(-c3ccc(-c4nnc(SCc5nnn[nH]5)[nH]4)o3)cc2c1] | 376.40 |
| 3-4 | 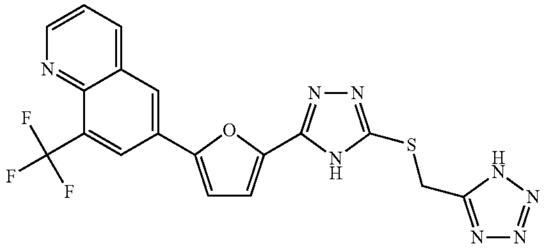 [SMILES: FC(F)(F)c1cc(-c2ccc(-c3nnc(SCc4nnn[nH]4)[nH]3)o2)cc2cccnc12] | 444.40 |
| 3-5 | 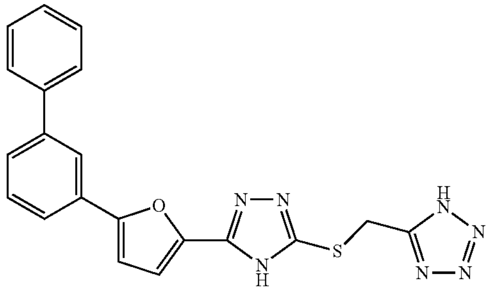 [SMILES: c1ccc(-c2cccc(-c3ccc(-c4nnc(SCc5nnn[nH]5)[nH]4)o3)c2)cc1] | 401.45 |

TABLE 9-continued
| # | Compound Structure | MW |
|---|---|---|
| 3-6 | 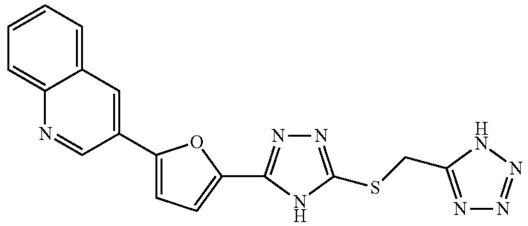 [SMILES: c1ccc2ncc(-c3ccc(-c4nnc(SCc5nnn[nH]5)[nH]4)o3)cc2c1] | 376.40 |
| 3-7 | 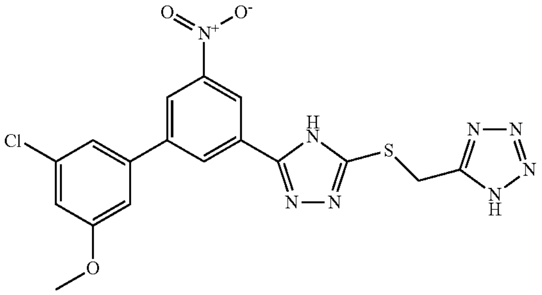 [SMILES: COc1cc(Cl)cc(-c2cc(-c3nnc(SCc4nnn[nH]4)[nH]3)cc([N+](=O)[O-])c2)c1] | 444.87 |
| 3-8 | 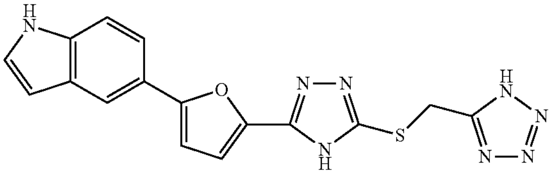 [SMILES: c1cc2cc(-c3ccc(-c4nnc(SCc5nnn[nH]5)[nH]4)o3)ccc2[nH]1] | 364.39 |
| 3-9 | 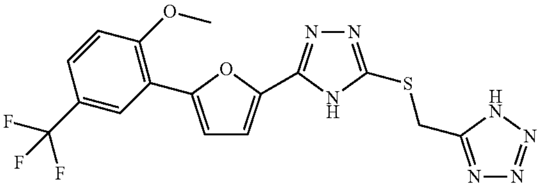 [SMILES: COc1ccc(C(F)(F)F)cc1-c1ccc(-c2nnc(SCc3nnn[nH]3)[nH]2)o1] | 423.37 |
| 3-10 | 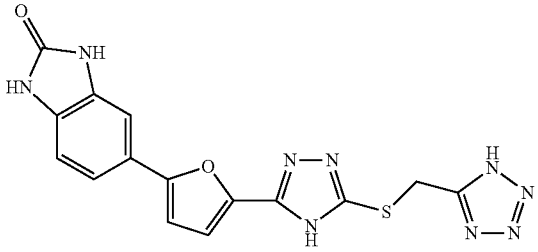 [SMILES: O=c1[nH]c2ccc(-c3ccc(-c4nnc(SCc5nnn[nH]5)[nH]4)o3)cc2[nH]1] | 381.37 |
| 3-11 | 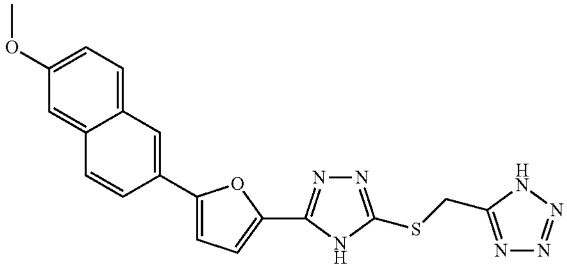 [SMILES: COc1ccc2cc(-c3ccc(-c4nnc(SCc5nnn[nH]5)[nH]4)o3)ccc2c1] | 405.44 |

TABLE 9-continued
| # | Compound Structure | MW |
| --- | --- | --- |
| 3-12 | 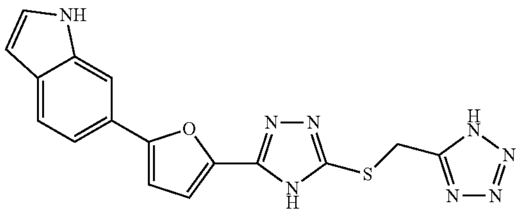 [SMILES: c1cc2ccc(-c3ccc(-c4nnc(SCc5nnn[nH]5)[nH]4)o3)cc2[nH]1] | 364.39 |
| 3-13 | 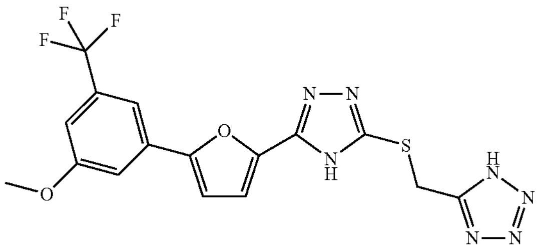 [SMILES: COc1cc(-c2ccc(-c3nnc(SCc4nnn[nH]4)[nH]3)o2)cc(C(F)(F)F)c1] | 423.37 |
| 3-14 | 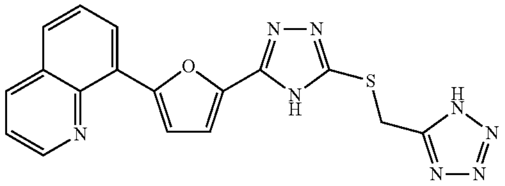 [SMILES: c1cnc2c(-c3ccc(-c4nnc(SCc5nnn[nH]5)[nH]4)o3)cccc2c1] | 376.40 |
| 3-15 | 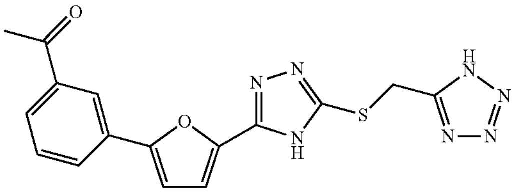 [SMILES: CC(=O)c1cccc(-c2ccc(-c3nnc(SCc4nnn[nH]4)[nH]3)o2)c1] | 367.39 |
| 3-16 | 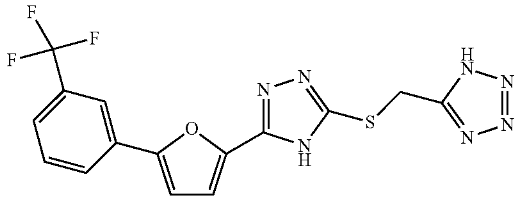 [SMILES: FC(F)(F)c1cccc(-c2ccc(-c3nnc(SCc4nnn[nH]4)[nH]3)o2)c1] | 393.35 |
| 3-17 | 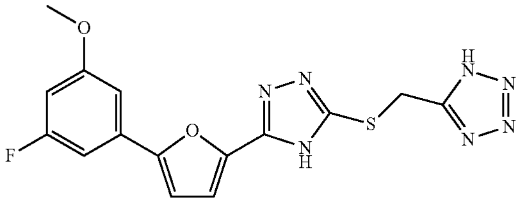 [SMILES: COc1cc(F)cc(-c2ccc(-c3nnc(SCc4nnn[nH]4)[nH]3)o2)c1] | 373.37 |
| 3-18 | 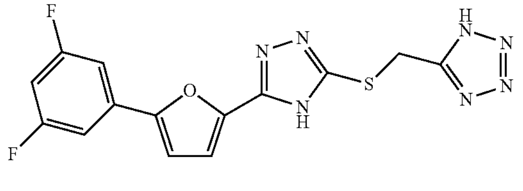 [SMILES: Fc1cc(F)cc(-c2ccc(-c3nnc(SCc4nnn[nH]4)[nH]3)o2)c1] | 361.33 |

TABLE 9-continued
| # | Compound Structure | MW |
|---|---|---|
| 3-19 | 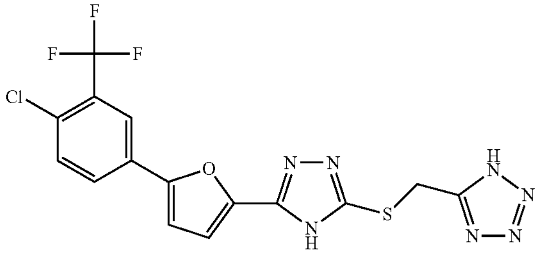 [SMILES: FC(F)(F)c1cc(-c2ccc(-c3nnc(SCc4nnn[nH]4)[nH]3)o2)ccc1Cl] | 427.80 |
| 3-20 | 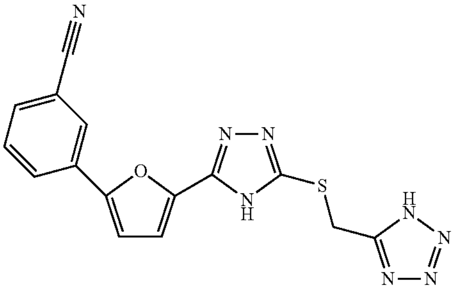 [SMILES: N#Cc1cccc(-c2ccc(-c3nnc(SCc4nnn[nH]4)[nH]3)o2)c1] | 350.36 |
| 3-21 | 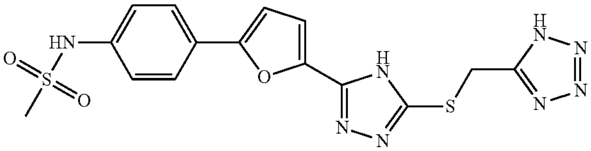 [SMILES: CS(=O)(=O)Nc1ccc(-c2ccc(-c3nnc(SCc4nnn[nH]4)[nH]3)o2)cc1] | 418.46 |
| 3-22 | 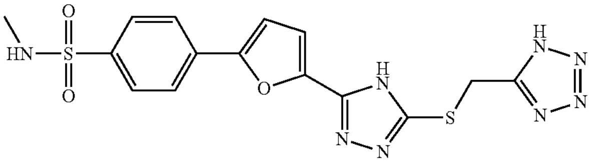 [SMILES: CNS(=O)(=O)c1ccc(-c2ccc(-c3nnc(SCc4nnn[nH]4)[nH]3)o2)cc1] | 418.46 |
| 3-23 | 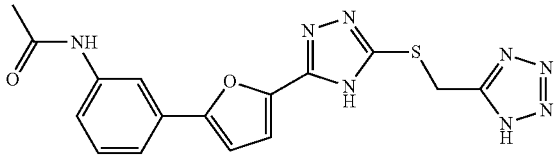 [SMILES: CC(=O)Nc1cccc(-c2ccc(-c3nnc(SCc4nnn[nH]4)[nH]3)o2)c1] | 382.40 |
| 3-24 | 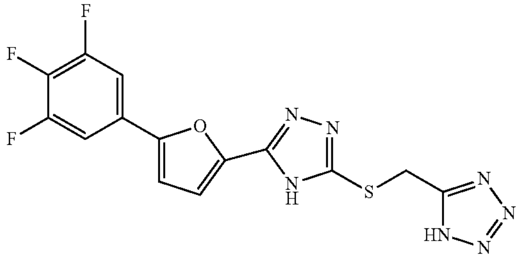 [SMILES: Fc1cc(-c2ccc(-c3nnc(SCc4nnn[nH]4)[nH]3)o2)cc(F)c1F] | 379.32 |
| 3-25 | 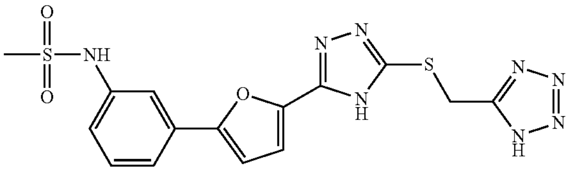 [SMILES: CS(=O)(=O)Nc1cccc(-c2ccc(-c3nnc(SCc4nnn[nH]4)[nH]3)o2)c1] | 418.46 |

TABLE 9-continued
| # | Compound Structure | MW |
|---|---|---|
| 3-26 | 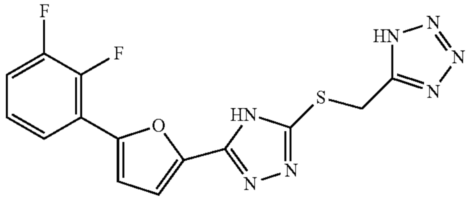 [SMILES: Fc1cccc(-c2ccc(-c3nnc(SCc4nnn[nH]4)[nH]3)o2)c1F] | 361.33 |
| 3-27 | 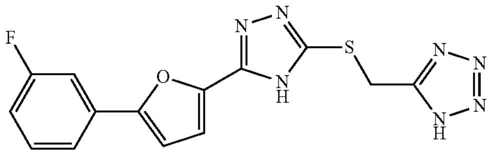 [SMILES: Fc1cccc(-c2ccc(-c3nnc(SCc4nnn[nH]4)[nH]3)o2)c1] | 343.34 |
| 3-28 | 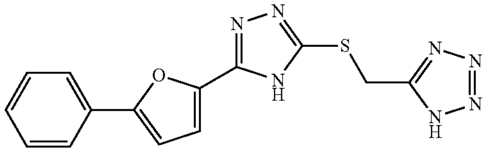 [SMILES: c1ccc(-c2ccc(-c3nnc(SCc4nnn[nH]4)[nH]3)o2)cc1] | 325.35 |
| 3-29 | 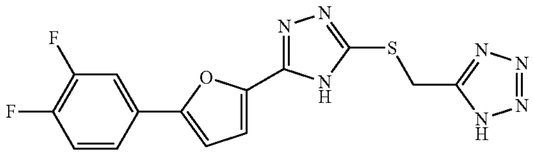 [SMILES: Fc1ccc(-c2ccc(-c3nnc(SCc4nnn[nH]4)[nH]3)o2)cc1F] | 361.33 |
| 3-30 | 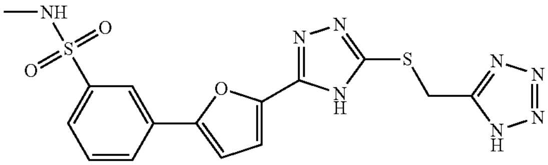 [SMILES: CNS(=O)(=O)c1cccc(-c2ccc(-c3nnc(SCc4nnn[nH]4)[nH]3)o2)c1] | 418.46 |
| 3-31 | 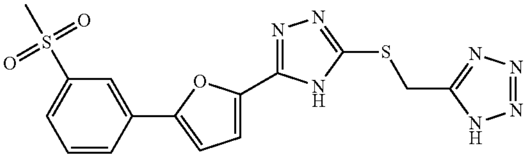 [SMILES: CS(=O)(=O)c1cccc(-c2ccc(-c3nnc(SCc4nnn[nH]4)[nH]3)o2)c1] | 403.44 |
| 3-32 | 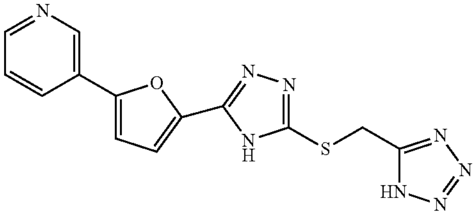 [SMILES: c1cncc(-c2ccc(-c3nnc(SCc4nnn[nH]4)[nH]3)o2)c1] | 326.34 |
| 3-33 | 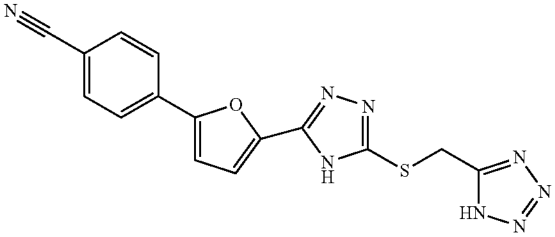 [SMILES: N#Cc1ccc(-c2ccc(-c3nnc(SCc4nnn[nH]4)[nH]3)o2)cc1] | 350.36 |

TABLE 9-continued

| # | Compound Structure | MW |
|---|---|---|
| 3-34 | 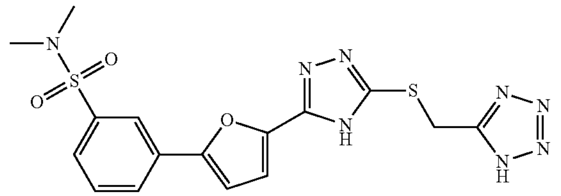 [SMILES: CN(C)S(=O)(=O)c1cccc(-c2ccc(-c3nnc(SCc4nnn[nH]4)[nH]3)o2)c1] | 432.48 |
| 3-35 | 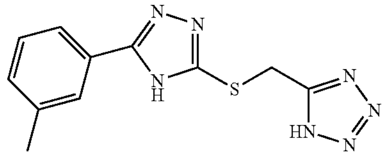 [SMILES: Cc1cccc(-c2nnc(SCc3nnn[nH]3)[nH]2)c1] | 273.32 |

Example 16

Preparation of 2-((5-(1-(3-chlorophenyl)-1H-pyrazol-4-yl)-4H-1,2,4-triazol-3-yl)thio)acetic acid (4-6)

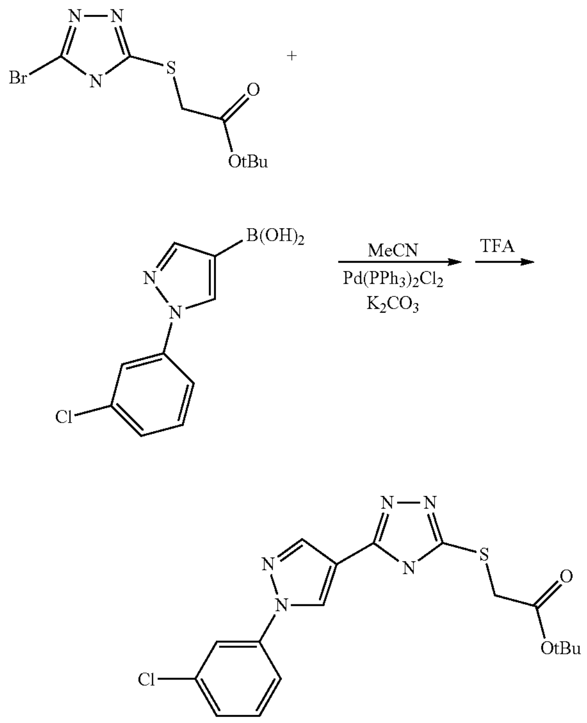

(5-Bromo-1H-pyrrol-2-ylsulfanyl)-acetic acid tert-butyl ester (30 mg, 0.1 mmol) was dissolved in acetonitrile (1 mL) in a microwave vessel, followed by addition of $Pd(PPh_3)_4$ (12 mg, 0.01 mmol), $K_2CO_3$ (0.5 ml, 2 N aq.) and 1-(3-chlorophenyl)pyrazole-4-boronic acid (34 mg, 0.15 mmol). The mixture was heated under microwave irradiation at 130° C. for 30 min. The mixture was subsequently concentrated and treated with trifluoroacetic acid (2 mL) for 2 h at room temperature. It was then concentrated and the residue was purified by prep HPLC to give the title compound (0.8 mg). MS: (m/z) calcd. 355.0, observed ($M+H^+$) 336.0.

Example 17

Preparation of Additional 5-heterocyclic- and hetero-biaryl substituted 2-(1H-1,2,4-triazol-3-yl)thio) acetic acid Derivatives The following examples (Table 10) can be prepared as shown above for the preparation of 2-((5-(1-(3-chlorophenyl)-1H-pyrazol-4-yl)-4H-1,2,4-triazol-3-yl)thio)acetic acid (Example 16) by substituting the appropriate starting materials.

TABLE 10

| # | Compound Structure | MW |
|---|---|---|
| 4-1 | 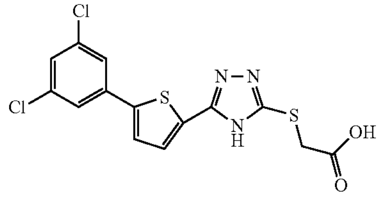 [SMILES: O=C(O)CSc1nnc(-c2ccc(-c3cc(Cl)cc(Cl)c3)s2)[nH]1] | 386.30 |
| 4-2 | 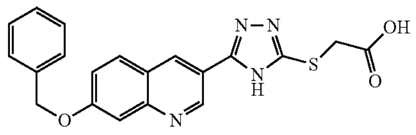 [SMILES: O=C(O)CSc1nnc(-c2cnc3cc(OCc4ccccc4)ccc3c2)[nH]1] | 392.43 |
| 4-3 | 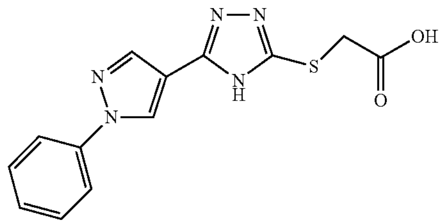 [SMILES: O=C(O)CSc1nnc(-c2cnn(-c3ccccc3)c2)[nH]1] | 301.33 |
| 4-4 | 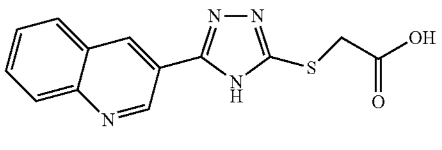 [SMILES: O=C(O)CSc1nnc(-c2cnc3ccccc3c2)[nH]1] | 286.31 |

TABLE 10-continued
| # | Compound Structure | MW |
|---|---|---|
| 4-5 | 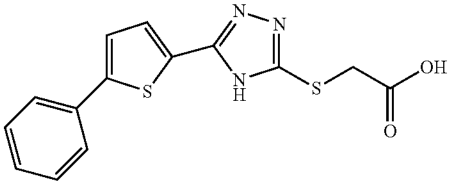 [SMILES: O=C(O)CSc1nnc(-c2ccc(-c3ccccc3)s2)[nH]1] | 317.39 |
| 4-6 | 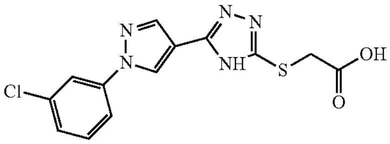 [SMILES: O=C(O)CSc1nnc(-c2cnn(-c3cccc(Cl)c3)c2)[nH]1] | 335.78 |
| 4-7 | 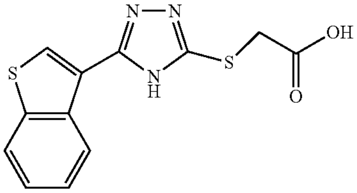 [SMILES: O=C(O)CSc1nnc(-c2csc3ccccc23)[nH]1] | 291.35 |
| 4-8 | 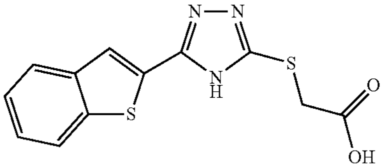 [SMILES: O=C(O)CSc1nnc(-c2cc3ccccc3s2)[nH]1] | 291.35 |
| 4-9 | 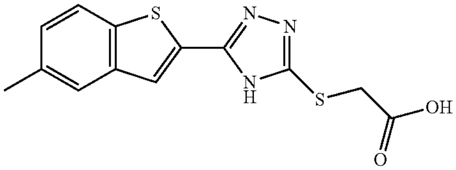 [SMILES: Cc1ccc2sc(-c3nnc(SCC(=O)O)[nH]3)cc2c1] | 305.38 |
| 4-10 | 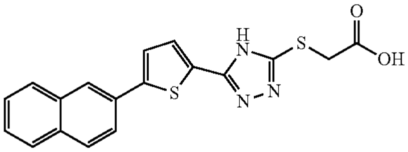 [SMILES: O=C(O)CSc1nnc(-c2ccc(-c3ccc4ccccc4c3)s2)[nH]1] | 367.45 |
| 4-11 | 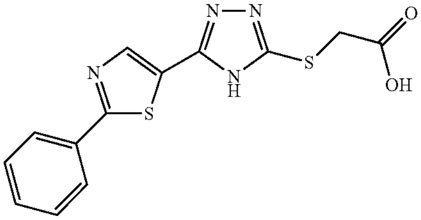 [SMILES: O=C(O)CSc1nnc(-c2cnc(-c3ccccc3)s2)[nH]1] | 318.38 |
| 4-12 | 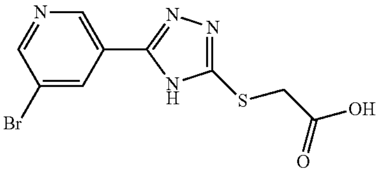 [SMILES: O=C(O)CSc1nnc(-c2cncc(Br)c2)[nH]1] | 315.15 |
| 4-13 | 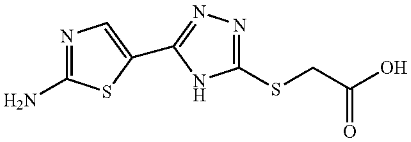 [SMILES: Nc1ncc(-c2nnc(SCC(=O)O)[nH]2)s1] | 257.30 |
| 4-14 | 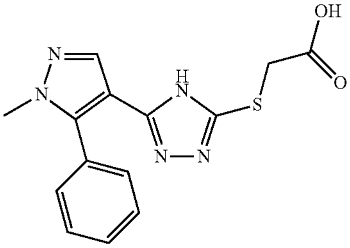 [SMILES: Cn1ncc(-c2nnc(SCC(=O)O)[nH]2)c1-c1ccccc1] | 315.35 |
| 4-15 | 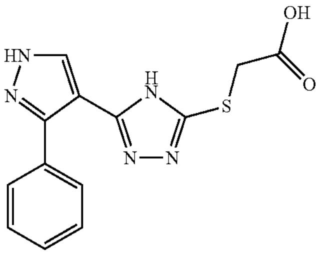 [SMILES: O=C(O)CSc1nnc(-c2c[nH]nc2-c2ccccc2)[nH]1] | 301.33 |
| 4-16 | 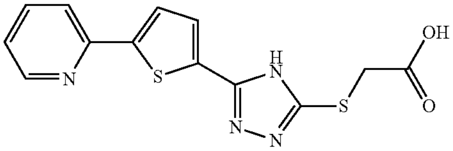 [SMILES: O=C(O)CSc1nnc(-c2ccc(-c3ccccn3)s2)[nH]1] | 318.38 |
| 4-18 | 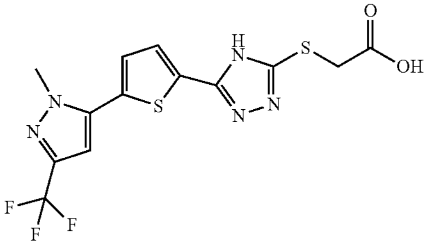 [SMILES: Cn1nc(C(F)(F)F)cc1-c1ccc(-c2nnc(SCC(=O)O)[nH]2)s1] | 389.38 |
| 4-19 | 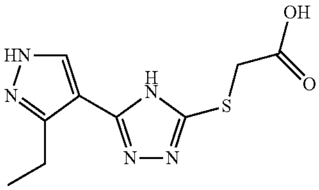 [SMILES: CCc1n[nH]cc1-c1nnc(SCC(=O)O)[nH]1] | 253.28 |
| 4-20 | 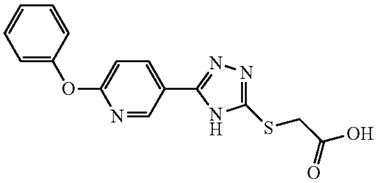 [SMILES: O=C(O)CSc1nnc(-c2ccc(Oc3ccccc3)nc2)[nH]1] | 328.35 |

TABLE 10-continued

| # | Compound Structure | MW |
|---|---|---|
| 4-22 | 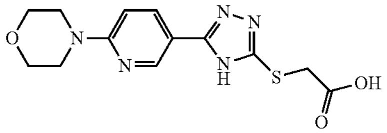 [SMILES: O=C(O)CSc1nnc(-c2ccc(N3CCOCC3)nc2)[nH]1] | 321.36 |
| 4-24 | 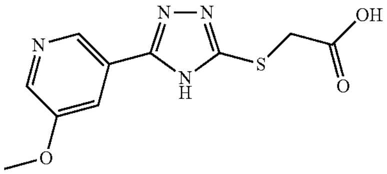 [SMILES: COc1cncc(-c2nnc(SCC(=O)O)[nH]2)c1] | 266.28 |
| 4-26 | 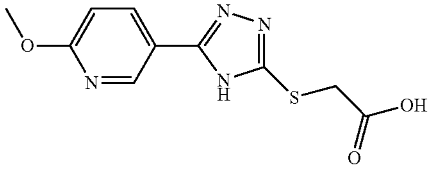 [SMILES: COc1ccc(-c2nnc(SCC(=O)O)[nH]2)cn1] | 266.28 |
| 4-29 | 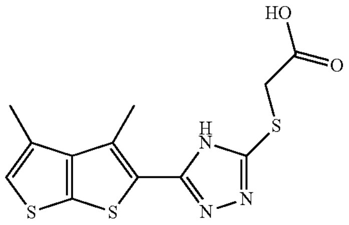 [SMILES: Cc1csc2sc(-c3nnc(SCC(=O)O)[nH]3)c(C)c12] | 325.43 |
| 4-38 | 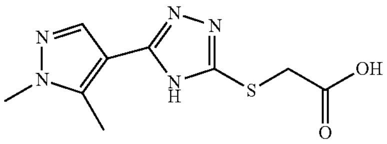 [SMILES: Cc1c(-c2nnc(SCC(=O)O)[nH]2)cnn1C] | 253.28 |
| 4-41 | 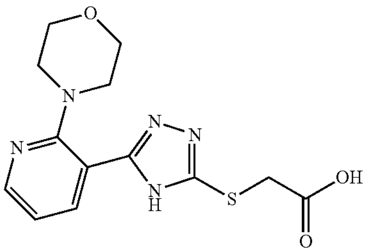 [SMILES: O=C(O)CSc1nnc(-c2cccnc2N2CCOCC2)[nH]1] | 321.36 |
| 4-43 | 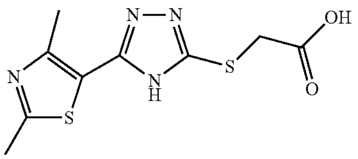 [SMILES: Cc1nc(C)c(-c2nnc(SCC(=O)O)[nH]2)s1] | 270.33 |
| 4-47 | 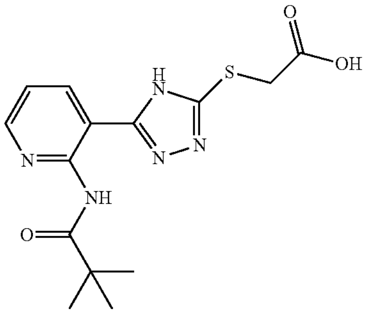 [SMILES: CC(C)(C)C(=O)Nc1ncccc1-c1nnc(SCC(=O)O)[nH]1] | 335.38 |
| 4-48 | 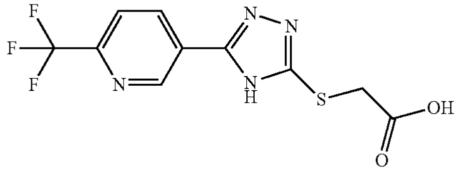 [SMILES: O=C(O)CSc1nnc(-c2ccc(C(F)(F)F)nc2)[nH]1] | 304.25 |
| 4-51 | 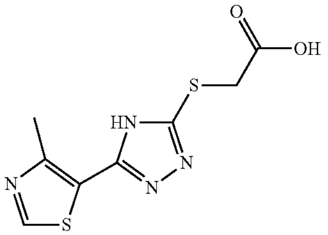 [SMILES: Cc1ncsc1-c1nnc(SCC(=O)O)[nH]1] | 256.31 |

Example 18

$IC_{50}$ Determination for Series 1

General Assay Conditions

The following assay conditions were used.

Buffer: 50 mM TRIS-HCl, pH 7.5, 5 mM $MgCl_2$, 2 mM DTT, 0.01% Triton X-100, 10 μM $Na_3VO_4$, 10 μM b-GP, 1% DMSO Enzyme: 20 nM GRK6, recombinant full-length GST-tagged human protein ATP: 12 μM (Km)

Peptide substrate (Peptide 216): 1 μM

Incubation Time: 7 h

One hundred two compounds (1-1-1-102) were further characterized by determining $IC_{50}$ values in a GRK6 assay. This screen has been previously described in WO 2013/063458, which is incorporated by reference in its entirety herein. Briefly, the following activities were performed: 8-point concentration-response determinations in singlicate wells (top concentration=60 μM, 3-fold dilution steps); Repeat tests for QC failed or inconclusive compounds; and Repeat tests (titrate down) for compounds with >50% inhibition at all tested concentrations.

Results of the testing are shown in Table 11.

TABLE 11

| # | $IC_{50}$ |
|---|---|
| 1-1 | 0.079 |
| 1-2 | 0.126 |
| 1-3 | 0.131 |

TABLE 11-continued

| # | $IC_{50}$ |
|---|---|
| 1-4 | 0.133 |
| 1-5 | 0.137 |
| 1-6 | 0.162 |
| 1-7 | 0.167 |
| 1-8 | 0.17 |
| 1-9 | 0.175 |
| 1-10 | 0.186 |
| 1-11 | 0.187 |
| 1-12 | 0.189 |
| 1-13 | 0.195 |
| 1-14 | 0.216 |
| 1-15 | 0.234 |
| 1-16 | 0.241 |
| 1-17 | 0.245 |
| 1-18 | 0.25 |
| 1-19 | 0.259 |
| 1-20 | 0.26 |
| 1-21 | 0.265 |
| 1-22 | 0.269 |
| 1-23 | 0.273 |
| 1-24 | 0.276 |
| 1-25 | 0.284 |
| 1-26 | 0.285 |
| 1-27 | 0.309 |
| 1-28 | 0.311 |
| 1-29 | 0.314 |
| 1-30 | 0.315 |
| 1-31 | 0.324 |
| 1-32 | 0.327 |
| 1-33 | 0.332 |
| 1-34 | 0.341 |
| 1-35 | 0.347 |
| 1-36 | 0.359 |
| 1-37 | 0.359 |
| 1-38 | 0.362 |
| 1-39 | 0.364 |
| 1-40 | 0.367 |
| 1-41 | 0.368 |
| 1-42 | 0.392 |
| 1-43 | 0.395 |
| 1-44 | 0.402 |
| 1-45 | 0.413 |
| 1-46 | 0.421 |
| 1-47 | 0.424 |
| 1-48 | 0.458 |
| 1-49 | 0.458 |
| 1-50 | 0.473 |
| 1-51 | 0.497 |
| 1-52 | 0.505 |
| 1-53 | 0.514 |
| 1-54 | 0.516 |
| 1-55 | 0.563 |
| 1-56 | 0.595 |
| 1-57 | 0.608 |
| 1-58 | 0.616 |
| 1-59 | 0.617 |
| 1-60 | 0.63 |
| 1-61 | 0.635 |
| 1-62 | 0.636 |
| 1-63 | 0.699 |
| 1-64 | 0.711 |
| 1-65 | 0.711 |
| 1-66 | 0.734 |
| 1-67 | 0.737 |
| 1-68 | 0.813 |
| 1-69 | 0.828 |
| 1-70 | 0.86 |
| 1-71 | 0.875 |
| 1-72 | 0.987 |
| 1-73 | 0.996 |
| 1-74 | 1.02 |
| 1-75 | 1.05 |
| 1-76 | 1.12 |
| 1-77 | 1.15 |
| 1-78 | 1.17 |
| 1-79 | 1.17 |
| 1-80 | 1.21 |
| 1-81 | 1.21 |

TABLE 11-continued

| # | $IC_{50}$ |
|---|---|
| 1-82 | 1.31 |
| 1-83 | 1.41 |
| 1-84 | 1.44 |
| 1-85 | 1.44 |
| 1-86 | 1.57 |
| 1-87 | 1.8 |
| 1-88 | 1.82 |
| 1-89 | 2.02 |
| 1-90 | 2.04 |
| 1-91 | 2.09 |
| 1-92 | 2.17 |
| 1-93 | 2.3 |
| 1-94 | 3.1 |
| 1-95 | 3.18 |
| 1-96 | 3.31 |
| 1-97 | 3.33 |
| 1-98 | 3.68 |
| 1-99 | 4.37 |
| 1-100 | 6.2 |
| 1-101 | 6.71 |
| 1-102 | 8.25 |

Example 19

$IC_{50}$ Determination for Series 2

Twelve compounds (2-1-2-12) were further characterized by determining the $IC_{50}$ values in a GRK6 assay. This screen has been previously described in WO 2013/063458, which is incorporated by reference in its entirety herein. Specific activities were performed as described above (Example 18).

Results of the testing are shown in Table 12.

TABLE 12

| # | $IC_{50}$ |
|---|---|
| 2-1 | 0.309 |
| 2-2 | 0.402 |
| 2-3 | 0.475 |
| 2-4 | 0.608 |
| 2-5 | 0.626 |
| 2-6 | 0.721 |
| 2-7 | 0.788 |
| 2-8 | 1.25 |
| 2-9 | 1.29 |
| 2-10 | 1.47 |
| 2-11 | 5.44 |
| 2-12 | 18.3 |

Example 20

$IC_{50}$ Determination for Series 3

Thirty-six compounds (3-1-3-36) were further characterized by determining the $IC_{50}$ values in a GRK6 assay. This screen has been previously described in WO 2013/063458, which is incorporated by reference in its entirety herein. Specific activities were performed as described above (Example 18).

Results of the testing are shown in Table 13.

TABLE 13

| # | $IC_{50}$ |
|---|---|
| 3-1 | 0.442 |
| 3-2 | 0.545 |

TABLE 13-continued

| # | $IC_{50}$ |
|---|---|
| 3-3 | 0.667 |
| 3-4 | 0.881 |
| 3-5 | 0.9 |
| 3-6 | 1.1 |
| 3-7 | 1.21 |
| 3-8 | 1.27 |
| 3-9 | 1.28 |
| 3-10 | 1.51 |
| 3-11 | 1.53 |
| 3-12 | 1.58 |
| 3-13 | 2.16 |
| 3-14 | 2.34 |
| 3-15 | 2.48 |
| 3-16 | 2.55 |
| 3-17 | 2.86 |
| 3-18 | 3.31 |
| 3-19 | 3.57 |
| 3-20 | 3.62 |
| 3-21 | 3.71 |
| 3-22 | 3.78 |
| 3-23 | 3.81 |
| 3-24 | 3.83 |
| 3-25 | 4.66 |
| 3-26 | 5.52 |
| 3-27 | 5.63 |
| 3-28 | 6.21 |
| 3-29 | 6.9 |
| 3-30 | 7.16 |
| 3-31 | 7.45 |
| 3-32 | 8.63 |
| 3-33 | 8.91 |
| 3-34 | 9.09 |
| 3-35 | 16.9 |
| 3-36 | 9.05 |

Example 21

$IC_{50}$ Determination for Series 4

Fifty-four compounds (4-1-4-54) were further characterized by determining the $IC_{50}$ values in a GRK6 assay. This screen has been previously described in WO 2013/063458, which is incorporated by reference in its entirety herein. Specific activities were performed as described above (Example 18).

Results of the testing are shown in Table 14.

TABLE 14

| # | $IC_{50}$ |
|---|---|
| 4-1 | 0.595 |
| 4-2 | 0.78 |
| 4-3 | 1.01 |
| 4-4 | 1.12 |
| 4-5 | 1.27 |
| 4-6 | 2.01 |
| 4-7 | 2.56 |
| 4-8 | 2.58 |
| 4-9 | 2.61 |
| 4-10 | 2.98 |
| 4-11 | 3.64 |
| 4-12 | 4.11 |
| 4-13 | 4.64 |
| 4-14 | 5.7 |
| 4-15 | 6.29 |
| 4-16 | 6.54 |
| 4-17 | 7.1 |
| 4-18 | 7.41 |
| 4-19 | 8.96 |
| 4-20 | 9.21 |
| 4-21 | 9.61 |
| 4-22 | 11.3 |
| 4-23 | 12.3 |
| 4-24 | 12.9 |
| 4-25 | 13 |
| 4-26 | 13 |
| 4-27 | 20.7 |
| 4-28 | 22.3 |
| 4-29 | 27.3 |
| 4-30 | 27.8 |
| 4-31 | 31.2 |
| 4-32 | 32.5 |
| 4-33 | 35.3 |
| 4-34 | 38.8 |
| 4-35 | 78.7 |
| 4-36 | 82.7 |
| 4-37 | 89.2 |
| 4-38 | 95.4 |
| 4-39 | >100.0 |
| 4-40 | >100.0 |
| 4-41 | >100.0 |
| 4-42 | >100.0 |
| 4-43 | >100.0 |
| 4-44 | >100.0 |
| 4-45 | >86.0 |
| 4-46 | >80.0 |
| 4-47 | >64.0 |
| 4-48 | >54.0 |
| 4-49 | >100.0 |
| 4-50 | >100.0 |
| 4-51 | >100.0 |
| 4-52 | >100.0 |
| 4-53 | >100.0 |
| 4-54 | 100.0 |

Other Embodiments

It is to be understood that while the invention has been described in conjunction with the detailed description thereof, the foregoing description is intended to illustrate and not limit the scope of the invention, which is defined by the scope of the appended claims Other aspects, advantages, and modifications are within the scope of the following claims.

What is claimed is:

1. A compound of Formula I:

Formula I

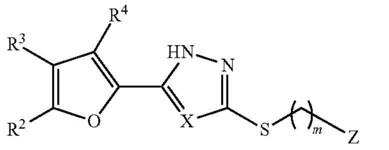

or a pharmaceutically acceptable salt thereof, wherein:

X is selected from the group consisting of CH and N;

Z is selected from the group consisting of —C(O)O$R^1$ and

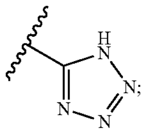 [SMILES: *c1nnn[nH]1]

$R^1$ is selected from the group consisting of H and ($C_1$-$C_6$)alkyl;

$R^2$ is selected from the group consisting of: a substituted $(C_1-C_6)$alkyl, a substituted or unsubstituted $(C_2-C_6)$alkenyl, a substituted or unsubstituted $(C_2-C_6)$alkynyl, $(C_1-C_6)$haloalkyl, a substituted or unsubstituted cycloalkyl, a substituted or unsubstituted heterocycloalkyl, a substituted or unsubstituted aryl, and a substituted or unsubstituted heteroaryl;

$R^3$ and $R^4$ are independently selected from the group consisting of: H, halo, a substituted $(C_1-C_6)$alkyl, a substituted or unsubstituted $(C_2-C_6)$alkenyl, a substituted or unsubstituted $(C_2-C_6)$alkynyl, $(C_1-C_6)$haloalkyl, a substituted or unsubstituted cycloalkyl, a substituted or unsubstituted heterocycloalkyl, a substituted or unsubstituted aryl, a substituted or unsubstituted heteroaryl, a substituted or unsubstituted aralkyl, and a substituted or unsubstituted heteroaralkyl;

or $R^2$ and $R^3$ or $R^3$ and $R^4$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and m is an integer from 1 to 2.

2. The compound of claim 1, wherein $R^2$ is a substituted or unsubstituted aryl.

3. The compound of claim 1, wherein $R^2$ is a substituted or unsubstituted heteroaryl.

4. The compound of claim 1, wherein:

$R^3$ is selected from a group consisting of: a substituted or unsubstituted $(C_1-C_6)$alkynyl, halo, and a substituted or unsubstituted aryl; and $R^4$ is H.

5. The compound of claim 1, wherein:

each of $R^1$, $R^3$, and $R^4$ is H; and $R^2$ is a substituted or unsubstituted heteroaryl.

6. The compound of claim 5, wherein $R^2$ is selected from a group consisting of pyridazinyl, pyridyl, carbazolyl, thiopheneyl, benzothiopheneyl, pyrrolyl, indolyl, quinolinyl, furanyl, and benzofuranyl.

7. The compound of claim 1, wherein:

each of $R^1$ and $R^4$ is H;

$R^2$ is selected from a group consisting of a substituted or unsubstituted aryl and a substituted or unsubstituted heteroaryl; and $R^3$ is selected from a group consisting of halo, a substituted $(C_1-C_6)$alkynyl, and a substituted or unsubstituted aryl.

8. The compound of claim 1, wherein the compound is selected from a group consisting of:

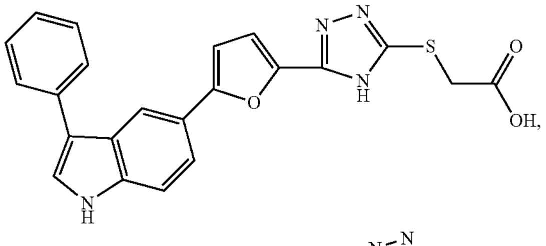

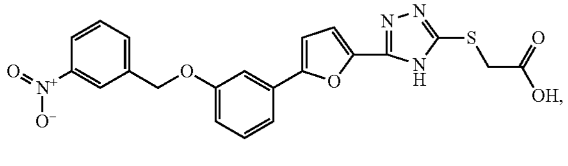

-continued

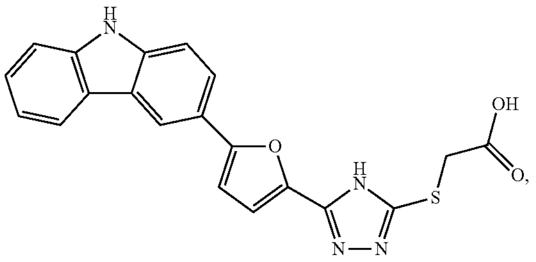

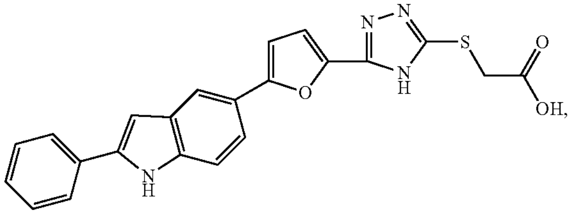

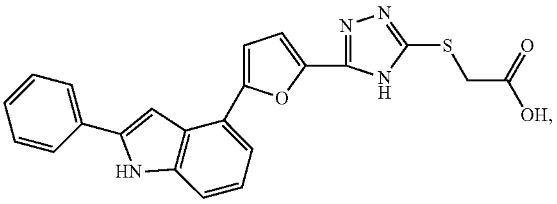

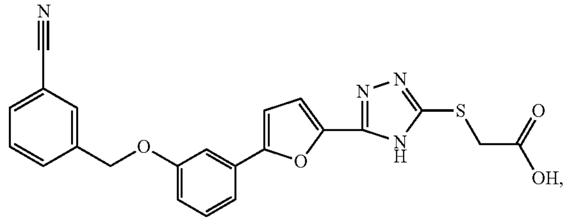

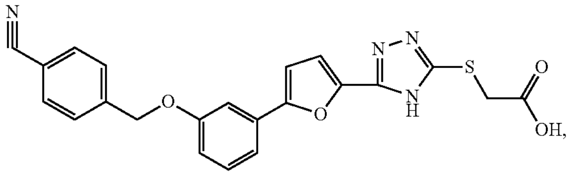

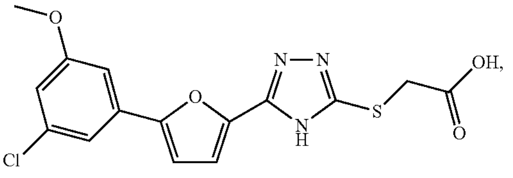

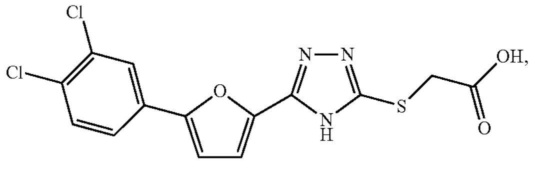

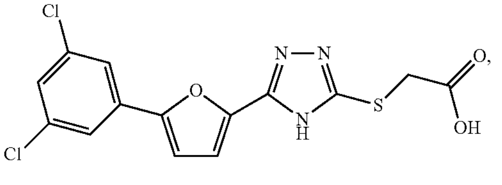

-continued
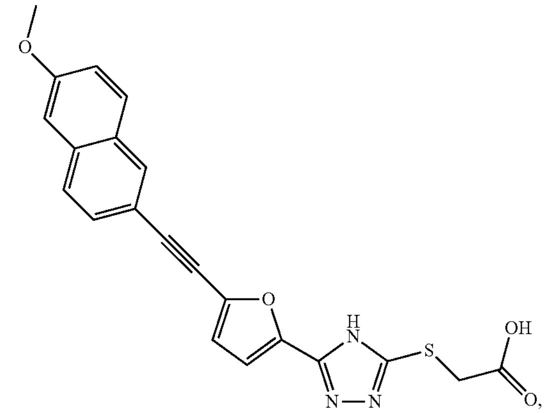
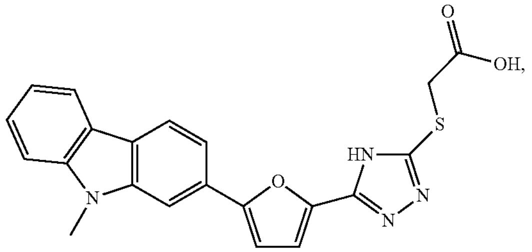
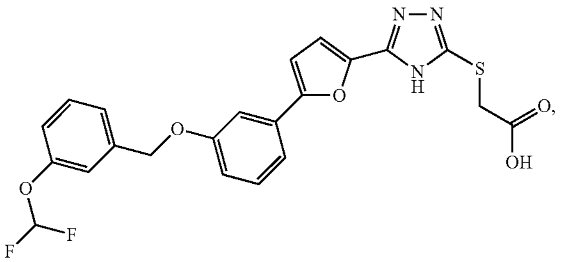
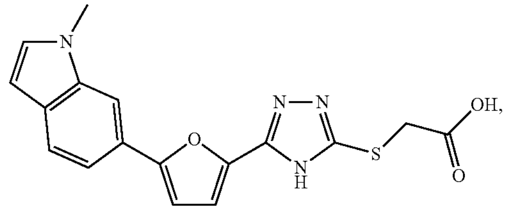
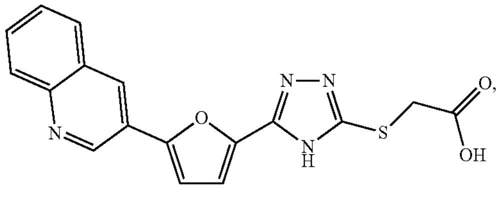
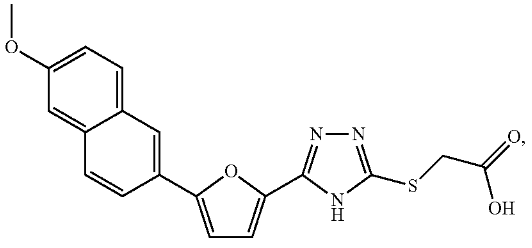
-continued
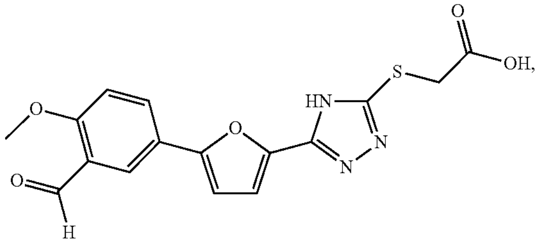
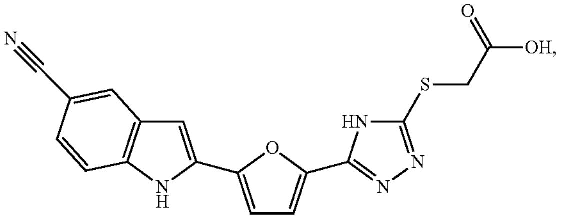
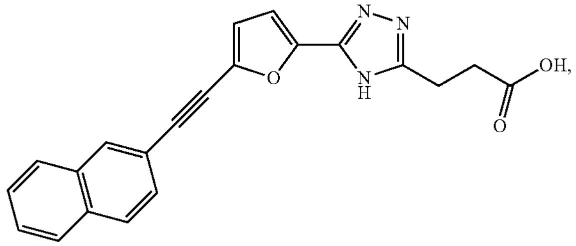
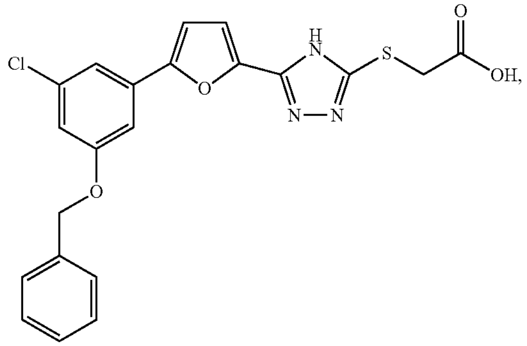
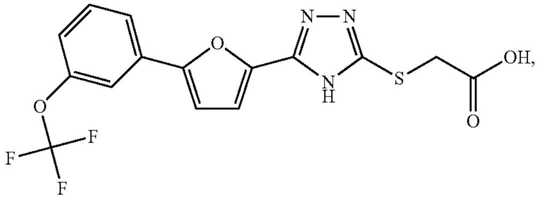
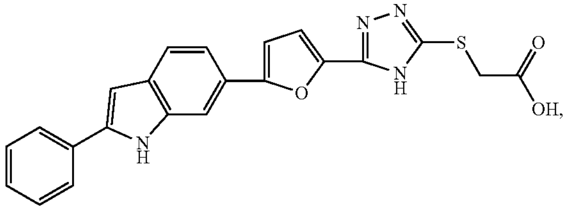
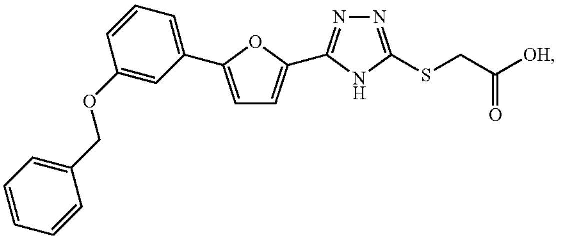

-continued
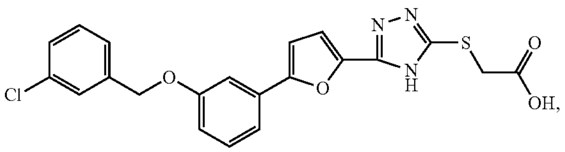
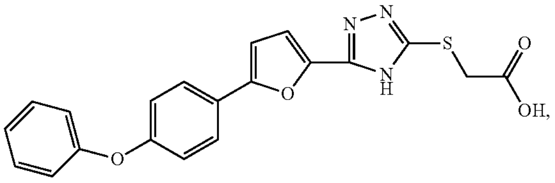
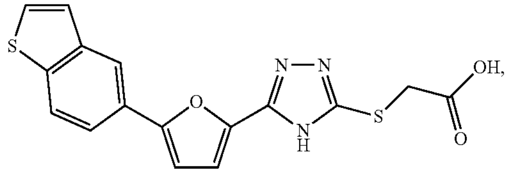
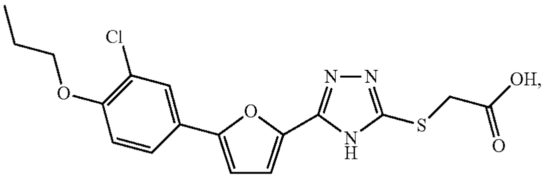
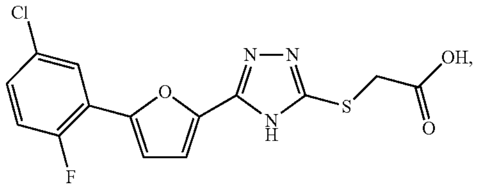
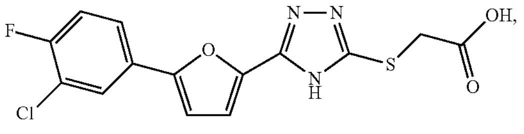
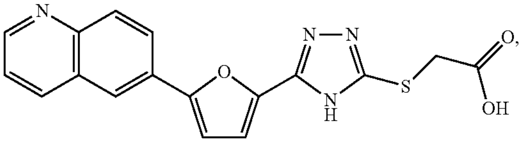
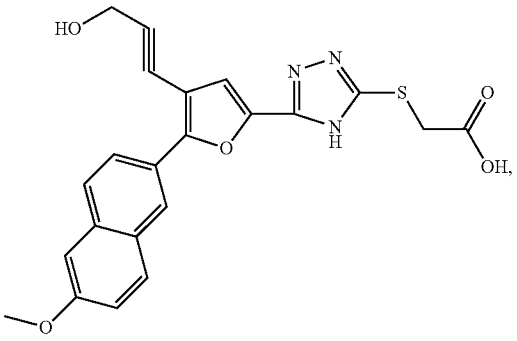
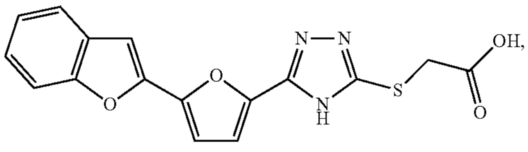
-continued
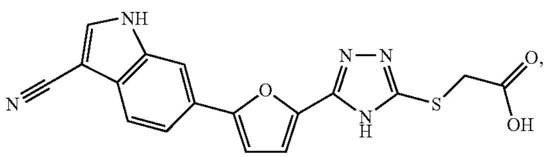
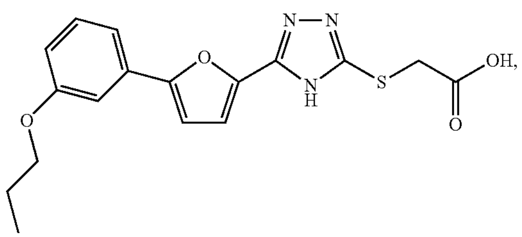
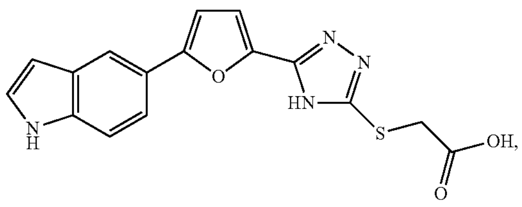
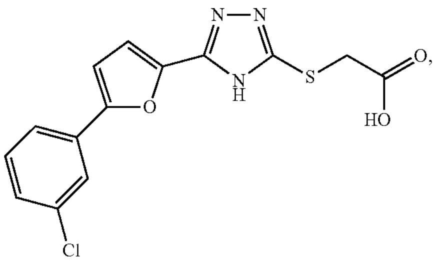
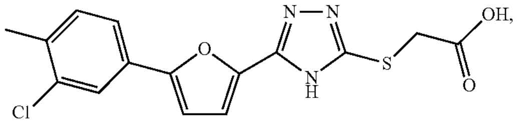
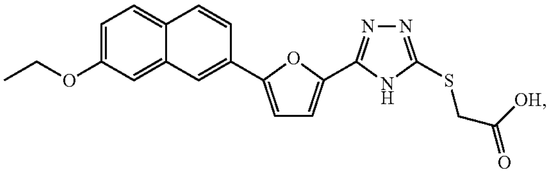
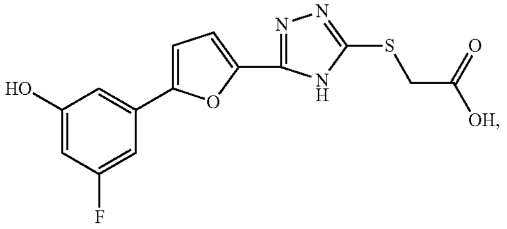
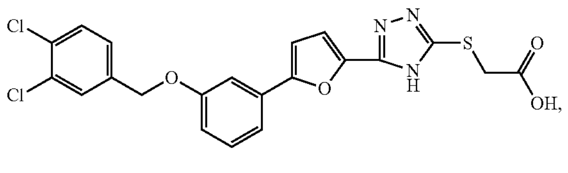

-continued
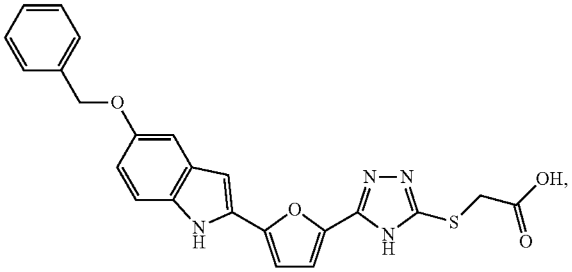
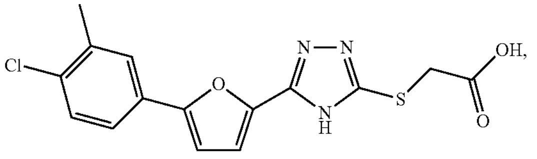
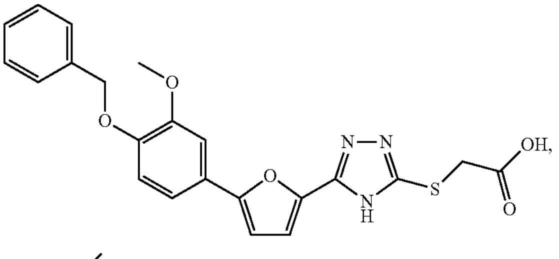
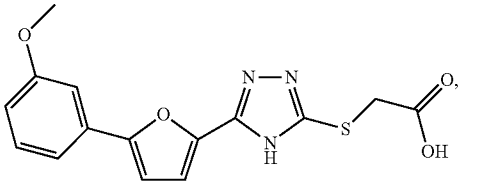
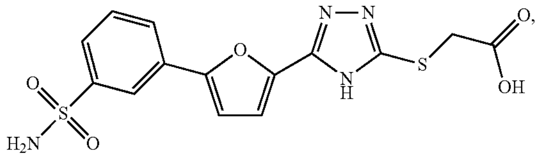
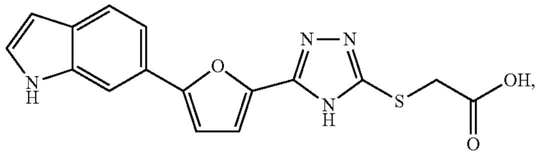
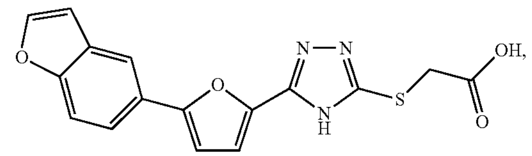
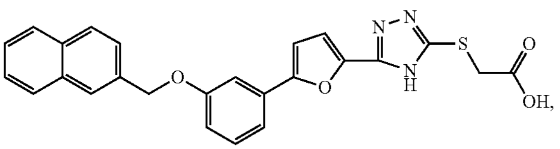
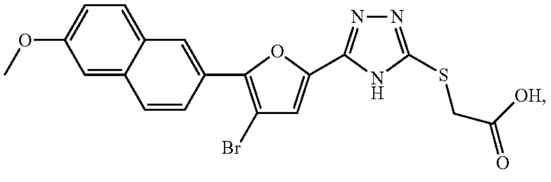
-continued
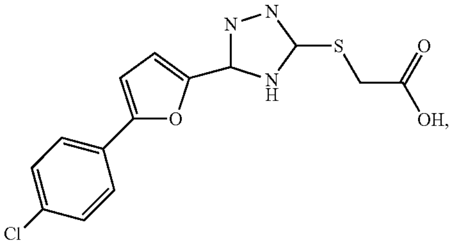
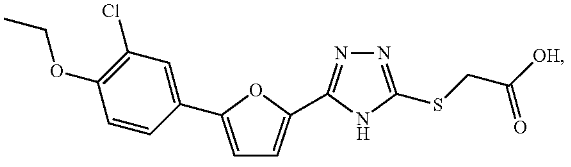
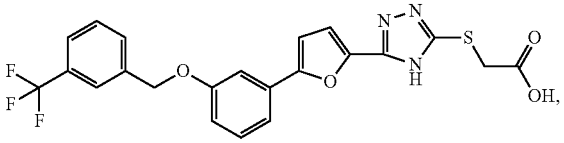
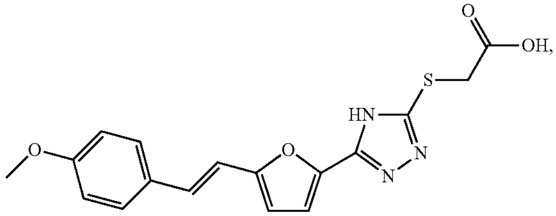
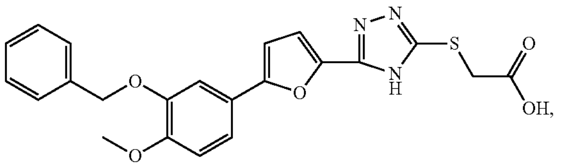
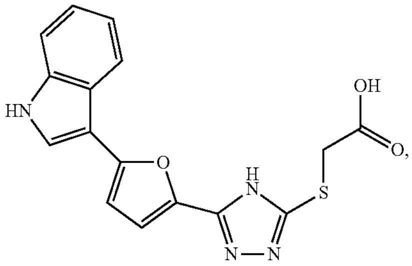
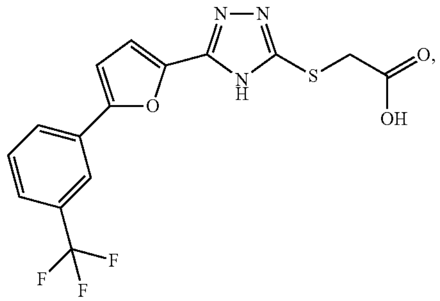
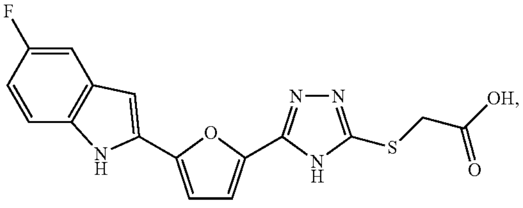

-continued
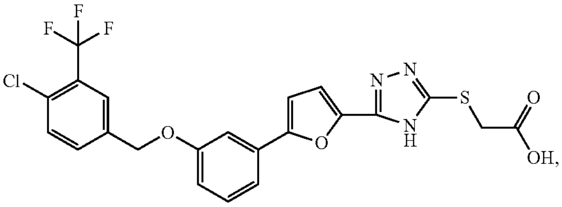
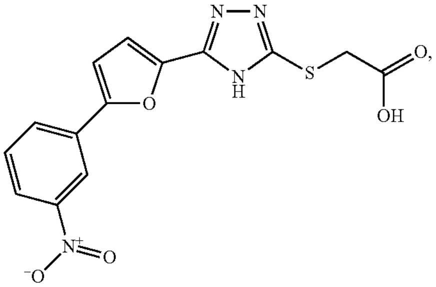
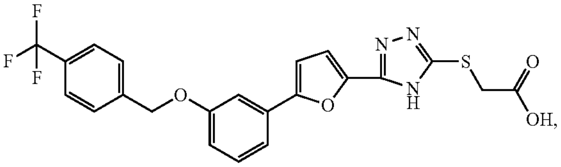
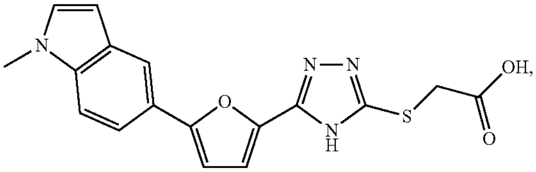
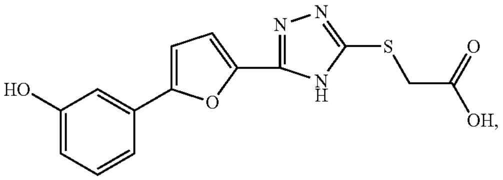
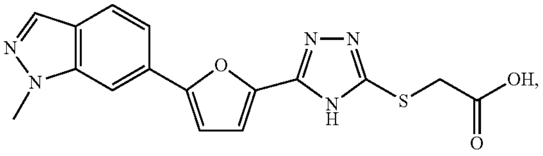
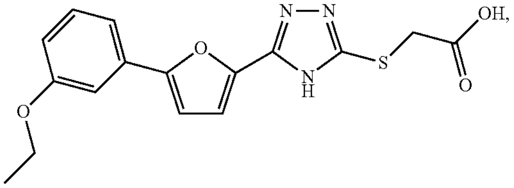
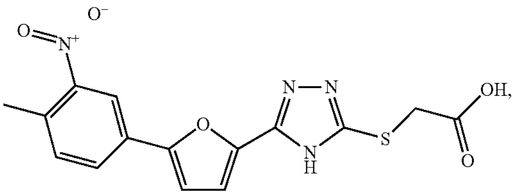
-continued
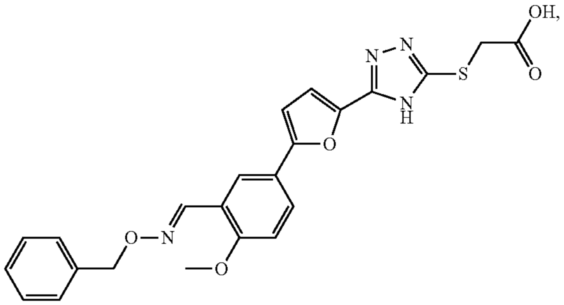
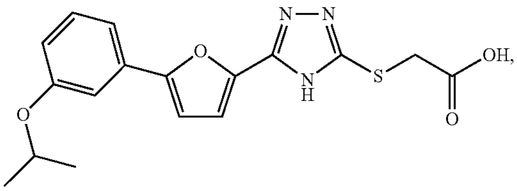
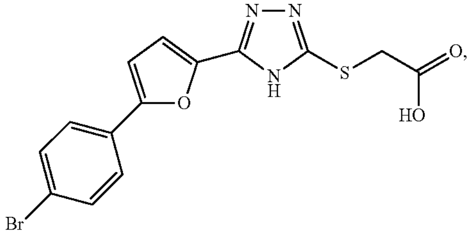
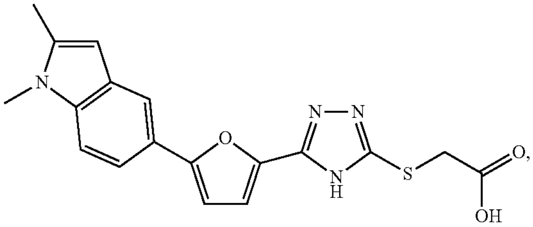
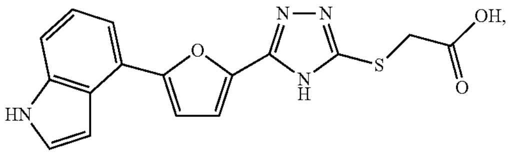
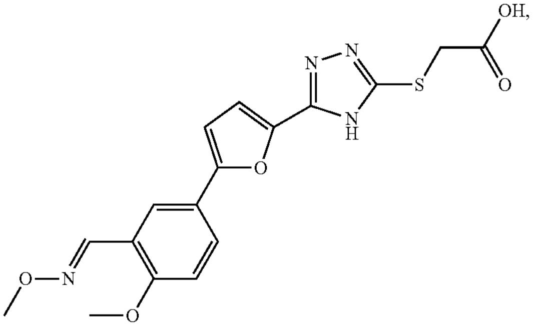
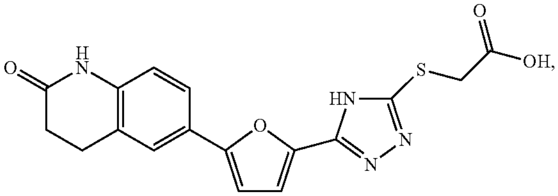

-continued
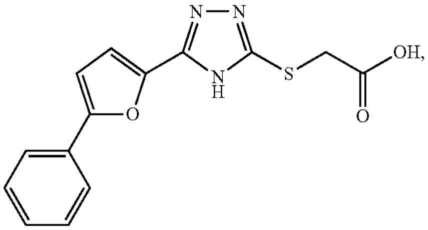
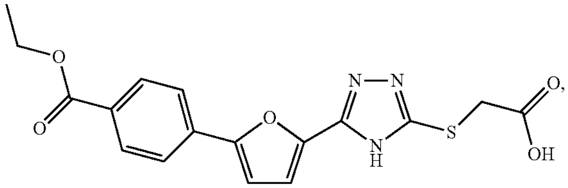
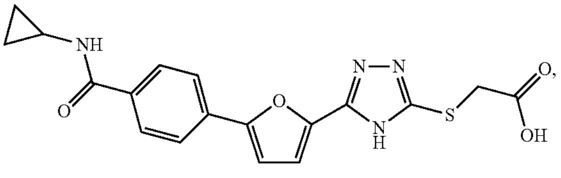
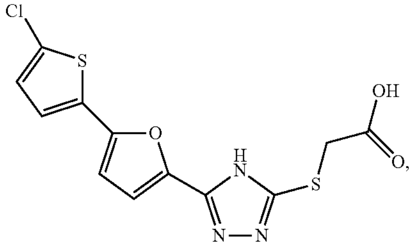
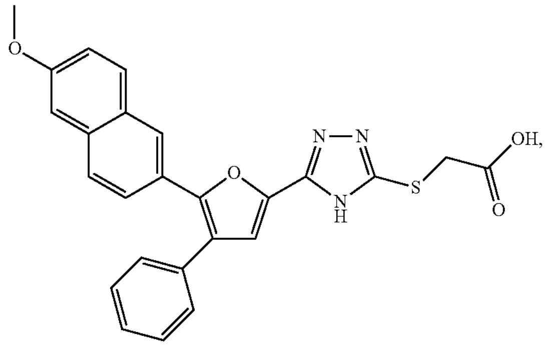
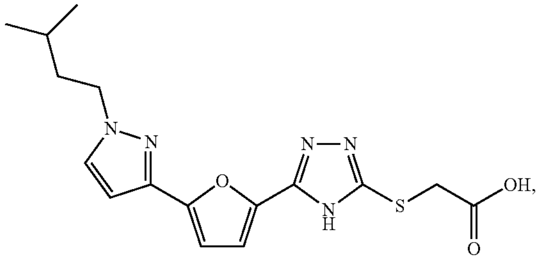
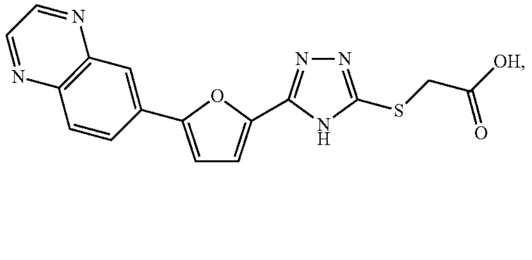
-continued
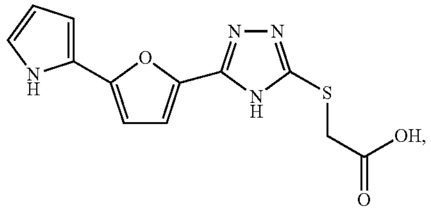
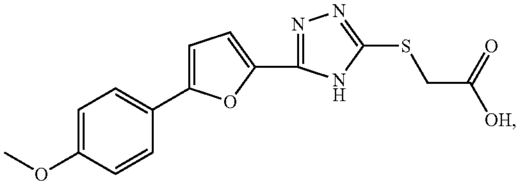
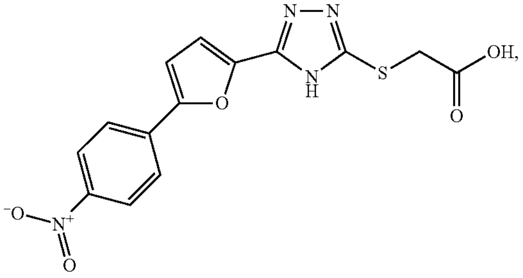
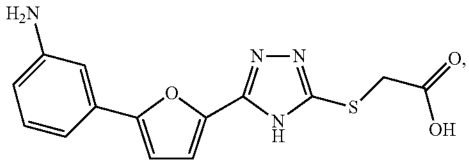
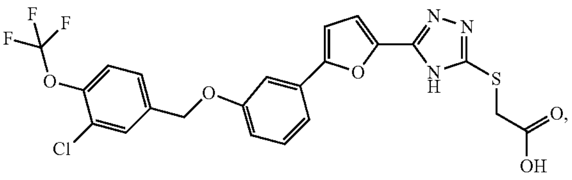
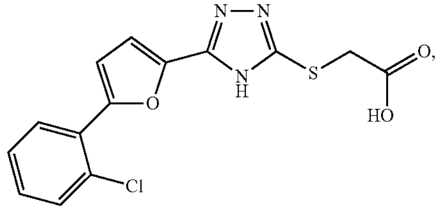
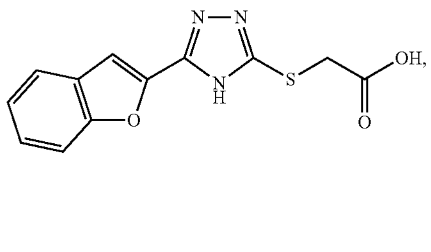

-continued
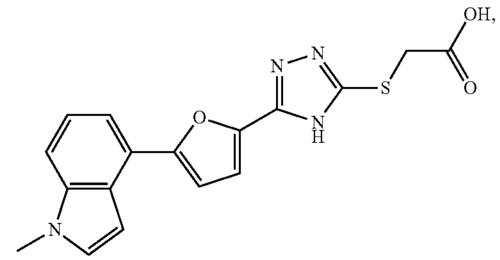
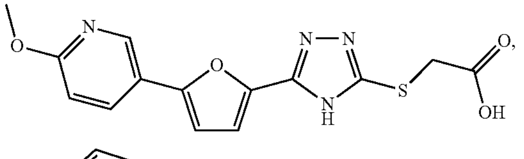
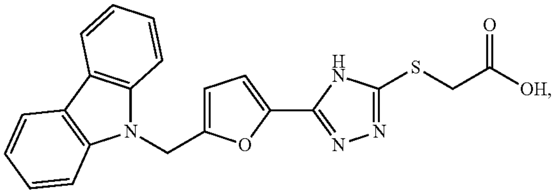
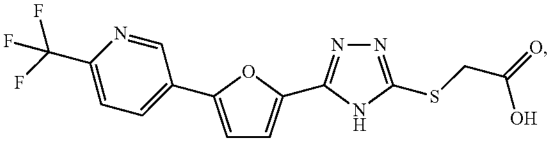
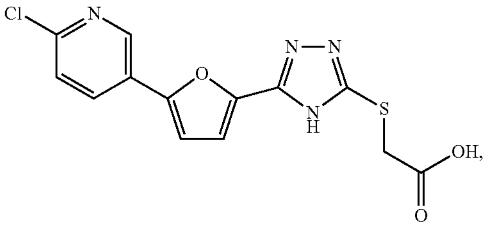
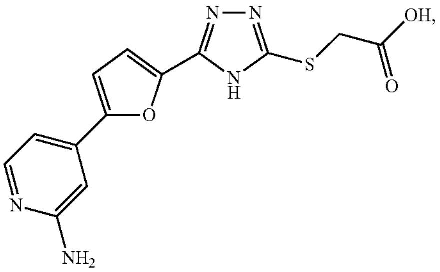
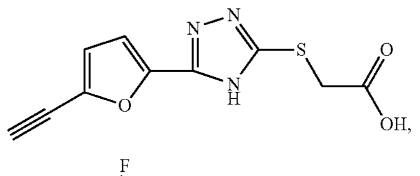
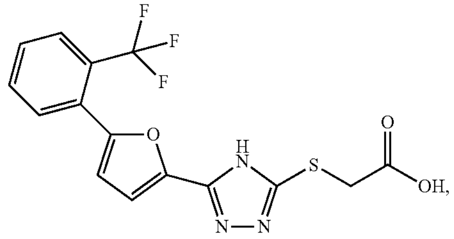
-continued
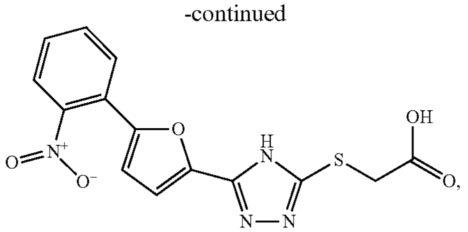
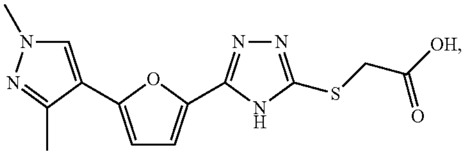
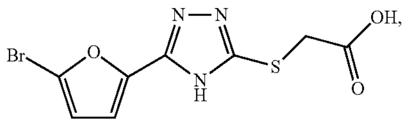
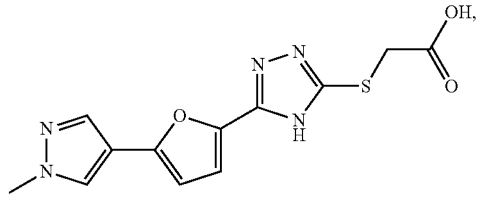
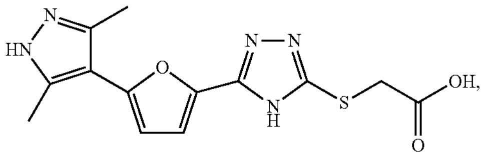
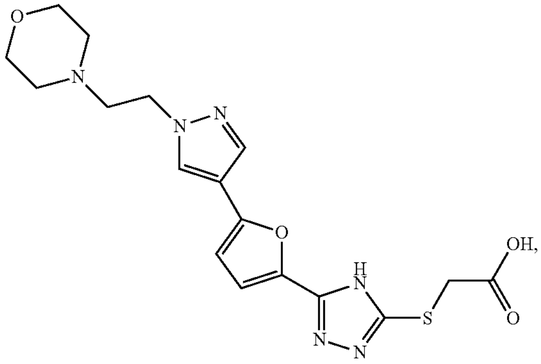
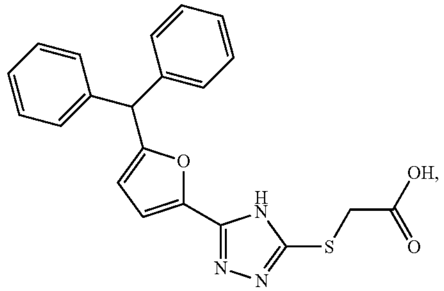
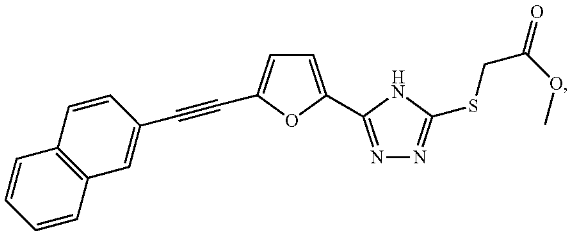

-continued

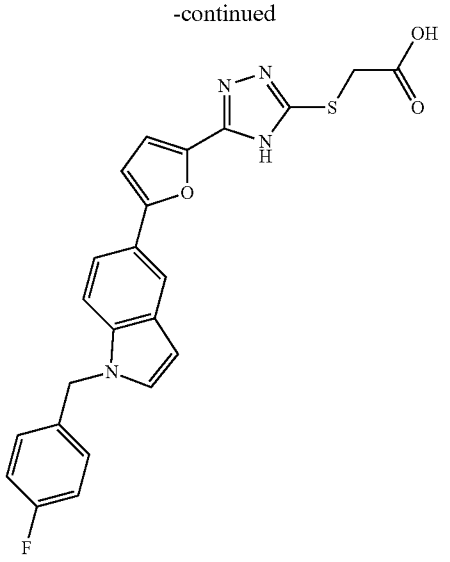

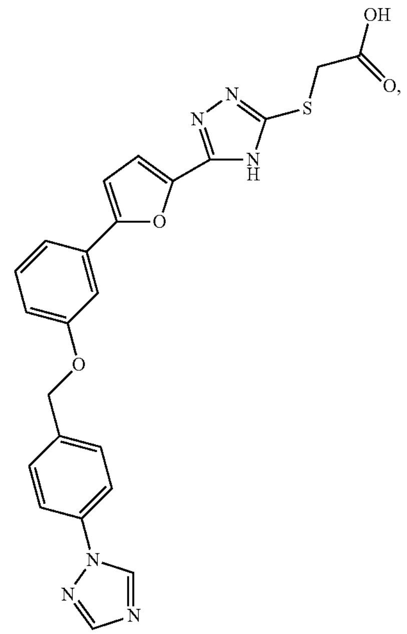

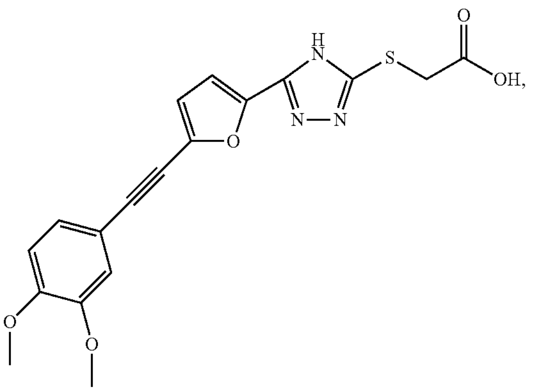

and

-continued

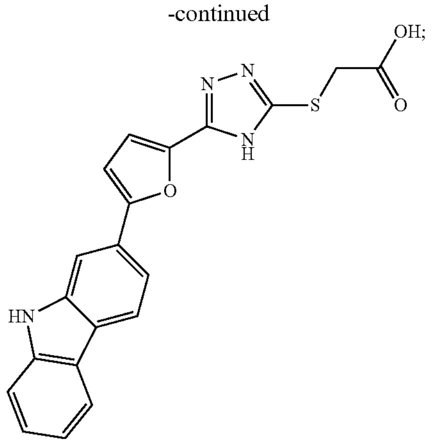

or a pharmaceutically acceptable salt thereof.

9. A compound of Formula II:

Formula II

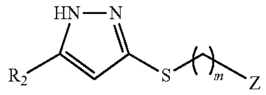

or a pharmaceutically acceptable salt thereof, wherein:

Z is selected from the group consisting of —C(O)OR$^1$ and

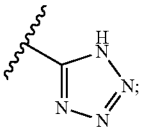 [SMILES: *c1nnn[nH]1]

$R^1$ is selected from the group consisting of H and ($C_1$-$C_6$)alkyl;

$R^2$ is a substituted or unsubstituted aryl, a substituted or unsubstituted heteroaryl; and m is an integer from 1 to 2.

10. The compound of claim 9, wherein $R^2$ is a substituted or unsubstituted furanyl, or a substituted or unsubstituted thiopheneyl.

11. The compound of claim 9, wherein the compound of Formula IIA is selected from a group consisting of:

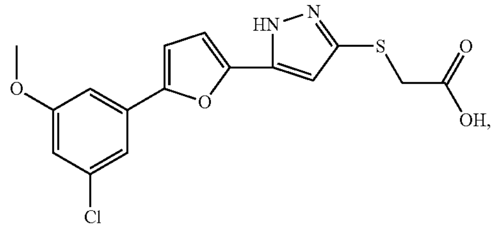

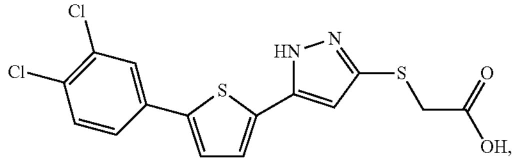

-continued

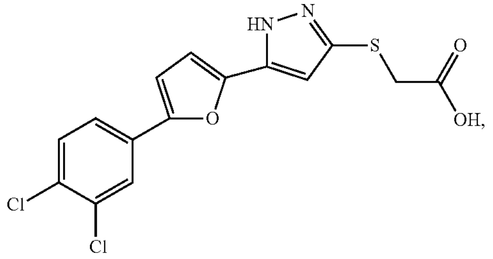

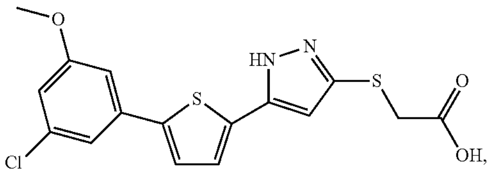

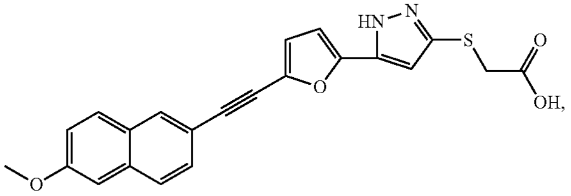

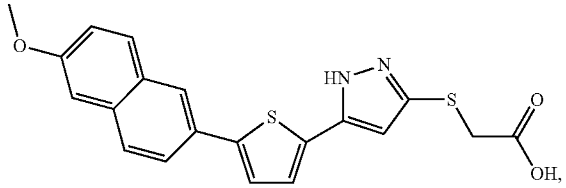

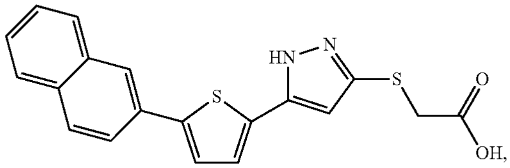

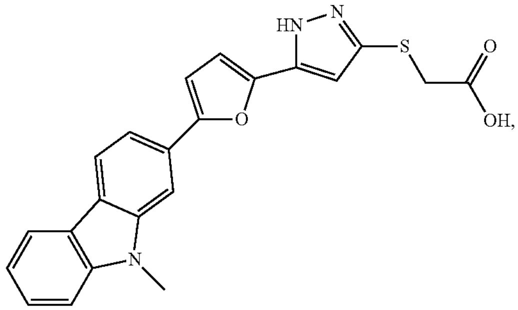

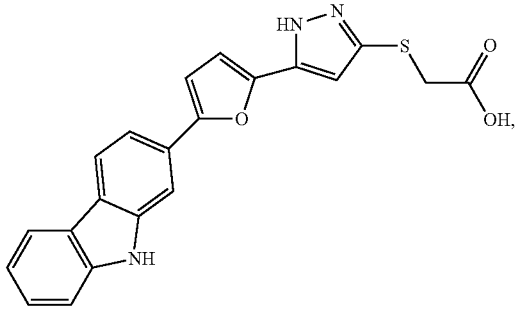

-continued

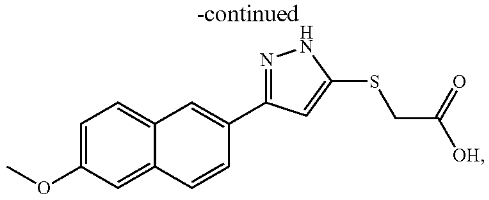

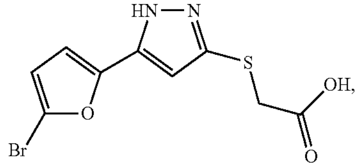

and

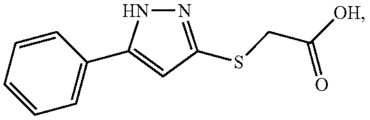

or a pharmaceutically acceptable salt thereof.

12. A compound of Formula III:

Formula III

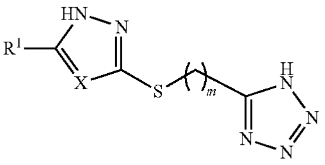

or a pharmaceutically acceptable salt thereof, wherein:

X is selected from the group consisting of CH and N;

$R^1$ is a substituted or unsubstituted aryl or a substituted or unsubstituted heteroaryl; and m is an integer from 1 to 2.

13. The compound of claim 12, wherein $R^1$ is:

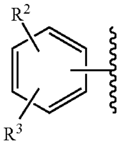

wherein:

each of $R^2$ and $R^3$ are independently selected from the group consisting of: H, halo, $(C_1\text{-}C_6)$alkyl, $(C_1\text{-}C_6)$haloalkyl, $OR^4$, $NO_2$, $NR^4R^5$, CN, a substituted or unsubstituted aryl, and a substituted or unsubstituted heteroaryl; and each of $R^4$ and $R^5$ are independently selected from the group consisting of H, $(C_1\text{-}C_6)$alkyl, and $(C_1\text{-}C_6)$haloalkyl.

14. The compound of claim 12, wherein $R^1$ is:

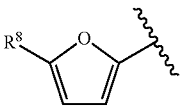

wherein:

$R^8$ is selected from the group consisting of: H, halo, $(C_1\text{-}C_6)$alkyl, $(C_1\text{-}C_6)$haloalkyl, $OR^{4b}$, $NO_2$, $NR^{4b}R^{5b}$, CN, a substituted or unsubstituted aryl, and a substituted or unsubstituted heteroaryl.

15. The compound of claim 14, wherein $R^8$ is:

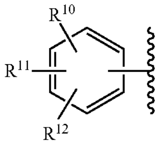

wherein:

each of $R^{10}$, $R^{11}$, and $R^{12}$ are independently selected from a group consisting of: H, halo, ($C_1$-$C_6$)alkyl, ($C_1$-$C_6$)haloalkyl, CN, $NO_2$, $OR^{13}$, $NR^{14}R^{15}$, $C(O)R^{16}$, $C(O)OR^{16}$, $—NR^{17}S(O)_2R^{18}$, $—S(O)_2NR^{19}R^{20}$, $—NR^{17}S(O)R^{18}$, $—S(O)_2NR^{19}R^{20}$, $—S(O)NR^{19}R^{20}$, $—NR^{21}C(O)R^{22}$, a substituted or unsubstituted aryl, a substituted or unsubstituted heteroaryl, and a substituted or unsubstituted heterocycloalkyl; or two of the groups $R^{10}$, $R^{11}$, and $R^{12}$ come together to form a substituted or unsubstituted fused cycloalkyl ring, a substituted or unsubstituted fused heterocycloalkyl ring, a substituted or unsubstituted fused aryl ring, or a substituted or unsubstituted fused heteroaryl ring; and each of $R^{13}$, $R^{14}$, $R^{15}$, $R^{16}$, $R^{17}$, $R^{18}$, $R^{19}$, $R^{20}$, $R^{21}$, and $R^{22}$ are independently selected from a group consisting of H, ($C_1$-$C_6$)alkyl, and ($C_1$-$C_6$)haloalkyl.

16. The compound of claim 12, wherein the compound of Formula IIIA is selected from the group consisting of:

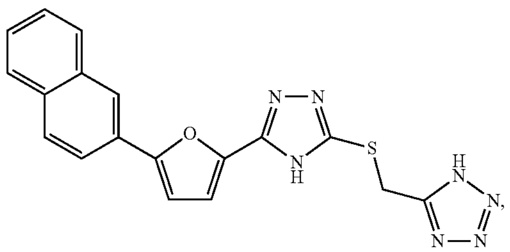

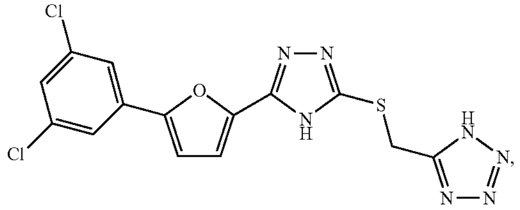

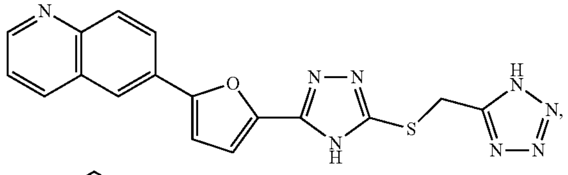

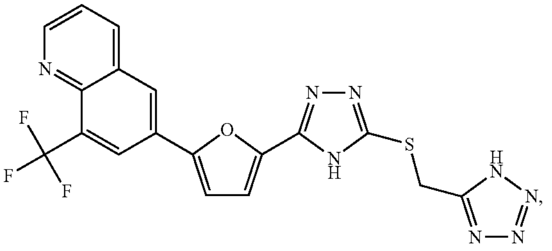

-continued

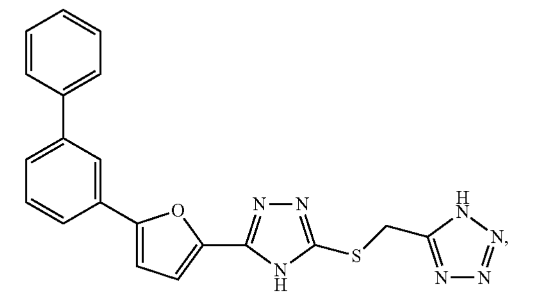

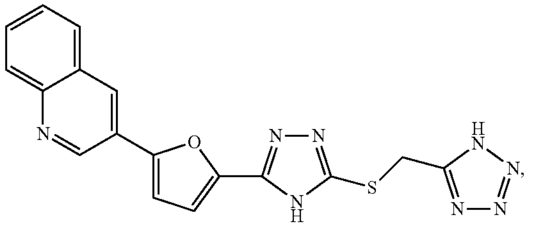

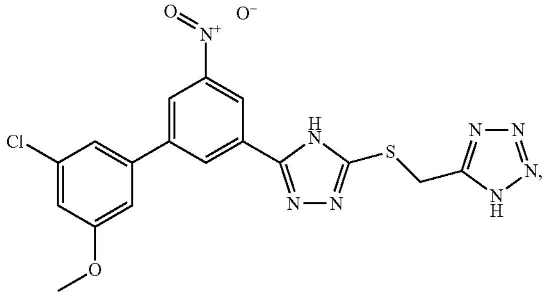

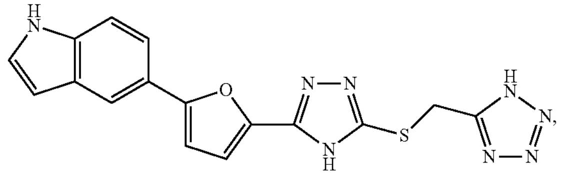

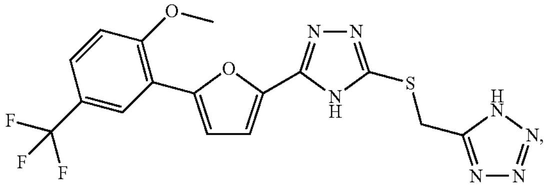

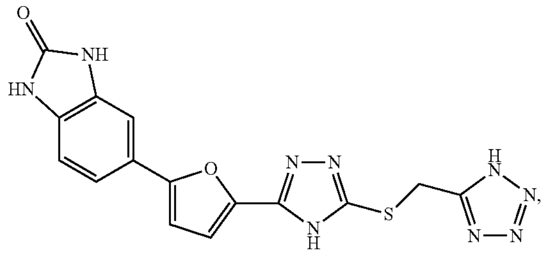

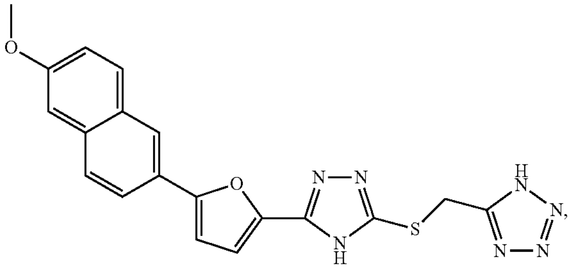

-continued
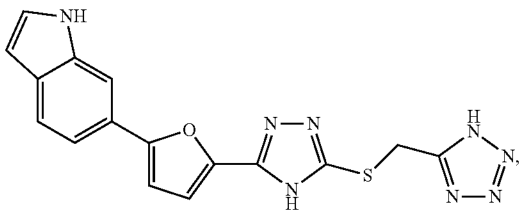
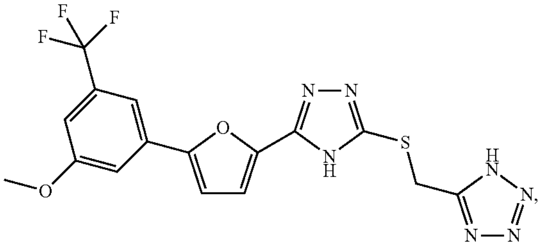
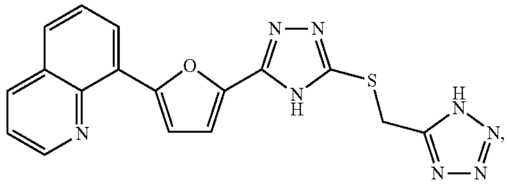
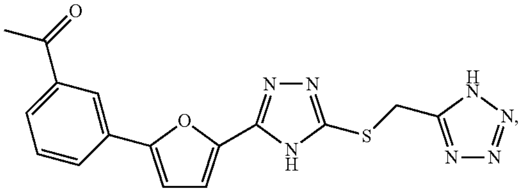
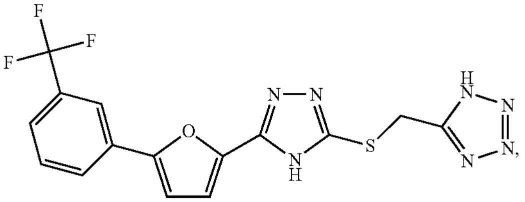
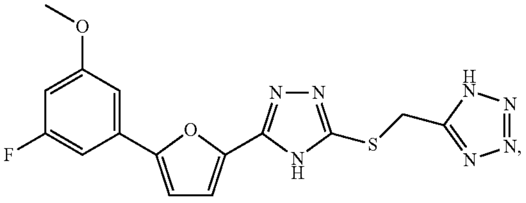
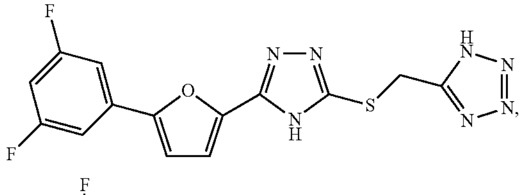
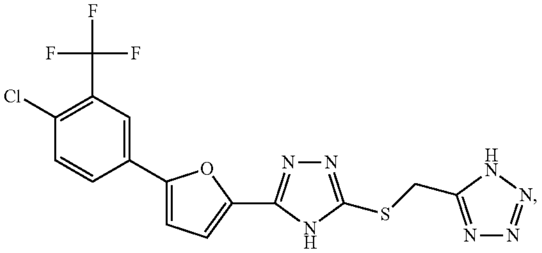
-continued
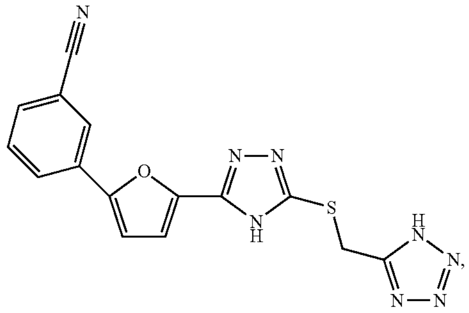
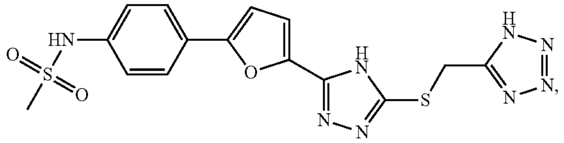
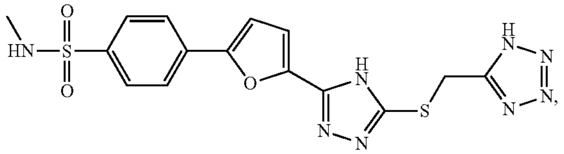
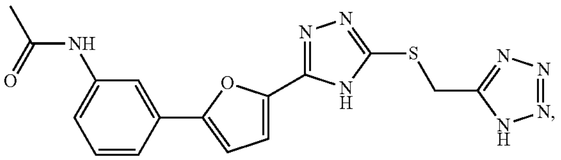
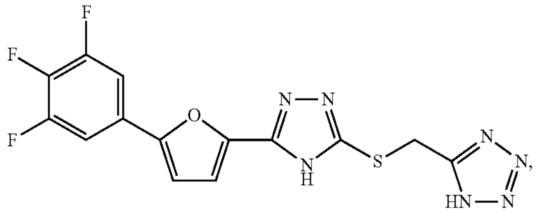
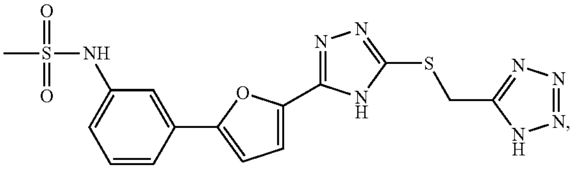
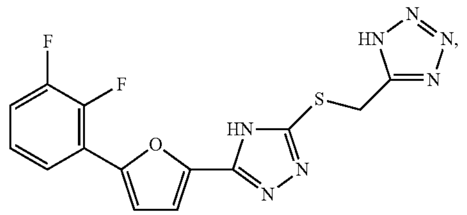
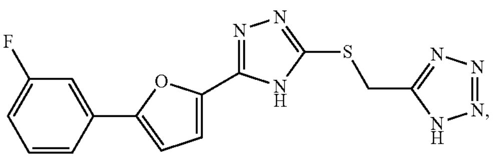
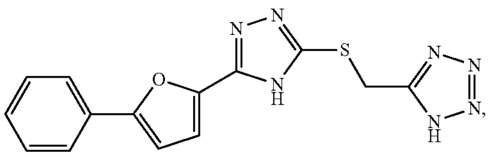

-continued
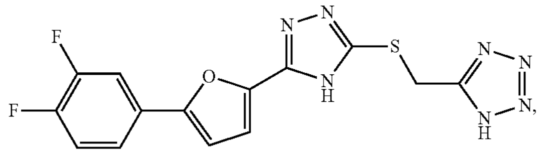
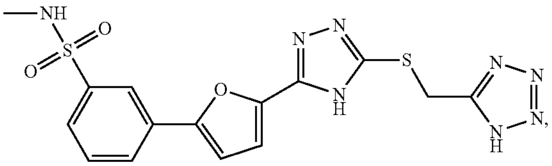
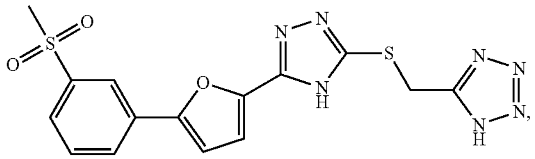
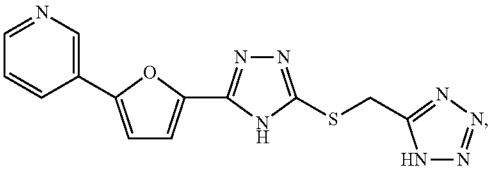
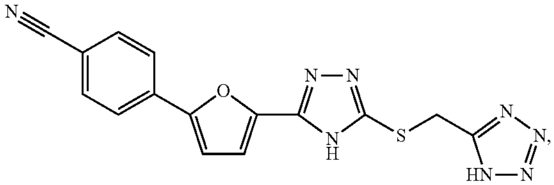
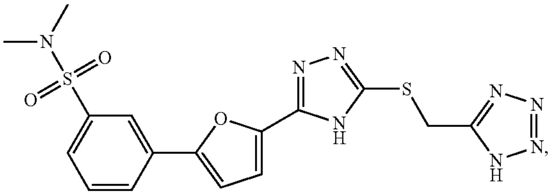
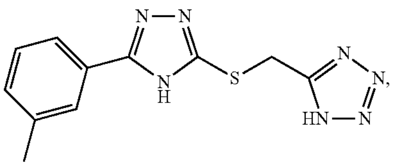
and
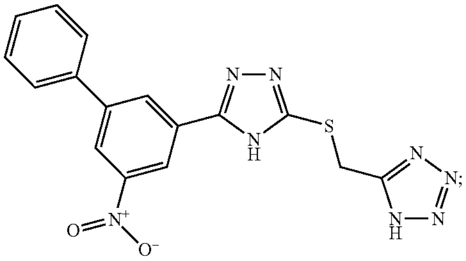
or a pharmaceutically acceptable salt thereof.
17. A compound selected from the group consisting of:
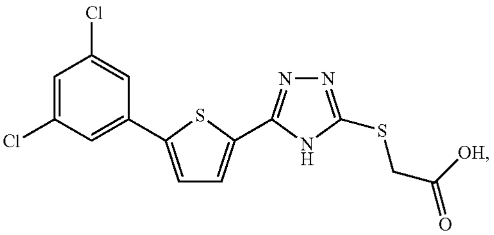
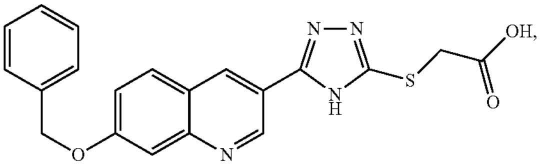
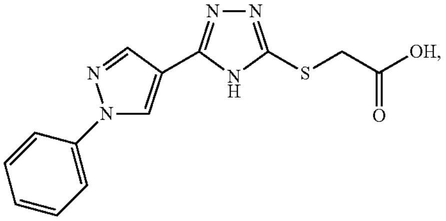
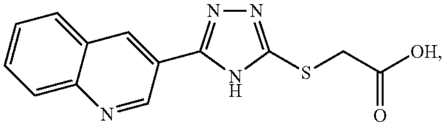
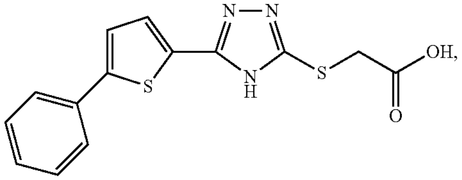
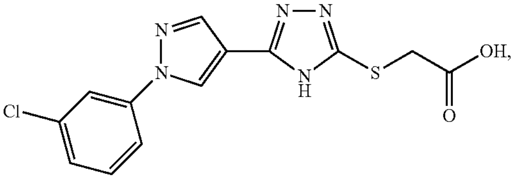
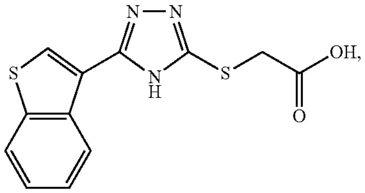
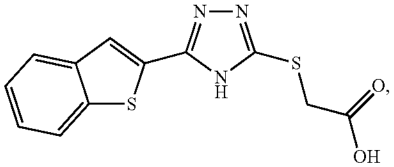
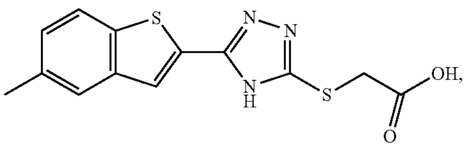

-continued
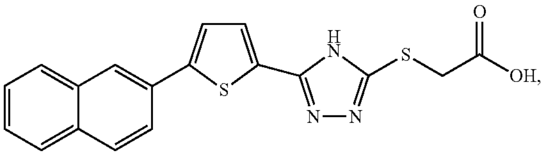
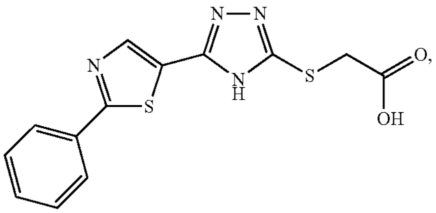
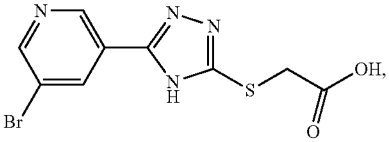
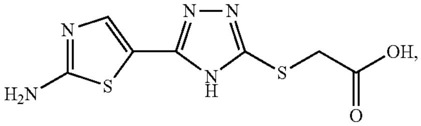
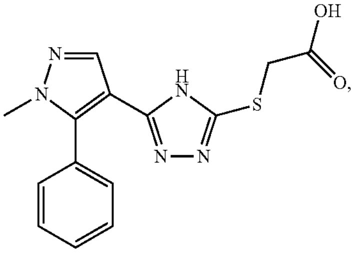
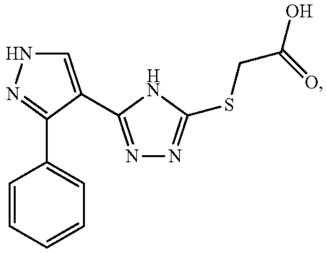
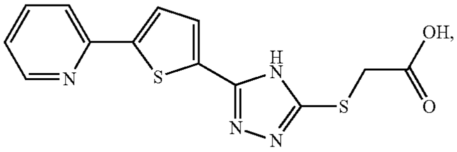
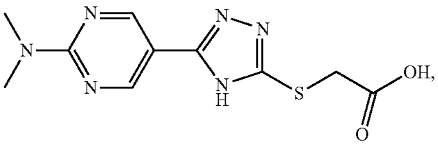
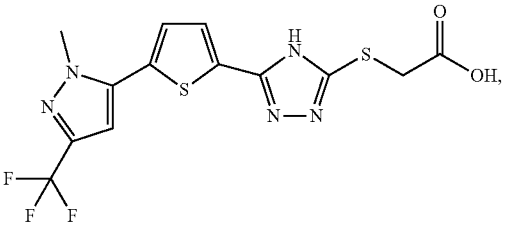
-continued
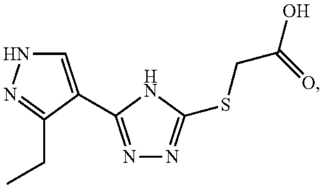
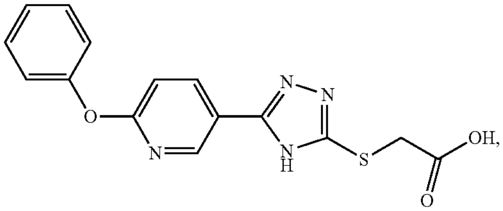
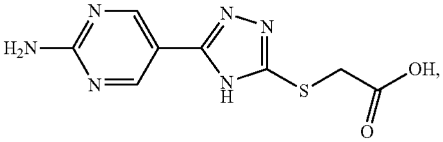
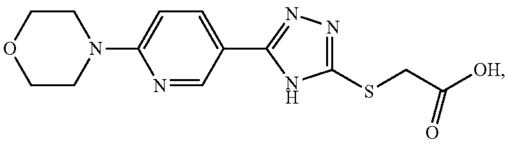
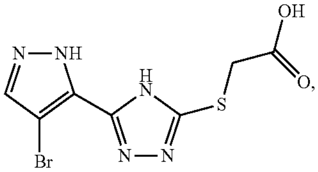
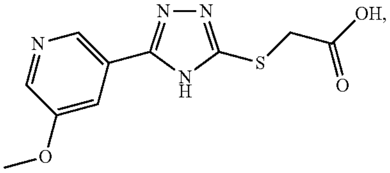
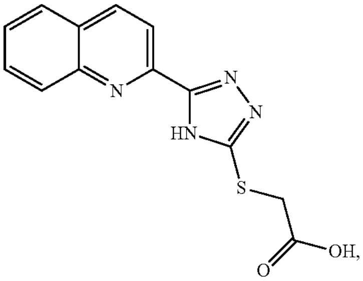
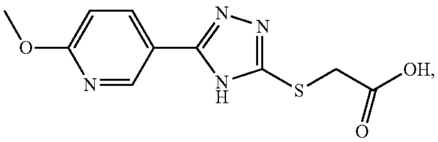
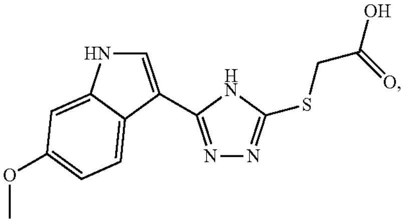

-continued
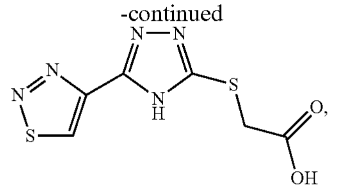
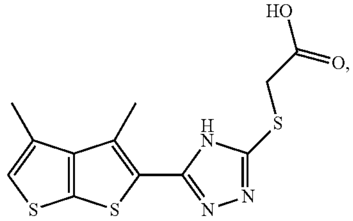
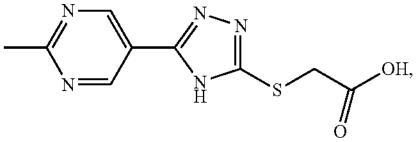
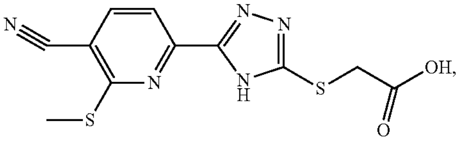
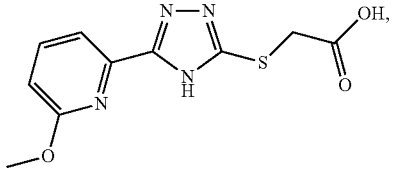
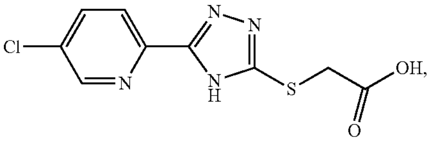
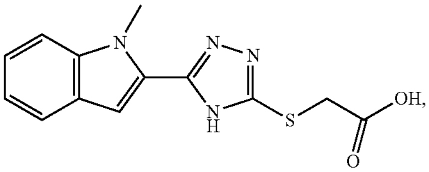
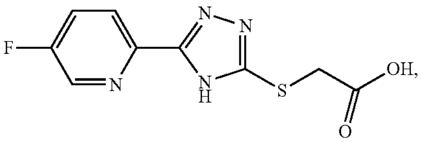
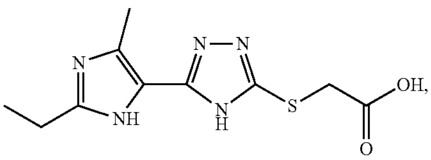
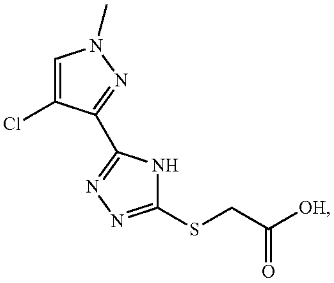
-continued
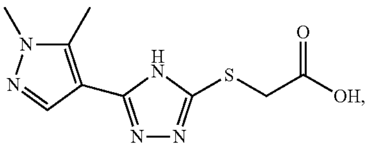
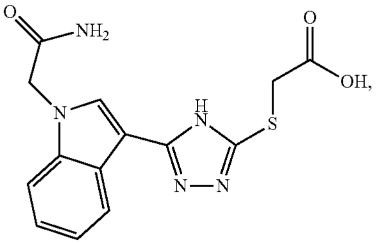
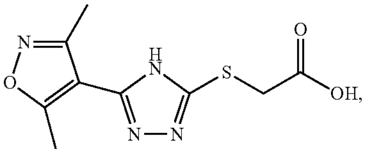
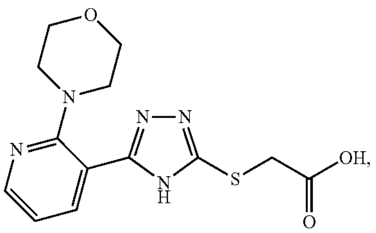
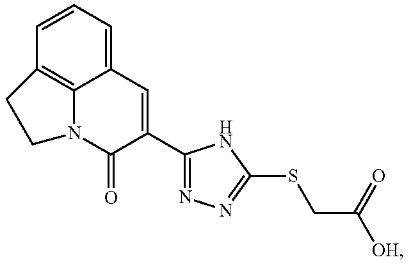
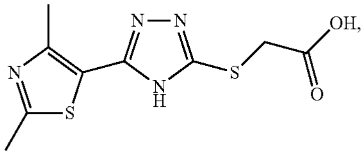
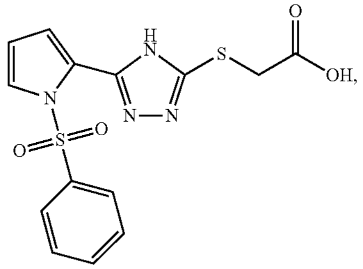
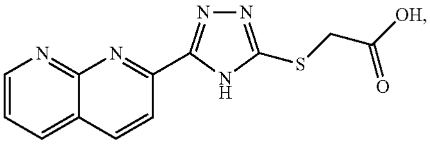

-continued

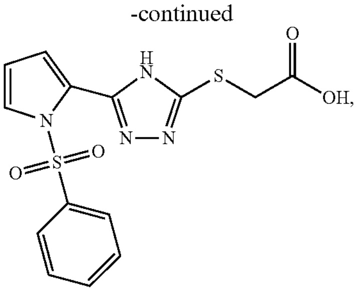

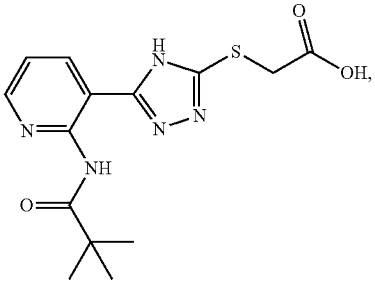

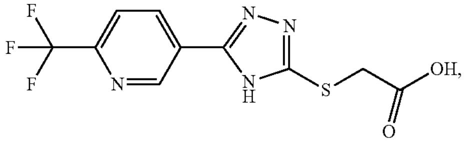

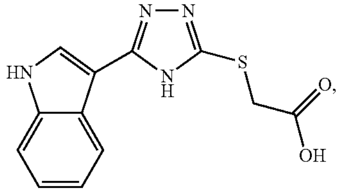

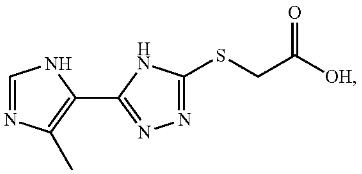

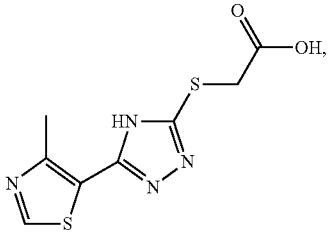

-continued

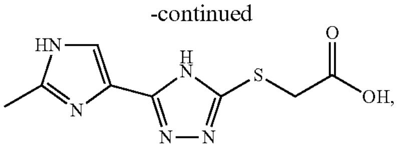

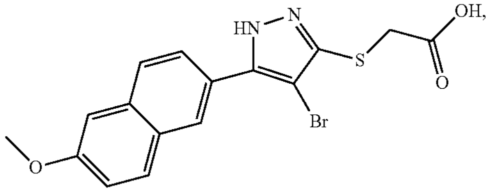

and

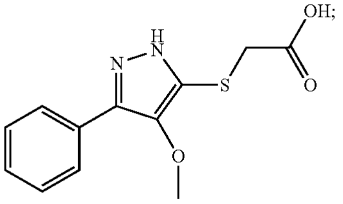

or a pharmaceutically acceptable salt thereof.

18. A pharmaceutical composition comprising a compound of claim 1, or a pharmaceutically acceptable salt thereof, and a pharmaceutically acceptable carrier.

19. A method for inhibiting a G protein coupled receptor 6 kinase polypeptide in a patient, the method comprising administering to the patient a therapeutically effective amount of a compound of claim 1, or a pharmaceutically acceptable salt thereof.

20. A method for treating a hematological malignancy exhibiting an overexpressed or over-active GRK6 polypeptide in a patient, the method comprising administering to the patient a therapeutically effective amount of a compound of claim 1, or a pharmaceutically acceptable salt thereof.

21. A method for treating an inflammation disease exhibiting an overexpressed or over-active GRK6 polypeptide in a patient, the method comprising administering to the patient a therapeutically effective amount of a compound of claim 1, or a pharmaceutically acceptable salt thereof.

22. A method of suppressing an immune response exhibiting an overexpressed or over-active GRK6 polypeptide in a patient, the method comprising administering to the patient a therapeutically effective amount of a compound of claim 1, or a pharmaceutically acceptable salt thereof.

* * * * *